United States Patent
Bruce et al.

(10) Patent No.: US 12,258,591 B2
(45) Date of Patent: *Mar. 25, 2025

(54) MODIFIED HELICASES

(71) Applicant: Oxford Nanopore Technologies PLC, Oxford (GB)

(72) Inventors: Mark Bruce, Oxford (GB); Andrew John Heron, Oxford (GB); Ruth Moysey, Oxford (GB); Szabolcs Soeroes, Oxford (GB); Elizabeth Jayne Wallace, Oxford (GB); James White, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 123 days.

This patent is subject to a terminal disclaimer.

(21) Appl. No.: 18/047,019

(22) Filed: Oct. 17, 2022

(65) Prior Publication Data

US 2023/0212535 A1    Jul. 6, 2023

Related U.S. Application Data

(60) Continuation of application No. 16/893,332, filed on Jun. 4, 2020, now Pat. No. 11,525,125, which is a division of application No. 15/028,651, filed as application No. PCT/GB2014/052736 on Sep. 10, 2014, now Pat. No. 10,724,018, and a continuation-in-part of application No. PCT/GB2014/050175, filed on Jan. 22, 2014.

(30) Foreign Application Priority Data

Oct. 18, 2013 (GB) .................................... 1318464
Mar. 17, 2014 (GB) .................................... 1404718
Apr. 4, 2014 (GB) .................................... 1406151

(51) Int. Cl.
*C12N 9/14* (2006.01)
*C12N 9/90* (2006.01)
*C12Q 1/6869* (2018.01)

(52) U.S. Cl.
CPC ............. *C12N 9/14* (2013.01); *C12N 9/90* (2013.01); *C12Q 1/6869* (2013.01); *C12Q 2565/631* (2013.01); *C12Y 306/04012* (2013.01)

(58) Field of Classification Search
None
See application file for complete search history.

(56) References Cited

U.S. PATENT DOCUMENTS

| | | | |
|---|---|---|---|
| 7,338,807 B2 | 3/2008 | Harris et al. | |
| 7,625,706 B2 | 12/2009 | Akeson et al. | |
| 7,745,116 B2 | 6/2010 | Williams | |
| 7,851,203 B2 | 12/2010 | Letant et al. | |
| 7,947,454 B2 | 5/2011 | Akeson et al. | |
| 8,105,846 B2 | 1/2012 | Bayley et al. | |
| 8,785,211 B2 | 7/2014 | Bayley et al. | |
| 8,828,208 B2 | 9/2014 | Canas et al. | |
| 9,617,591 B2 | 4/2017 | Moysey et al. | |
| 9,758,823 B2 | 9/2017 | Moysey et al. | |
| 9,797,009 B2 | 10/2017 | Heron et al. | |
| 10,221,450 B2 | 3/2019 | Heron et al. | |
| 10,322,150 B2 | 6/2019 | Honda et al. | |
| 10,385,382 B2 | 8/2019 | Moysey et al. | |
| 10,392,658 B2 | 8/2019 | Bowen et al. | |
| 10,443,097 B2 | 10/2019 | Jayasinghe et al. | |
| 10,480,026 B2 | 11/2019 | Garalde et al. | |
| 10,724,018 B2 | 7/2020 | Bruce et al. | |
| 10,724,087 B2 | 7/2020 | Moysey et al. | |
| 10,808,231 B2 | 10/2020 | Heron et al. | |
| 10,844,432 B2 | 11/2020 | Jayasinghe et al. | |
| 11,180,741 B2 | 11/2021 | Heron et al. | |
| 11,525,125 B2 | 12/2022 | Bruce et al. | |
| 11,525,126 B2 | 12/2022 | Heron et al. | |
| 11,634,763 B2 | 4/2023 | Moysey et al. | |
| 11,965,183 B2 | 4/2024 | Heron et al. | |
| 2003/0010638 A1 | 1/2003 | Hansford et al. | |
| 2004/0058378 A1 | 3/2004 | Kong et al. | |
| 2004/0248114 A1 | 12/2004 | Taira et al. | |
| 2006/0063171 A1 | 3/2006 | Akeson et al. | |
| 2008/0293045 A1 | 11/2008 | Piepenburg et al. | |
| 2008/0311582 A1 | 12/2008 | Bayley et al. | |
| 2009/0256116 A1 | 10/2009 | Shumaker-Parry et al. | |
| 2009/0269744 A1 | 10/2009 | Krause et al. | |
| 2010/0035260 A1 | 2/2010 | Olasagasti et al. | |
| 2010/0092960 A1 | 4/2010 | Fehr | |

(Continued)

FOREIGN PATENT DOCUMENTS

CA    2927728 A1    4/2015
CA    2937411 A1    7/2015

(Continued)

OTHER PUBLICATIONS

U.S. Appl. No. 18/762,324, filed Jul. 2, 2024, Heron et al.

(Continued)

*Primary Examiner* — Suzanne M Noakes
*Assistant Examiner* — Jae W Lee
(74) *Attorney, Agent, or Firm* — Wolf, Greenfield & Sacks, P.C.

(57) ABSTRACT

The invention relates to a new method of characterising a target polynucleotide. The method uses a pore and a Dda helicase. The helicase controls the movement of the target polynucleotide through the pore. The invention also relates to modified Dda helicases which can be used to control the movement of polynucleotides and are particularly useful for sequencing polynucleotides.

15 Claims, 34 Drawing Sheets

Specification includes a Sequence Listing.

(56) References Cited

U.S. PATENT DOCUMENTS

| | | |
|---|---|---|
| 2010/0120098 A1 | 5/2010 | Grunenwald et al. |
| 2010/0221212 A1 | 9/2010 | Stagliano et al. |
| 2010/0331194 A1 | 12/2010 | Turner et al. |
| 2011/0177498 A1 | 7/2011 | Clarke et al. |
| 2011/0229877 A1 | 9/2011 | Jayasinghe et al. |
| 2011/0311965 A1 | 12/2011 | Maglia et al. |
| 2012/0058468 A1 | 3/2012 | Mckeown |
| 2012/0107802 A1 | 5/2012 | Stoddart et al. |
| 2013/0048499 A1 | 2/2013 | Mayer et al. |
| 2013/0118902 A1 | 5/2013 | Akeson et al. |
| 2013/0149769 A1 | 6/2013 | Kizaki et al. |
| 2013/0225421 A1 | 8/2013 | Li et al. |
| 2013/0327644 A1 | 12/2013 | Turner et al. |
| 2014/0051069 A1 | 2/2014 | Jayasinghe et al. |
| 2014/0186823 A1 | 7/2014 | Clarke et al. |
| 2014/0255921 A1 | 9/2014 | Moysey et al. |
| 2014/0262784 A1 | 9/2014 | Clarke et al. |
| 2014/0335512 A1 | 11/2014 | Moysey et al. |
| 2015/0008126 A1 | 1/2015 | Maglia et al. |
| 2015/0031020 A1 | 1/2015 | Jayasinghe et al. |
| 2015/0065354 A1 | 3/2015 | Moysey et al. |
| 2015/0152492 A1 | 6/2015 | Brown et al. |
| 2015/0191709 A1 | 7/2015 | Heron et al. |
| 2015/0197796 A1 | 7/2015 | White et al. |
| 2015/0218629 A1 | 8/2015 | Heron et al. |
| 2016/0257942 A1 | 9/2016 | Bruce et al. |
| 2017/0002406 A1 | 1/2017 | Bowen et al. |
| 2018/0030530 A1 | 2/2018 | Moysey et al. |
| 2018/0037874 A9 | 2/2018 | Bruce et al. |
| 2018/0179500 A1 | 6/2018 | Heron et al. |
| 2018/0230526 A1 | 8/2018 | Heron et al. |
| 2019/0203288 A1 | 7/2019 | Gutierrez et al. |
| 2019/0345550 A1 | 11/2019 | Bowen et al. |
| 2021/0009971 A1 | 1/2021 | Bruce et al. |
| 2021/0123032 A1 | 4/2021 | Heron et al. |
| 2021/0139972 A1 | 5/2021 | Jayasinghe et al. |
| 2021/0172011 A1 | 6/2021 | Moysey et al. |
| 2022/0135956 A1 | 5/2022 | Heron et al. |
| 2022/0372568 A1 | 11/2022 | Moysey et al. |
| 2023/0227799 A1 | 7/2023 | Heron et al. |
| 2024/0060126 A1 | 2/2024 | Jayasinghe et al. |
| 2024/0287485 A1 | 8/2024 | Heron et al. |
| 2024/0301484 A1 | 9/2024 | Moysey et al. |

FOREIGN PATENT DOCUMENTS

| | | |
|---|---|---|
| CN | 104039979 A | 9/2014 |
| JP | 2006-500028 A | 1/2006 |
| WO | WO 2000/028312 A1 | 5/2000 |
| WO | WO 2002/092821 A1 | 11/2002 |
| WO | WO 2004/027025 A2 | 4/2004 |
| WO | WO 2005/124888 A1 | 12/2005 |
| WO | WO 2006/028508 A2 | 3/2006 |
| WO | WO 2006/100484 A2 | 9/2006 |
| WO | WO 2007/057668 A1 | 5/2007 |
| WO | WO 2008/102120 A1 | 8/2008 |
| WO | WO 2008/102121 A1 | 8/2008 |
| WO | WO 2008/124107 A1 | 10/2008 |
| WO | WO 2009/035647 A1 | 3/2009 |
| WO | WO 2009/044170 A1 | 4/2009 |
| WO | WO 2009/077734 A2 | 6/2009 |
| WO | WO 2010/004265 A1 | 1/2010 |
| WO | WO 2010/004273 A1 | 1/2010 |
| WO | WO 2010/034018 A2 | 3/2010 |
| WO | WO 2010/086602 A1 | 8/2010 |
| WO | WO 2010/086603 A1 | 8/2010 |
| WO | WO 2010/086622 A1 | 8/2010 |
| WO | WO 2010/109197 A2 | 9/2010 |
| WO | WO 2010/117470 A2 | 10/2010 |
| WO | WO 2010/122293 A1 | 10/2010 |
| WO | WO 2011/067559 A1 | 6/2011 |
| WO | WO 2012/033524 A2 | 3/2012 |
| WO | WO 2012/164270 A1 | 12/2012 |
| WO | WO 2013/014451 A1 | 1/2013 |
| WO | WO 2013/041878 A1 | 3/2013 |
| WO | WO 2013/057495 A2 | 4/2013 |
| WO | WO 2013/098561 A1 | 7/2013 |
| WO | WO 2013/098562 A2 | 7/2013 |
| WO | WO 2013/153359 A1 | 10/2013 |
| WO | WO 2013/185137 A1 | 12/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/064443 A2 | 5/2014 |
| WO | WO 2014/064444 A1 | 5/2014 |
| WO | WO 2014/135838 A1 | 9/2014 |
| WO | WO 2014/158665 A1 | 10/2014 |
| WO | WO 2015/022544 A1 | 2/2015 |
| WO | WO 2015/055981 A2 | 4/2015 |
| WO | WO 2015/110777 A1 | 7/2015 |
| WO | WO 2015/110813 A1 | 7/2015 |
| WO | WO 2015/124935 A1 | 8/2015 |
| WO | WO 2015/150786 A1 | 10/2015 |
| WO | WO 2016/034591 A2 | 3/2016 |
| WO | WO 2016/055777 A2 | 4/2016 |
| WO | WO 2016/059363 A1 | 4/2016 |
| WO | WO 2018/060740 A1 | 4/2018 |
| WO | WO 2018/100370 A1 | 6/2018 |

OTHER PUBLICATIONS

International Search Report and Written Opinion for PCT/GB2014/052736, mailed Apr. 17, 2015.

International Preliminary Report on Patentability for PCT/GB2014/052736, mailed Apr. 28, 2016.

[No Author Listed] Antibodies bind specific molecules through their hypervariable loops. 33.3 Antibody Binding. 6th edition. 2007;953-954.

[No Author Listed] Data sheet Seq ID No. 10 search results from STIC, printed on Oct. 29, 2018, pp. 1-38 (Year: 2018).

[No Author Listed] Enterobacteria phage T4 helicase Dda E94C/A360C mutant, Seq ID 8., XP055978108, Oct. 23, 2014, Retrieved from EBI accession No. GSP: BBM82447, Database accession No. BBM82447, Geneseq [online].

[No Author Listed] *Escherichia* phage PBECO4 DNA helicase, XP055978026, Jan. 25, 2013, retrieved from EBI accession No. UPI0002AB07E2, Database accession No. AGC35141.

[No Author Listed] Data sheet Seq ID No. 2 search results from STIC, printed on Oct. 29, 2018, pp. 1-24 (Year: 2018).

[No Author Listed] Press release: Oxford Nanopore introduces DNA 'strand sequencing' on the high-throughput GridION platform and presents MinION, a sequencer the size of a USB; memory stick, Feb. 2012.

[No Author Listed] UniProt Database accession No. 17J3V8 sequence. Oct. 3, 2012.

[No Author Listed] UniProt Database accession No. k7nri8 sequence. Feb. 6, 2013.

Ali et al., Kinetic measurement of the step size of DNA unwinding by *Escherichia coli* UvrD helicase. Science. Jan. 17, 1997;275(5298):377-80. doi: 10.1126/science.275.5298.377. Erratum in: Science Apr. 4, 1997;276(5309):21.

Allen et al., The genome sequence of the psychrophilic archaeon, Methanococcoides burtonii: the role of genome evolution in cold adaptation. ISME J. Sep. 2009;3(9):1012-35. doi: 10.1038/ismej.2009.45.

Altschul et al., Basic local alignment search tool. J Mol Biol. Oct. 5, 1990;215(3):403-10.

Altschul, A protein alignment scoring system sensitive at all evolutionary distances. J Mol Evol. Mar. 1993;36(3):290-300.

Arslan et al., Protein structure. Engineering of a superhelicase through conformational control. Science. Apr. 17, 2015;348(6232):344-7. doi: 10.1126/science.aaa0445.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

(56) References Cited

OTHER PUBLICATIONS

Balakrishnan et al., Dna2 exhibits a unique strand end-dependent helicase function. J Biol Chem Dec. 10, 2010;285(50):38861-8. doi: 10.1074/jbc.M110.165191. Epub Oct. 6, 2010.
Balci et al., Single-molecule nanopositioning: structural transitions of a helicase-DNA complex during ATP hydrolysis. Biophys J. Aug. 17, 2011;101(4):976-84. doi: 10.1016/j.bpj.2011.07.010.
Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.
Bennett et al., Association of yeast DNA topoisomerase III and Sgs1 DNA helicase: studies of fusion proteins. Proc Natl Acad Sci U S A. Sep. 25, 2001;98(20):11108-13. Epub Sep. 1, 2001.
Berger, SnapShot: nucleic acid helicases and translocases. Cell. Sep. 5, 2008;134(5):888-888.e1. doi: 10.1016/j.cell.2008.08.027.
Bessler et al., The amino terminus of the *Saccharomyces cerevisiae* DNA helicase Rrm3p modulates protein function ltering replication and checkpoint activity. Genetics. Nov. 2004;168(3):1205-18.
Blast ® NCBI. Sequence ID No. 10; ZSYBNHWV114. Sep. 18, 2015.
Blast ® NCBI. Sequence ID No. 52; ZT1133A811N. Sep. 18, 2015.
Braha et al., Designed protein pores as components for biosensors. Chem Biol. Jul. 1997;4(7):497-505.
Breyer et al., A structural basis for processivity. Protein Sci. Sep. 2001; 10(9):1699-711. doi: 10.1110/ps.10301.
Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.
Buttner et al., Structural basis for DNA duplex separation by a superfamily-2 helicase. Nat Struct Mol Biol. Jul. 2007; 14(7):647-52.
Byrd et al., A parallel quadruplex DNA is bound tightly but unfolded slowly by pif1 helicase. J Biol Chem. Mar. 6, 2015;290(10):6482-94. doi: 10.1074/jbc.M114.630749. Epub Jan. 14, 2015.
Byrd et al., Dda helicase tightly couples translocation on single-stranded DNA to unwinding of duplex DNA: Dda is an optimally active helicase. J Mol Biol. Jul. 13, 2012;420(3):141-54. doi: 10.1016/j.jmb.2012.04.007. Epub Apr. 11, 2012.
Byrd et al., Superfamily 2 helicases. Front Biosci (Landmark Ed). Jun. 1, 2012;17:2070-88.
Chandler et al., A new microparticle size calibration standard for use in measuring smaller microparticles using a new flow cytometer. J Thromb Haemost. Jun. 2011;9(6):1216-24. doi: 10.1111/j.1538-7836.2011.04283.x.
Cheng et al., Functional characterization of the multidomain F plasmid TraI relaxase-helicase. J Biol Chem. Apr. 8, 2011;286(14):12670-82. doi: 10.1074/jbc.M110.207563. Epub Feb. 2, 2011.
Colas et al., Microscopical investigations of nisin-loaded nanoliposomes prepared by Mozafari method and their bacterial targeting. Micron. 2007;38(8):841-7.
Comer et al., Microscopic mechanics of hairpin DNA translocation through synthetic nanopores. Biophys J. Jan. 2009;96(2):593-608. doi: 10.1016/j.bpj.2008.09.023.
Deamer, Nanopore analysis of nucleic acids bound to exonucleases and polymerases. Annu Rev Biophys. 2010;39:79-90. doi: 10.1146/annurev.biophys.093008.131250.
Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.
Devereux et al., A comprehensive set of sequence analysis programs for the VAX. Nucleic Acids Res. Jan. 11, 1984;12(1 Pt 1):387-95.
Dong et al., Wza the translocon for *E. coli* capsular polysaccharides defines a new class of membrane protein. Nature. Nov. 9, 2006;444(7116):226-9. doi: 10.1038/nature05267. Epub Nov. 1, 2006. Author Manuscript, 14 pages.

Dostál et al., Tracking F plasmid TraI relaxase processing reactions provides insight into F plasmid transfer. Nucleic Acids Res. Apr. 2011;39(7):2658-70. doi: 10.1093/nar/gkq1137. Epub Nov. 24, 2010.
Dou et al., The DNA binding properties of the *Escherichia coli* RecQ helicase. J Biol Chem. Feb. 20, 2004;279(8):6354-63. Epub Dec. 9, 2003.
Durrieu et al., Interactions between neuronal fusion proteins explored by molecular dynamics. Biophys J. May 1, 2008;94(9):3436-46. doi: 10.1529/biophysj.107.123117. Epub Jan. 22, 2008.
Eliseev et al., Molecular Recognition of Nucleotides, Nucleosides, and Sugars by Aminocyclodextrins. J. Am. Chem. Soc., vol. 116:6081-6088 (1994).
Eoff et al., The Kinetic Mechanism for DNA Unwinding by Multiple Molecules of Dda Helicase Aligned on DNA. Biochemistry. Jun. 1, 2010; 49(21): 4543-4553. doi:10.1021/bi100061v. Author Manuscript.
Fairman-Williams et al., SF1 and SF2 helicases: family matters. Curr Opin Struct Biol. Jun. 2010;20(3):313-24. doi:10.1016/j.sbi.2010.03.011. Epub Apr. 22, 2010.
Farah et al., The RecBCD enzyme initiation complex for DNA unwinding:enzyme positioning and DNA opening. J Mol Biol. Oct. 10, 1997;272(5):699-715.
Garalde et al., Highly parallel direct RNA sequencing on an array of nanopores. bioRxiv. 2016. doi: http://dx.doi.org/10.1101/068809.
Garcillán-barcia et al., The diversity of conjugative relaxases and its application in plasmid classification. FEMS Microbiol Rev. May 2009;33(3):657-87.
Genbank accession No. AEA72977 sequence. Apr. 6, 2011.
Genbank Submission. NCBI; Accession No. AM778123. Richards et al.; Sep. 18, 2008.
GenPept Accession No. XP 003728286. Jun. 7, 2012.
Gonzalez-Perez et al., Biomimetic triblock copolymer membrane arrays: a stable template for functional membrane proteins. Langmuir. Sep. 15, 2009;25(18):10447-50. doi: 10.1021/la902417m.
Graham et al., Sequence-specific assembly of FtsK hexamers establishes directional translocation on DNA. Proc Natl Acad Sci U S A. Nov. 23, 2010;107(47):20263-8. doi:10.1073/pnas.1007518107. Epub Nov. 3, 2010.
Grant et al., A facile method for attaching nitroxide spin labels at the 5' terminus of nucleic acids. Nucleic Acids Res. 2007;35(10):e77. Epub May 21, 2007.
Green et al., Quantitative evaluation of the lengths of homobifunctional protein cross-linking reagents used as molecular rulers. Protein Sci. Jul. 2001;10(7):1293-304.
Guo et al., Protein tolerance to random amino acid change. Proc Natl Acad Sci U S A. Jun. 22, 2004;101(25):9205-10. doi: 10.1073/pnas.0403255101. Epub Jun. 14, 2004.
Guo et al., The linker region between the helicase and primase domains of the bacteriophage T7 gene 4 protein is critical for hexamer formation. J Biol Chem. Oct. 15, 1999;274(42):30303-9.
Hammerstein et al., Subunit dimers of alpha-hemolysin expand the engineering toolbox for protein nanopores. J Biol Chem. Apr. 22, 2011;286(16):14324-34. doi: 10.1074/jbc.M111.218164. Epub Feb. 15, 2011.
He et al, The T4 phage SF1B helicase Dda is structurally optimized to perform DNA strand separation. Structure. Jul. 3, 2012;20(7):1189-200. doi:10.1016/j.str.2012.04.013. Epub May 31, 2012.
Heron et al., Simultaneous measurement of ionic current and fluorescence from single protein pores. J Am Chem Soc. Feb. 11, 2009;131(5):1652-3. doi: 10.1021/ja808128s.
Holden et al., Direct introduction of single protein channels and pores into lipid bilayers. J Am Chem Soc. May 11, 2005;127(18):6502-3.
Holden et al., Functional bionetworks from nanoliter water droplets. J Am Chem Soc. Jul. 11, 2007;129(27):8650-5. Epub Jun. 16, 2007.
Hopfner et al., Mechanisms of nucleic acid translocases: lessons from structural biology and single-molecule biophysics. Curr Opin Struct Biol. Feb. 2007;17(1):87-95. Epub Dec. 6, 2006.
Hornblower et al., Single-molecule analysis of DNA-protein complexes using nanopores. Nat Methods. Apr. 2007;4(4):315-7. Epub Mar. 4, 2007.

(56) References Cited

OTHER PUBLICATIONS

Howorka et al., Nanopore analytics: sensing of single molecules. Chem Soc Rev. Aug. 2009;38(8):2360-84. doi: 10.1039/b813796j. Epub Jun. 15, 2009.

Ivanov et al., DNA tunneling detector embedded in a nanopore. Nano Lett. Jan. 12, 2011;11(1):279-85. doi: 10.1021/nl103873a. Epub Dec. 6, 2010.

James, Aptamers. Encyclopedia of Analytical Chemistry. R.A. Meyers (Ed.). 4848-4871. John Wiley & Sons Ltd, Chichester, 2000.

Jankowsky, RNA helicases at work: binding and rearranging. Trends Biochem Sci. Jan. 2011;36(1):19-29. doi: 10.1016/j.tibs.2010.07.008.

Japrung et al., Urea facilitates the translocation of single-stranded DNA and RNA through the alpha-hemolysin nanopore. Biophys J. May 19, 2010;98(9):1856-63. doi: 10.1016/j.bpj.2009.12.4333.

Jezewska et al., Interactions of *Escherichia coli* replicative helicase PriA protein with single-stranded DNA. Biochemistry. Aug. 29, 2000;39(34):10454-67.

Jia et al., Rotations of the 2B Sub-domain of *E. coli* UvrD Helicase/Translocase Coupled to Nucleotide and DNA Binding. J Mol Biol. Aug. 19, 2011; 411(3): 633-648. EPub Jun. 17, 2011. doi: 10.1016/j.jmb.2011.06.019.

Jones et al., Protein secondary structure prediction based on position-specific scoring matrices. J Mol Biol. Sep. 17, 1999;292(2):195-202. doi: 10.1006/jmbi.1999.3091.

Kabsch et al., Dictionary of protein secondary structure: pattern recognition of hydrogen-bonded and geometrical features. Biopolymers. Dec. 1983;22(12):2577-637. doi: 10.1002/bip.360221211.

Kafri et al., Dynamics of molecular motors and polymer translocation with sequence heterogeneity. Biophys J. Jun. 2004;86(6):3373-91.

Kalli et al., Conformational changes in talin on binding to anionic phospholipid membranes facilitate signaling by integrin transmembrane helices. PLoS Comput Biol. Oct. 2013;9(10):e1003316. doi:10.1371/journal.pcbi.1003316. Epub Oct. 31, 2013.

Kankia et al., Folding of the thrombin aptamer into a G-quadruplex with Sr(2+): stability, heat, and hydration. J Am Chem Soc. Nov. 7, 2001;123(44):10799-804.

Kar et al., Defining the structure-function relationships of bluetongue virus helicase protein VP6. J Virol. Nov. 2003;77(21):11347-56.

Keyser, Controlling molecular transport through nanopores. J R Soc Interface. Oct. 7, 2011;8(63):1369-78. doi: 10.1098/rsif.2011.0222. Epub Jun. 29, 2011.

Khafizov, Single Molecule Force Spectroscopy Of Single Stranded Dna Binding Protein And Rep Helicase. University of Illinois at Urbana-Champaign Dissertation. 2012.

Korolev et al., Major domain swiveling revealed by the crystal structures of complexes of *E. coli* Rep helicase bound to single-stranded DNA and ADP. Cell. Aug. 22, 1997;90(4):635-47.

Kumar et al., Nonradioactive labeling of synthetic oligonucleotide probes with terminal deoxynucleotidyl transferase. Anal Biochem. Mar. 1988; 169(2):376-82. Erratum in: Anal Biochem Sep. 1988;173(2):469.

Kuper et al., Functional and structural studies of the nucleotide excision repair helicase XPD suggest a polarity for DNA translocation. EMBO J. Jan. 18, 2012;31(2):494-502. doi: 10.1038/emboj.2011.374.

Kutyavin et al., Oligonucleotides containing 2-aminoadenine and 2-thiothymine act as selectively binding complementary agents. Biochemistry. Aug. 27, 1996;35(34):11170-6.

Langecker et al., Synthetic lipid membrane channels formed by designed DNA nanostructures. Science. Nov. 16, 2012;338(6109):932-6. doi: 10.1126/science.1225624.

Lee et al., Cooperative translocation enhances the unwinding of duplex DNA by SARS coronavirus helicase nsP13. Nucleic Acids Res. Nov. 2010;38(21):7626-36. doi:10.1093/nar/gkq647. Epub Jul. 29, 2010.

Lee et al., Direct imaging of single UvrD helicase dynamics on long single-stranded DNA. Nat Commun. 2013;4:1878. doi:10.1038/ncomms2882.

Levin et al., Helicase from hepatitis C virus, energetics of DNA binding. J Biol Chem. Aug. 16, 2002;277(33):29377-85. Epub May 28, 2002.

Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.

Liu et al., Adding new chemistries to the genetic code. Annu Rev Biochem. 2010;79:413-44. doi: 10.1146/annurev.biochem.052308.105824.

Liu et al., Structure of the DNA repair helicase XPD. Cell. May 30, 2008;133(5):801-12. doi: 10.1016/j.cell.2008.04.029.

Lohman et al., Mechanisms of helicase-catalyzed DNA unwinding. Annu Rev Biochem. 1996;65:169-214.

Lohman et al., Non-hexameric DNA helicases and translocases:mechanisms and regulation. Nat Rev Mol Cell Biol. May 2008;9(5):391-401. doi:10.1038/nrm2394.

Ma et al., Bright functional rotaxanes. Chem Soc Rev. Jan. 2010;39(1):70-80. doi:10.1039/b901710k. Epub Jul. 21, 2009.

Maddox et al., Elevated serum levels in human pregnancy of a molecule immunochemically similar to eosinophil granule major basic protein. J Exp Med. Oct. 1, 1983;158(4):1211-26.

Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.

Marathias et al., Structures of the potassium-saturated, 2:1, and intermediate, 1:1, forms of a quadruplex DNA. Nucleic Acids Res. May 1, 2000;28(9):1969-77.

Marini et al., A human DNA helicase homologous to the DNA cross-link sensitivity protein Mus308. J Biol Chem. Mar. 8, 2002;277(10):8716-23. Epub Dec. 18, 2001.

Marsault et al., Macrocycles are great cycles: applications, opportunities, and challenges of synthetic macrocycles in drug discovery. J Med Chem. Apr. 14, 2011;54(7):1961-2004. doi: 10.1021/jm1012374. Epub Mar. 7, 2011.

Marušič et al., Solution-state structure of an intramolecular G-quadruplex with propeller, diagonal and edgewise loops. Nucleic Acids Res. Aug. 2012;40(14):6946-56. doi: 10.1093/nar/gks329. Epub Apr. 24, 2012.

Mechanic et al., *Escherichia coli* DNA helicase II is active as a monomer. J Biol Chem. Apr. 30, 1999;274(18):12488-98.

Miles et al., Properties of Bacillus cereus hemolysin II: a heptameric transmembrane pore. Protein Sci. Jul. 2002;11(7):1813-24.

Montal et al., Formation of bimolecular membranes from lipid monolayers and a study of their electrical properties. Proc Natl Acad Sci U S A. Dec. 1972;69(12):3561-6.

Morris et al., Evidence for a functional monomeric form of the bacteriophage T4 DdA helicase. Dda does not form stable oligomeric structures. J Biol Chem. Jun. 8, 2001;276(23):19691-8. Epub Feb. 27, 2001.

Ngo et al., Computational complexity, protein structure prediction, and the levinthal paradox. 14. The protein folding problem teritary structure prediction. Ed(s):Merz et al. Birkhauser, Boston, Ma. 1994. 433, 492-5.

Nikolov et al., Behavior of giant vesicles with anchored DNA molecules. Biophys J. Jun. 15, 2007;92(12):4356-68. Epub Mar. 23, 2007.

Nishikiori et al., Crystal structure of the superfamily 1 helicase from Tomato mosaic virus. J Virol. Jul. 2012;86(14):7565-76. doi: 10.1128/JVI.00118-12. Epub May 9, 2012.

O'Shea et al., X-ray structure of the GCN4 leucine zipper, a two-stranded, parallel coiled coil. Science. Oct. 25, 1991;254(5031):539-44.

Pfeiffer et al., Bivalent cholesterol-based coupling of oligonucletides to lipid membrane assemblies. J Am Chem Soc. Aug. 25, 2004;126(33):10224-5.

Pinero-Fernandez et al., Indole transport across *Escherichia coli* membranes. J Bacteriol. Apr. 2011;193(8):1793-8. doi:10.1128/JB.01477-10. Epub Feb. 4, 2011.

Portakal et al., Construction of recB-recD genetic fusion and functional analysis of RecBDC fusion enzyme in *Escherichia coli*. BMC Biochem. Oct. 10, 2008;9:27. doi: 10.1186/1471-2091-9-27.

(56) References Cited

OTHER PUBLICATIONS

Raney et al., Structure and Mechanisms of SF1 DNA Helicases. Adv Exp Med Biol. 2013;767:17-46. doi: 10.1007/978-1-4614-5037-5_2.
Remaut et al., Protein-protein interaction through beta-strand addition. Trends Biochem Sci. Aug. 2006;31(8):436-44. Epub Jul. 7, 2006.
Richards et al., Structure of the DNA repair helicase hel308 reveals DNA binding and autoinhibitory domains. J Biol Chem. Feb. 22, 2008;283(8):5118-26. Epub Dec. 4, 2007.
Rudolf et al., The DNA repair helicases XPD and FancJ have essential iron-sulfur domains. Mol Cell. Sep. 15, 2006;23(6):801-8.
Rudolf et al., The helicase XPD unwinds bubble structures and is not stalled by DNA lesions removed by the nucleotide excision repair pathway. Nucleic Acids Res. Jan. 2010;38(3):931-41. doi:10.1093/nar/gkp1058.
Saariaho et al., Characteristics of MuA transposase-catalyzed processing of model transposon end DNA hairpin substrates. Nucleic Acids Res. Jun. 6, 2006;34(10):3139-49. Print 2006.
Satapathy et al., ATPase activity of RecD is essential for growth of the Antarctic Pseudomonas syringae Lz4W at low temperature. FEBS J. Apr. 2008;275(8):1835-51. doi:10.1111/j.1742-4658.2008.06342.x. Epub Mar. 9, 2008.
Sathiyamoorthy et al., The crystal structure of *Escherichia coli* group 4 capsule protein GfcC reveals a domain organization resembling that of Wza. Biochemistry. Jun. 21, 2011;50(24):5465-76. doi: 10.1021/bi101869h.
Schneider et al., DNA sequencing with nanopores. Nat Biotechnol. Apr. 10, 2012;30(4):326-8. doi: 10.1038/nbt.2181.
Sequence ID No. 2 Search Results. US-14-351-038-2. Sep. 16, 2015. 69 pages.
Singleton et al., Structure and mechanism of helicases and nucleic acid translocases. Annu Rev Biochem. 2007;76:23-50.
Soni et al., Synchronous optical and electrical detection of biomolecules traversing through solid-state nanopores. Rev Sci Instrum. Jan. 2010;81(1):014301. doi: 10.1063/1.3277116.
Stelter et al., Structural and mechanistic insight into DNA unwinding by Deinococcus radiodurans UvrD. PLoS One. Oct. 15, 2013;8(10):e77364. doi: 10.1371/journal.pone.0077364.
Stoddart et al., Single-nucleotide discrimination in immobilized DNA oligonucleotides with a biological nanopore. Proc Natl Acad Sci U S A. May 12, 2009;106(19):7702-7 and Supplementary Info. doi: 10.1073/pnas.0901054106. Epub Apr. 20, 2009.
Theissen et al., Cooperative binding of ATP and RNA induces a closed conformation in a DEAD box RNA helicase. Proc Natl Acad Sci U S A. Jan. 15, 2008;105(2):548-53. doi: 10.1073/pnas.0705488105. Epub Jan. 9, 2008.
Troutt et al., Ligation-anchored PCR: a simple amplification technique with single-sided specificity. Proc Natl Acad Sci U S A. Oct. 15, 1992;89(20):9823-5. Erratum in: Proc Natl Acad Sci U S A Apr. 15, 1993;90(8):3775.
Tuteja et al., Unraveling DNA helicases. Motif, structure, mechanism and function. Eur J Biochem. May 2004;271(10):1849-63. Review. Erratum in: Eur J Biochem. Aug. 2004;271(15):3283.
UniProt Database accession No. a4s1e1 sequence. May 15, 2007.
UniProt Database accession No. b4kac8 sequence. Sep. 23, 2008.
UniProt Database accession No. D0KN27. Dec. 15, 2009.
UniProt Database accession No. D7RM26 sequence. Aug. 10, 2010.
UniProt Database accession No. elqus6 sequence. Nov. 30, 2010.
UniProt Database accession No. i3d0e7 sequence. Jul. 11, 2012.
UniProt Database accession No. 16ZR75 sequence. Oct. 3, 2012.
UniProt Database accession No. k0im99 sequence. Nov. 28, 2012.
UniProt Database accession No. Q12WZ6 sequence. Apr. 12, 2017.
UniProt Database accession No. Q7Y5C3 sequence. Oct. 1, 2003.
Utama et al., Role of the DExH motif of the Japanese encephalitis virus and hepatitis C virus NS3 proteins in the ATPase and RNA helicase activities. Virology. Aug. 1, 2000;273(2):316-24. doi: 10.1006/viro.2000.0417.
Van Heel et al., Single-particle electron cryo-microscopy:towards atomic resolution. Q Rev Biophys. Nov. 2000;33(4):307-69.
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.
Venkatesan et al., Nanopore sensors for nucleic acid analysis. Nat Nanotechnol. Sep. 18, 2011;6(10):615-24. doi: 10.1038/nnano.2011.129.
Vinson, Proteins in motion. Introduction. Science. Apr. 10, 2009;324(5924):197. doi: 10.1126/science.324.5924.197.
Von Ossowski et al., Engineering the exo-loop of Trichoderma reesei cellobiohydrolase, Cel7A. A comparison with Phanerochaete chrysosporium Cel7D. J Mol Biol. Oct. 31, 2003;333(4):817-29. doi: 10.1016/s0022-2836(03)00881-7.
Wang et al., DNA helicase activity of the RecD protein from Deinococcus radiodurans. J Biol Chem. Dec. 10, 2004;279(50):52024-32.
White, Structure, function and evolution of the XPD family of iron-sulfur-containing 5'→3' DNA helicases. Biochem Soc Trans. 2009;37:547-551.
Woodman et al., Archaeal Hel308 domain V couples DNA binding to ATP hydrolysis and positions DNA for unwinding over the helicase ratchet. J Mol Biol. Dec. 14, 2007;374(5):1139-44. Epub Oct. 10, 2007.
Woodman et al., Molecular biology of Hel308 helicase in archaea. Biochem Soc Trans. Feb. 2009;37(Pt 1):74-8. doi: 10.1042/BST0370074.
Woodman et al., Winged helix domains with unknown function in Hel308 and related helicases. Biochem Soc Trans. Jan. 2011;39(1):140-4. doi:10.1042/BST0390140.
Yoshina-Ishii et al., Arrays of mobile tethered vesicles on supported lipid bilayers. J Am Chem Soc. Apr. 2, 2003;125(13):3696-7.
Yusko et al., Controlling the translocation of proteins through nanopores with bioinspired fluid walls. Nat Nanotechnol. Nat Nanotechnol. Apr. 2011; 6(4): 253-260. EPub Feb. 20, 2011. doi: 10.1038/nnano.2011.12 Author manuscript; available in PMC Oct. 1, 2011.
Zhang et al., DNA Binding and Unwinding Functional Analyses of Recombinant *E. coli* Helicase II (UvrD). Chinese J. of Biochem. Mol. Biol. 2007;23(9):764-9.
Zhang et al., Structural evidence for consecutive Hel308-like modules in the spliceosomal ATPase Brr2. Nat Struct Mol Biol. Jul. 2009;16(7):731-9. doi: 10.1038/nsmb.1625.

Figure 23A

```
Dda-Rma-DSM    1 - - - - - - - - - - - - - - - - - - - - - - - - - - - - - - - - -
Dda-Csp        1 M S Q S V V V P D E L G E I I T A V I E F Y Q D A V D K I E P
Dda-Sru        1 - - - - - - - - - - - - - - - - - - - - - - - - - - - - - - - - -
Dda-Sgo        1 - - - - - - - - - - - - - - - - - - - - - - - - - - - - - - - - -
Dda-Vph12B8    1 - - - - - - - - - - - - - - - - - - - - - - - - - - - - - - - - -
Dda-Vph        1 - - - - - - - - - - - - - - - - - - - - - - - - - - - - - - - - -
Dda-Aph65      1 - - - - - - - - - - - - - - - - - - - - - - - - - - - - - - - - -
Dda-AphCC2     1 - - - - - - - - - - - - - - - - - - - - - - - - - - - - - - - - -
Dda-Cph        1 - - - - - - - - - - - - - - - - - - - - - - - - - - - - - - - - -
Dda-Kph        1 - - - - - - - - - - - - - - - - - - - - - - - - - - - - - - - - -
Dda-SphME13    1 - - - - - - - - - - - - - - - - - - - - - - - - - - - - - - - - -
Dda-AphAc42    1 - - - - - - - - - - - - - - - - - - - - - - - - - - - - - - - - -
Dda-SphSP18    1 - - - - - - - - - - - - - - - - - - - - - - - - - - - - - - - - -
Dda-Yph        1 - - - - - - - - - - - - - - - - - - - - - - - - - - - - - - - - -
Dda-SphS16     1 - - - - - - - - - - - - - - - - - - - - - - - - - - - - - - - - -
Dda-1993       1 - - - - - - - - - - - - - - - - - - - - - - - - - - - - - - - - -   TO
                                                                                    Figure
Dda-Rma-DSM   59 A A P T G R A A R I L S E R T - - - - - - G D H A R T L H S       23B
Dda-Csp      117 A A P T N K A A K N L T Q I A R S Q G I - - K I E A T T V A K
Dda-Sru       62 C A P T H K A V Q V L S D E L G D A - - - - P V Q M Q T L H S
Dda-Sgo       85 T A P T H K A V G V L S K L L R E N N I - - Q S S C K T T H S
Dda-Vph12B8   64 C S P T H K S V K V I R R M A R E A G I S H R V D I R T T H S
Dda-Vph       52 V T P T H Q A K N V L H K A T G Q - - - - - - E V S T T H S
Dda-Aph65     56 A A P T H Q A K I V L T E M S G I - - - - - - E A C T T H S
Dda-AphCC2    43 A A P T H Q A K I V L T E M S G I - - - - - - E A C T T H S
Dda-Cph       62 T A P T H Q A K N V L A A A T G M - - - - - - D A T T T H S
Dda-Kph       62 T A P T H Q A K N V L S E A V G M - - - - - - D A T T T H S
Dda-SphME13   60 T A P T H Q A K K E L S K H A L R - - - - - - K S Y T T Q S
Dda-AphAc42   66 A A P T H Q A K K V L S Q H A G M - - - - - - E A S T T H S
Dda-SphSP18   62 A A P T H Q A K K V L S K L S G Q - - - - - - T A N T T H S
Dda-Yph       61 C A P T H Q A K K V L S K L S G M - - - - - - D A S T T H S
Dda-SphS16    61 T A P T H A A K K V L T K L S G M - - - - - - E A N T T H K
Dda-1993      60 A A P T H A A K K I L S K L S G K - - - - - - E A S T T H S
```

Figure 23B

```
                                             MEE SNE QRV
KIVFLELRKNVVDWVSRTQLKIEEKEIQATGL RQQ T A
                              MSTFADAPF ED QEEA
                MKILNKETYKLSLHQEEVFTQIVSQ
                           MADFE TL G QKTV
                              MG TNC QQGA
                       MSESEIT PS QNSA
                                          MA
                       MSELTFDD SDD KSA
                       MSELTFDD SED QKNA
                      MV-TYDD  VG QKDA
                         MNFED EG QKNA
                        MIKFED NT G QKEA
                         MITYDD TD G QKSA
                        MITFEQ TS G QKLA
                         MTFDD  EG QKNA
```

FROM Figure 23A

```
LIY FDRYQLVEEADRQTDEPLSL LHFALRSAEH---D
L K LQ TIDVDT---------GQ SFEFNSEKELELKD
F GLRLQPK-QD---------GE YELVAEEERNF---A
F G K FIDYTTGE-------EKFVVD TNKRKD---R
A GLVMKPV-RG---------DE VLVKEPFAER----I
L K HP DTYEDQKH------FT S--GEVEG D---E
LM K HP ET LEDIQI-------FD Q---SKLP LS---N
LM K HP ET LEDIQI-------FD-Q---SKMP LS---T
A K S P VTNEELRV------FE QKGKKAP LS---T
A K S P VTNEELRV------FE QKGKKAA LS---E
V K N P STLEENQI------FE Q---KGTP FS---K
L K N P TTYEDSTT------FE Q---KDVP MS---E
I K N P TTYEDQNI------FE Q---REMP MS---K
V K N P TTYEENQI------FE Q---REVP A---A
I K N P TTYEESML------FE Q---KEVP LA---S
I K N P VTYEENVL------FE Q---KEVP LA---K
```

```
        LDHVLAWLERNDA----PPIFILTGSAGTGKLLIRHLV
        YKEMINFIENSSE-----QYFRLSGYAGTGKSFLMAKVI
        YDHVYDRLAQ-GE-----RFTGLRGYAGTGKTYLVSRLV
        LDTKVSSILKSTNI--EDYLLSLTGPAGTGKTFLTTQIA
        LGEVISTILKPVNLNDTSRFHTMHGPAGSGKTVLQRI
        MDAFLESD---G-------HMTISGPAGSGKTFLMKSIL
        VNEVKNGT---G-------HITISGPPGSGKTFLVKYLI
        VDAVQSGT---G-------HITISGPPGSGKTFLVKYI
        HDRVIHNIQNAI-------HTTITGGPGVGKTLVKFVF
        HDRVIKNIRNKI-------HTTITGGPGVGKTLVKFVF
        IEKALQAMRTKR-------HITIRGPAGSGKTMTRFLL
        YTAAIKAIETVPSSSAEKRHLTINGPAGTGKTLTKFLI
        FDYITEAIQRRS-----GECITLNGPAGTGKTLTKFVI
        FDNTMEAIKNKK------GHITINGPAGTGKTLTKFII
        FDETIRAIKE-K-----KNHVTINGPAGTGKTLTKFIM
FROM    FNIVMKAIKEKK-----HHVTINGPAGTGKTLTKFII     TO
Figure                                             Figure
23B     ARLIIVDEASMVSDTAGEEELYRFGSGRLLNDLLTFARL    23D
        YDVIIIDEYSMLNKDNFRDLQQAVKGGES-----------
        EGVVIVDEASMIGREEWSHIQDAPF--WV-----------
        TSILIVDESSMIGNTLYEYILEAIEDKRV-----------
        YDVLIIDEAGMLNDELIMYILESQ---SS-----------
        IDVLVVEEASMVDEELFQITGRTMPRKC------------
        IRYLIVEEASMHSKTLFKITMKSIPPTC------------
        VRYLIIEEASMHSKALFNITMKSIPPTC------------
        CRVFVVEEVSMVDMDLFRIIRRSIPSNA------------
        CRVFVVEEVSMVDKELFRIIKRTIPSCA------------
        TRVLICDEVSFYTRKLFDILMRNVPSHC------------
        CRVLICDEASMYDLKLFQILMSSIPLCC------------
        CNVLVCDEASMYDGSLFKITCNSVPEWC------------
        CRVLICDEASFYDRKLFGILATVPSWC------------
        CRVLICDEASMWDRKLFKILMASIPKWC------------
        CRVLICDEVSMYDRKLFKILLSTIPPWC------------
```

Figure 23D

```
        R A L Q D R R - - - - - - - - - - - I H Y A L  58
        E W L K Q E D - - - - - - - - - - - Y K Y S V 116
        E Q L L D E D - - - - - - - - - - - C T V T V  61
        K Y L V E K R K E S E Y P M S S D F D F I I   84
        S Q I P A Y K - - - - - - - - - - - T I G F  63
        E A L E S K G - - - - - - - - - - - K N V T M 51
        K M L G D E - - - - - - - - - - - - L G T V L 55
        K M L G D E - - - - - - - - - - - - L G T V L 42
        N T L K G L G I - - - - - - - - - - S G I W L 61
        E T L K K L G I - - - - - - - - - - S G I W L 61
        E R L F Q T G Q - - - - - - - - - - Q G I V L 59
        A E L I R R G E - - - - - - - - - - R G V Y L 65
        D H L V R N G V - - - - - - - - - - M G I V L 61
        D H L I K T G E - - - - - - - - - - A G I I L 60
        E H L V S T G E - - - - - - - - - - T G I I L 60
FROM    E A L I S T G E - - - - - - - - - - T G I I L 59   TO
Figure                                                     Figure
23C     I P K R D R P P T T R L L F V G D P A Q L - 178    23E
        - - - - - - - - - - - K F I F V G D S S Q L - 214
        - - - - - - - - - - Q W L F V G D P A Q L - 151
        - - - - - - - - - - N V V L F I G D P Y Q L - 182
        - - - - - - - - - - K V I F V G D M C Q I - 156
        - - - - - - - - - - R I L A V G D K Y Q L - 140
        - - - - - - - - - - R I I A I G D K D Q I Q 144
        - - - - - - - - - - R I I A I G D K D Q I - 130
        - - - - - - - - - - V I L G L G D K D Q I - 152
        - - - - - - - - - - V I L G L G D K D Q I - 152
        - - - - - - - - - - V V I G I G D K A Q I - 147
        - - - - - - - - - - T V I A L G D I A Q I - 153
        - - - - - - - - - - T I L G I G D M H Q L - 149
        - - - - - - - - - - T V I A L G D K D Q L - 148
        - - - - - - - - - - T I V A I G D V A Q I - 148
        - - - - - - - - - - T I I G I G D N K Q I - 147
```

Figure 23E

```
Dda-Rma-DSM  179 P P V G Q S V S P A L S A Q Y L R D T F G L S A E - - - - - -
Dda-Csp      215 P P V - - - - - - - K E K E P I V A N H P D I R - - - - - -
Dda-Sru      152 P P V - - - - - - - N E D P S P A L D V P - - - - - - - -
Dda-Sgo      183 L P I E - - - - - - N S K N E I Y D L P N - - - - - - - -
Dda-Vph12B8  157 G P I - - - - - - - Q S N L P E E D G Y T P T S T D D V S K V
Dda-Vph      141 Q P V K H - - - D - P - - G V I S P F F T K - F T - - - - - -
Dda-Aph65    145 P E E H A - - - Q - G - - E L S P Y F T D P R F S - - - - - -
Dda-AphCC2   131 Q P V D H - - - A - P G - E L S P Y F T D S R F T - - - - - -
Dda-Cph      153 R P V N A - - - D - G R V E L S P F F D E E I F D - - - - - -
Dda-Kph      153 R P V N T - - - E - G I T E L S P F F D E E I F D - - - - - -
Dda-SphiME13 148 R G V S E - - - D - D T H E L S P F F T D N R F E - - - - - -
Dda-AphAc42  154 R P V E P - - - G A F E G Q V S P F F T Y E K F E - - - - - -
Dda-SphSP18  150 Q P V D P - - - G S T Q Q K I S P F F T H P K F K - - - - - -
Dda-Yph      149 R P V T P - - - G E S E Q Q L S P F F S H A K F K - - - - - -
Dda-SphS16   149 R P V D P - - - G E T E A H I S P F F I H K D F K - - - - - -
Dda-1993     148 R P V D P - - - G E N T A Y I S P F F T H K D F Y - - - - - -

Dda-Rma-DSM  288 A R L W G R E G L P P Q P G D L L L V N R N A - - - - - - - - -
Dda-Csp      321 E A L Y G E N V E Q L V V G D R L I A L K P V F R S L P G G K
Dda-Sru      254 A E R Y G A D A D R F V E G E W L V G T E T W Y Y D - - - - -
Dda-Sgo      287 N K F W E Q K G N T T - P S T L L A G D M I R - - - - - - - - -
Dda-Vph12B8  281 K R L F G A D V P E W L E D E I L V A C E - - - - - - - - - - -
Dda-Vph      244 E H V Y - N T S E P F I P G E Y L V T Q M P V M V - S N - - - -
Dda-Aph65    249 E H V Y - K T K L P F I E G E K I V L Q E P V M V - - - E H E
Dda-AphCC2   236 K H V Y - K T D L P F I E G E K L V L Q E P V M V E Y D - - -
Dda-Cph      257 K H L Y - K T T E P F I L D E V I V M Q E P L V Q E M R L N G
Dda-Kph      257 K H L Y - K T D Q P F I V G E V V V M Q E P L V T E G R V N G
Dda-SphiME13 251 K Q L Y G A N A A P F L P D E I L V M Q E P L M F D I D I G G
Dda-AphAc42  260 K K I Y - N T L E P F I D G E V L V M Q E P L I K S Y T Y E G
Dda-SphSP18  256 R K L Y - E T D K A F L P Y E V L M Q E P H M K E L E F E G
Dda-Yph      255 R K L Y - E T D K P F I N G E V L V M Q E P L M K E L E F D G
Dda-SphS16   255 R R L Y - Q T E E A F V V G E V L V M Q E P L M R E L V F E G
Dda-1993     254 K K I F - E T D K D F I V G E I I V M Q E P L F K T Y K I D G
```

FROM Figure 23D

FROM Figure 23E

```
        TFRLPE---------QPPDLRPVGLEEAIETTATDFRR
        FETVADGT-------IIKLNTEDWLQQALSHFEKEDWLSN
        TFEDGKGV-------AVTRNREEFLDSILRAFDADAFAED
        SLQQFFQEN------MEDEITFFHNKEAFLEDFYKEEEWY
        LPRIVTNTTPDGNGIITMPNGNWVDSAVARFQSDQFKED
        SKE-RR---------QGVLHVPNVNKMLDTYLSKVNSPED
        NRD-TK---------TGVYKVSGITDLVNSYLRAVKTPED
        NKE-KK---------SGVYKVKSITDLINSYLRVVKTPED
        -SV-GD---------LGVFQHANAVDFLRQYFRRVKTPDD
        -MN-GE---------LGVMKHENASDFLRRYFSRVKTPDD
        LDD-SG---------NGVKQFHTVKDFLSKYFERTKTPND
        IDGAGV---------HNLTSERSVKSFMEKYFSIVKTPED
        YDGHGV---------QGFTSQTALKDFMVNYFGIVKDADM
        VDGEGV---------HAFNSNTALKDFMIRYFDVVKTSDD
        VDGHGV---------HGFTSTTALKDFMMQYFSIVKSPED
FROM    VDGHGV---------RGFTGDTALRDFMVNYFSIVKSLDD    TO
Figure                                              Figure
23F     YFRDVELLYPHEKPRNRIRCKLLENLLESPDGQLSPDII    23H
        -----------VKVRTDEGGMIELRILTSESEEKRQKKLK
        -----------KIRTPGRGLTRTIHVLHEEERERYE----
        -------IEYWECKSIYALEQQVFRVVNPDSEAVFNQKLQ
        -----------QLESVEDHKLHNALVVKGDYIEDFKFR--
        DVAVLTVE-KEDGN----VYEFTVLWDDLQKERFARYLS
        KLSVSSD----YSGI---EHDFCVLYGSESRLEFEYQLS
        SVAKLKVT-SDFSGV---THDIMSVYGEDSKAEFNYQLS
        EFYLLKTV-SLEEET---EAQIQVVVDPVMKDRLGNYLA
        DYFLMKTE-SMFEDT---KADIQVIADPVMQERLGDYLN
        ECTMLECE-SYEEDE---DDYRRAWFTVVHDQNTQYAIN
        RYWQLDLQ-SLDDPDL--TGSINVIVDEAEINKLNLVLG
        NYWDLEVE-SIDEDEEY-QVDRIKVLPEDQQPKFQAYLA
        RYWNLEVE-TADSDDDYATSQIQVICDPAEMTKFQMFLA
        RHWVLDVE-TYDDEEYA-REKINVISDEQEMNKFQFFLA
        RHWDLTVE-TYGDDEYY-REKIKIISSDEELYKFNLFLG
```

FROM Figure 23G

FROM Figure 23H

| | | | | | | | | | | | | | | | | | | | | | | | | | | | |
|---|---|---|---|---|---|---|---|---|---|---|---|---|---|---|---|---|---|---|---|---|---|---|---|---|---|---|---|
| Dda-Rma-DSM | 406 | L | M | L | A | N | D | A | Y | F | N | A | L | H | W | R | Y | G | Y | A | M | T | V | F | K | A | D | G | E | W | K |
| Dda-Csp | 433 | M | A | I | Y | Y | E | L | D | E | L | F | D | N | M | A | Y | A | Y | A | L | T | C | H | R | A | D | G | S | S | I | D |
| Dda-Sru | 355 | M | D | R | F | F | E | L | R | E | R | F | A | R | W | D | Y | A | Y | A | T | T | V | H | R | A | D | G | S | T | Y | D |
| Dda-Sgo | 392 | M | K | L | Y | Y | E | T | R | N | M | F | A | N | W | Q | Y | I | H | A | S | T | I | H | K | L | D | G | S | T | Y | D |
| Dda-Vph12B8 | 378 | M | K | E | F | W | G | M | R | K | K | F | N | T | F | K | N | V | Y | A | G | T | A | H | K | S | Q | G | S | T | F | D |
| Dda-Vph | 356 | M | R | A | F | W | G | L | K | E | Q | M | I | E | T | K | S | L | G | A | S | T | V | H | K | S | Q | G | T | T | V | K |
| Dda-Aph65 | 365 | M | K | S | F | W | A | A | K | K | M | F | I | E | T | K | S | L | G | A | S | T | I | H | K | S | Q | G | S | T | V | K |
| Dda-AphCC2 | 351 | M | A | S | F | W | D | A | K | K | T | F | T | E | T | K | S | L | G | A | C | T | I | H | K | S | Q | G | S | T | V | K |
| Dda-Cph | 377 | M | H | S | F | W | A | I | K | N | K | F | Q | D | W | K | P | L | P | V | C | T | Y | H | K | S | Q | G | S | T | Y | D |
| Dda-Kph | 376 | M | Y | S | F | W | Q | I | K | N | K | F | Q | T | W | K | A | L | P | V | C | T | Y | H | K | G | Q | G | S | T | Y | D |
| Dda-SphME13 | 371 | M | K | D | F | W | A | I | R | N | T | F | V | K | W | R | P | L | G | A | M | T | F | H | K | S | Q | G | S | T | F | D |
| Dda-AphAc42 | 377 | M | A | D | W | W | K | L | K | R | N | F | H | K | W | K | A | L | P | C | S | T | I | H | K | S | Q | G | T | S | V | D |
| Dda-SphSP18 | 377 | M | K | D | F | W | K | A | R | R | T | F | L | K | W | R | A | L | P | V | S | T | I | H | K | A | D | G | V | S | V | D |
| Dda-Yph | 374 | M | K | D | F | W | S | V | K | N | K | F | K | K | W | K | A | L | P | V | S | T | I | H | K | S | Q | G | C | T | V | N |
| Dda-SphS16 | 375 | M | S | E | F | W | D | A | K | R | K | F | H | K | W | K | A | L | P | C | S | T | F | H | K | A | D | G | I | S | V | D |
| Dda-1993 | 374 | M | S | D | F | W | D | A | K | S | Q | F | S | K | W | K | A | L | P | A | S | T | F | H | K | A | D | G | M | S | V | D |

```
              R A T V V F N D W R H F - - - R H A E F F R W A T T A I T R A R E E L L T I G
              N V F L L V S - D M H Y - - - - C R D K T K M I V T G L T R A K K C C Y V G -
              T V F V D H R - D L R V - - C R G E E R G A L L V A V T R P S R R L A L L V
              V S Y I D I F S L V H N H Y M S D E E K Y R L L V A I T R A S K D I K I F M
              Y T Y V F T P D F Y K F - - G A T M T I K R L L V T A I T R S R Y T T Y F A M
              G V C L Y T Q D M G Y A - - - E P E I L Q Q L V V V G L T R P T D W A L Y N -
              G V W L A L H D I H Y A - - - D E E L K Q Q L V V V G V T R P T D F C L Y F D
FROM          G V W L G L H D I S Y A - - - D T D L Q Q Q L V V V G V T R P T D F C L Y F D    TO
Figure        H A Y M Y T R D A Y A F - - A D Y D L C K Q L I V V G V T R A R Y T V D Y V -    Figure
23I           H S Y M Y T R D A Y A Y - - A D Y E L C K Q L L V V G T T R A R F T V D Y V -    23K
              N A Y L F T P C L H Q Y - C R D P D V A Q E L I V V G N T R A R K N V C F V -
              N V F L Y T P C I H K A - - - D S Q L A Q Q L L V V G A T R A R H N V Y Y I -
              K A F I Y T P C I H M A - - - E A S L A S Q L A V V G I T R A R Y D A Y Y V -
              N T F L Y T P C I H M A - - - D A Q L A K Q L L V V G A T R A R T N L Y Y I -
              S S F I Y T P C I H V S - - S D N K F K L E L L V V G A T R G R H D V F F V -
              R A F I Y T P C I H Y A - - - D V E L A Q Q L L V V G V T R G R Y D V F Y V -
```

Figure 23K

```
         A - - - P S F E A L S D M R W Q P A P S V P A P E Q A A E N A T R F P L K A L
         . . . . . . . . . . . . . . . . . . . . . . . . . . . . . . . . . . . . . .
         . . . . . . . . . . . . . . . . . . . . . . . . . . . . . . . . . . . . . .
         S A F D R T S D E K V I I N N Q - - - - - - N S E T M N T L - - - - - K Q L
         N - - - T G A Q - . . . . . . . . . . . . . . . . . . . . . . . . . . . . .
         . . . . . . . . . . . . . . . . . . . . . . . . . . . . . . . . . . . . . .
         G - - - T K - . . . . . . . . . . . . . . . . . . . . . . . . . . . . . . .
FROM     G - - - S K - . . . . . . . . . . . . . . . . . . . . . . . . . . . . . . .     TO
Figure   . . . . . . . . . . . . . . . . . . . . . . . . . . . . . . . . . . . . . .     Figure
23J      . . . . . . . . . . . . . . . . . . . . . . . . . . . . . . . . . . . . . .     23L
         . . . . . . . . . . . . . . . . . . . . . . . . . . . . . . . . . . . . . .
         . . . . . . . . . . . . . . . . . . . . . . . . . . . . . . . . . . . . . .
         . . . . . . . . . . . . . . . . . . . . . . . . . . . . . . . . . . . . . .
         . . . . . . . . . . . . . . . . . . . . . . . . . . . . . . . . . . . . . .
         . . . . . . . . . . . . . . . . . . . . . . . . . . . . . . . . . . . . . .
```

Figure 23L

```
ETYHQRLSEALTAAGIETTGVE 530
. . . . . . . . . . . . . . . . . . . . . 496
. . . . . . . . . . . . . . . . . . . . . 421
HDIDIILKDLDL- - - - - - - - - - 500
. . . . . . . . . . . . . . . . . . . . . 450
. . . . . . . . . . . . . . . . . . . . . 421
. . . . . . . . . . . . . . . . . . . . . 434
. . . . . . . . . . . . . . . . . . . . . 420
. . . . . . . . . . . . . . . . . . . . . 443
. . . . . . . . . . . . . . . . . . . . . 442
. . . . . . . . . . . . . . . . . . . . . 438
. . . . . . . . . . . . . . . . . . . . . 442
. . . . . . . . . . . . . . . . . . . . . 442
. . . . . . . . . . . . . . . . . . . . . 439
. . . . . . . . . . . . . . . . . . . . . 441
. . . . . . . . . . . . . . . . . . . . . 439
```

FROM Figure 23K

MODIFIED HELICASES

FIELD OF THE INVENTION

The invention relates to a new method of characterising a target polynucleotide. The method uses a pore and a DNA-dependent ATPase (Dda) helicase. The helicase controls the movement of the target polynucleotide through the pore. The invention also relates to modified Dda helicases which can be used to control the movement of polynucleotides and are particularly useful for sequencing polynucleotides.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the "strand sequencing" method, a single polynucleotide strand is passed through the pore and the identity of the nucleotides are derived. Strand sequencing can involve the use of a nucleotide handling protein, such as a helicase, to control the movement of the polynucleotide through the pore.

SUMMARY OF THE INVENTION

The inventors have demonstrated that a Dda helicase can control the movement of a polynucleotide through a pore especially when a potential, such as a voltage, is applied. The helicase is capable of moving a target polynucleotide in a controlled and stepwise fashion against or with the field resulting from the applied voltage.

The inventors have also surprisingly identified specific Dda mutants which have an improved ability to control the movement of a polynucleotide through a pore. Such mutants typically comprise one or more modifications in (i) the tower domain and/or (ii) the pin domain and/or (iii) the 1A (RecA-like motor) domain.

Accordingly, the invention provides a Dda helicase in which at least one cysteine residue and/or at least one non-natural amino acid have been introduced into (i) the tower domain and/or (ii) the pin domain and/or (iii) the 1A (RecA-like motor) domain, wherein the helicase retains its ability to control the movement of a polynucleotide.

The invention also provides:
- a Dda helicase in which at least one cysteine residue and/or at least one non-natural amino acid have been introduced into the hook domain and/or the 2A (RecA-like motor) domain, wherein the helicase retains its ability to control the movement of a polynucleotide;
- a Dda helicase which is modified to reduce its surface negative charge, wherein the helicase retains its ability to control the movement of a polynucleotide;
- a first polypeptide comprising the pin domain and the 1A (RecA-like motor) domain from a Dda helicase and not comprising any other domains from a Dda helicase, wherein at least one cysteine residue and/or at least one non-natural amino acid have been introduced into the pin domain and/or the 1A (RecA-like motor) domain;
- a second polypeptide comprising the 2A (RecA-like motor) domain, tower domain and hook domain from a Dda helicase and not comprising any other domains from a Dda helicase, wherein at least one cysteine residue and/or at least one non-natural amino acid have been introduced into the tower domain;
- a helicase comprising a first polypeptide of the invention covalently attached to a second polypeptide of the invention, wherein the helicase has the ability to control the movement of a polynucleotide;
- a construct comprising a Dda helicase or a helicase of the invention and an additional polynucleotide binding moiety, wherein the helicase is attached to the polynucleotide binding moiety and the construct has the ability to control the movement of a polynucleotide;
- a polynucleotide comprising a sequence which encodes a helicase of the invention, a polypeptide of the invention or a construct of the invention;
- a vector which comprises a polynucleotide of the invention operably linked to a promoter;
- a host cell comprising a vector of the invention;
- a method of making a helicase of the invention, a polypeptide of the invention or a construct of the invention, which comprises expressing a polynucleotide of the invention, transfecting a cell with a vector of the invention or culturing a host cell of the invention; a method of controlling the movement of a polynucleotide, comprising contacting the polynucleotide with a Dda helicase or a construct of the invention and thereby controlling the movement of the polynucleotide;
- a method of characterising a target polynucleotide, comprising (a) contacting the target polynucleotide with a transmembrane pore and a Dda helicase or a construct of the invention such that the helicase controls the movement of the target polynucleotide through the pore and (b) taking one or more measurements as the polynucleotide moves with respect to the pore wherein the measurements are indicative of one or more characteristics of the target polynucleotide and thereby characterising the target polynucleotide;
- method of forming a sensor for characterising a target polynucleotide, comprising forming a complex between (a) a pore and (b) a Dda helicase or a construct of the invention and thereby forming a sensor for characterising the target polynucleotide;
- sensor for characterising a target polynucleotide, comprising a complex between (a) a pore and (b) a Dda helicase or a construct of the invention;
- use of a Dda helicase or a construct of the invention to control the movement of a target polynucleotide through a pore;
- a kit for characterising a target polynucleotide comprising (a) a pore and (b) a Dda helicase or a construct of the invention;
- an apparatus for characterising target polynucleotides in a sample, comprising (a) a plurality of pores and (b) a plurality of Dda helicases or a plurality of constructs of the invention; and
- a series of two or more helicases attached to a polynucleotide, wherein at least one of the two or more helicases is a Dda helicase of the invention.

of when a helicase (T4 Dda E94C/A360C (SEQ ID NO: 8 with mutations E94C/A360C)) controlled the translocation of the Lambda DNA construct (0.2 nM, SEQ ID NO: 60 attached by its 3' end to four iSpC3 spacers which are attached to the 5' end of SEQ ID NO: 61 which is attached at its 3' end to SEQ ID NO: 62, the SEQ ID NO: 61 region of this construct is hybridised to SEQ ID NO: 63 (which has a 3' cholesterol tether)) through a nanopore (MS(B1-G75S/G77S/L88N/Q126R)8 MspA (SEQ ID NO: 2 with mutations G75S/G77S/L88N/Q26R)).

Figure 1:
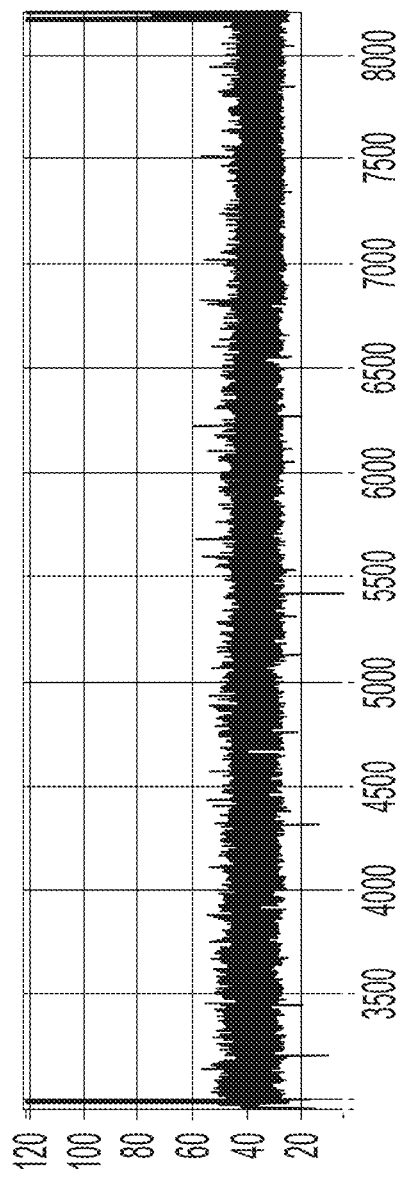
FIG. 1 shows an example current trace (y-axis label Current (pA, 20 to 120), x-axis label Time (s, 3500 to 8000))
Figure 2A:
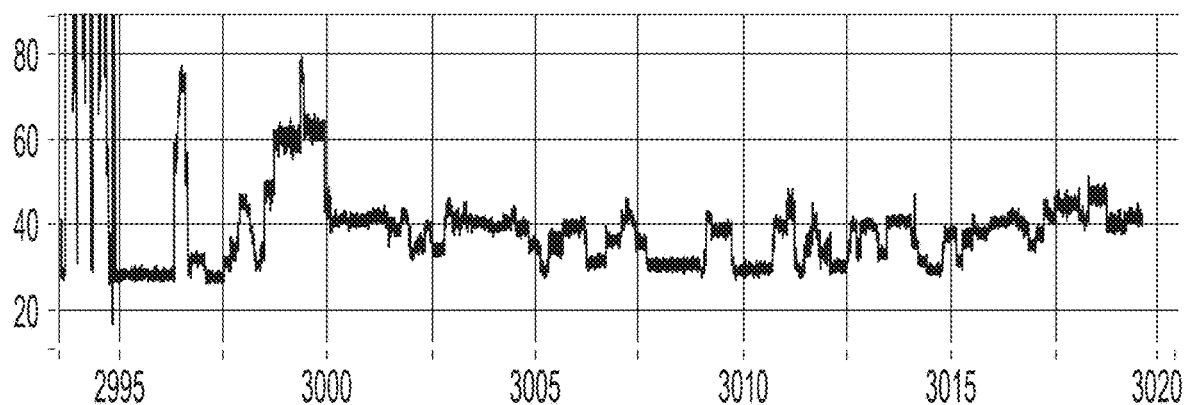
Figure 2B:
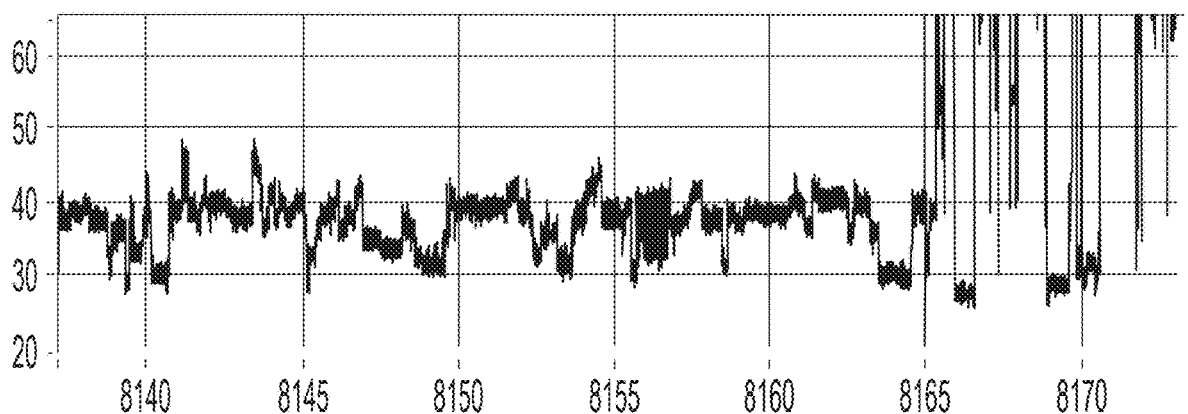

FIG. 2 shows zoomed in regions of the helicase-controlled DNA movement shown in the current trace in FIG. 1 (y-axis label Current (pA, upper trace 20 to 80, lower trace 20 to 60), x-axis label Time (s, upper trace 2995 to 3020, lower trace 8140 to 8170) upper and lower trace). A) shows the beginning of the helicase-controlled DNA movement and B) shows the end of the helicase controlled DNA movement.

Figures 3A, 3B:
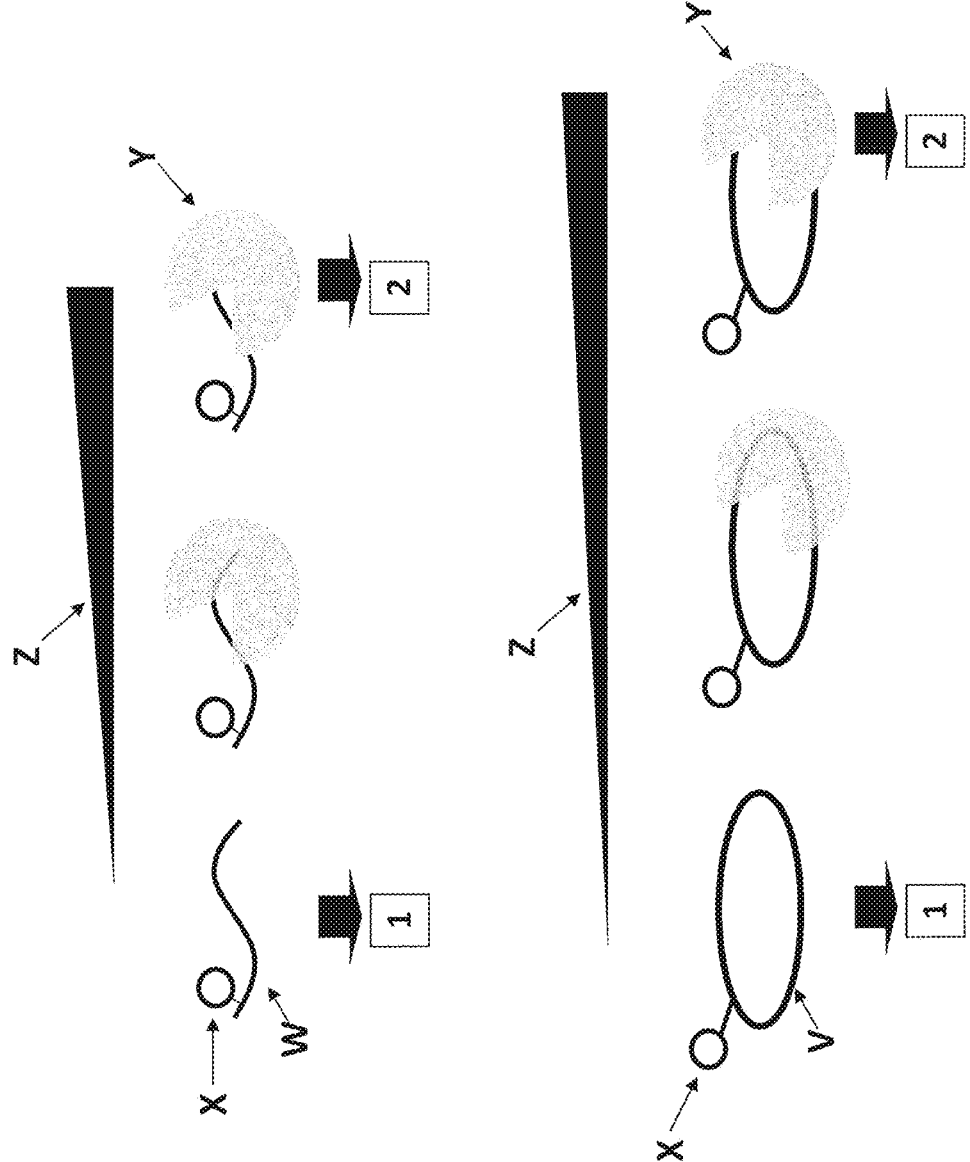

FIG. 3 shows a fluorescence assay for testing helicase binding to linear (A) or circular (B) single-stranded DNA. (A) shows a custom fluorescent substrate used to assay the ability of T4 Dda E94C/A360C (SEQ ID NO: 8 with mutations E94C/A360C) helicase to bind to linear single-stranded DNA. The 44 nt single-stranded DNA substrate (1 nM final, SEQ ID NO: 64, labelled W) has a carboxyfluorescein (FAM) attached to the thymine base at position 37 in SEQ ID NO: 64 (circle labelled X). As the helicase (labelled Y) bound to the DNA substrate in buffered solution (25 mM potassium phosphate, 151.5 mM KCl, pH8.0, 10 mM $MgCl_2$), the fluorescence anisotropy (a property relating to the speed of tumbling of the DNA substrate in solution) increased. The lower the amount of helicase needed to affect an increase in anisotropy, the tighter the binding affinity between the DNA and helicase. In situation 1 with no enzyme bound the DNA substrate exhibited faster tumbling and low anisotropy, whereas, in situation 2 with enzyme bound to the DNA substrate it exhibited slower tumbling and high anisotropy (this was attributed to the mass increase upon binding of a large protein molecule to the DNA). The black bar labelled Z corresponds to increasing helicase concentration (the thicker the bar the higher the helicase concentration). (B) shows a custom fluorescent substrate used to assay the ability of T4 Dda E94C/A360C (SEQ ID NO: 8 with mutations E94C/A360C) helicase to bind to circular single-stranded DNA. The 75 nt circular single-stranded DNA substrate (1 nM final, SEQ ID NO: 65, labelled V) had a carboxyfluorescein (FAM) attached to one of the thymine bases in SEQ ID NO: 65 (circle labelled X). As the helicase (labelled Y) bound to the oligonucleotide in buffered solution (25 mM potassium phosphate, 151.5 mM KCl, pH8.0, 10 mM $MgCl_2$), the fluorescence anisotropy (a property relating to the rate of tumbling of the oligonucleotide in solution) increased. The lower the amount of helicase needed to affect an increase in anisotropy, the tighter the binding affinity between the DNA and helicase. In situation 1 with no enzyme bound the DNA substrate exhibited faster tumbling and low anisotropy, whereas, in situation 2 with enzyme bound to the DNA substrate it exhibited slower tumbling and high anisotropy (this was attributed to the mass increase upon binding of a large protein molecule to the DNA). The black bar labelled Z corresponds to increasing helicase concentration (the thicker the bar the higher the helicase concentration).

Figure 4:
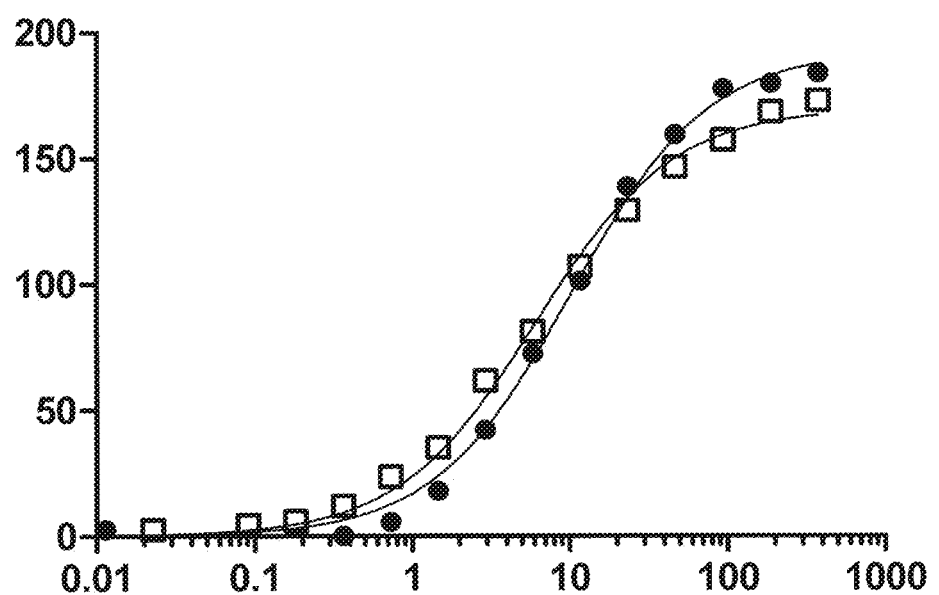

FIG. 4 shows the change in anisotropy of the linear and circular single-stranded DNA oligonucleotides (SEQ ID NO: 64 or 65) with increasing amounts of T4 Dda E94C/A360C (SEQ ID NO: 8 with mutations E94C/A360C) (y-axis label Anisotropy (blank subtracted, 50 to 200), x-axis label Concentration T4 Dda (nM, 0.01 to 1000)) at the end of a 60 min incubation period. The data with black circles corresponded to the linear ssDNA construct. The data with the empty squares corresponded to the circular ssDNA construct.

Figure 5:
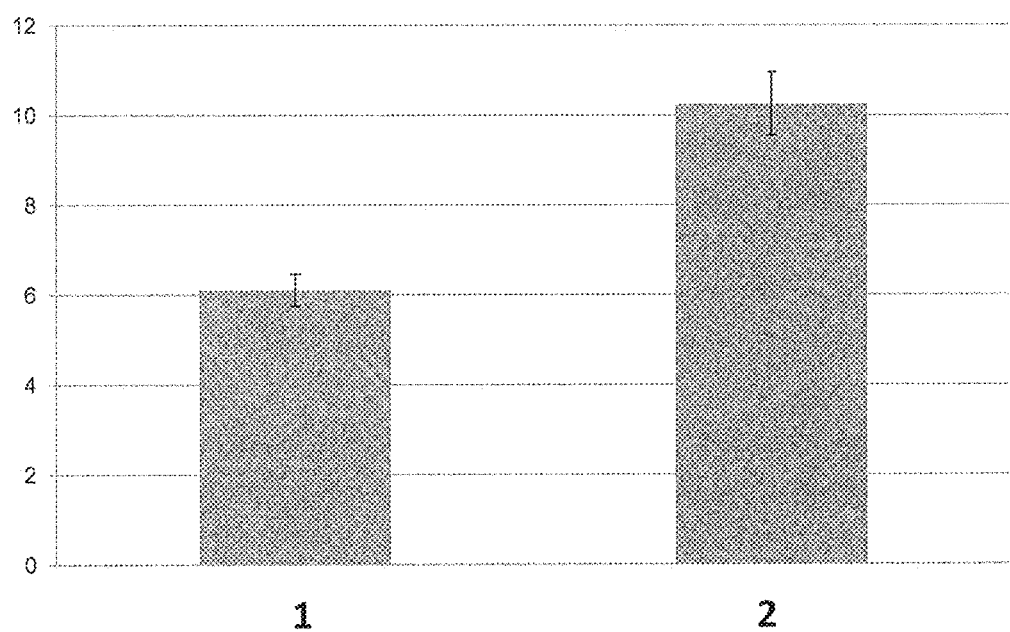

FIG. 5 shows the equilibrium dissociation constants ($K_d$) for T4 Dda E94C/A360C (SEQ ID NO: 8 with mutations E94C/A360C) binding to linear or circular single-stranded DNA after a 60 minute incubation. The graph was obtained through fitting one phase dissociation binding curves through the data shown in FIG. 4 using Graphpad Prism software (y-axis label dissociation constant Kd (nM, 0 to 12), x-axis label Ref. Number, where Ref. Number 1 corresponded to the linear single-stranded DNA oligonucleotide and Ref. Number 2 corresponded to the circular single-stranded DNA oligonucleotide).

Figure 6:
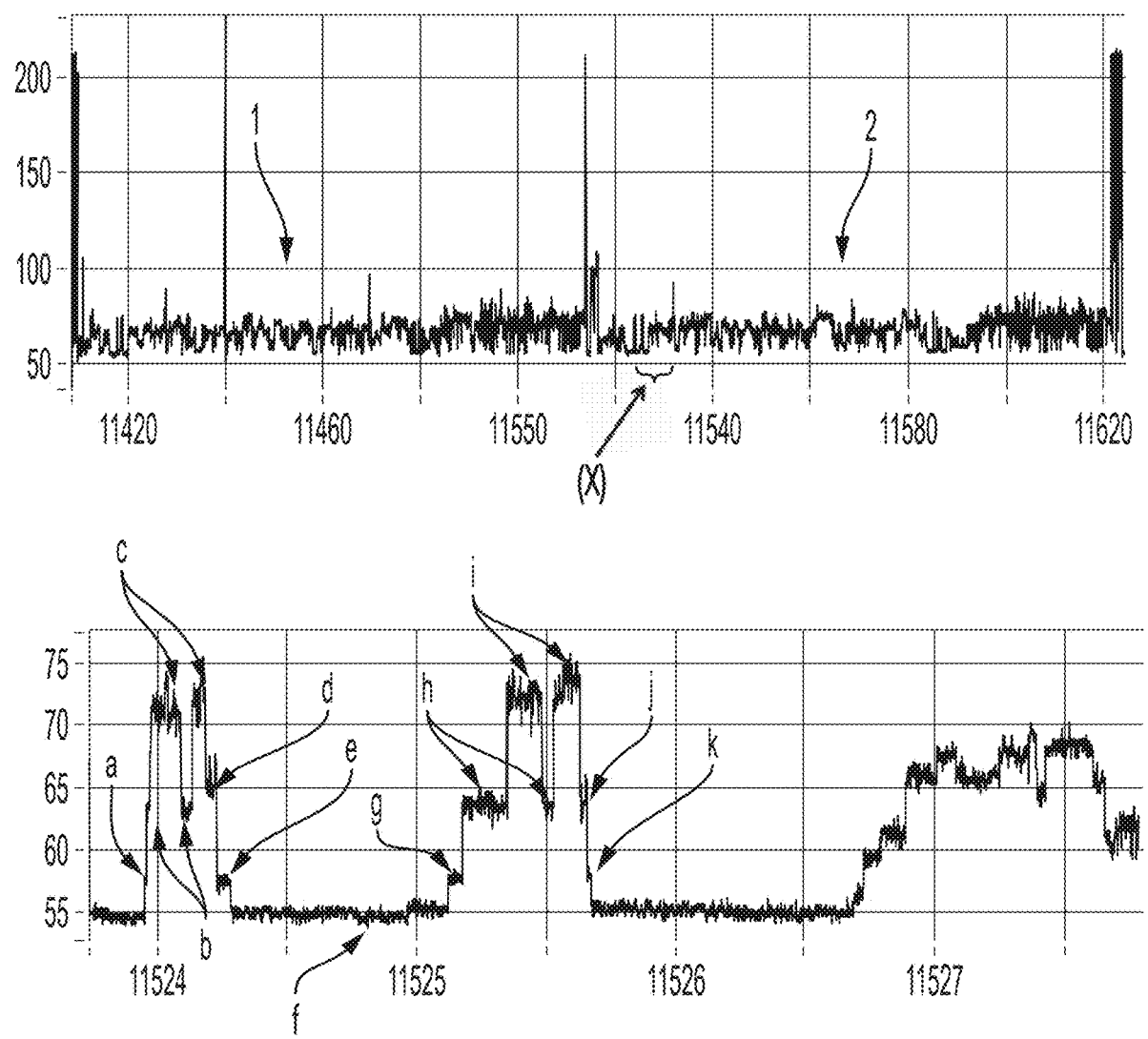

FIG. 6 shows an example current trace (y-axis label Current (pA, upper trace 50 to 200, lower trace 55 to 75), x-axis label Time (s, upper trace 11420 to 11620, lower trace 11524 to 11527)) of when a helicase (TrwC Cba (SEQ ID NO: 66)) controlled the translocation of DNA (0.2 nM, SEQ ID NO: 67 attached by its 3' end to four iSpC3 spacers which are attached to the 5' end of SEQ ID NO: 61 which is attached at its 3' end to four 5-nitroindoles the last of which is attached to the 5' end of SEQ ID NO: 68, in addition SEQ ID NO: 63 is hybridised to SEQ ID NO: 61) through a nanopore (MS(B1-G75S/G77S/L88N/Q126R)8 MspA (SEQ ID NO: 2 with mutations G75S/G77S/L88N/Q126R)). The upper trace shows two helicase controlled DNA movements and the lower trace shows a zoomed in region labelled X in the upper level. As the helicase moved the DNA through the nanopore the current levels detected have been labelled a to k. When TrwC Cba controlled translocation through the nanopore, the DNA stepped back and therefore levels corresponding to b, c, h and i were observed several times.

Figure 7:
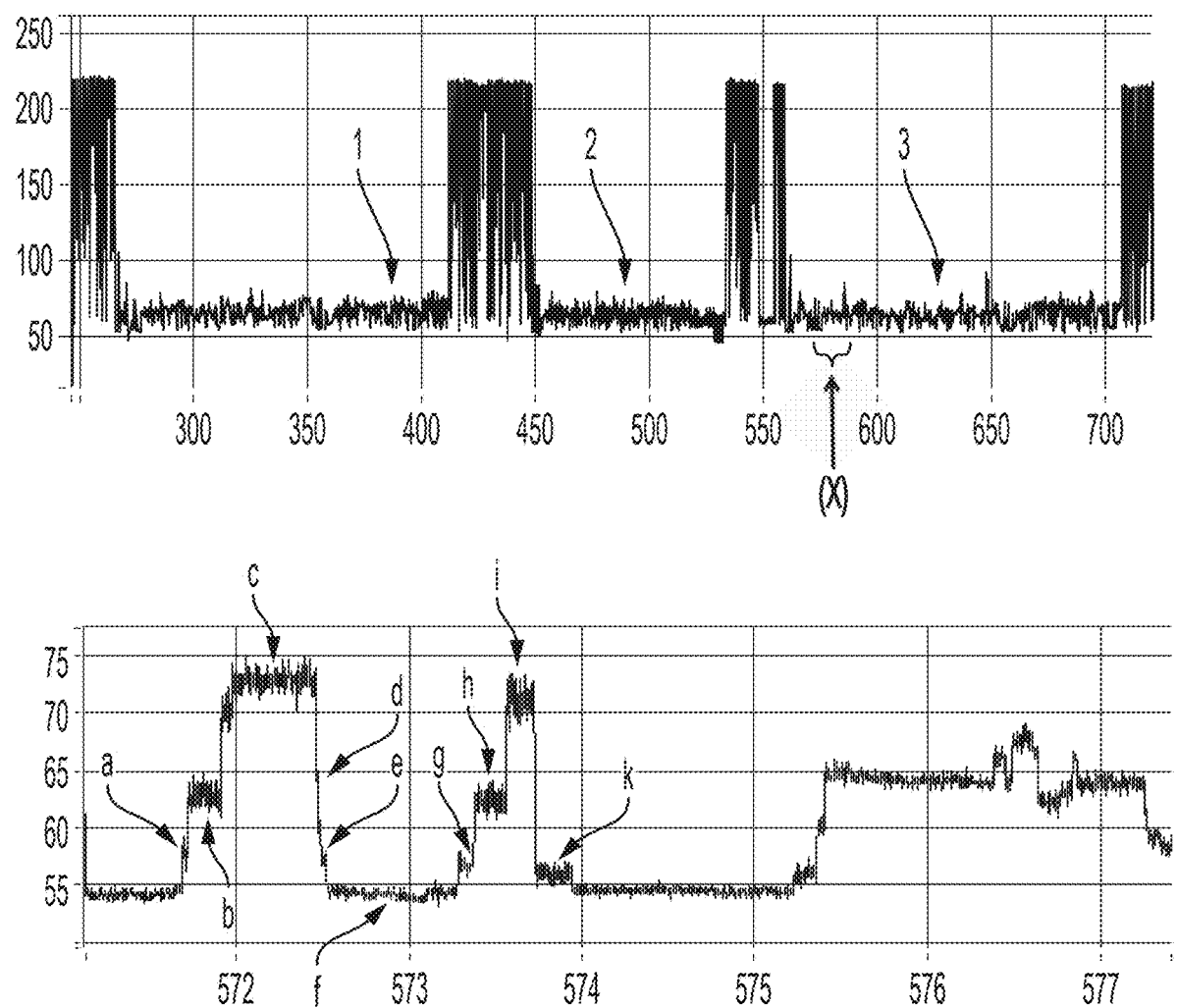

FIG. 7 shows an example current trace (y-axis label Current (pA, upper trace 50 to 250, lower trace 55 to 75), x-axis label Time (s, upper trace 300 to 700, lower trace 572 to 577)) of when a helicase (T4 Dda E94C/A360C (SEQ ID NO: 8 with mutations E94C/A360C)) controlled the translocation of DNA (0.2 nM, SEQ ID NO: 67 attached by its 3' end to four iSpC3 spacers which are attached to the 5' end of SEQ ID NO: 61 which is attached at its 3' end to four 5-nitroindoles the last of which is attached to the 5' end of SEQ ID NO: 68, in addition SEQ ID NO: 63 is hybridised to SEQ ID NO: 61) through a nanopore (MS(B1-G75S/G77S/L88N/Q126R)8 MspA (SEQ ID NO: 2 with mutations G75S/G77S/L88N/Q126R)). The upper trace shows three helicase controlled DNA movements and the lower trace shows a zoomed in region labelled X in the upper level. As the helicase moved the DNA through the nanopore the current levels detected have been labelled a to k. When T4 Dda E94C/A360C (SEQ ID NO: 8 with mutations E94C/A360C) controlled translocation through the nanopore, the DNA did not step back and therefore single current levels corresponding to levels a to i were observed.

Figure 8:
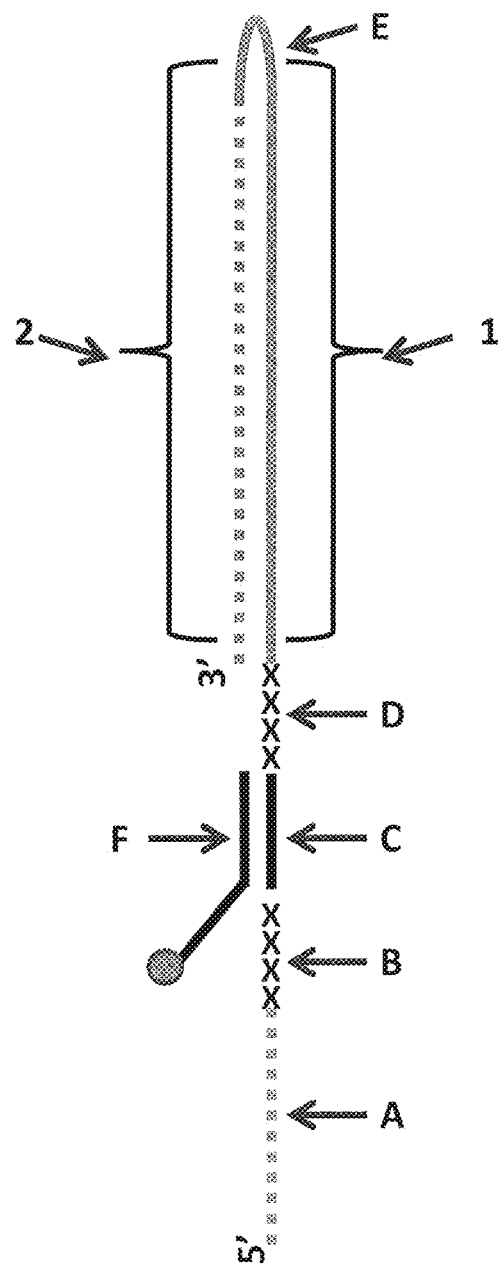

FIG. 8 shows a diagram of the lambda DNA construct used in Examples 1 and 4. SEQ ID NO: 60 (labelled A) is attached at its 3' end to four iSpC3 spacers (labelled B). The four iSpC3 spacers are attached to the 5' end of SEQ ID NO: 61 (labelled C). SEQ ID NO: 61 is attached to four iSpC3 spacers (labelled D) which are attached to SEQ ID NO: 62 (labelled E) at its 5' end. SEQ ID NO: 61 is hybridised to SEQ ID NO: 63 (labelled F, which has a 3' cholesterol tether). Two separate sections of labelled region E are highlighted as region 1 (shown as a solid grey line) and region 2 (shown as a dotted grey line) in the figure and are referred to in Example 4.

Figure 9:
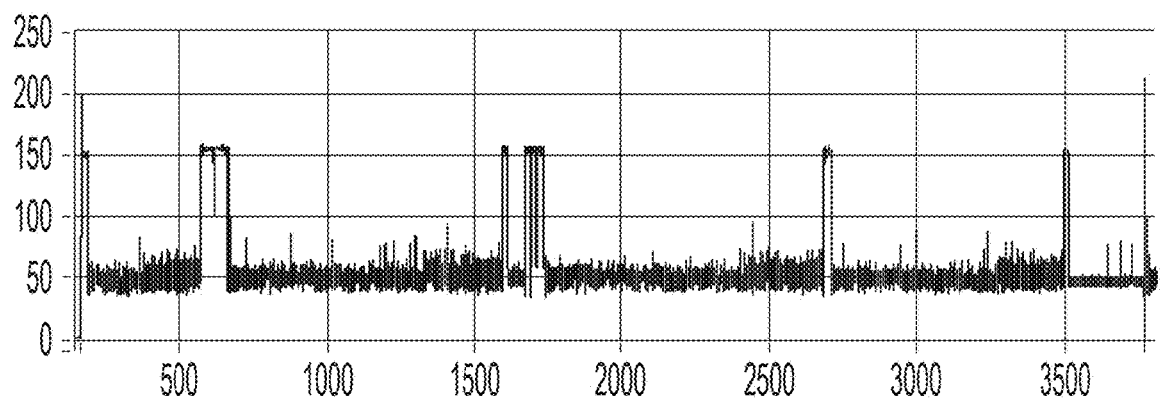
Figure 9:
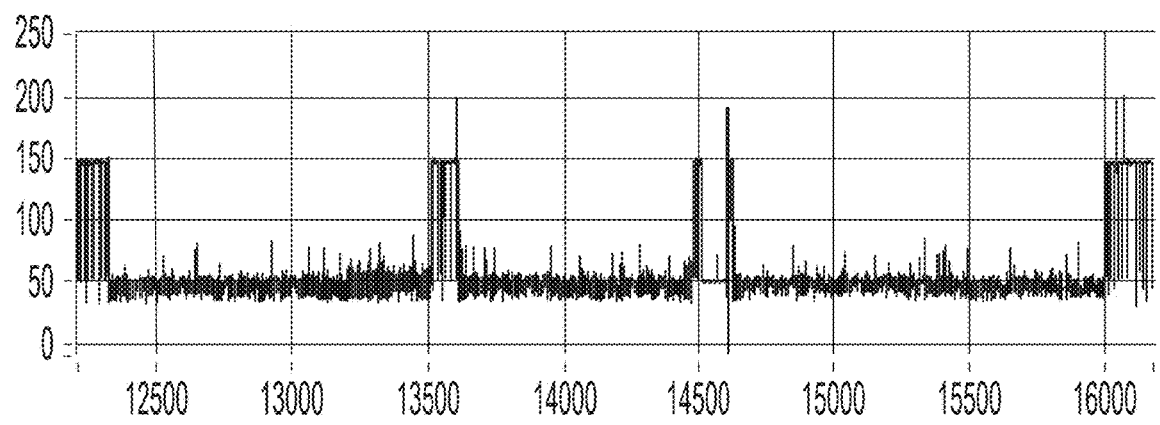

FIG. 9 shows example current traces (both traces have the following axes labels y-axis label Current (pA), x-axis label Time (s)) of when a helicase (T4 Dda E94C/A360C/C109A/C136A (SEQ ID NO: 8 with mutations E94C/A360C/C109A/C136A and then (ΔM1)G1G2)) controlled the translocation of DNA (0.1 nM, SEQ ID NO: 67 attached by its 3' end to four iSpC3 spacers which are attached to the 5' end of SEQ ID NO: 61 which is attached at its 3' end to four four 5-nitroindoles spacers which are attached to the 5' end of SEQ ID NO: 69, the SEQ ID NO: 61 region of this construct is hybridised to SEQ ID NO: 63 (which has a 3' cholesterol tether)) through an MspA nanopore. Both traces showed multiple helicase controlled DNA movements.

Figure 10:
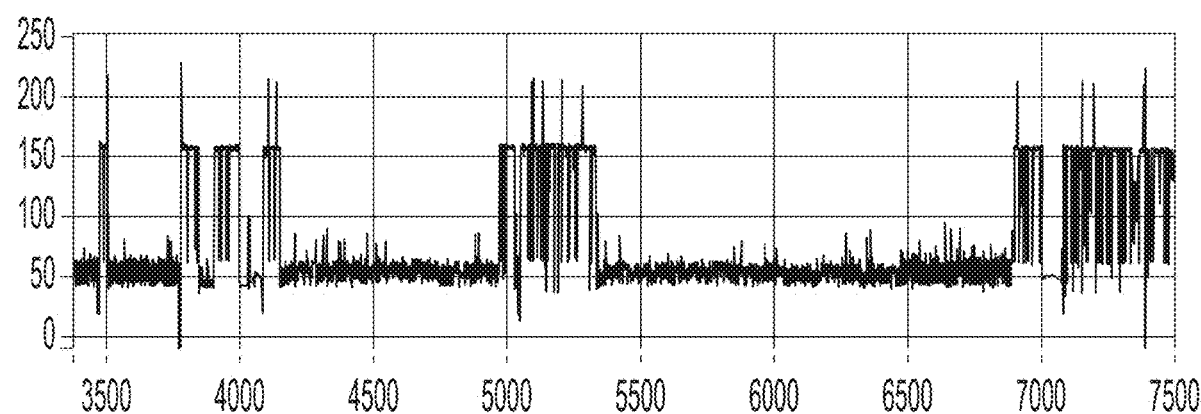
Figure 10:
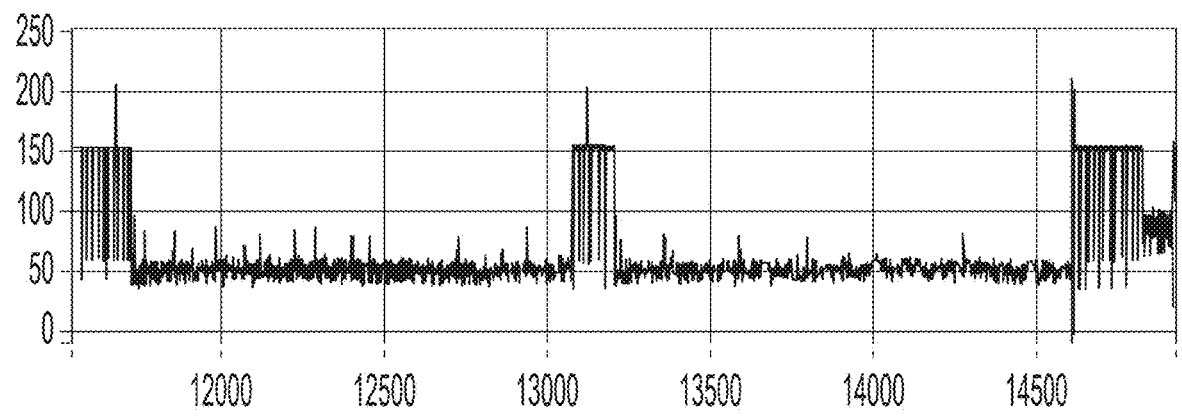

FIG. 10 shows example current traces (both traces have the following axes labels y-axis label Current (pA), x-axis label Time (s)) of when a helicase (T4 Dda E94C/A360C/C114A/C171A/C421D (SEQ ID NO: 8 with mutations E94C/A360C/C114A/C171A/C421D and then (ΔM1)G1G2)) controlled the translocation of DNA (0.1 nM, SEQ ID NO: 67 attached by its 3' end to four iSpC3 spacers which are attached to the 5' end of SEQ ID NO: 61 which is attached at its 3' end to four four 5-nitroindoles spacers which are attached to the 5' end of SEQ ID NO: 69, the SEQ ID NO: 61 region of this construct is hybridised to SEQ ID NO: 63 (which has a 3' cholesterol tether)) through an MspA nanopore. Both traces showed multiple helicase controlled DNA movements.

Figure 11:
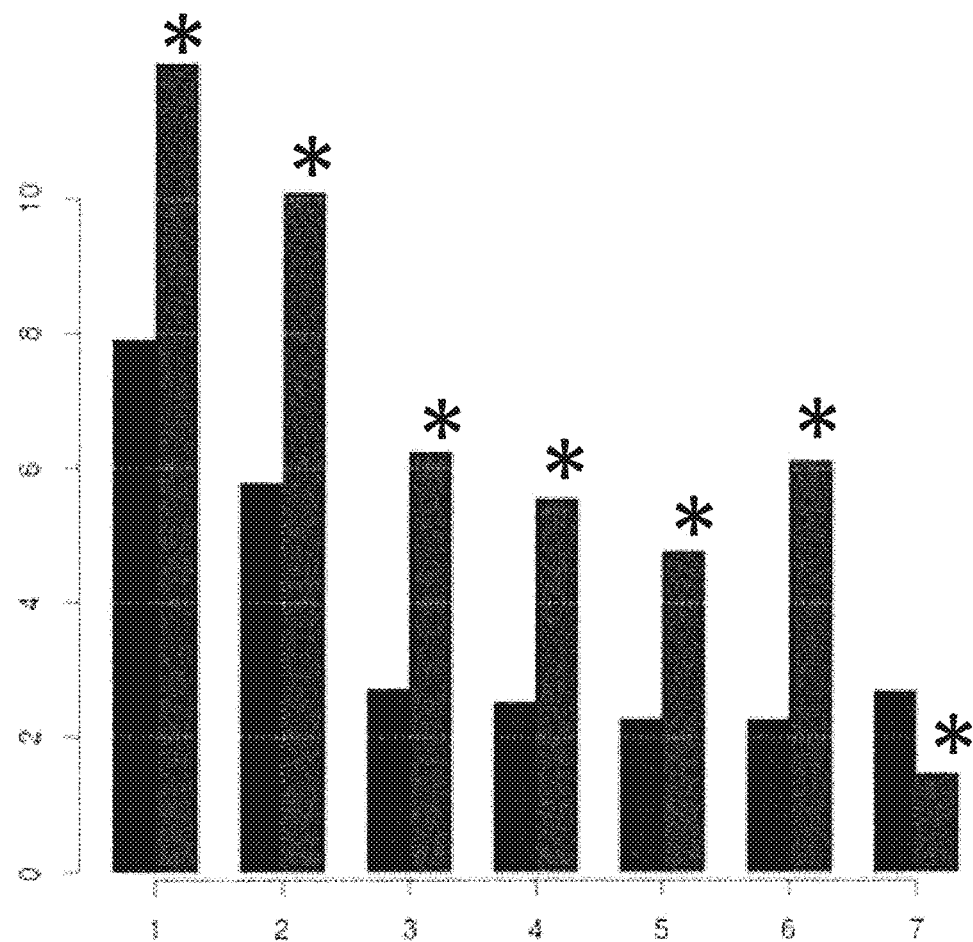

FIG. 11 shows how the helicase controlled DNA movement speed for the mutant T4 Dda E94C/A360C varied during the course of a 6 hour 5 minute experimental run (y-axis label events per second, x-axis label time (hours)). The bars in the graph labelled with a star (*) corresponded to helicase controlled movement speed of region 2 of the lambda DNA construct (shown in FIG. 8) passing through the nanopore and those without a star corresponded to the helicase controlled movement speed of of region 1 of the lambda DNA construct (shown in FIG. 8) passing through the nanopore. Events per second was used in the examples as a measure of the speed of translocation of DNA movement through the nanopore.

Figure 12:
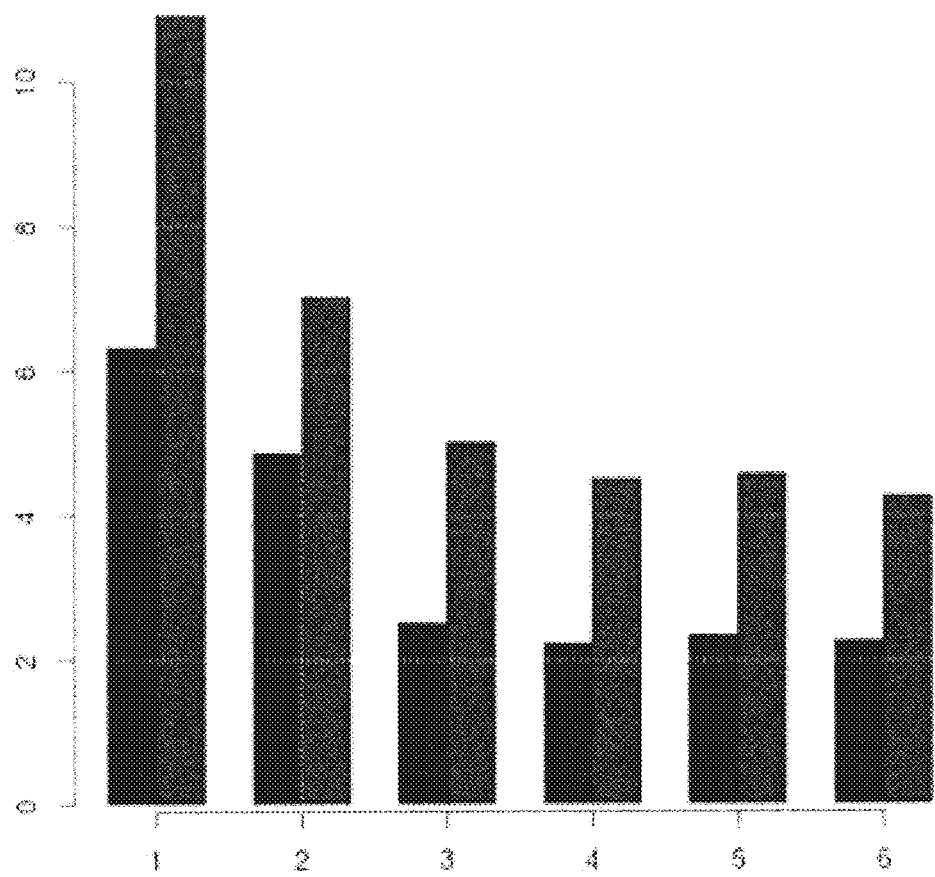

FIG. 12 shows how the helicase controlled DNA movement speed for the mutant T4 Dda E94C/A360C/C114A/C171A/C421D varied during the course of a six hour five minute experimental run (y-axis label events per second, x-axis label time (hours)). The bars in the graph labelled with a star (*) corresponded to helicase controlled movement speed of region 2 of the lambda DNA construct (shown in FIG. 8) passing through the nanopore and those without a star corresponded to the helicase controlled movement speed of of region 1 of the lambda DNA construct (shown in FIG. 8) passing through the nanopore. Events per second was used in the examples as a measure of the speed of translocation of DNA movement through the nanopore.

Figure 13:
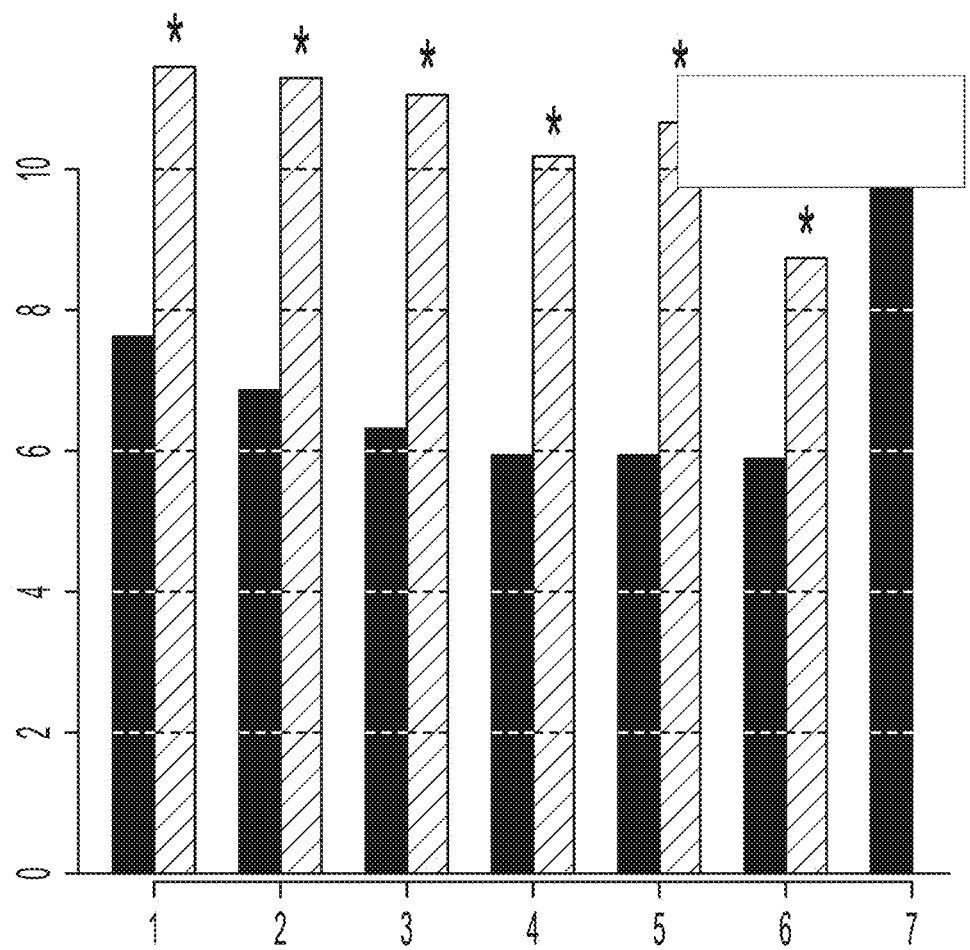

FIG. 13 shows how the helicase controlled DNA movement speed for the mutant T4 Dda E94C/A360C/C109A/C136A varied during the course of a six hour five minute experimental run (y-axis label events per second, x-axis label time (hours)). The bars in the graph labelled with a star (*) corresponded to helicase controlled movement speed of region 2 of the lambda DNA construct (shown in FIG. 8) passing through the nanopore and those without a star corresponded to the helicase controlled movement speed of of region 1 of the lambda DNA construct (shown in FIG. 8) passing through the nanopore. Events per second was used in the examples as a measure of the speed of translocation of DNA movement through the nanopore.

Figure 14:
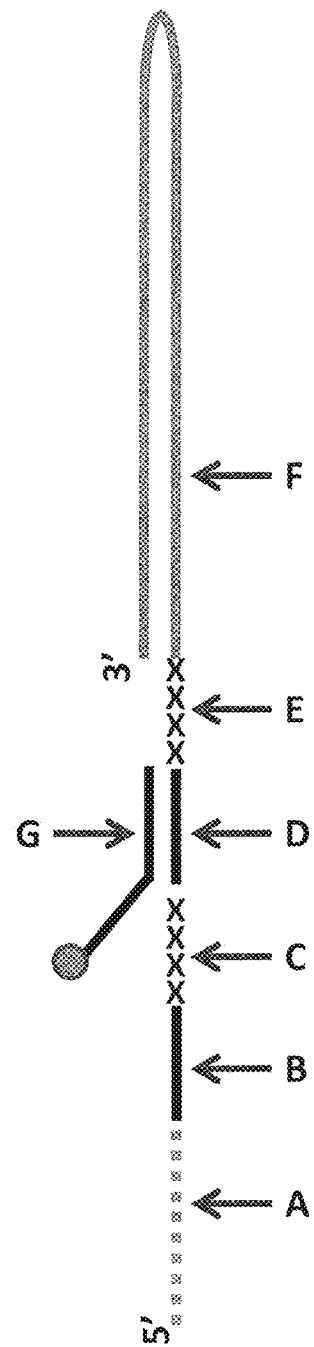

FIG. 14 shows a diagram of the DNA construct used in Example 5. Label A corresponds to 25iSpC3 spacers which are attached at the 3' end to SEQ ID NO: 70 (labelled B). Label B is attached at its 3' end to four iSp18 spacers (labelled C). The four iSp18 spacers are attached to the 5' end of SEQ ID NO: 61 (labelled D). SEQ ID NO: 61 is attached to four 5-nitroindoles (labelled E) which are attached to SEQ ID NO: 71 (labelled F) at its 5' end. SEQ ID NO: 61 is hybridised to SEQ ID NO: 63 (labelled G). SEQ ID NO: 63 has six iSp18 spacers, two thymines and a 3' cholesterol TEG attached at its 3' end.

Figure 15:
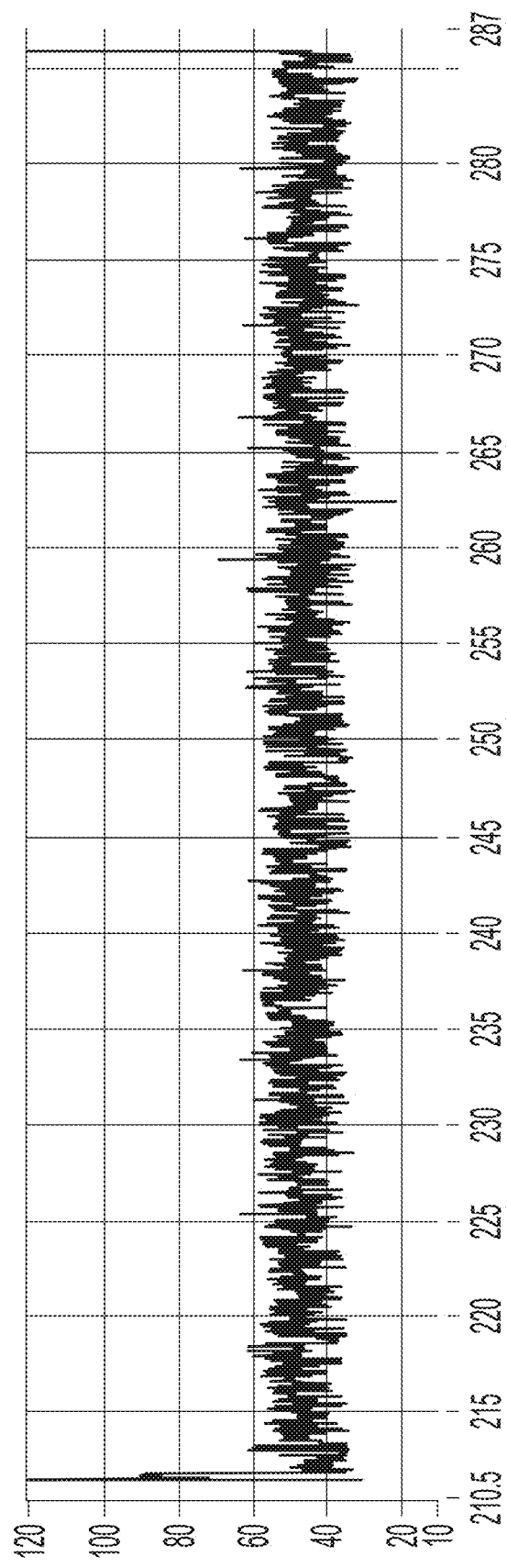

FIG. 15 shows an example current trace (y-axis label Current (pA, 10 to 120), x-axis label Time (s, 210.5 to 287)) of when a helicase (T4 Dda E94C/C109A/C136A/A360C/W378A (SEQ ID NO: 8 with mutations E94C/C109A/C136A/A360C/W378A)) controlled the translocation of DNA construct Z (shown in FIG. 8) through an MspA nanopore.

Figure 16A:
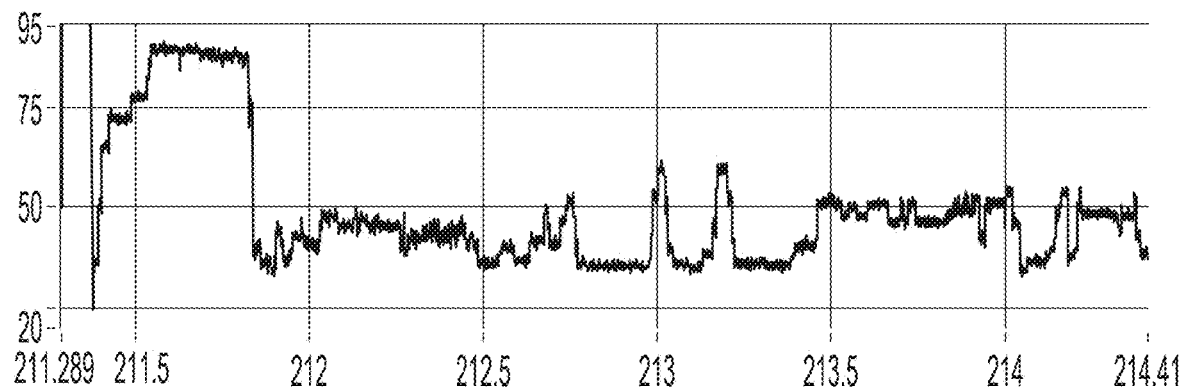
Figure 16B:
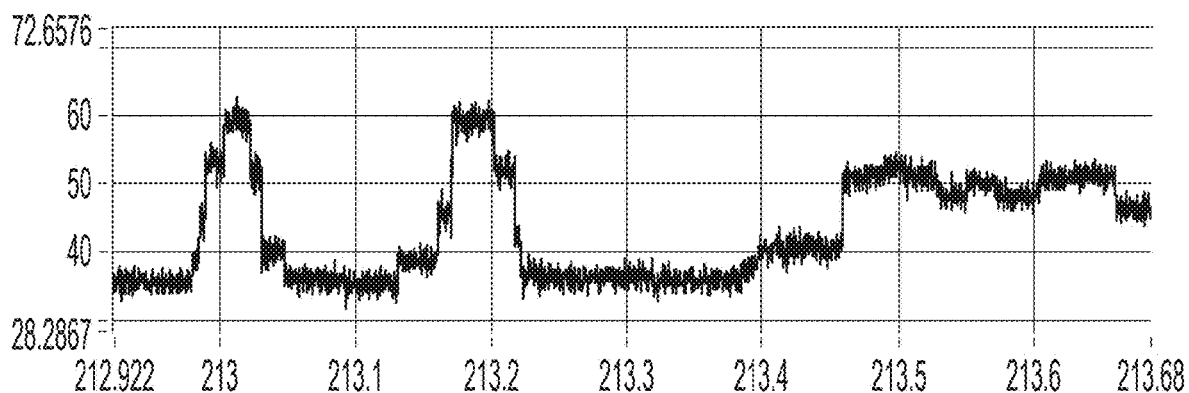
Figure 16C:
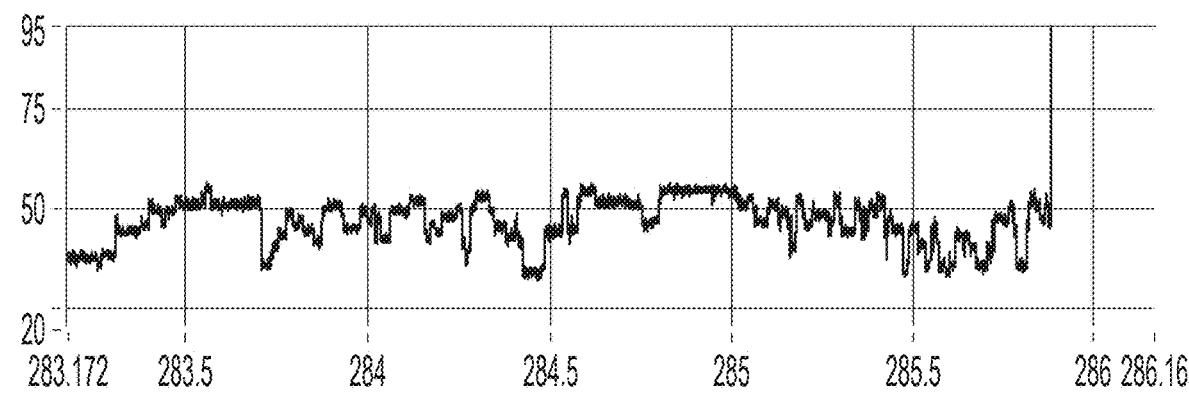

FIG. 16 shows zoomed in regions of the helicase-controlled DNA movement shown in the current trace in FIG. 15 (y-axis label Current (pA, upper trace 20 to 95, middle trace 28.3 to 72.7 and lower trace 20 to 95), x-axis label Time (s, upper trace 211.3 to 214.4, middle trace 212.9 to 213.7 and lower trace 283.2 to 286.2). A) shows the beginning of the helicase-controlled DNA movement B) shows a zoomed in region of trace A and C) shows the end of the helicase controlled DNA movement.

Figure 17:
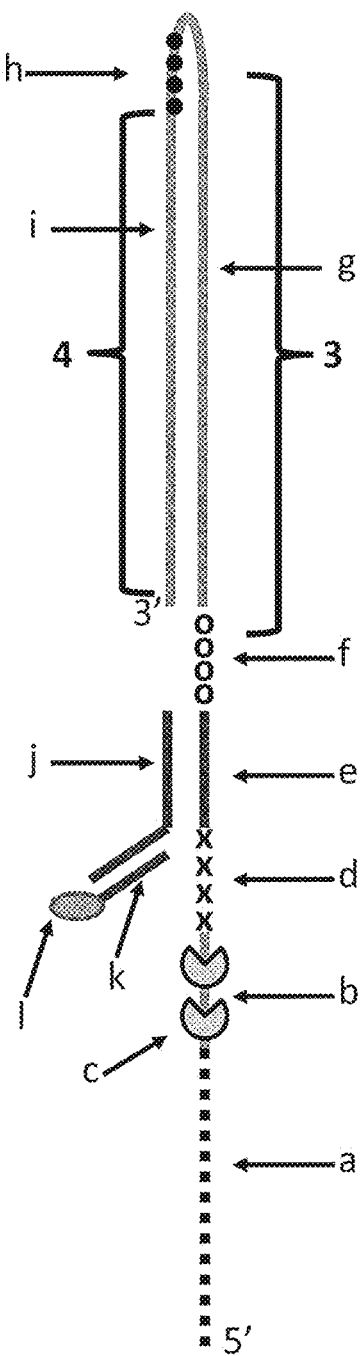

FIG. 17 shows DNA construct X which was used in Example 6. Section a of DNA construct X corresponds to 25 iSpC3 spacers, which are attached to the 5' end of SEQ ID NO: 70 (labelled b). Section b is the region of construct X to which the helicase enzymes T4 Dda E94C/A360C or T4 Dda E94C/C109A/C136A/A360C (depending on the experiment) bound (labelled c). The length of section b corresponded to the footprint (binding region) of two enzymes e.g. it was long enough to allow two enzymes to bind to this region. Section d corresponds to four iSp18 spacers. Section e corresponds to SEQ ID NO: 61. Section f corresponds to four 5'-nitroindoles. Section g corresponds to SEQ ID NO: 72 (this section of the strand was referred to as region 3 of DNA construct X). Section h (shown by black dots) corresponds to four iSpC3 spacers, which are attached to the 5' end of SEQ ID NO: 73 (labelled in which was referred to as region 4 of DNA construct X). Section j corresponds to SEQ ID NO: 74 and section k corresponds to SEQ ID NO: 75 which is attached to a 5' cholesterol TEG. It was possible to distinguish between regions 3 and 4 as they translocated through a nanopore as they produced different characteristics. Furthermore, the section h spacers (four iSpC3 spacers) produced a current spike in the current trace which aided identification of the transition from region 3 to region 4.

FIG. 18 shows example plots of when the helicase T4 Dda E94C/A360C (SEQ ID NO: 24 with mutations E94C/A360C) controlled the translocation of DNA construct X (see FIG. 17 for details) through an MspA nanopore. The x-axis corresponds to the movement index and the y-axis corresponds to the current (pA). For each DNA strand which moved through the pore the current was measured as a function of time. The moving DNA resulted in stepwise changes in the measured current levels. The observed current levels were fitted to obtain a mean current for each step, and assigned an incrementing movement index point. The mean current against movement index therefore closely approximated the original current signal, and was used to characterise the translocated DNA. Plots A and B each showed a single DNA strand moving through the nanopore under the control of helicases, the labelled regions 3 and 4 corresponded to the translocation of region 3 and 4 of DNA construct X (see FIG. 17). Trace A shows the movement index observed when construct X was translocated through the pore under the control of a single T4 Dda E94C/A360C helicase. Trace B shows the movement index observed when construct X was translocated through the pore under the control of two T4 Dda E94C/A360C helicases. As region 3 and region 4 were approximately the same length, the movement index observed for each region would have been expected to have had approximately the same number of points in the movement index. Plot A shows a significantly reduced number of points in the movement index for region 4 when compared to region 3, therefore, less information was derived from region 4 than region 3. However, plot B (where the movement of construct X was controlled by two T4 Dda E94C/A360C helicases) showed many more points in the movement index of region 4, which indicated that approximately the same amount of information was derived from region 4 as region 3. Using two helicases to control the movement of construct X provided improved movement as more information was derived from region 4 than when a single helicase controlled the movement.

FIG. 19 shows example plots of when the helicase T4 Dda E94C/C109A/C136A/A360C (SEQ ID NO: 24 with mutations E94C/C109A/C136A/A360C) controlled the translocation of DNA construct X (see FIG. 17 for details) through an MspA nanopore. The x-axis corresponds to the movement index (see FIG. 18's figure legend for description of movement index) and the y-axis corresponds to the current (pA). Plots A and B each showed a single DNA strand moving through the nanopore under the control of helicases, the labelled regions 3 and 4 corresponded to the translocation of region 3 and 4 of DNA construct X (see FIG. 17). Trace A shows the movement index observed when construct X was translocated through the pore under the control of a single T4 Dda E94C/C109A/C136A/A360C. Trace B shows the movement index observed when construct X was translocated through the pore under the control of two T4 Dda E94C/C109A/C136A/A360C helicases. As region 3 and region 4 were approximately the same length, the movement index observed for each region would have been expected to have had approximately the same number of points in the movement index. Plot A shows a significantly reduced number of points in the movement index for region 4 when compared to region 3, therefore, less information was derived from region 4 than region 3. However, plot B (where the movement of construct X was controlled by two T4 Dda E94C/C109A/C136A/A360C helicases) showed approximately the same number of points in both sections of the movement index, and therefore approximately the same amount of information was derived from region 4 as region 3. Using two helicases to control the movement of construct X provided improved movement as more information was derived from region 4 than when a single helicase controlled the movement.

Figure 20:
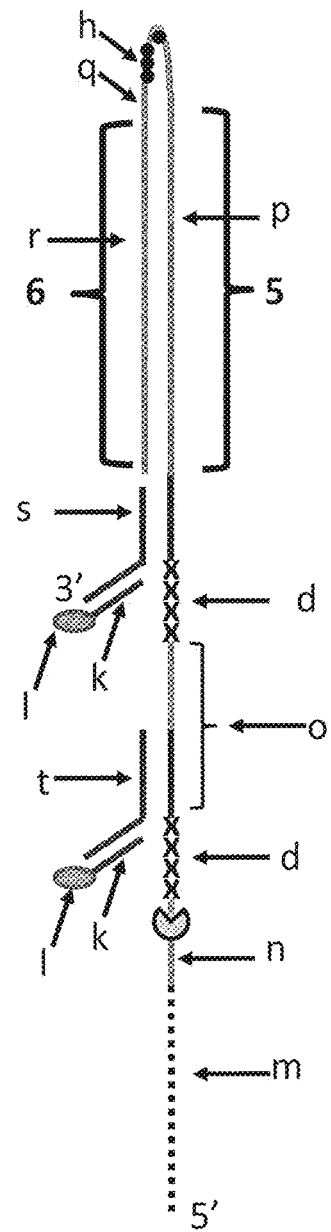

FIG. 20 shows DNA construct Z which was used in Example 7 and 8. Section m of DNA construct Z corresponds to 40 iSpC3 spacers, which are attached to the 5' end of SEQ ID NO: 76 (labelled n). Section n is a region of construct Z to which the helicase enzyme T4 Dda E94C/C109A/C136A/A360C or T4 Dda E94C/C109A/C136A/A360C/W378A bound. The length of section n corresponded to the footprint (binding region) of one enzyme e.g. it was long enough to allow one enzyme to bind to this region. The sections labelled d correspond to four iSp18 spacers. Section o corresponds to SEQ ID NO: 77, part of this section was a region of construct Z to which the helicase enzyme T4 Dda E94C/C109A/C136A/A360C/W378A bound. Section p corresponds to SEQ ID NO: 78 (part of this section of the strand was referred to as region 5 of DNA construct Z). Section h (shown by black dots) corresponds to four iSpC3 spacers, which are attached to the 5' end of SEQ ID NO: 79 (labelled q). Section r corresponds to the complementary sequence of SEQ ID NO: 78 (labelled r, which was referred to as region 6 of DNA construct Z). Section s corresponds to SEQ ID NO: 74. Section k corresponds to SEQ ID NO: 75 which is attached to a 5' cholesterol TEG (labelled 1). Section t corresponds to SEQ ID NO: 80. It was possible to distinguish between regions 5 and 6 as they translocated through a nanopore as they produced different characteristics. Furthermore, the section h spacers (four iSpC3 spacers) produced a current spike in the current trace which aided identification of the transition from region 5 to region 6.

Figure 21A:
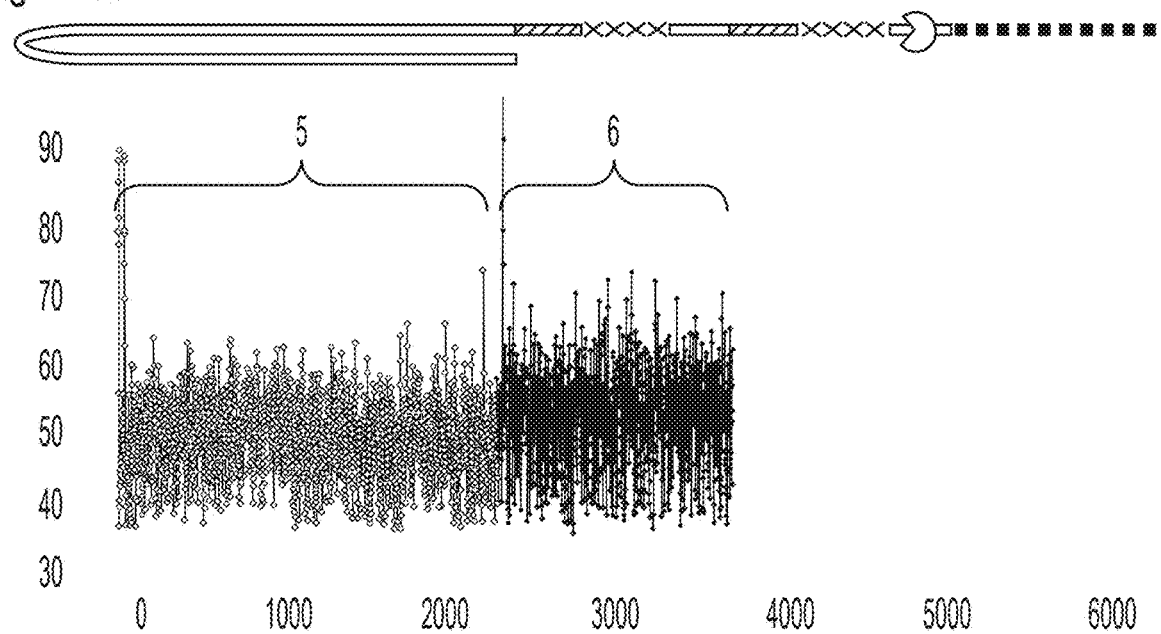

FIG. 21 shows example plots of when either the helicase T4 Dda E94C/C109A/C136A/A360C (section (A), SEQ ID NO: 24 with mutations E94C/C109A/C136A/A360C) or the helicases T4 Dda E94C/C109A/C136A/A360C and T4 Dda E94C/C109A/C136A/A360C/W378A (section (B)) controlled the translocation of DNA construct Z (FIG. 20) through an MspA nanopore. The x-axis corresponds to the movement index and the y-axis corresponds to the current (pA). For each DNA strand which moved through the pore the current was measured as a function of time. The moving DNA resulted in stepwise changes in the measured current levels. The observed current levels were fitted to obtain a mean current for each step, and assigned an incrementing movement index point. The mean current against movement index therefore closely approximated the original current signal, and was used to characterise the translocated DNA. Plots A and B each showed a single DNA strand moving through the nanopore under the control of helicases, the labelled regions 5 and 6 corresponded to the translocation of region 5 and 6 of DNA construct Z (see FIG. 20). Trace A shows the movement index observed when construct Z was translocated through the pore under the control of a single T4 Dda E94C/C109A/C136A/A360C helicase. Trace B shows the movement index observed when construct Z was translocated through the pore under the control of both T4 Dda E94C/C109A/C136A/A360C and T4 Dda E94C/C109A/C136A/A360C/W378A. As region 5 and region 6 were approximately the same length, the movement index observed for each region would have been expected to have had approximately the same number of points in the movement index. Plot A shows a significantly reduced number of points in the movement index for region 6 when compared to region 5, therefore, less information was derived from region 6 than region 5. However, plot B (where the movement of construct Z was controlled by both T4 Dda E94C/C109A/C136A/A360C and T4 Dda E94C/C109A/C136A/A360C/W378A) showed many more points in the movement index of region 6, which indicated that approximately the same amount of information was derived from region 6 as region 5. Using two different helicases to control the movement of construct Z provided improved movement as more information was derived from region 6 than when a single helicase controlled the movement.

Figure 22A:
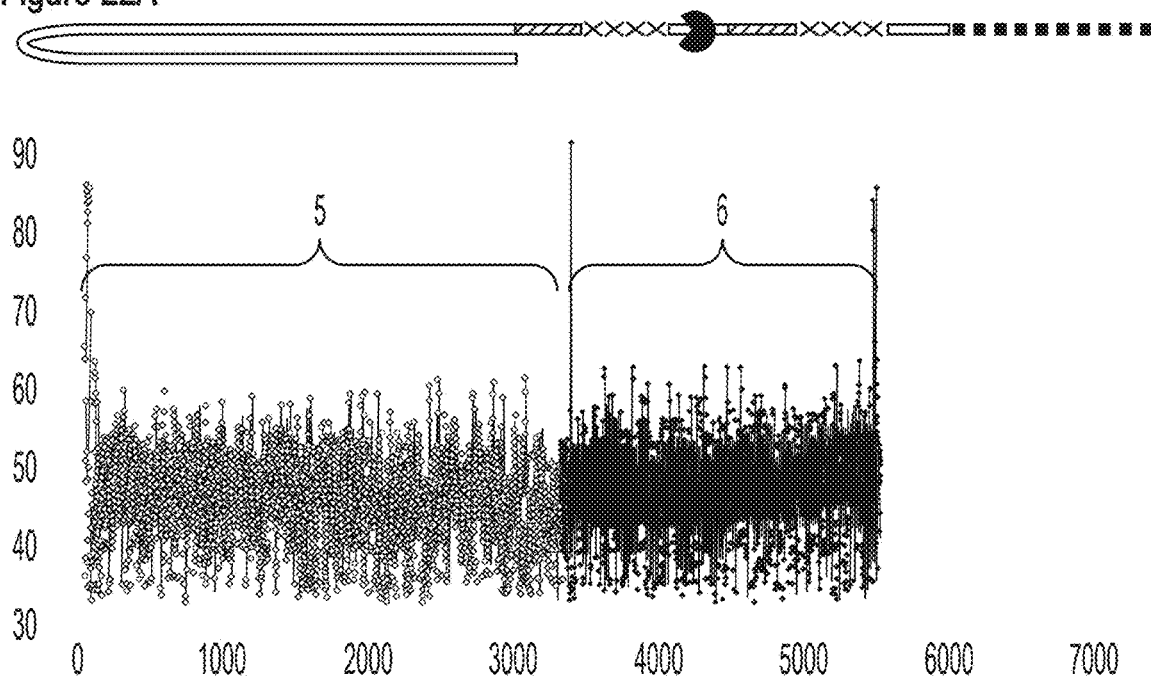

FIG. 22 shows example plots of when either the single helicase T4 Dda E94C/C109A/C136A/A360C/W378A (section (a), SEQ ID NO: 24 with mutations E94C/C109A/C136A/A360C/W378A) or two T4 Dda E94C/C109A/C136A/A360C/W378A helicases (section (b)) were used to controlled the translocation of DNA construct Z (FIG. 20) through an MspA nanopore. The x-axis corresponds to the movement index and the y-axis corresponds to the current (pA). For each DNA strand which moved through the pore the current was measured as a function of time. The moving DNA resulted in stepwise changes in the measured current levels. The observed current levels were fitted to obtain a mean current for each step, and assigned an incrementing movement index point. The mean current against movement index therefore closely approximated the original current signal, and was used to characterise the translocated DNA. Plots (A) and (B) showed a single DNA strand moving through the nanopore under the control of either one or two a helicases, the labelled regions 5 and 6 corresponded to the translocation of region 5 and 6 of DNA construct Z (see FIG. 20). Trace A shows the movement index observed when construct Z was translocated through the pore under the control of a single T4 Dda E94C/C109A/C136A/A360C/W378A helicase. Trace B shows the movement index observed when construct Z was translocated through the pore under the control of two T4 Dda E94C/C109A/C136A/A360C/W378A helicases. As region 5 and 6 were approximately the same length, the movement index observed for each region would have been expected to have had approximately the same number of points in the movement index. Plot A shows a significantly reduced number of points in the movement index for region 6 when compared to region 5, therefore, less information was derived from region 6 than region 5. However, plot B (where the movement of construct Z was controlled by two T4 Dda E94C/C109A/C136A/A360C/W378A helicases) showed many more points in the movement index of region 6, which indicated that approximately the same amount of information was derived from region 6 as region 5. Therefore, using two helicases to control the movement of construct Z provided improved movement as more information was derived from region 6 than when a single helicase controlled the movement.

DESCRIPTION OF THE SEQUENCE LISTING

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows the polynucleotide sequence encoding one monomer of α-hemolysin-E111N/K147N (α-HL-NN; Stoddart et al., PNAS, 2009; 106(19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NOs: 8 to 23 show the amino acid sequences of the Dda helicases shown in Tables 1 and 2.

SEQ ID NO: 24 shows the amino acid sequence of a preferred HhH domain.

SEQ ID NO: 25 shows the amino acid sequence of the ssb from the bacteriophage RB69, which is encoded by the gp32 gene.

SEQ ID NO: 26 shows the amino acid sequence of the ssb from the bacteriophage T7, which is encoded by the gp2.5 gene.

SEQ ID NO: 27 shows the amino acid sequence of the UL42 processivity factor from Herpes virus 1.

SEQ ID NO: 28 shows the amino acid sequence of subunit 1 of PCNA.

SEQ ID NO: 29 shows the amino acid sequence of subunit 2 of PCNA.

SEQ ID NO: 30 shows the amino acid sequence of subunit 3 of PCNA.

SEQ ID NO: 31 shows the amino acid sequence of Phi29 DNA polymerase.

SEQ ID NO: 32 shows the amino acid sequence (from 1 to 319) of the UL42 processivity factor from the Herpes virus 1.

SEQ ID NO: 33 shows the amino acid sequence of the ssb from the bacteriophage RB69, i.e. SEQ ID NO: 25, with its C terminus deleted (gp32RB69CD).

SEQ ID NO: 34 shows the amino acid sequence (from 1 to 210) of the ssb from the bacteriophage T7 (gp2.5T7-R211Del). The full length protein is shown in SEQ ID NO: 96.

SEQ ID NO: 35 shows the amino acid sequence of the 5$^{th}$ domain of Hel308 Hla.

SEQ ID NO: 36 shows the amino acid sequence of the 5$^{th}$ domain of Hel308 Hvo.

SEQ ID NO: 37 shows the amino acid sequence of the (HhH)2 domain.

SEQ ID NO: 38 shows the amino acid sequence of the (HhH)2-(HhH)2 domain.

SEQ ID NO: 39 shows the amino acid sequence of the human mitochondrial SSB (HsmtSSB).

SEQ ID NO: 40 shows the amino acid sequence of the p5 protein from Phi29 DNA polymerase.

SEQ ID NO: 41 shows the amino acid sequence of the wild-type SSB from *E. coli*.

SEQ ID NO: 42 shows the amino acid sequence of the ssb from the bacteriophage T4, which is encoded by the gp32 gene.

SEQ ID NO: 43 shows the amino acid sequence of EcoSSB-CterAla.

SEQ ID NO: 44 shows the amino acid sequence of EcoSSB-CterNGGN.

SEQ ID NO: 45 shows the amino acid sequence of EcoSSB-Q152del.

SEQ ID NO: 46 shows the amino acid sequence of EcoSSB-G117del.

SEQ ID NO: 47 shows the amino acid sequence of Topoisomerase V Mka (*Methanopyrus kandleri*).

SEQ ID NO: 48 shows the amino acid sequence of domains H-L of Topoisomerase V Mka (*Methanopyrus kandleri*).

SEQ ID NO: 49 shows the amino acid sequence of Mutant S (*Escherichia coli*).

SEQ ID NO: 50 shows the amino acid sequence of Sso7d (*Sulfolobus solfataricus*).

SEQ ID NO: 51 shows the amino acid sequence of Sso10b1 (*Sulfolobus solfataricus* P2).

SEQ ID NO: 52 shows the amino acid sequence of Sso10b2 (*Sulfolobus solfataricus* P2).

SEQ ID NO: 53 shows the amino acid sequence of Tryptophan repressor (*Escherichia coli*).

SEQ ID NO: 54 shows the amino acid sequence of Lambda repressor (Enterobacteria phage lambda).

SEQ ID NO: 55 shows the amino acid sequence of Cren7 (Histone crenarchaea Cren7 Sso).

SEQ ID NO: 56 shows the amino acid sequence of human histone (*Homo sapiens*).

SEQ ID NO: 57 shows the amino acid sequence of dsbA (Enterobacteria phage T4).

SEQ ID NO: 58 shows the amino acid sequence of Rad51 (*Homo sapiens*).

SEQ ID NO: 59 shows the amino acid sequence of PCNA sliding clamp (*Citromicrobium bathyomarinum* JL354).

SEQ ID NO: 60 shows a polynucleotide sequence used in Example 1. SEQ ID NO: 60 is attached by its 3' end to four iSpC3 spacers which are attached to the 5' end of SEQ ID NO: 61.

SEQ ID NO: 61 shows a polynucleotide sequence used in Example 1, 3, 4 and 6.

SEQ ID NO: 62 shows a polynucleotide sequence used in Example 1. SEQ ID NO: 62 is attached by its 5' end to three iSpC3 spacers which are attached to the 3' end of SEQ ID NO: 61.

SEQ ID NO: 63 shows a polynucleotide sequence used in Example 1 which at the 3' end of the sequence has six iSp18 spacers attached to two thymine residues and a 3' cholesterol TEG.

SEQ ID NO: 64 shows a polynucleotide sequence used in Example 2. The sequence has a carboxyfluorescein (FAM) attached to the thymine at position 37 in the sequence.

SEQ ID NO: 65 shows a circular polynucleotide sequence used in Example 2. The sequence has a carboxyfluorescein (FAM) attached to one thymine in the sequence.

SEQ ID NO: 66 shows the amino acid sequence for the Trwc Cba helicase.

SEQ ID NO: 67 shows a polynucleotide sequence used in Example 3 and 4.

SEQ ID NO: 68 shows a polynucleotide sequence used in Example 3. SEQ ID NO: 68 is attached by its 5' end to four 5-nitroindoles which are attached to the 3' end of SEQ ID NO: 61.

SEQ ID NO: 69 shows a polynucleotide sequence used in Example 4.

SEQ ID NO: 70 shows a polynucleotide sequence used in Example 5 and 6.

SEQ ID NO: 71 shows a polynucleotide sequence used in Example 5.

SEQ ID NO: 72 shows a polynucleotide sequence used in Example 6.

SEQ ID NO: 73 shows a polynucleotide sequence used in Example 6.

SEQ ID NO: 74 shows a polynucleotide sequence used in Example 6, 7 and 8.

SEQ ID NO: 75 shows a polynucleotide sequence used in Example 6, 7 and 8.

SEQ ID NO: 76 shows a polynucleotide sequence used in Example 7 and 8.

SEQ ID NO: 77 shows a polynucleotide sequence used in Example 7 and 8.

SEQ ID NO: 78 shows a polynucleotide sequence used in Example 7 and 8.

SEQ ID NO: 79 shows a polynucleotide sequence used in Example 7 and 8.

SEQ ID NO: 80 shows a polynucleotide sequence used in Example 7 and 8.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a helicase" includes "helicases", reference to "a modification" includes two or more such modifications, reference to "a transmembrane protein pore" includes two or more such pores, and the like.

All publications, patents and patent applications cited herein, whether supra or infra, are hereby incorporated by reference in their entirety.

Modified Dda Helicases

The present invention provides a modified Dda helicase. The one or more specific modifications are discussed in more detail below. The modification(s) allows the modified helicase to remain bound to the polynucleotide for longer. The modified helicase retains its ability to control the movement of a polynucleotide. In other words, the modified helicase is still capable of controlling the movement of a polynucleotide. The extent to which the helicase can control the movement of a polynucleotide is typically altered by the modifications as discussed in more detail below.

The Dda helicase of the invention is modified. The modified helicase is typically modified compared with the corresponding wild-type helicase or natural helicase. The helicase of the invention is artificial or non-natural.

The ability of a helicase to bind to and unbind from a polynucleotide can be determined using any method known in the art. Suitable binding/unbinding assays include, but are not limited to, native polyacrylamide gel electrophoresis (PAGE), fluorescence anisotropy, calorimetry and Surface plasmon resonance (SPR, such as Biacore™). The ability of a helicase to unbind from a polynucleotide can of course be determined by measuring the time for which the helicase can control the movement of a polynucleotide. This may also be determined using any method known in the art. The ability of a helicase to control the movement of a polynucleotide is typically assayed in a nanopore system, such as the ones described below. The ability of a helicase to control the movement of a polynucleotide can be determined as described in the Examples.

A modified helicase of the invention is a useful tool for controlling the movement of a polynucleotide during Strand Sequencing. The Dda helicase can control the movement of DNA in at least two active modes of operation (when the helicase is provided with all the necessary components to facilitate movement e.g. ATP and $Mg^{2+}$) and one inactive mode of operation (when the helicase is not provided with the necessary components to facilitate movement). When provided with all the necessary components to facilitate movement the Dda helicase moves along the DNA in the 5'-3' direction, but the orientation of the DNA in the nanopore (dependent on which end of the DNA is captured) means that the enzyme can be used to either move the DNA out of the nanopore against the applied field, or move the DNA into the nanopore with the applied field. When the 3' end of the DNA is captured the helicase works against the direction of the field applied by the voltage, pulling the threaded DNA out of the nanopore and into the cis chamber. However, when the DNA is captured 5'-down in the nanopore, the helicase works with the direction of the field applied by the voltage, pushing the threaded DNA into the nanopore and into the trans chamber. When the Dda helicase is not provided with the necessary components to facilitate movement it can bind to the DNA and act as a brake slowing the movement of the DNA when it is pulled into the pore by the applied field. In the inactive mode it does not matter whether the DNA is captured either 3' or 5' down, it is the applied field which pulls the DNA into the nanopore towards the trans side with the enzyme acting as a brake. When in the inactive mode the movement control of the DNA by the helicase can be described in a number of ways including ratcheting, sliding and braking.

A problem which occurs in sequencing polynucleotides, particularly those of 500 nucleotides or more, is that the molecular motor which is controlling the movement of the polynucleotide may disengage from the polynucleotide. This allows the polynucleotide to be pulled through the pore rapidly and in an uncontrolled manner in the direction of the applied field. A modified helicase of the invention is less likely to unbind or disengage from the polynucleotide being sequenced. The modified helicase can provide increased read lengths of the polynucleotide as they control the movement of the polynucleotide through a nanopore. The ability to move an entire polynucleotide through a nanopore under the control of a modified helicase of the invention allows characteristics of the polynucleotide, such as its sequence, to be estimated with improved accuracy and speed over known methods. This becomes more important as strand lengths increase and molecular motors are required with improved processivity. A modified helicase of the invention is particularly effective in controlling the movement of target polynucleotides of 500 nucleotides or more, for example 1000 nucleotides, 5000, 10000, 20000, 50000, 100000 or more.

In addition, using a modified helicase in accordance with the invention means that a lower concentration of helicase may be used. For instance, in Example 3, 1 nM of a modified helicase of the invention is used. In contrast, in Example 3, 1 µM of TrwC Cba, which is not a modified Dda helicase of the invention, is used.

A modified helicase of the invention is also a useful tool for isothermal polymerase chain reaction (PCR). In such methods, the strands of double stranded DNA are typically first separated by a helicase of the invention and coated by single stranded DNA (ssDNA)-binding proteins. In the second step, two sequence specific primers typically hybridise to each border of the DNA template. DNA polymerases may then be used to extend the primers annealed to the templates to produce a double stranded DNA and the two newly synthesised DNA products may then be used as substrates by the helicases of the invention, entering the next round of the reaction. Thus, a simultaneous chain reaction develops, resulting in exponential amplification of the selected target sequence.

The modified helicase has the ability to control the movement of a polynucleotide. The ability of a helicase to control the movement of a polynucleotide can be assayed using any method known in the art. For instance, the helicase may be contacted with a polynucleotide and the position of the polynucleotide may be determined using standard methods. The ability of a modified helicase to control the movement of a polynucleotide is typically assayed in a nanopore system, such as the ones described below and, in particular, as described in the Examples.

A modified helicase of the invention may be isolated, substantially isolated, purified or substantially purified. A helicase is isolated or purified if it is completely free of any other components, such as lipids, polynucleotides, pore monomers or other proteins. A helicase is substantially isolated if it is mixed with carriers or diluents which will not interfere with its intended use. For instance, a helicase is substantially isolated or substantially purified if it is present in a form that comprises less than 10%, less than 5%, less than 2% or less than 1% of other components, such as lipids, polynucleotides, pore monomers or other proteins.

Any Dda helicase may be modified in accordance with the invention. Preferred Dda helicases are discussed below.

Dda helicases typically comprises the following five domains: 1A (RecA-like motor) domain, 2A (RecA-like motor) domain, tower domain, pin domain and hook domain (Xiaoping He et al., 2012, Structure; 20: 1189-1200). The domains may be identified using protein modelling, x-ray diffraction measurement of the protein in a crystalline state (Rupp B (2009). Biomolecular Crystallography: Principles, Practice and Application to Structural Biology. New York: Garland Science.), nuclear magnetic resonance (NMR) spectroscopy of the protein in solution (Mark Rance; Cavanagh, John; Wayne J. Fairbrother; Arthur W. Hunt III; Skelton, NNicholas J. (2007). Protein NMR spectroscopy: principles and practice (2nd ed.). Boston: Academic Press.) or cryo-electron microscopy of the protein in a frozen-hydrated state (van Heel M, Gowen B, Matadeen R, Orlova E V, Finn R, Pape T, Cohen D, Stark H, Schmidt R, Schatz M, Patwardhan A (2000). "Single-particle electron cryo-microscopy: towards atomic resolution.". Q Rev Biophys. 33: 307 69). Structural information of proteins determined by above mentioned methods are publicly available from the protein bank (PDB) database.

Protein modelling exploits the fact that protein structures are more conserved than protein sequences amongst homologues. Hence, producing atomic resolution models of proteins is dependent upon the identification of one or more protein structures that are likely to resemble the structure of the query sequence. In order to assess whether a suitable protein structure exists to use as a "template" to build a protein model, a search is performed on the protein data bank (PDB) database. A protein structure is considered a suitable template if it shares a reasonable level of sequence identity with the query sequence. If such a template exists, then the template sequence is "aligned" with the query sequence, i.e. residues in the query sequence are mapped onto the template residues. The sequence alignment and template structure are then used to produce a structural model of the query sequence. Hence, the quality of a protein model is dependent upon the quality of the sequence alignment and the template structure.

Modifications in the Tower Domain and/or Pin Domain and/or 1A Domain

In one embodiment, the Dda helicase of the invention is one in which at least one cysteine residue (i.e. one or more cysteine residues) and/or at least one non-natural amino acid (i.e. one or more non-natural amino acids) have been introduced into (i) the tower domain and/or (ii) the pin domain and/or the (iii) 1A (RecA-like motor) domain, wherein the helicase retains its ability to control the movement of a polynucleotide. At least one cysteine residue and/or at least one non-natural amino acid may be introduced into the tower domain, the pin domain, the 1A domain, the tower domain and the pin domain, the tower domain and the 1A domain or the tower domain, the pin domain and the 1A domain.

The Dda helicase of the invention is preferably one in which at least one cysteine residue and/or at least one non-natural amino acid have been introduced into each of (i) the tower domain and (ii) the pin domain and/or the 1A (RecA-like motor) domain, i.e. into the tower domain and the pin domain, the tower domain and the 1A domain or the tower domain, the pin domain and the 1A domain.

Any number of cysteine residues and/or non-natural amino acids may be introduced into each domain. For instance, 1, 2, 3, 4, 5, 6, 7, 8, 9, 10 or more cysteine residues may be introduced and/or 1, 2, 3, 4, 5, 6, 7, 8, 9, 10 or more non-natural amino acids may be introduced. Only one or more cysteine residues may be introduced. Only one or more non-natural amino acids may be introduced. A combination of one or more cysteine residues and one or more non-natural amino acids may be introduced.

The at least one cysteine residue and/or at least one non-natural amino acid are/is preferably introduced by substitution. Methods for doing this are known in the art.

These modifications do not prevent the helicase from binding to a polynucleotide. These modifications decrease the ability of the polynucleotide to unbind or disengage from the helicase. In other words, the one or more modifications increase the processivity of the Dda helicase by preventing dissociation from the polynucleotide strand. The thermal stability of the enzyme is typically also increased by the one or more modifications giving it an improved structural stability that is beneficial in Strand Sequencing.

A non-natural amino acid is an amino that is not naturally found in a Dda helicase. The non-natural amino acid is preferably not histidine, alanine, isoleucine, arginine, leucine, asparagine, lysine, aspartic acid, methionine, cysteine, phenylalanine, glutamic acid, threonine, glutamine, tryptophan, glycine, valine, proline, serine or tyrosine. The non-natural amino acid is more preferably not any of the twenty amino acids in the previous sentence or selenocysteine Preferred non-natural amino acids for use in the invention include, but are not limited to 4-Azido-L-phenylalanine (Faz), 4-Acetyl-L-phenylalanine, 3-Acetyl-L-phenylalanine, 4-Acetoacetyl-L-phenylalanine, O-Allyl-L-tyrosine, 3-(Phenylselanyl)-L-alanine, O-2-Propyn-1-yl-L-tyrosine, 4-(Dihydroxyboryl)-L-phenylalanine, 4-[(Ethylsulfanyl)carbonyl]-L-phenylalanine, (2S)-2-amino-3-{4-[(propan-2-ylsulfanyl)carbonyl]phenyl}propanoic acid, (2S)-2-amino-3-{4-[(2-amino-3-sulfanylpropanoyl)amino]phenyl} propanoic acid, O-Methyl-L-tyrosine, 4-Amino-L-phenylalanine, 4-Cyano-L-phenylalanine, 3-Cyano-L-phenylalanine, 4-Fluoro-L-phenylalanine, 4-Iodo-L-phenylalanine, 4-Bromo-L-phenylalanine, O-(Trifluor- omethyl)tyrosine, 4-Nitro-L-phenylalanine, 3-Hydroxy-L-tyrosine, 3-Amino-L-tyrosine, 3-Iodo-L-tyrosine, 4-Isopropyl-L-phenylalanine, 3-(2-Naphthyl)-L-alanine, 4-Phenyl-L-phenylalanine, (2S)-2-amino-3-(naphthalen-2-ylamino)propanoic acid, 6-(Methylsulfanyl)norleucine, 6-Oxo-L-lysine, D-tyrosine, (2R)-2-Hydroxy-3-(4-hydroxyphenyl)propanoic acid, (2R)-2-Ammoniooctanoate3-(2,2'-Bipyridin-5-yl)-D-alanine, 2-amino-3-(8-hydroxy-3-quinolyl)propanoic acid, 4-Benzoyl-L-phenylalanine, S-(2-Nitrobenzyl)cysteine, (2R)-2-amino-3-[(2-nitrobenzyl)sulfanyl]propanoic acid, (2S)-2-amino-3-[(2-nitrobenzyl)oxy]propanoic acid, 0-(4,5-Dimethoxy-2-nitrobenzyl)-L-serine, (2S)-2-amino-6-({[(2-nitrobenzyl)oxy]carbonyl}amino)hexanoic acid, O-(2-Nitrobenzyl)-L-tyrosine, 2-Nitrophenylalanine, 4-[(E)-Phenyldiazenyl]-L-phenylalanine, 4-[3-(Trifluoromethyl)-3H-diaziren-3-yl]-D-phenylalanine, 2-amino-3-[[5-(dimethylamino)-1-naphthyl]sulfonylamino]propanoic acid, (2S)-2-amino-4-(7-hydroxy-2-oxo-2H-chromen-4-yl)butanoic acid, (2S)-3-[(6-acetylnaphthalen-2-yl)amino]-2-aminopropanoic acid, 4-(Carboxymethyl)phenylalanine, 3-Nitro-L-tyrosine, O-Sulfo-L-tyrosine, (2R)-6-Acetamido-2-ammoniohexanoate, 1-Methylhistidine, 2-Aminononanoic acid, 2-Aminodecanoic acid, L-Homocysteine, 5-Sulfanylnorvaline, 6-Sulfanyl-L-norleucine, 5-(Methylsulfanyl)-L-norvaline, $N^6$-{[(2R,3R)-3-Methyl-3,4-dihydro-2H-pyrrol-2-yl]carbonyl}-L-lysine, $N^6$-[(Benzyloxy)carbonyl]lysine, (2S)-2-amino-6-[(cyclopentylcarbonyl)amino]hexanoic acid, $N^6$-[(Cyclopentyloxy)carbonyl]-L-lysine, (2S)-2-amino-6-{[(2R)-tetrahydrofuran-2-ylcarbonyl]amino}hexanoic acid, (2S)-2-amino-8-[(2R,3S)-3-ethynyltetrahydrofuran-2-yl]-8-oxooctanoic acid, $N^6$-(tert-Butoxycarbonyl)-L-lysine, (2S)-2-Hydroxy-6-({[(2-methyl-2-propanyl)oxy]carbonyl}amino)hexanoic acid, $N^6$-[(Allyloxy)carbonyl]lysine, (2S)-2-amino-6-({[(2-azidobenzyl)oxy]carbonyl}amino)hexanoic acid, $N^6$-L-Prolyl-L-lysine, (2S)-2-amino-6-{[(prop-2-yn-1-yloxy)carbonyl]amino}hexanoic acid and $N^6$-[(2-Azidoethoxy)carbonyl]-L-lysine. The most preferred non-natural amino acid is 4-azido-L-phenylalanine (Faz).

Table 1 below summarises the preferred Dda helicases which may be modified in accordance with the invention.

| Dda Homologue (SEQ ID NO:) | | Habitat | Uniprot | Length | Sequence Identity to 1993/% | Number of D/E vs. K/R amino acids | # C |
|---|---|---|---|---|---|---|---|
| Rma-DSM (SEQ ID NO: 9) | Rhodothermus marinus | Mild halophile, moderate thermophile >65° C. | D0MKQ2 | 678 | 21 | −84/+85 | 2 |
| Csp (SEQ ID NO: 10) | Cyanothece sp. (strain ATCC 51142) | Marine bacterium | B1X365 | 496 | 24 | −76/+76 | 5 |
| Sru (SEQ ID NO: 11) | Salinibacter ruber | Extremely halophilic, 35-45° C. | Q2S429 | 421 | 26 | −78/+54 | 3 |
| Sgo (SEQ ID NO: 12) | Sulfurimonas gotlandica GD1 | Habitat: hydrothermal vents, coastal sediments | B6BJ43 | 500 | 27 | −72/+64 | 2 |
| Vph12B8 (SEQ ID NO: 13) | Vibrio phage henriette 12B8 | Host found in saltwater, stomach bug | M4MBC3 | 450 | 27 | −62/+47 | 6 |
| Vph (SEQ ID NO: 14) | Vibrio phage phi-pp2 | Host found in saltwater, stomach bug | I6XGX8 | 421 | 39 | −55/+45 | 5 |
| Aph65 (SEQ ID NO: 15) | Aeromonas phage 65 | Host found in fresh/brackish water, stomach bug | E5DRP6 | 434 | 40 | −57/+48 | 4 |
| AphCC2 (SEQ ID NO: 16) | Aeromonas phage CC2 | Host found in fresh/brackish water, stomach bug | I6XH64 | 420 | 41 | −53/+44 | 4 |

-continued

| Dda Homologue (SEQ ID NO:) | Habitat | Uniprot | Length | Sequence Identity to 1993/% | Number of D/E vs. K/R amino acids | # C |
|---|---|---|---|---|---|---|
| Cph (SEQ ID NO: 17) | Cronobacter phage vB CsaM GAP161 | Host member of enterobacteriaceae | K4FBD0 | 443 | 42 | −59/+57 | 4 |
| Kph (SEQ ID NO: 18) | Klebsiella phage KP15 | Host member of enterobacteriaceae | D5JF67 | 442 | 44 | −59/+58 | 5 |
| SphIME13 (SEQ ID NO: 19) | Stenotrophomonas phage IME13 | Host found in soil | J7HXT5 | 438 | 51 | −58/+59 | 7 |
| AphAc42 (SEQ ID NO: 20) | Acinetobacter phage Ac42 | Host found in soil | E5EYE6 | 442 | 59 | −53/+49 | 9 |
| SphSP18 (SEQ ID NO: 21) | Shigella phage SP18 | Host member of enterobacteriaceae | E3SFA5 | 442 | 59 | −55/+55 | 9 |
| Yph (SEQ ID NO: 22) | Yersinia phage phiR1-RT | Host member of enterobacteriaceae | I7J3V8 | 439 | 64 | −52/+52 | 7 |
| SphS16 (SEQ ID NO: 23) | Salmonella phage S16 | Host member of enterobacteriaceae | M1EA88 | 441 | 72 | −56/+55 | 5 |
| 1993 (SEQ ID NO: 8) | Enterobateria phage T4 | Host member of enterobacteriaceae | P32270 | 439 | 100 | −57/+58 | 5 |

Table 2 below (which is separated in two parts) identifies the residues making up each domain in each Dda homologue (SEQ ID NOs: 8 to 23).

| Homologue | SEQ ID NO | 1A | 2A |
|---|---|---|---|
| Dda-Rma-DSM | 9 | M1-I84 + R113-Y211 | R212-E294 + G422-S678 |
| Dda-Csp | 10 | M1-L147 + S166-V240 | R241-N327 + A449-G496 |
| Dda-Sru | 11 | M1-L90 + E108-H173 | R174-D260 + A371-V421 |
| Dda-Sgo | 12 | M1-L115 + N136-V205 | R206-K293 + I408-L500 |
| Dda-Vph12B8 | 13 | M1-L96 + F114-V194 | R195-D287 + V394-Q450 |
| Dda-Vph | 14 | M1-L77 + V96-V166 | R167-T249 + L372-N421 |
| Dda-Aph65 | 15 | M1-M81 + L99-M171 | R172-T254 + L381-K434 |
| Dda-AphCC2 | 16 | M1-M68 + M86-M158 | R159-T241 + L367-K420 |
| Dda-Cph | 17 | M1-L87 + A108-M181 | R182-T262 + L393-V443 |
| Dda-Kph | 18 | M1-L87 + A108-M181 | R182-T262 + L392-V442 |
| Dda-SphIME13 | 19 | M1-L85 + T103-K176 | R177-N257 + L387-V438 |
| Dda-AphAc42 | 20 | M1-L91 + V109-M183 | R184-T265 + L393-I442 |
| Dda-SphSP18 | 21 | M1-L87 + M105-M179 | R180-T261 + L393-V442 |
| Dda-Yph | 22 | M1-L86 + V104-K178 | R179-T260 + L390-I439 |
| Dda-SphS16 | 23 | M1-L86 + V104-M178 | R179-T260 + L391-V441 |
| Dda-1993 | 8 | M1-L85 + V103-K177 | R178-T259 + L390-V439 |

| Homologue | SEQ ID | tower | pin | hook |
|---|---|---|---|---|
| Dda-Rma-DSM | 9 | G295-N309 + F316-Y421 | Y85-L112 | A310-L315 |
| Dda-Csp | 10 | V328-P342 + N360-Y448 | K148-N165 | V343-L359 |
| Dda-Sru | 11 | A261-T275 + T285-Y370 | G91-E107 | W276-L284 |
| Dda-Sgo | 12 | G294-I307 + T314-Y407 | G116-T135 | R308-Y313 |
| Dda-Vph12B8 | 13 | V288-E301 + N307-N393 | G97-P113 | M302-W306 |
| Dda-Vph | 14 | S250-P264 + E278-S371 | K78-E95 | V265-I277 |
| Dda-Aph65 | 15 | K255-P269 + T284-S380 | K82-K98 | V270-F283 |
| Dda-AphCC2 | 16 | D242-P256 + T271-S366 | K69-K85 | V257-F270 |
| Dda-Cph | 17 | T263-P277 + N295-P392 | K88-K107 | L278-Y294 |
| Dda-Kph | 18 | D263-P277 + N295-A391 | K88-K107 | L278-Y294 |
| Dda-SpHIME13 | 19 | A258-P272 + N290-P386 | K86-G102 | L273-F289 |
| Dda-AphAc42 | 20 | L266-P280 + N298-A392 | K92-D108 | L281-F297 |
| Dda-SphSP18 | 21 | D262-P276 + N294-A392 | K88-E104 | H277-F293 |
| Dda-Yph | 22 | D261-P275 + N293-A389 | K87-E103 | L276-F292 |
| Dda-SphS16 | 23 | E261-P275 + T293-A390 | K87-E103 | L276-F292 |
| Dda-1993 | 8 | D260-P274 + N292-A389 | K86-E102 | L275-F291 |

The helicase of the invention preferably comprises a variant of SEQ ID NO: 8 in which at least one cysteine residue and/or at least one non-natural amino acid have been introduced into (i) the tower domain (residues D260-P274 and N292-A389) and/or (ii) the pin domain (residues K86-E102) and/or the (iii) 1A domain (residues M1-L85 and V103-K177). The at least one cysteine residue and/or at least one non-natural amino acid are preferably introduced into residues N292-A389 of the tower domain.

The helicase of the invention preferably comprises a variant of SEQ ID NO: 9 in which at least one cysteine residue and/or at least one non-natural amino acid have been introduced into (i) the tower domain (residues G295-N309 and F316-Y421) and/or (ii) the pin domain (residues Y85-L112) and/or the (iii) 1A domain (residues M1-I84 and R113-Y211). The at least one cysteine residue and/or at least one non-natural amino acid are preferably introduced into residues F316-Y421 of the tower domain.

The helicase of the invention preferably comprises a variant of SEQ ID NO: 10 in which at least one cysteine residue and/or at least one non-natural amino acid have been introduced into (i) the tower domain (residues V328-P342 and N360-Y448) and/or (ii) the pin domain (residues K148-N165) and/or the (iii) 1A domain (residues M1-L147 and 5166-V240). The at least one cysteine residue and/or at least one non-natural amino acid are preferably introduced into residues N360-Y448 of the tower domain.

The helicase of the invention preferably comprises a variant of SEQ ID NO: 11 in which at least one cysteine residue and/or at least one non-natural amino acid have been introduced into (i) the tower domain (residues A261-T275 and T285-Y370) and/or (ii) the pin domain (residues G91-E107) and/or the (iii) 1A domain (residues M1-L90 and E108-H173). The at least one cysteine residue and/or at least one non-natural amino acid are preferably introduced into residues T285-Y370 of the tower domain.

The helicase of the invention preferably comprises a variant of SEQ ID NO: 12 in which at least one cysteine residue and/or at least one non-natural amino acid have been introduced into (i) the tower domain (residues G294-I307 and T314-Y407) and/or (ii) the pin domain (residues G116-T135) and/or the (iii) 1A domain (residues M1-L115 and N136-V205). The at least one cysteine residue and/or at least one non-natural amino acid are preferably introduced into residues T314-Y407 of the tower domain.

The helicase of the invention preferably comprises a variant of SEQ ID NO: 13 in which at least one cysteine residue and/or at least one non-natural amino acid have been introduced into (i) the tower domain (residues V288-E301 and N307-N393) and/or (ii) the pin domain (residues G97-P113) and/or the (iii) 1A domain (residues M1-L96 and F114-V194). The at least one cysteine residue and/or at least one non-natural amino acid are preferably introduced into residues N307-N393 of the tower domain.

The helicase of the invention preferably comprises a variant of SEQ ID NO: 14 in which at least one cysteine residue and/or at least one non-natural amino acid have been introduced into (i) the tower domain (residues S250-P264 and E278-S371) and/or (ii) the pin domain (residues K78-E95) and/or the (iii) 1A domain (residues M1-L77 and V96-V166). The at least one cysteine residue and/or at least one non-natural amino acid are preferably introduced into residues E278-S371 of the tower domain.

The helicase of the invention preferably comprises a variant of SEQ ID NO: 15 in which at least one cysteine residue and/or at least one non-natural amino acid have been introduced into (i) the tower domain (residues K255-P269 and T284-S380) and/or (ii) the pin domain (residues K82-K98) and/or the (iii) 1A domain (residues M1-M81 and L99-M171). The at least one cysteine residue and/or at least one non-natural amino acid are preferably introduced into residues T284-S380 of the tower domain.

The helicase of the invention preferably comprises a variant of SEQ ID NO: 16 in which at least one cysteine residue and/or at least one non-natural amino acid have been introduced into (i) the tower domain (residues D242-P256 and T271-S366) and/or (ii) the pin domain (residues K69-K85) and/or the (iii) 1A domain (residues M1-M68 and M86-M158). The at least one cysteine residue and/or at least one non-natural amino acid are preferably introduced into residues T271-S366 of the tower domain.

The helicase of the invention preferably comprises a variant of SEQ ID NO: 17 in which at least one cysteine residue and/or at least one non-natural amino acid have been introduced into (i) the tower domain (residues T263-P277 and N295-P392) and/or (ii) the pin domain (residues K88-K107) and/or the (iii) 1A domain (residues M1-L87 and A108-M181). The at least one cysteine residue and/or at least one non-natural amino acid are preferably introduced into residues N295-P392 of the tower domain.

The helicase of the invention preferably comprises a variant of SEQ ID NO: 18 in which at least one cysteine residue and/or at least one non-natural amino acid have been introduced into (i) the tower domain (residues D263-P277 and N295-A391) and/or (ii) the pin domain (residues K88-K107) and/or the (iii) 1A domain (residues M1-L87 and A108-M181). The at least one cysteine residue and/or at least one non-natural amino acid are preferably introduced into residues N295-A391 of the tower domain.

The helicase of the invention preferably comprises a variant of SEQ ID NO: 19 in which at least one cysteine residue and/or at least one non-natural amino acid have been introduced into (i) the tower domain (residues A258-P272 and N290-P386) and/or (ii) the pin domain (residues K86-G102) and/or the (iii) 1A domain (residues M1-L85 and T103-K176). The at least one cysteine residue and/or at least one non-natural amino acid are preferably introduced into residues N290-P386 of the tower domain.

The helicase of the invention preferably comprises a variant of SEQ ID NO: 20 in which at least one cysteine residue and/or at least one non-natural amino acid have been introduced into (i) the tower domain (residues L266-P280 and N298-A392) and/or (ii) the pin domain (residues K92-D108) and/or the (iii) 1A domain (residues M1-L91 and V109-M183). The at least one cysteine residue and/or at least one non-natural amino acid are preferably introduced into residues N298-A392 of the tower domain.

The helicase of the invention preferably comprises a variant of SEQ ID NO: 21 in which at least one cysteine residue and/or at least one non-natural amino acid have been introduced into (i) the tower domain (residues D262-P276 and N294-A392) and/or (ii) the pin domain (residues K88-E104) and/or the (iii) 1A domain (residues M1-L87 and M105-M179). The at least one cysteine residue and/or at least one non-natural amino acid are preferably introduced into residues N294-A392 of the tower domain.

The helicase of the invention preferably comprises a variant of SEQ ID NO: 22 in which at least one cysteine residue and/or at least one non-natural amino acid have been introduced into (i) the tower domain (residues D261-P275 and N293-A389) and/or (ii) the pin domain (residues K87-E103) and/or the (iii) 1A domain (residues M1-L86 and V104-K178). The at least one cysteine residue and/or at least one non-natural amino acid are preferably introduced into residues N293-A389 of the tower domain.

The helicase of the invention preferably comprises a variant of SEQ ID NO: 23 in which at least one cysteine residue and/or at least one non-natural amino acid have been introduced into (i) the tower domain (residues E261-P275 and T293-A390) and/or (ii) the pin domain (residues K87-E103) and/or the (iii) 1A domain (residues M1-L86 and V104-M178). The at least one cysteine residue and/or at least one non-natural amino acid are preferably introduced into residues T293-A390 of the tower domain.

The helicase of the invention preferably comprises a variant of any one of SEQ ID NOs: 8 to 23 in which at least one cysteine residue and/or at least one non-natural amino acid have been introduced into each of (i) the tower domain and (ii) the pin domain and/or the 1A domain. The helicase of the invention more preferably comprises a variant of any one of SEQ ID NOs: 8 to 23 in which at least one cysteine residue and/or at least one non-natural amino acid have been introduced into each of (i) the tower domain, (ii) the pin domain and (iii) the 1A domain. Any number and combination of cysteine residues and non-natural amino acids may be introduced as discussed above.

The helicase of the invention preferably comprises a variant of SEQ ID NO: 8 which comprises (or only comprises) (i) E94C and/or A360C; (ii) E93C and/or K358C; (iii) E93C and/or A360C; (iv) E93C and/or E361C; (v) E93C and/or K364C; (vi) E94C and/or L354C; (vii) E94C and/or K358C; (viii) E93C and/or L354C; (ix) E94C and/or E361C; (x) E94C and/or K364C; (xi) L97C and/or L354C; (xii) L97C and/or K358C; (xiii) L97C and/or A360C; (xiv) L97C and/or E361C; (xv) L97C and/or K364C; (xvi) K123C and/or L354C; (xvii) K123C and/or K358C; (xviii) K123C and/or A360C; (xix) K123C and/or E361C; (xx) K123C and/or K364C; (xxi) N155C and/or L354C; (xxii) N155C and/or K358C; (xxiii) N155C and/or A360C; (xxiv) N155C and/or E361C; (xxv) N155C and/or K364C; (xxvi) any of (i) to (xxv) and G357C; (xxvii) any of (i) to (xxv) and Q100C; (xxviii) any of (i) to (xxv) and I127C; (xxix) any of (i) to (xxv) and Q100C and I127C; (xxx) E94C and/or F377C; (xxxi) N95C; (xxxii) T91C; (xxxiii) Y92L, E94Y, Y350N, A360C and Y363N; (xxxiv) E94Y and A360C; (xxxv) A360C; (xxxvi) Y92L, E94C, Y350N, A360Y and Y363N; (xxxvii) Y92L, E94C and A360Y; (xxxviii) E94C and/or A360C and F276A; (xxxix) E94C and/or L356C; (xl) E93C and/or E356C; (xli) E93C and/or G357C; (xlii) E93C and/or A360C; (xliii) N95C and/or W378C; (xliv) T91C and/or S382C; (xlv) T91C and/or W378C; (xlvi) E93C and/or N353C; (xlvii) E93C and/or S382C; (xlviii) E93C and/or K381C; (xlix) E93C and/or D379C; (l) E93C and/or S375C; (li) E93C and/or W378C; (lii) E93C and/or W374C; (liii) E94C and/or N353C; (liv) E94C and/or S382C; (lv) E94C and/or K381C; (lvi) E94C and/or D379C; (lvii) E94C and/or S375C; (lviii) E94C and/or W378C; (lix) E94C and/or W374C; (lx) E94C and A360Y; (lxi) E94C, G357C and A360C or (lxii) T2C, E94C and A360C. In any one of (i) to (lxii), and/or is preferably and.

The helicase of the invention preferably comprises a variant of any one of SEQ ID NOs: 9 to 23 which comprises a cysteine residue at the positions which correspond to those in SEQ ID NO: 8 as defined in any of (i) to (lxii). Positions in any one of SEQ ID NOs: 9 to 23 which correspond to those in SEQ ID NO: 8 can be identified using the alignment of SEQ ID NOs: 8 to 23 below. The helicase of the invention preferably comprises a variant of SEQ ID NO: 11 which comprises (or only comprises) (a) D99C and/or L341C, (b) Q98C and/or L341C or (d) Q98C and/or A340C. The helicase of the invention preferably comprises a variant of SEQ ID NO: 15 which comprises (or only comprises) D90C and/or A349C. The helicase of the invention preferably comprises a variant of SEQ ID NO: 21 which comprises (or only comprises) D96C and/or A362C.

The helicase of the invention preferably comprises a variant of any one of SEQ ID NOs: 8 to 23 as defined in any one of (i) to (lxii) in which Faz is introduced at one or more of the specific positions instead of cysteine. Faz may be introduced at each specific position instead of cysteine. The helicase of the invention preferably comprises a variant of SEQ ID NO: 8 which comprises (or only comprises) (i) E94Faz and/or A360C; (ii) E94C and/or A360Faz; (iii) E94Faz and/or A360Faz; (iv) Y92L, E94Y, Y350N, A360Faz and Y363N; (v) A360Faz; (vi) E94Y and A360Faz; (vii) Y92L, E94Faz, Y350N, A360Y and Y363N; (viii) Y92L, E94Faz and A360Y; (ix) E94Faz and A360Y; and (x) E94C, G357Faz and A360C.

The helicase of the invention preferably further comprises one or more single amino acid deletions from the pin domain. Any number of single amino acid deletions may be made, such as 1, 2, 3, 4, 5, 6, 7, 8, 9, 10 or more. The helicase more preferably comprises a variant of SEQ ID NO: 8 which comprises deletion of E93, deletion of E95 or deletion of E93 and E95. The helicase more preferably comprises a variant of SEQ ID NO: 8 which comprises (or only comprises) (a) E94C, deletion of N95 and A360C; (b) deletion of E93, deletion of E94, deletion of N95 and A360C; (c) deletion of E93, E94C, deletion of N95 and A360C or (d) E93C, deletion of N95 and A360C. The helicase of the invention preferably comprises a variant of any one of SEQ ID NOs: 9 to 23 which comprises deletion of the position corresponding to E93 in SEQ ID NO: 8, deletion of the position corresponding to E95 in SEQ ID NO: 8 or deletion of the positions corresponding to E93 and E95 in SEQ ID NO: 8.

The helicase of the invention preferably further comprises one or more single amino acid deletions from the hook domain. Any number of single amino acid deletions may be made, such as 1, 2, 3, 4, 5, 6, 7, 8, 9, 10 or more. The helicase more preferably comprises a variant of SEQ ID NO: 8 which comprises deletion of any number of positions T278 to S287. The helicase more preferably comprises a variant of SEQ ID NO: 8 which comprises (a) E94C, deletion of Y279 to K284 and A360C, (b) E94C, deletion of T278, Y279, V286 and S287 and A360C, (c) E94C, deletion of I281 and K284 and replacement with a single G and A360C, (d) E94C, deletion of K280 and P2845 and replacement with a single G and A360C, or (e) deletion of Y279 to K284, E94C, F276A and A230C. The helicase of the invention preferably comprises a variant of any one of SEQ ID NOs: 9 to 23 which comprises deletion of any number of the positions corresponding to 278 to 287 in SEQ ID NO: 8.

The helicase of the invention preferably further comprises one or more single amino acid deletions from the pin domain and one or more single amino acid deletions from the hook domain.

The helicase of the invention is preferably one in which at least one cysteine residue and/or at least one non-natural amino acid have been further introduced into the hook domain and/or the 2A (RecA-like) domain. Any number and combination of cysteine residues and non-natural amino acids may be introduced as discussed above for the tower, pin and 1A domains.

The helicase of the invention preferably comprises a variant of SEQ ID NO: 8 in which at least one cysteine residue and/or at least one non-natural amino acid have further been introduced into the hook domain (residues L275-F291) and/or the 2A (RecA-like) domain (residues R178-T259 and L390-V439).

The helicase of the invention preferably comprises a variant of SEQ ID NO: 9 in which at least one cysteine residue and/or at least one non-natural amino acid have further been introduced into the hook domain (residues A310-L315) and/or the 2A (RecA-like) domain (residues R212-E294 and G422-S678).

The helicase of the invention preferably comprises a variant of SEQ ID NO: 10 in which at least one cysteine residue and/or at least one non-natural amino acid have further been introduced into the hook domain (residues V343-L359) and/or the 2A (RecA-like) domain (residues R241-N327 and A449-G496).

The helicase of the invention preferably comprises a variant of SEQ ID NO: 11 in which at least one cysteine residue and/or at least one non-natural amino acid have further been introduced into the hook domain (residues W276-L284) and/or the 2A (RecA-like) domain (residues R174-D260 and A371-V421).

The helicase of the invention preferably comprises a variant of SEQ ID NO: 12 in which at least one cysteine residue and/or at least one non-natural amino acid have further been introduced into the hook domain (residues R308-Y313) and/or the 2A (RecA-like) domain (residues R206-K293 and I408-L500).

The helicase of the invention preferably comprises a variant of SEQ ID NO: 13 in which at least one cysteine residue and/or at least one non-natural amino acid have further been introduced into the hook domain (residues M302-W306) and/or the 2A (RecA-like) domain (residues R195-D287 and V394-Q450).

The helicase of the invention preferably comprises a variant of SEQ ID NO: 14 in which at least one cysteine residue and/or at least one non-natural amino acid have further been introduced into the hook domain (residues V265-1277) and/or the 2A (RecA-like) domain (residues R167-T249 and L372-N421).

The helicase of the invention preferably comprises a variant of SEQ ID NO: 15 in which at least one cysteine residue and/or at least one non-natural amino acid have further been introduced into the hook domain (residues V270-F283) and/or the 2A (RecA-like) domain (residues R172-T254 and L381-K434).

The helicase of the invention preferably comprises a variant of SEQ ID NO: 16 in which at least one cysteine residue and/or at least one non-natural amino acid have further been introduced into the hook domain (residues V257-F270) and/or the 2A (RecA-like) domain (residues R159-T241 and L367-K420).

The helicase of the invention preferably comprises a variant of SEQ ID NO: 17 in which at least one cysteine residue and/or at least one non-natural amino acid have further been introduced into the hook domain (residues L278-Y294) and/or the 2A (RecA-like) domain (residues R182-T262 and L393-V443).

The helicase of the invention preferably comprises a variant of SEQ ID NO: 18 in which at least one cysteine residue and/or at least one non-natural amino acid have further been introduced into the hook domain (residues L278-Y294) and/or the 2A (RecA-like) domain (residues R182-T262 and L392-V442).

The helicase of the invention preferably comprises a variant of SEQ ID NO: 19 in which at least one cysteine residue and/or at least one non-natural amino acid have further been introduced into the hook domain (residues L273-F289) and/or the 2A (RecA-like) domain (residues R177-N257 and L387-V438).

The helicase of the invention preferably comprises a variant of SEQ ID NO: 20 in which at least one cysteine residue and/or at least one non-natural amino acid have further been introduced into the hook domain (residues L281-F297) and/or the 2A (RecA-like) domain (residues R184-T265 and L393-I442).

The helicase of the invention preferably comprises a variant of SEQ ID NO: 21 in which at least one cysteine residue and/or at least one non-natural amino acid have further been introduced into the hook domain (residues H277-F293) and/or the 2A (RecA-like) domain (residues R180-T261 and L393-V442).

The helicase of the invention preferably comprises a variant of SEQ ID NO: 22 in which at least one cysteine residue and/or at least one non-natural amino acid have further been introduced into the hook domain (residues L276-F292) and/or the 2A (RecA-like) domain (residues R179-T260 and L390-1439).

The helicase of the invention preferably comprises a variant of SEQ ID NO: 23 in which at least one cysteine residue and/or at least one non-natural amino acid have further been introduced into the hook domain (residues L276-F292) and/or the 2A (RecA-like) domain (residues R179-T260 and L391-V441).

The helicase of the invention preferably comprises a variant of SEQ ID NO: 8 which comprises one or more of (i) I181C; (ii) Y279C; (iii) I281C; and (iv) E288C. The helicase may comprise any combination of (i) to (iv), such as (i); (ii); (iii); (iv); (i) and (ii); (i) and (iii); (i) and (iv); (ii) and (iii); (ii) and (iv); (iii) and (iv); or (i), (ii), (iii) and (iv). The helicase more preferably comprises a variant of SEQ ID NO: 8 which comprises (or only comprises) (a) E94C, I281C and A360C or (b) E94C, I281C, G357C and A360C. The helicase of the invention preferably comprises a variant of any one of SEQ ID NOs: 9 to 23 which comprises a cysteine residue at one or more of the position(s) which correspond to those in SEQ ID NO: 8 as defined in (i) to (iv), (a) and (b). The helicase may comprise any of these variants in which Faz is introduced at one or more of the specific positions (or each specific position) instead of cysteine.

The helicase of the invention is further modified to reduce its surface negative charge. Surface residues can be identified in the same way as the Dda domains disclosed above. Surface negative charges are typically surface negatively-charged amino acids, such as aspartic acid (D) and glutamic acid (E).

The helicase is preferably modified to neutralise one or more surface negative charges by substituting one or more negatively charged amino acids with one or more positively charged amino acids, uncharged amino acids, non-polar amino acids and/or aromatic amino acids or by introducing one or more positively charged amino acids, preferably adjacent to one or more negatively charged amino acids. Suitable positively charged amino acids include, but are not limited to, histidine (H), lysine (K) and arginine (R). Uncharged amino acids have no net charge. Suitable uncharged amino acids include, but are not limited to, cysteine (C), serine (S), threonine (T), methionine (M), asparagine (N) and glutamine (Q). Non-polar amino acids have non-polar side chains. Suitable non-polar amino acids include, but are not limited to, glycine (G), alanine (A), proline (P), isoleucine (I), leucine (L) and valine (V). Aromatic amino acids have an aromatic side chain. Suitable aromatic amino acids include, but are not limited to, histidine (H), phenylalanine (F), tryptophan (W) and tyrosine (Y).

Preferred substitutions include, but are not limited to, substitution of E with R, substitution of E with K, substitution of E with N, substitution of D with K and substitution of D with R.

The helicase of the invention preferably comprises a variant of SEQ ID NO: 8 and the one or more negatively charged amino acids are one or more of D5, E8, E23, E47, D167, E172, D202, D212 and E273. Any number of these amino acids may be neutralised, such as 1, 2, 3, 4, 5, 6, 7 or 8 of them. Any combination may be neutralised. The helicase of the invention preferably comprises a variant of any one of SEQ ID NOs: 9 to 23 and the one or more negatively charged amino acids correspond to one or more of D5, E8, E23, E47, D167, E172, D202, D212 and E273 in SEQ ID NO: 8. Amino acids in SEQ ID NOs: 9 to 23 which correspond to D5, E8, E23, E47, D167, E172, D202, D212 and E273 in SEQ ID NO: 8 can be determined using the alignment below. The helicase of the invention preferably comprises a variant of SEQ ID NO: 8 which comprises (or only comprises) (a) E94C, E273G and A360C or (b) E94C, E273G, N292G and A360C.

The helicase of the invention is preferably further modified by the removal of one or more native cysteine residues. Any number of native cysteine residues may be removed. The number of cysteine residues in each of SEQ ID NOs: 9 to 23 is shown in Table 1 (as #C). The one or more cysteine residues are preferably removed by substitution. The one or more cysteine residues are preferably substituted with alanine (A), serine (S) or valine (V). The helicase of the invention preferably comprises a variant of SEQ ID NO: 8 and the one or more native cysteine residues are one or more of C109, C114, C136, C171 and C412. Any number and combination of these cysteine residues may be removed. For instance, the variant of SEQ ID NO: 8 may comprise {C109}; {C114}; {C136}; {C171}; {C412}; {C109 and C114}; {C109 and C136}; {C109 and C171}; {C109 and C412}; {C114 and C136}; {C114 and C171}; {C114 and C412}; {C136 and C171}; {C136 and C412}; {C171 and C412}; {C109, C114 and C136}; {C109, C114 and C171}; {C109, C114 and C412}; {C109, C136 and C171}; {C109, C136 and C412}; {C109, C171 and C412}; {C114, C136 and C171}; {C114, C136 and C412}; {C114, C171 and C412}; {C136, C171 and C412}; {C109, C114, C136 and C171}; {C109, C114, C136 and C412}; {C109, C114, C171 and C412}; {C109, C136, C171 and C412}; {C114, C136, C171 and C412}; or {C109, C114, C136, C171 and C412}.

The helicase of the invention is preferably one in which at least one cysteine residue (i.e. one or more cysteine residues) and/or at least one non-natural amino acid (i.e. one or more non-natural amino acids) have been introduced into the tower domain only. Suitable modifications are discussed above.

The helicase of the invention preferably comprises a variant of SEQ ID NO: 8 comprising (or comprising only) the following mutations:

E93C and K364C;
E94C and K364C;
E94C and A360C;
L97C and $E^{361}C$;
L97C and E361C and C412A;
K123C and E361C;
K123C, E361C and C412A;
N155C and K358C;
N155C, K358C and C412A;
N155C and L354C;
N155C, L354C and C412A;
deltaE93, E94C, deltaN95 and A360C;
E94C, deltaN95 and A360C;
E94C, Q100C, I127C and A360C;
L354C;
G357C;
E94C, G357C and A360C;
E94C, Y279C and A360C;
E94C, I281C and A360C;
E94C, Y279Faz and A360C;
Y279C and G357C;
I281C and G357C;
E94C, Y279C, G357C and A360C;
E94C, I281C, G357C and A360C;
E8R, E47K, E94C, D202K and A360C;
D5K, E23N, E94C, D167K, E172R, D212R and A360C;
D5K, E8R, E23N, E47K, E94C, D167K, E172R, D202K, D212R and A360C;
E94C, C114A, C171A, A360C and C412D;
E94C, C114A, C171A, A360C and C412S;
E94C, C109A, C136A and A360C;
E94C, C109A, C114A, C136A, C171A, A360C and C412S;
E94C, C109V, C114V, C171A, A360C and C412S;
C109A, C114A, C136A, G153C, C171A, E361C and C412A;
C109A, C114A, C136A, G153C, C171A, E361C and C412D;
C109A, C114A, C136A, G153C, C171A, E361C and C412S;
C109A, C114A, C136A, G153C, C171A, K358C and C412A;
C109A, C114A, C136A, G153C, C171A, K358C and C412D
C109A, C114A, C136A, G153C, C171A, K358C and C412S;
C109A, C114A, C136A, N155C, C171A, K358C and C412A;
C109A, C114A, C136A, N155C, C171A, K358C and C412D;
C109A, C114A, C136A, N155C, C171A, K358C and C412S;
C109A, C114A, C136A, N155C, C171A, L354C and C412A;
C109A, C114A, C136A, N155C, C171A, L354C and C412D;
C109A, C114A, C136A, N155C, C171A, L354C and C412S;
C109A, C114A, K123C, C136A, C171A, E361C and C412A;
C109A, C114A, K123C, C136A, C171A, E361C and C412D;
C109A, C114A, K123C, C136A, C171A, E361C and C412S;
C109A, C114A, K123C, C136A, C171A, K358C and C412A;
C109A, C114A, K123C, C136A, C171A, K358C and C412D;
C109A, C114A, K123C, C136A, C171A, K358C and C412S;
C109A, C114A, C136A, G153C, C171A, E361C and C412A;
E94C, C109A, C114A, C136A, C171A, A360C and C412D;
E94C, C109A, C114V, C136A, C171A, A360C and C412D;
E94C, C109V, C114A, C136A, C171A, A360C and C412D;
L97C, C109A, C114A, C136A, C171A, E361C and C412A;
L97C, C109A, C114A, C136A, C171A, E361C and C412D; or
L97C, C109A, C114A, C136A, C171A, E361C and C412S.

Modifications in the Hook Domain and/or 2A Domain

In one embodiment, the Dda helicase of the invention is one in which at least one cysteine residue and/or at least one non-natural amino acid have been introduced into the hook domain and/or the 2A (RecA-like motor) domain, wherein the helicase retains its ability to control the movement of a polynucleotide. At least one cysteine residue and/or at least one non-natural amino acid is preferably introduced into the hook domain and the 2A (RecA-like motor) domain.

Any number of cysteine residues and/or non-natural amino acids may be introduced into each domain. For instance, 1, 2, 3, 4, 5, 6, 7, 8, 9, 10 or more cysteine residues may be introduced and/or 1, 2, 3, 4, 5, 6, 7, 8, 9, 10 or more non-natural amino acids may be introduced. Only one or more cysteine residues may be introduced. Only one or more non-natural amino acids may be introduced. A combination of one or more cysteine residues and one or more non-natural amino acids may be introduced.

The at least one cysteine residue and/or at least one non-natural amino acid are preferably introduced by substitution. Methods for doing this are known in the art. Suitable modifications of the hook domain and/or the 2A (RecA-like motor) domain are discussed above.

The helicase of the invention is preferably a variant of SEQ ID NO: 8 comprising (or comprising only) (a) Y279C, I181C, E288C, Y279C and I181C, (b) Y279C and E288C, (c) I181C and E288C or (d) Y279C, I181C and E288C. The helicase of the invention preferably comprises a variant of any one of SEQ ID NOs: 9 to 23 which comprises a mutation at one or more of the position(s) which correspond to those in SEQ ID NO: 8 as defined in (a) to (d).

Surface Modification

In one embodiment, the Dda helicase is modified to reduce its surface negative charge, wherein the helicase retains its ability to control the movement of a polynucleotide. Suitable modifications are discussed above. Any number of surface negative charges may be neutralised.

The helicase of the invention preferably comprises a variant of SEQ ID NO: 8 comprising (or comprising only) the following mutations:

E273G;
E8R, E47K and D202K;
D5K, E23N, D167K, E172R and D212R;
D5K, E8R, E23N, E47K, D167K, E172R, D202K and D212R.

Other Modified Helicases

In one embodiment, the Dda helicase of the invention comprises a variant of SEQ ID NO: 8 comprising (or comprising only):

A360K;
Y92L and/or A360Y;
Y92L, Y350N and Y363N;
Y92L and/or Y363N; or
Y92L.

Other Modifications

In addition to the specific mutations disclosed above, a variant of SEQ ID NO: 8 may comprise (or may only comprise) one or more of the following mutations:

K38A;
H64N;
H64K;
H64Q;
H64S;
H64W;
T80K;
T80N;
H82A;
H82F;
H82Q;
H82R;
H82W;
H82Y;
S83K;
S83N;
S83T;
N88H;
N88Q;
P89A;
P89F;
P89S;
P89T;
P89W;
P89Y;
T91F;
T91N;

-continued

T91Q;
T91W;
V96E;
V96F;
V96L
V96Q;
V96R;
V96W;
V96Y;
F98A
F98L;
F98V;
F98W;
F98Y;
V150A;
V150F;
V150I;
V150K;
V150L;
V150S;
V150T;
V150W;
V150Y;
F240W;
F240Y;
N242K;
P274G;
F276A;
F276I;
F276M;
F276V;
F276W;
F276Y;
V286F;
V286W;
V286Y;
S287F;
S287W;
S287Y;
F291G;
N292F;
N292G;
N292P;
N292Y;
N293F;
N293K;
N293Q;
N293Y;
G294Y;
G294F;
K364A;
W378A;
T394K;
T394N;
H396Q;
H396S;
H396W;
Y415F;
Y415K;
Y415M; or
Y415W.

The helicase of the invention preferably comprises a variant of SEQ ID NO: 8 which comprises (or only comprises):

K38A, E94C and A360C;
H64K; E94C and A360C;
H64N; E94C and A360C;
H64Q; E94C and A360C;
H64S; E94C and A360C;
H64W, E94C and A360C;
T80K, E94C and A360C;
T80K, S83K, E94C, N242K, N293K and A360C;
T80K, S83K, E94C, N242K, N293K, A360C and T394K;

T80K, S83K, E94C, N293K and A360C;
T80K, S83K, E94C, A360C and T394K;
T80K, S83K, E94C, A360C and T394N;
T80K, E94C, N242K and A360C;
T80K, E94C, N242K, N293K and A360C;
T80K, E94C, N293K and A360C;
T80N, E94C and A360C;
H82A, E94C and A360C;
H82A, P89A, E94C, F98A and A360C;
H82F, E94C and A360C;
H82Q, E94C, A360C;
H82R, E94C and A360C;
H82W, E94C and A360C;
H82W, P89W, E94C, F98W and A360C;
H82Y, E94C and A360C;
S83K, E94C and A360C;
S83K, T80K, E94C, A360C and T394K;
S83N, E94C and A360C;
S83T, E94C and A360C;
N88H, E94C and A360C;
N88Q, E94C and A360C;
P89A, E94C and A360C;
P89A, F98W, E94C and A360C;
P89A, E94C, F98Y and A360C;
P89A, E94C, F98A and A360C;
P89F, E94C and A360C;
P89S, E94C and A360C;
P89T, E94C and A360C;
P89W, E94C, F98W and A360C;
P89Y, E94C and A360C;
T91F, E94C and A360C;
T91N, E94C and A360C;
T91Q, E94C and A360C;
T91W, E94C and A360C;
E94C, V96E and A360C;
E94C, V96F and A360C;
E94C, V96L and A360C;
E94C, V96Q and A360C;
E94C, V96R and A360C;
E94C, V96W and A360C;
E94C, V96Y and A360C;
E94C, F98A and A360C;
E94C, F98L and A360C;
E94C, F98V and A360C;
E94C, F98Y and A360C;
E94C; F98W and A360C;
E94C, V150A and A360C;
E94C, V150F and A360C;
E94C, V150I and A360C;
E94C, V150K and A360C;
E94C, V150L and A360C;
E94C, V150S and A360C;
E94C, V150T and A360C;
E94C, V150W and A360C;
E94C, V150Y and A360C;
E94C, F240Y and A360C;
E94C, F240W and A360C;
E94C, N242K and A360C;
E94C, N242K, N293K and A360C;
E94C, P274G and A360C;
E94C, L275G and A360C
E94C, F276A and A360C;
E94C, F276I and A360C;
E94C, F276M and A360C;
E94C, F276V and A360C;
E94C, F276W and A360C;
E94C, F276Y and A360C;
E94C, V286F and A360C;
E94C, V286W and A360C;
E94C, V286Y and A360C;
E94C, S287F and A360C;
E94C, S287W and A360C;
E94C, S287Y and A360C;
E94C, F291G and A360C;
E94C, N292F and A360C;
E94C, N292G and A360C;
E94C, N292P and A360C;
E94C, N292Y and A360C;
E94C, N293F and A360C;
E94C, N293K and A360C;
E94C, N293Q and A360C;
E94C, N293Y and A360C;
E94C, G294F and A360C;
E94C, G294Y and A360C;
E94C, A36C and K364A;
E94C, A360C, W378A;
E94C, A360C and T394K;
E94C, A360C and H396Q;
E94C, A360C and H396S;
E94C, A360C and H396W;
E94C, A360C and Y415F;
E94C, A360C and Y415K;
E94C, A360C and Y415M; or
E94C, A360C and Y415W.

The helicase of the invention preferably comprises a variant of SEQ ID NO: 8 which comprises (or only comprises) (a) E94C/A360C/W378A, (b) E94C/A360C/W378A W378A and then (ΔM1)G1G2 (i.e. deletion of M1 and then addition G1 and G2), (c) E94C/A360C/C109A/C136A/W378A or (d) E94C/A360C/C109A/C136A/W378A and then (ΔM1)G1G2 (i.e. deletion of M1 and then addition G1 and G2).

Variants

A variant of a Dda helicase is an enzyme that has an amino acid sequence which varies from that of the wild-type helicase and which retains polynucleotide binding activity. In particular, a variant of any one of SEQ ID NOs: 8 to 23 is an enzyme that has an amino acid sequence which varies from that of any one of SEQ ID NOs: 8 to 23 and which retains polynucleotide binding activity. Polynucleotide binding activity can be determined using methods known in the art. Suitable methods include, but are not limited to, fluorescence anisotropy, tryptophan fluorescence and electrophoretic mobility shift assay (EMSA). For instance, the ability of a variant to bind a single stranded polynucleotide can be determined as described in the Examples.

The variant retains helicase activity. This can be measured in various ways. For instance, the ability of the variant to translocate along a polynucleotide can be measured using electrophysiology, a fluorescence assay or ATP hydrolysis.

The variant may include modifications that facilitate handling of the polynucleotide encoding the helicase and/or facilitate its activity at high salt concentrations and/or room temperature.

Over the entire length of the amino acid sequence of any one of SEQ ID NOs: 8 to 23, a variant will preferably be at least 20% homologous to that sequence based on amino acid identity. More preferably, the variant polypeptide may be at least 30%, at least 40%, at least 45%, at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of any one of SEQ ID NOs: 8 to 23 over the entire sequence. There may be at least 70%, for example at least 80%, at least 85%, at least 90% or at least 95%, amino acid identity over a stretch of 100 or more, for example 150, 200, 300, 400 or 500 or more, contiguous amino acids ("hard homology"). Homology is determined as described below. The variant may differ from the wild-type sequence in any of the ways discussed below with reference to SEQ ID NOs: 2 and 4. In particular, in addition to the specific modifications discussed above, the variant of any one of SEQ ID NOs: 8 to 23 may comprise one or more substitutions, one or more deletions and/or one or more additions as discussed below.

Preferred variants of any one of SEQ ID NOs: 8 to 23 have a non-natural amino acid, such as Faz, at the amino- (N-) terminus and/or carboxy (C-) terminus. Preferred variants of any one of SEQ ID NOs: 8 to 23 have a cysteine residue at the amino- (N-) terminus and/or carboxy (C-) terminus. Preferred variants of any one of SEQ ID NOs: 8 to 23 have a cysteine residue at the amino- (N-) terminus and a non-natural amino acid, such as Faz, at the carboxy (C-) terminus or vice versa.

Preferred variants of SEQ ID NO: 8 contain one or more of, such as all of, the following modifications E54G, D151E, I196N and G357A.

The most preferred variants of any one of SEQ ID NOs: 8 to 23 have (in addition to the modifications of the invention) the N-terminal methionine (M) deleted and replaced with two glycine residues (GG). In the examples this is shown as (ΔM1)G1G2. For instance, preferred variants of SEQ ID NO: 8 comprise (or only comprise):

E94C, A360C and then (ΔM1)G1G2; and
E94C, C109A, C136A, A360C and then (ΔM1)G1G2.

Dda Helicase Fragments

The invention also provides fragments of Dda helicases which may be used to produce a helicase of the invention. In a first embodiment, the polypeptide comprises the pin domain and the 1A (RecA-like motor) domain from a Dda helicase and does not comprise any other domains from a Dda helicase, wherein at least one cysteine residue and/or at least one non-natural amino acid have been introduced into the pin domain and/or the 1A (RecA-like motor) domain. Preferred helicases from which the domains may be derived include any of SEQ ID NOs: 8 to 23. The relevant domains of these helicases are defined in Table 2 above. The pin domain and/or the 1A domain may be modified in any of the ways discussed above for the helicases of the invention. In particular, the polypeptide may comprise any of the variants of the pin domains and the 1A domains defined above and any of the pin domain and/or 1A domain mutations defined above.

In a second embodiment, the polypeptide comprises the 2A (RecA-like motor) domain, tower domain and hook domain from a Dda helicase and does not comprise any other domains from a Dda helicase, wherein at least one cysteine residue and/or at least one non-natural amino acid have been introduced into the tower domain. Preferred helicases from which the domains may be derived include any of SEQ ID NOs: 8 to 23. The relevant domains of these helicases are defined in Table 2 above. The tower domain may be modified in any of the ways discussed above for the helicases of the invention. In particular, the polypeptide may comprise any of the variants of the tower defined above and any of the tower mutations defined above.

In addition to the specific modifications discussed above, a polypeptide of the invention may comprise one or more substitutions, one or more deletions and/or one or more additions as discussed below with reference to SEQ ID NOs: 2 and 4.

The invention also provides a helicase comprising a polypeptide of the first embodiment covalently attached to a polypeptide of the second embodiment, wherein the helicase has the ability to control the movement of a polynucleotide. The ability of the helicase to control the movement of a polynucleotide may be determined as discussed above.

No Connection

In one preferred embodiment, none of the introduced cysteines and/or non-natural amino acids in a modified Dda helicase of the invention are connected to one another.

Connecting Two or More of the Introduced Cysteines and/or Non-Natural Amino Acids In another preferred embodiment, two or more of the introduced cysteines and/or non-natural amino acids in a modified Dda helicase of the invention are connected to one another. This typically reduces the ability of the helicase of the invention to unbind from a polynucleotide.

Any number and combination of two or more of the introduced cysteines and/or non-natural amino acids may be connected to one another. For instance, 3, 4, 5, 6, 7, 8 or more cysteines and/or non-natural amino acids may be connected to one another. One or more cysteines may be connected to one or more cysteines. One or more cysteines may be connected to one or more non-natural amino acids, such as Faz. One or more non-natural amino acids, such as Faz, may be connected to one or more non-natural amino acids, such as Faz.

The two or more cysteines and/or non-natural amino acids may be connected in any way. The connection can be transient, for example non-covalent. Even transient connection will reduce unbinding of the polynucleotide from the helicase.

The two or more cysteines and/or non-natural amino acids are preferably connected by affinity molecules. Suitable affinity molecules are known in the art. The affinity molecules are preferably (a) complementary polynucleotides (International Application No. PCT/GB10/000132 (published as WO 2010/086602), (b) an antibody or a fragment thereof and the complementary epitope (Biochemistry 6th Ed, W.H. Freeman and co (2007) pp 953-954), (c) peptide zippers (O'Shea et al., Science 254 (5031): 539-544), (d) capable of interacting by β-sheet augmentation (Remaut and Waksman Trends Biochem. Sci. (2006) 31 436-444), (e) capable of hydrogen bonding, pi-stacking or forming a salt bridge, (f) rotaxanes (Xiang Ma and He Tian Chem. Soc. Rev., 2010, 39, 70-80), (g) an aptamer and the complementary protein (James, W. in Encyclopedia of Analytical Chemistry, R. A. Meyers (Ed.) pp. 4848 4871 John Wiley & Sons Ltd, Chichester, 2000) or (h) half-chelators (Hammerstein et al. J Biol Chem. 2011 Apr. 22; 286(16): 14324 14334). For (e), hydrogen bonding occurs between a proton bound to an electronegative atom and another electronegative atom. Pi-stacking requires two aromatic rings that can stack together where the planes of the rings are parallel. Salt bridges are between groups that can delocalize their electrons over several atoms, e.g. between aspartate and arginine.

The two or more parts may be transiently connected by a hexa-his tag or Ni-NTA.

The two or more cysteines and/or non-natural amino acids are preferably permanently connected. In the context of the invention, a connection is permanent if is not broken while the helicase is used or cannot be broken without intervention on the part of the user, such as using reduction to open S—S— bonds.

The two or more cysteines and/or non-natural amino acids are preferably covalently-attached. The two or more cysteines and/or non-natural amino acids may be covalently attached using any method known in the art.

The two or more cysteines and/or non-natural amino acids may be covalently attached via their naturally occurring amino acids, such as cysteines, threonines, serines, aspartates, asparagines, glutamates and glutamines. Naturally occurring amino acids may be modified to facilitate attachment. For instance, the naturally occurring amino acids may be modified by acylation, phosphorylation, glycosylation or farnesylation. Other suitable modifications are known in the art. Modifications to naturally occurring amino acids may be post-translation modifications. The two or more cysteines and/or non-natural amino acids may be attached via amino acids that have been introduced into their sequences. Such amino acids are preferably introduced by substitution. The introduced amino acid may be cysteine or a non-natural amino acid that facilitates attachment. Suitable non-natural amino acids include, but are not limited to, 4-azido-L-phenylalanine (Faz), any one of the amino acids numbered 1-71 included in FIG. 1 of Liu C. C. and Schultz P. G., Annu. Rev. Biochem., 2010, 79, 413-444 or any one of the amino acids listed below. The introduced amino acids may be modified as discussed above.

In a preferred embodiment, the two or more cysteines and/or non-natural amino acids are connected using linkers. Linker molecules are discussed in more detail below. One suitable method of connection is cysteine linkage. This is discussed in more detail below. The two or more cysteines and/or non-natural amino acids are preferably connected using one or more, such as two or three, linkers. The one or more linkers may be designed to reduce the size of, or close, the opening as discussed above. If one or more linkers are being used to close the opening as discussed above, at least a part of the one or more linkers is preferably oriented such that it is not parallel to the polynucleotide when it is bound by the helicase. More preferably, all of the linkers are oriented in this manner. If one or more linkers are being used to close the opening as discussed above, at least a part of the one or more linkers preferably crosses the opening in an orientation that is not parallel to the polynucleotide when it bound by the helicase. More preferably, all of the linkers cross the opening in this manner. In these embodiments, at least a part of the one or more linkers may be perpendicular to the polynucleotide. Such orientations effectively close the opening such that the polynucleotide cannot unbind from the helicase through the opening.

Each linker may have two or more functional ends, such as two, three or four functional ends. Suitable configurations of ends in linkers are well known in the art.

One or more ends of the one or more linkers are preferably covalently attached to the helicase. If one end is covalently attached, the one or more linkers may transiently connect the two or more cysteines and/or non-natural amino acids as discussed above. If both or all ends are covalently attached, the one or more linkers permanently connect the two or more cysteines and/or non-natural amino acids.

The one or more linkers are preferably amino acid sequences and/or chemical crosslinkers.

Suitable amino acid linkers, such as peptide linkers, are known in the art. The length, flexibility and hydrophilicity of the amino acid or peptide linker are typically designed such that it reduces the size of the opening, but does not to disturb the functions of the helicase. Preferred flexible peptide linkers are stretches of 2 to 20, such as 4, 6, 8, 10 or 16, serine and/or glycine amino acids. More preferred flexible linkers include $(SG)_1$, $(SG)_2$, $(SG)_3$, $(SG)_4$, $(SG)_5$, $(SG)_8$, $(SG)_{10}$, $(SG)_{15}$ or $(SG)_{20}$ wherein S is serine and G is glycine. Preferred rigid linkers are stretches of 2 to 30, such as 4, 6, 8, 16 or 24, proline amino acids. More preferred rigid linkers include $(P)_{12}$ wherein P is proline. The amino acid sequence of a linker preferably comprises a polynucleotide binding moiety. Such moieties and the advantages associated with their use are discussed below.

Suitable chemical crosslinkers are well-known in the art. Suitable chemical crosslinkers include, but are not limited to, those including the following functional groups: maleimide, active esters, succinimide, azide, alkyne (such as dibenzocyclooctynol (DIBO or DBCO), difluoro cycloalkynes and linear alkynes), phosphine (such as those used in traceless and non-traceless Staudinger ligations), haloacetyl (such as iodoacetamide), phosgene type reagents, sulfonyl chloride reagents, isothiocyanates, acyl halides, hydrazines, disulphides, vinyl sulfones, aziridines and photoreactive reagents (such as aryl azides, diaziridines).

Reactions between amino acids and functional groups may be spontaneous, such as cysteine/maleimide, or may require external reagents, such as Cu(I) for linking azide and linear alkynes.

Linkers can comprise any molecule that stretches across the distance required. Linkers can vary in length from one carbon (phosgene-type linkers) to many Angstroms. Examples of linear molecules, include but are not limited to, are polyethyleneglycols (PEGs), polypeptides, polysaccharides, deoxyribonucleic acid (DNA), peptide nucleic acid (PNA), threose nucleic acid (TNA), glycerol nucleic acid (GNA), saturated and unsaturated hydrocarbons, polyamides. These linkers may be inert or reactive, in particular they may be chemically cleavable at a defined position, or may be themselves modified with a fluorophore or ligand. The linker is preferably resistant to dithiothreitol (DTT).

Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2-yldisulfanyl)octanoate, di-maleimide PEG 1k, di-maleimide PEG 3.4k, di-maleimide PEG 5k, di-maleimide PEG 10k, bis(maleimido)ethane (BMOE), bis-maleimidohexane (BMH), 1,4-bis-maleimidobutane (BMB), 1,4 bis-maleimidyl-2,3-dihydroxybutane (BMDB), BM[PEO]2 (1,8-bis-maleimidodiethyleneglycol), BM[PEO]3 (1,11-bis-maleimidotriethylene glycol), tris[2-maleimidoethyl]amine (TMEA), DTME dithiobismaleimidoethane, bis-maleimide PEG3, bis-maleimide PEG11, DBCO-maleimide, DBCO-PEG4-maleimide, DBCO-PEG4-NH2, DBCO-PEG4-NHS, DBCO-NHS, DBCO-PEG-DBCO 2.8 kDa, DBCO-PEG-DBCO 4.0 kDa, DBCO-15 atoms-DBCO, DBCO-26 atoms-DBCO, DBCO-35 atoms-DBCO, DBCO-PEG4-S—S-PEG3-biotin, DBCO-S—S-PEG3-biotin, DBCO-S—S-PEG11-biotin, (succinimidyl 3-(2-pyridyldithio)propionate (SPDP) and maleimide-PEG(2 kDa)-maleimide (ALPHA,OMEGA-BIS-MALEIMIDO POLY (ETHYLENE GLYCOL)). The most preferred crosslinker is maleimide-propyl-SRDFWRS-(1,2-diaminoethane)-propyl-maleimide.

The one or more linkers may be cleavable. This is discussed in more detail below.

The two or more cysteines and/or non-natural amino acids may be connected using two different linkers that are specific for each other. One of the linkers is attached to one part and the other is attached to another part. The linkers should react to form a modified helicase of the invention. The two or more cysteines and/or non-natural amino acids may be connected using the hybridization linkers described in International Application No. PCT/GB10/000132 (published as WO 2010/086602). In particular, the two or more cysteines and/or non-natural amino acids may be connected using two or more linkers each comprising a hybridizable region and a group capable of forming a covalent bond. The hybridizable regions in the linkers hybridize and link the two or more cysteines and/or non-natural amino acids. The linked cysteines and/or non-natural amino acids are then coupled via the formation of covalent bonds between the groups. Any of the specific linkers disclosed in International Application No. PCT/GB10/000132 (published as WO 2010/086602) may be used in accordance with the invention.

The two or more cysteines and/or non-natural amino acids may be modified and then attached using a chemical crosslinker that is specific for the two modifications. Any of the crosslinkers discussed above may be used.

The linkers may be labeled. Suitable labels include, but are not limited to, fluorescent molecules (such as Cy3 or AlexaFluor®555), radioisotopes, e.g. $^{125}$I, $^{35}$S, enzymes, antibodies, antigens, polynucleotides and ligands such as biotin. Such labels allow the amount of linker to be quantified. The label could also be a cleavable purification tag, such as biotin, or a specific sequence to show up in an identification method, such as a peptide that is not present in the protein itself, but that is released by trypsin digestion.

A preferred method of connecting two or more cysteines is via cysteine linkage. This can be mediated by a bi-functional chemical crosslinker or by an amino acid linker with a terminal presented cysteine residue.

The length, reactivity, specificity, rigidity and solubility of any bi-functional linker may be designed to ensure that the size of the opening is reduced sufficiently and the function of the helicase is retained. Suitable linkers include bismaleimide crosslinkers, such as 1,4-bis(maleimido)butane (BMB) or bis(maleimido)hexane. One drawback of bi-functional linkers is the requirement of the helicase to contain no further surface accessible cysteine residues if attachment at specific sites is preferred, as binding of the bi-functional linker to surface accessible cysteine residues may be difficult to control and may affect substrate binding or activity. If the helicase does contain several accessible cysteine residues, modification of the helicase may be required to remove them while ensuring the modifications do not affect the folding or activity of the helicase. This is discussed in International Application No. PCT/GB10/000133 (published as WO 2010/086603). The reactivity of cysteine residues may be enhanced by modification of the adjacent residues, for example on a peptide linker. For instance, the basic groups of flanking arginine, histidine or lysine residues will change the pKa of the cysteines thiol group to that of the more reactive S group. The reactivity of cysteine residues may be protected by thiol protective groups such as 5,5'-dithiobis-(2-nitrobenzoic acid) (dTNB). These may be reacted with one or more cysteine residues of the helicase before a linker is attached. Selective deprotection of surface accessible cysteines may be possible using reducing reagents immobilized on beads (for example immobilized tris(2-carboxyethyl) phosphine, TCEP). Cysteine linkage is discussed in more detail below.

Another preferred method of attachment via Faz linkage. This can be mediated by a bi-functional chemical linker or by a polypeptide linker with a terminal presented Faz residue.

Other Modified Helicases of the Invention

The invention also provides a Dda helicase which has been modified to increase the attraction between (i) the tower domain and (ii) the pin domain and/or the 1A domain. Any known chemical modifications can be made in accordance with the invention.

In particular, the invention provides a Dda helicase in which at least one charged amino acid has been introduced into (i) the tower domain and/or (ii) the pin domain and/or (iii) the 1A (RecA-like motor) domain, wherein the helicase retains its ability to control the movement of a polynucleotide. The ability of the helicase to control the movement of a polynucleotide may be measured as discussed above. The invention preferably provides a Dda helicase in which at least one charged amino acid has been introduced into (i) the tower domain and (ii) the pin domain and/or the 1A domain.

The at least one charged amino acid may be negatively charged or positively charged. The at least one charged amino acid is preferably oppositely charged to any amino acid(s) with which it interacts in the helicase. For instance, at least one positively charged amino acid may be introduced into the tower domain at a position which interacts with a negatively charged amino acid in the pin domain. The at least one charged amino acid is typically introduced at a position which is not charged in the wild-type (i.e. unmodified) helicase. The at least one charged amino acid may be used to replace at least one oppositely charged amino acid in the helicase. For instance, a positively charged amino acid may be used to replace a negatively charged amino acid.

Suitable charged amino acids are discussed above. The at least one charged amino acid may be natural, such as arginine (R), histidine (H), lysine (K), aspartic acid (D) or glutamic acid (D). Alternatively, the at least one charged amino acid may be artificial or non-natural. Any number of charged amino acids may be introduced into each domain. For instance, 1, 2, 3, 4, 5, 6, 7, 8, 9, 10 or more charged amino acids may be introduced into each domain.

The helicase preferably comprises a variant of SEQ ID NO: 8 which comprises a positively charged amino acid at one or more of the following positions: (i) 93; (ii) 354; (iii) 360; (iv) 361; (v) 94; (vi) 97; (vii) 155; (viii) 357; (ix) 100; and (x) 127. The helicase preferably comprises a variant of SEQ ID NO: 8 which comprises a negatively charged amino acid at one or more of the following positions: (i) 354; (ii) 358; (iii) 360; (iv) 364; (v) 97; (vi) 123; (vii) 155; (viii); 357; (ix) 100; and (x) 127. The helicase preferably comprises a variant of any one of SEQ ID NOs: 9 to 23 which comprises a positively charged amino acid or negatively charged amino acid at the positions which correspond to those in SEQ ID NO: 8 as defined in any of (i) to (x). Positions in any one of SEQ ID NOs: 9 to 23 which correspond to those in SEQ ID NO: 8 can be identified using the alignment of SEQ ID NOs: 8 to 23 below.

The helicase preferably comprises a variant of SEQ ID NO: 8 which is modified by the introduction of at least one charged amino acid such that it comprises oppositely charged amino acid at the following positions: (i) 93 and 354; (ii) 93 and 358; (iii) 93 and 360; (iv) 93 and 361; (v) 93 and 364; (vi) 94 and 354; (vii) 94 and 358; (viii) 94 and 360; (ix) 94 and 361; (x) 94 and 364; (xi) 97 and 354; (xii) 97 and 358; (xiii) 97 and 360; (xiv) 97 and 361; (xv) 97 and 364; (xvi) 123 and 354; (xvii) 123 and 358; (xviii) 123 and 360; (xix) 123 and 361; (xx) 123 and 364; (xxi) 155 and 354; (xxii) 155 and 358; (xxiii) 155 and 360; (xxiv) 155 and 361; (xxv) 155 and 364. The helicase of the invention preferably comprises a variant of any one of SEQ ID NOs: 9 to 23 which comprises oppositely charged amino acids at the positions which correspond to those in SEQ ID NO: 8 as defined in any of (i) to (xxv).

The invention also provides a Dda helicase in which (i) at least one charged amino acid has been introduced into the tower domain and (ii) at least one oppositely charged amino acid has been introduced into the pin domain and/or the 1A (RecA-like motor) domain, wherein the helicase retains its ability to control the movement of a polynucleotide. The at least one charged amino acid may be negatively charged and the at least one oppositely charged amino acid may be positively charged or vice versa. Suitable charged amino acids are discussed above. Any number of charged amino acids and any number of oppositely charged amino acids may be introduced. For instance, 1, 2, 3, 4, 5, 6, 7, 8, 9, 10 or more charged amino acids may be introduced and/or 1, 2, 3, 4, 5, 6, 7, 8, 9, 10 or more oppositely charged amino acids may be introduced.

The charged amino acids are typically introduced at positions which are not charged in the wild-type helicase. One or both of the charged amino acids may be used to replace charged amino acids in the helicase. For instance, a positively charged amino acid may be used to replace a negatively charged amino acid. The charged amino acids may be introduced at any of the positions in the (i) tower domain and (ii) pin domain and/or 1A domain discussed above. The oppositely charged amino acids are typically introduced such that they will interact in the resulting helicase. The helicase preferably comprises a variant of SEQ ID NO: 8 in which oppositely charged amino acids have been introduced at the following positions: (i) 97 and 354; (ii) 97 and 360; (iii) 155 and 354; or (iv) 155 and 360. The helicase of the invention preferably comprises a variant of any one of SEQ ID NOs: 9 to 23 which comprises oppositely charged amino acids at the positions which correspond to those in SEQ ID NO: 8 as defined in any of (i) to (iv).

Construct

The invention also provides a construct comprising a Dda helicase or a modified Dda helicase of the invention and an additional polynucleotide binding moiety, wherein the helicase is attached to the polynucleotide binding moiety and the construct has the ability to control the movement of a polynucleotide. The construct is artificial or non-natural.

A construct of the invention is a useful tool for controlling the movement of a polynucleotide during Strand Sequencing. A construct of the invention is even less likely than a modified helicase of the invention to disengage from the polynucleotide being sequenced. The construct can provide even greater read lengths of the polynucleotide as it controls the translocation of the polynucleotide through a nanopore.

A targeted construct that binds to a specific polynucleotide sequence can also be designed. As discussed in more detail below, the polynucleotide binding moiety may bind to a specific polynucleotide sequence and thereby target the helicase portion of the construct to the specific sequence.

The construct has the ability to control the movement of a polynucleotide. This can be determined as discussed above.

A construct of the invention may be isolated, substantially isolated, purified or substantially purified. A construct is isolated or purified if it is completely free of any other components, such as lipids, polynucleotides or pore monomers. A construct is substantially isolated if it is mixed with carriers or diluents which will not interfere with its intended use. For instance, a construct is substantially isolated or substantially purified if it is present in a form that comprises less than 10%, less than 5%, less than 2% or less than 1% of other components, such as lipids, polynucleotides or pore monomers.

The Dda helicase may be any Dda helicase. Preferred Dda helicases include, but are not limited to, any one of SEQ ID NOs: 8 to 23 and variants thereof. Variants are defined above. Variants are preferably at least 20% homologous to any one of SEQ ID NOs: 8 to 23 based on amino acid identity. The Dda helicase in the construct does not have to comprise the specific modification(s) discussed above with reference to the modified Dda helicases of the invention (i.e. does not have to be modified in accordance with the invention). For instance, the construct may comprise a Dda helicase which comprises the sequence shown in any one of SEQ ID NOs: 8 to 23 or a variant thereof, wherein:
    no cysteine residues and no non-natural amino acids have been introduced into the tower domain, the pin domain and the 1A (RecA-like motor) domain of the variant;
    the variant does not comprise one or more single amino acid deletions from the pin domain;
    no cysteine residues and no non-natural amino acids have been introduced into the hook domain and the 2A (RecA-like) domain;
    the variant is not modified to reduce its surface negative charge;
    the variant is not modified by the removal of one or more native cysteine residues;
    no cysteine residues and no non-natural amino acids have been introduced into the tower domain only; or
    no charged amino acids have introduced into the tower domain, the pin domain and the 1A domain of the variant.

The helicase is preferably a modified Dda helicase of the invention. Any of the helicases of the invention may be present in a construct of the invention.

The helicase is preferably covalently attached to the additional polynucleotide binding moiety. The helicase may be attached to the moiety at more than one, such as two or three, points.

The helicase can be covalently attached to the moiety using any method known in the art. Suitable methods are discussed above with reference to connecting the two or more parts.

The helicase and moiety may be produced separately and then attached together. The two components may be attached in any configuration. For instance, they may be attached via their terminal (i.e. amino or carboxy terminal) amino acids. Suitable configurations include, but are not limited to, the amino terminus of the moiety being attached to the carboxy terminus of the helicase and vice versa. Alternatively, the two components may be attached via amino acids within their sequences. For instance, the moiety may be attached to one or more amino acids in a loop region of the helicase. In a preferred embodiment, terminal amino acids of the moiety are attached to one or more amino acids in the loop region of a helicase.

In a preferred embodiment, the helicase is chemically attached to the moiety, for instance via one or more linker molecules as discussed above. In another preferred embodiment, the helicase is genetically fused to the moiety. A helicase is genetically fused to a moiety if the whole construct is expressed from a single polynucleotide sequence. The coding sequences of the helicase and moiety may be combined in any way to form a single polynucleotide sequence encoding the construct. Genetic fusion of a pore to a nucleic acid binding protein is discussed in International Application No. PCT/GB09/001679 (published as WO 2010/004265).

The helicase and moiety may be genetically fused in any configuration. The helicase and moiety may be fused via their terminal amino acids. For instance, the amino terminus of the moiety may be fused to the carboxy terminus of the helicase and vice versa. The amino acid sequence of the moiety is preferably added in frame into the amino acid sequence of the helicase. In other words, the moiety is preferably inserted within the sequence of the helicase. In such embodiments, the helicase and moiety are typically attached at two points, i.e. via the amino and carboxy terminal amino acids of the moiety. If the moiety is inserted within the sequence of the helicase, it is preferred that the amino and carboxy terminal amino acids of the moiety are in close proximity and are each attached to adjacent amino acids in the sequence of the helicase or variant thereof. In a preferred embodiment, the moiety is inserted into a loop region of the helicase.

The helicase may be attached directly to the moiety. The helicase is preferably attached to the moiety using one or more, such as two or three, linkers as discussed above. The one or more linkers may be designed to constrain the mobility of the moiety. The helicase and/or the moiety may be modified to facilitate attachment of the one or more linker as discussed above.

Cleavable linkers can be used as an aid to separation of constructs from non-attached components and can be used to further control the synthesis reaction. For example, a hetero-bifunctional linker may react with the helicase, but not the moiety. If the free end of the linker can be used to bind the helicase protein to a surface, the unreacted helicases from the first reaction can be removed from the mixture. Subsequently, the linker can be cleaved to expose a group that reacts with the moiety. In addition, by following this sequence of linkage reactions, conditions may be optimised first for the reaction to the helicase, then for the reaction to the moiety after cleavage of the linker. The second reaction would also be much more directed towards the correct site of reaction with the moiety because the linker would be confined to the region to which it is already attached.

The helicase may be covalently attached to the bifunctional crosslinker before the helicase/crosslinker complex is covalently attached to the moiety. Alternatively, the moiety may be covalently attached to the bifunctional crosslinker before the bifunctional crosslinker/moiety complex is attached to the helicase. The helicase and moiety may be covalently attached to the chemical crosslinker at the same time.

Preferred methods of attaching the helicase to the moiety are cysteine linkage and Faz linkage as described above. In a preferred embodiment, a reactive cysteine is presented on a peptide linker that is genetically attached to the moiety. This means that additional modifications will not necessarily be needed to remove other accessible cysteine residues from the moiety.

Cross-linkage of helicases or moieties to themselves may be prevented by keeping the concentration of linker in a vast excess of the helicase and/or moiety. Alternatively, a "lock and key" arrangement may be used in which two linkers are used. Only one end of each linker may react together to form a longer linker and the other ends of the linker each react with a different part of the construct (i.e. helicase or moiety). This is discussed in more detail below.

The site of attachment is selected such that, when the construct is contacted with a polynucleotide, both the helicase and the moiety can bind to the polynucleotide and control its movement.

Attachment can be facilitated using the polynucleotide binding activities of the helicase and the moiety. For instance, complementary polynucleotides can be used to bring the helicase and moiety together as they hybridize. The helicase can be bound to one polynucleotide and the moiety can be bound to the complementary polynucleotide. The two polynucleotides can then be allowed to hybridise to each other. This will bring the helicase into close contact with the moiety, making the linking reaction more efficient. This is especially helpful for attaching two or more helicases in the correct orientation for controlling movement of a target polynucleotide. An example of complementary polynucleotides that may be used are shown below.

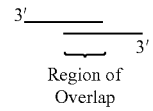

Region of Overlap

For helicase-Phi29 constructs the DNA below could be used.

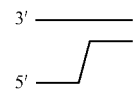

Tags can be added to the construct to make purification of the construct easier. These tags can then be chemically or enzymatically cleaved off, if their removal is necessary. Fluorophores or chromophores can also be included, and these could also be cleavable.

A simple way to purify the construct is to include a different purification tag on each protein (i.e. the helicase and the moiety), such as a hexa-His-tag and a Strep-Tag®. If the two proteins are different from one another, this method is particularly useful. The use of two tags enables only the species with both tags to be purified easily.

If the two proteins do not have two different tags, other methods may be used. For instance, proteins with free surface cysteines or proteins with linkers attached that have not reacted to form a construct could be removed, for instance using an iodoacetamide resin for maleimide linkers.

Constructs of the invention can also be purified from unreacted proteins on the basis of a different DNA processivity property. In particular, a construct of the invention can be purified from unreacted proteins on the basis of an increased affinity for a polynucleotide, a reduced likelihood of disengaging from a polynucleotide once bound and/or an increased read length of a polynucleotide as it controls the translocation of the polynucleotide through a nanopore A targeted construct that binds to a specific polynucleotide sequence can also be designed. As discussed in more detail below, the polynucleotide binding moiety may bind to a specific polynucleotide sequence and thereby target the helicase portion of the construct to the specific sequence.

Polynucleotide Binding Moiety

The constructs of the invention comprise a polynucleotide binding moiety. A polynucleotide binding moiety is a polypeptide that is capable of binding to a polynucleotide. The moiety is preferably capable of specific binding to a defined polynucleotide sequence. In other words, the moiety preferably binds to a specific polynucleotide sequence, but displays at least 10 fold less binding to different sequences or more preferably at least 100 fold less binding to different sequences or most preferably at least 1000 fold less binding to different sequences. The different sequence may be a random sequence. In some embodiments, the moiety binds to a specific polynucleotide sequence, but binding to different sequences cannot be measured. Moieties that bind to specific sequences can be used to design constructs that are targeted to such sequences.

The moiety typically interacts with and modifies at least one property of a polynucleotide. The moiety may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the target polynucleotide can be oxidized or methylated. One or more nucleotides in the target polynucleotide may be damaged. For instance, the polynucleotide may comprise a pyrimidine dimer. Such dimers are typically associated with damage by ultraviolet light and are the primary cause of skin melanomas. One or more nucleotides in the target polynucleotide may be modified, for instance with a label or a tag. Suitable labels are described above. The target polynucleotide may comprise one or more spacers.

A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), guanosine monophosphate (GMP), thymidine monophosphate (TMP), uridine monophosphate (UMP), cytidine monophosphate (CMP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP) and deoxycytidine monophosphate (dCMP). The nucleotides are preferably selected from AMP, TMP, GMP, CMP, UMP, dAMP, dTMP, dGMP, dCMP and dUMP.

A nucleotide may be abasic (i.e. lack a nucleobase). A nucleotide may also lack a nucleobase and a sugar (i.e. is a C3 spacer).

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be single stranded or double stranded. At least a portion of the polynucleotide is preferably double stranded.

The polynucleotide can be a nucleic acid, such as deoxyribonucleic acid (DNA) or ribonucleic acid (RNA). The target polynucleotide can comprise one strand of RNA hybridized to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains.

It is preferred that the tertiary structure of the moiety is known. Knowledge of the three dimensional structure of the moiety allows modifications to be made to the moiety to facilitate its function in the construct of the invention.

The moiety may be any size and have any structure. For instance, the moiety may be an oligomer, such as a dimer or trimer. The moiety is preferably a small, globular polypeptide formed from one monomer. Such moieties are easy to handle and are less likely to interfere with the ability of the helicase to control the movement of the polynucleotide, particularly if fused to or inserted into the sequence of the helicase.

The amino and carboxy terminii of the moiety are preferably in close proximity. The amino and carboxy terminii of the moiety are more preferably presented on same face of the moiety. Such embodiments facilitate insertion of the moiety into the sequence of the helicase. For instance, if the amino and carboxy terminii of the moiety are in close proximity, each can be attached by genetic fusion to adjacent amino acids in the sequence of the helicase.

It is also preferred that the location and function of the active site of the moiety is known. This prevents modifications being made to the active site that abolish the activity of the moiety. It also allows the moiety to be attached to the helicase so that the moiety binds to the polynucleotide and controls its movement. Knowledge of the way in which a moiety may bind to and orient polynucleotides also allows an effective construct to be designed.

The constructs of the invention are useful in Strand Sequencing. The moiety preferably binds the polynucleotide in a buffer background which is compatible with Strand Sequencing and the discrimination of the nucleotides. The moiety preferably has at least residual activity in a salt concentration well above the normal physiological level, such as from 100 mM to 2M. The moiety is more preferably modified to increase its activity at high salt concentrations. The moiety may also be modified to improve its processivity, stability and shelf life.

Suitable modifications can be determined from the characterisation of polynucleotide binding moieties from extremphiles such as halophilic, moderately halophilic bacteria, thermophilic and moderately thermophilic organisms, as well as directed evolution approaches to altering the salt tolerance, stability and temperature dependence of mesophilic or thermophilic exonucleases.

The polynucleotide binding moiety preferably comprises one or more domains independently selected from helix-hairpin-helix (HhH) domains, eukaryotic single-stranded binding proteins (SSBs), bacterial SSBs, archaeal SSBs, viral SSBs, double-stranded binding proteins, sliding clamps, processivity factors, DNA binding loops, replication initiation proteins, telomere binding proteins, repressors, zinc fingers and proliferating cell nuclear antigens (PCNAs).

The helix-hairpin-helix (HhH) domains are polypeptide motifs that bind DNA in a sequence non-specific manner. They have been shown to confer salt stability and processivity when fused to polymerases, as well as increasing their thermal stability. Suitable domains include domain H (residues 696-751) and domain HI (residues 696-802) from Topoisomerase V from *Methanopyrus kandleri* (SEQ ID NO: 47). As discussed below, the polynucleotide binding moiety may be domains H-L of SEQ ID NO: 47 as shown in SEQ ID NO: 48. Topoisomerase V from *Methanopyrus kandleri* is an example of a double-stranded binding protein as discussed below.

The HhH domain preferably comprises the sequence shown in SEQ ID NO: 24 or 37 or 38 or a variant thereof. This domain increases the processivity and the salt tolerance of a helicase when used in a construct of the invention. A variant of SEQ ID NO: 24 or 37 or 38 is a protein that has an amino acid sequence which varies from that of SEQ ID NO: 24 or 37 or 38 and which retains polynucleotide binding activity. This can be measured as described above. A variant typically has at least 50% homology to SEQ ID NO: 24 or 37 or 38 based on amino acid identity over its entire sequence (or any of the % homologies discussed above in relation to helicases) and retains polynucleotide binding activity. A variant may differ from SEQ ID NO: 24 or 37 or 38 in any of the ways discussed above in relation to helicases or below in relation to pores. A variant preferably comprises one or more substituted cysteine residues and/or one or more substituted Faz residues to facilitate attachment to the helicase as discussed above.

SSBs bind single stranded DNA with high affinity in a sequence non-specific manner. They exist in all domains of life in a variety of forms and bind DNA either as monomers or multimers. Using amino acid sequence alignment and logarithms (such as Hidden Markov models) SSBs can be classified according to their sequence homology. The Pfam family, PF00436, includes proteins that all show sequence similarity to known SSBs. This group of SSBs can then be further classified according to the Structural Classification of Proteins (SCOP). SSBs fall into the following lineage: Class; All beta proteins, Fold; OB-fold, Superfamily: Nucleic acid-binding proteins, Family; Single strand DNA-binding domain, SSB. Within this family SSBs can be classified according to subfamilies, with several type species often characterised within each subfamily.

The SSB may be from a eukaryote, such as from humans, mice, rats, fungi, protozoa or plants, from a prokaryote, such as bacteria and archaea, or from a virus.

Eukaryotic SSBs are known as replication protein A (RPAs). In most cases, they are hetero-trimers formed of different size units. Some of the larger units (e.g. RPA70 of *Saccharomyces cerevisiae*) are stable and bind ssDNA in monomeric form.

Bacterial SSBs bind DNA as stable homo-tetramers (e.g. *E. coli, Mycobacterium smegmatis* and *Helicobacter pylori*) or homo-dimers (e.g. *Deinococcus radiodurans* and *Thermotoga maritima*). The SSBs from archaeal genomes are considered to be related with eukaryotic RPAs. Few of them, such as the SSB encoded by the crenarchaeote *Sulfolobus solfataricus*, are homo-tetramers. The SSBs from most other species are closer related to the replication proteins from eukaryotes and are referred to as RPAs. In some of these species they have been shown to be monomeric (*Methanococcus jannaschii* and *Methanothermobacter thermoautotrophicum*). Still, other species of Archaea, including *Archaeoglobus fulgidus* and *Methanococcoides burtonii*, appear to each contain two open reading frames with sequence similarity to RPAs. There is no evidence at protein level and no published data regarding their DNA binding capabilities or oligomeric state. However, the presence of two oligonucleotide/oligosaccharide (OB) folds in each of these genes (three OB folds in the case of one of the *M. burtonii* ORFs) suggests that they also bind single stranded DNA.

Viral SSBs bind DNA as monomers. This, as well as their relatively small size renders them amenable to genetic fusion to other proteins, for instance via a flexible peptide linker. Alternatively, the SSBs can be expressed separately and attached to other proteins by chemical methods (e.g. cysteines, unnatural amino-acids). This is discussed in more detail below.

The SSB is preferably either (i) an SSB comprising a carboxy-terminal (C-terminal) region which does not have a net negative charge or (ii) a modified SSB comprising one or more modifications in its C-terminal region which decreases the net negative charge of the C-terminal region. Such SSBs do not block the transmembrane pore and therefore allow characterization of the target polynucleotide.

Examples of SSBs comprising a C-terminal region which does not have a net negative charge include, but are not limited to, the human mitochondrial SSB (HsmtSSB; SEQ ID NO: 39, the human replication protein A 70 kDa subunit, the human replication protein A 14 kDa subunit, the telomere end binding protein alpha subunit from *Oxytricha nova*, the core domain of telomere end binding protein beta subunit from *Oxytricha nova*, the protection of telomeres protein 1 (Pot1) from *Schizosaccharomyces pombe*, the human Pot1, the OB-fold domains of BRCA2 from mouse or rat, the p5 protein from phi29 (SEQ ID NO: 40) or a variant of any of those proteins. A variant is a protein that has an amino acid sequence which varies from that of the wild-type protein and which retains single stranded polynucleotide binding activity. Polynucleotide binding activity can be determined using methods known in the art (and as described above). For instance, the ability of a variant to bind a single stranded polynucleotide can be determined as described in the Examples.

A variant of SEQ ID NO: 39 or 40 typically has at least 50% homology to SEQ ID NO: 39 or 40 based on amino acid identity over its entire sequence (or any of the % homologies discussed above in relation to helicases) and retains single stranded polynucleotide binding activity. A variant may differ from SEQ ID NO: 39 or 40 in any of the ways discussed above in relation to helicases. In particular, a variant may have one or more conservative substitutions as shown in Tables 5 and 6.

Examples of SSBs which require one or more modifications in their C-terminal region to decrease the net negative charge include, but are not limited to, the SSB of *E. coli* (EcoSSB; SEQ ID NO: 41, the SSB of *Mycobacterium tuberculosis*, the SSB of *Deinococcus radiodurans*, the SSB of *Thermus thermophiles*, the SSB from *Sulfolobus solfataricus*, the human replication protein A 32 kDa subunit (RPA32) fragment, the CDC13 SSB from *Saccharomyces cerevisiae*, the Primosomal replication protein N (PriB) from *E. coli*, the PriB from *Arabidopsis thaliana*, the hypothetical protein At4g28440, the SSB from T4 (gp32; SEQ ID NO: 42), the SSB from RB69 (gp32; SEQ ID NO: 25), the SSB from T7 (gp2.5; SEQ ID NO: 26) or a variant of any of these proteins. Hence, the SSB used in the method of the invention may be derived from any of these proteins.

In addition to the one or more modifications in the C-terminal region, the SSB used in the method may include additional modifications which are outside the C-terminal region or do not decrease the net negative charge of the C-terminal region. In other words, the SSB used in the method of the invention is derived from a variant of a wild-type protein. A variant is a protein that has an amino acid sequence which varies from that of the wild-type protein and which retains single stranded polynucleotide binding activity. Polynucleotide binding activity can be determined as discussed above.

The SSB used in the invention may be derived from a variant of SEQ ID NO: 25, 26, 41 or 42. In other words, a variant of SEQ ID NO: 25, 26, 41 or 42 may be used as the starting point for the SSB used in the invention, but the SSB actually used further includes one or more modifications in its C-terminal region which decreases the net negative charge of the C-terminal region. A variant of SEQ ID NO: 25, 26, 41 or 42 typically has at least 50% homology to SEQ ID NO: 25, 26, 41 or 42 based on amino acid identity over its entire sequence (or any of the % homologies discussed above in relation to helicases) and retains single stranded polynucleotide binding activity. A variant may differ from SEQ ID NO: 25, 26, 41 or 42 in any of the ways discussed above in relation to helicases. In particular, a variant may have one or more conservative substitutions as shown in Tables 5 and 6.

It is straightforward to identify the C-terminal region of the SSB in accordance with normal protein N to C nomenclature. The C-terminal region of the SSB is preferably about the last third of the SSB at the C-terminal end, such as the last third of the SSB at the C-terminal end. The C-terminal region of the SSB is more preferably about the last quarter, fifth or eighth of the SSB at the C-terminal end, such as the last quarter, fifth or eighth of the SSB at the C-terminal end. The last third, quarter, fifth or eighth of the SSB may be measured in terms of numbers of amino acids or in terms of actual length of the primary structure of the SSB protein. The length of the various amino acids in the N to C direction are known in the art.

The C-terminal region is preferably from about the last 10 to about the last 60 amino acids of the C-terminal end of the SSB. The C-terminal region is more preferably about the last 15, about the last 20, about the last 25, about the last 30, about the last 35, about the last 40, about the last 45, about the last 50 or about the last 55 amino acids of the C-terminal end of the SSB.

The C-terminal region typically comprises a glycine and/or proline rich region. This proline/glycine rich region gives the C-terminal region flexibility and can be used to identify the C-terminal region.

Suitable modifications for decreasing the net negative charge are disclosed in International Application No. PCT/GB2013/051924 (published as WO 2014/013259). The SSB may be any of the SSBs disclosed in this International application.

The modified SSB most preferably comprises a sequence selected from those shown in SEQ ID NOs: 33, 34, 43 to 46.

Double-stranded binding proteins bind double stranded DNA with high affinity. Suitable double-stranded binding proteins include, but are not limited to Mutator S (MutS; NCBI Reference Sequence: NP 417213.1; SEQ ID NO: 49), Sso7d (*Siufolobus solfataricus* P2; NCBI Reference Sequence: NP 343889.1; SEQ ID NO: 50; Nucleic Acids Research, 2004, Vol 32, No. 3, 1197-1207), Sso10b1 (NCBI Reference Sequence: NP 342446.1; SEQ ID NO: 51), Sso10b2 (NCBI Reference Sequence: NP 342448.1; SEQ ID NO: 52), Tryptophan repressor (Trp repressor; NCBI Reference Sequence: NP 291006.1; SEQ ID NO: 53), Lambda repressor (NCBI Reference Sequence: NP 040628.1; SEQ ID NO: 54), Cren7 (NCBI Reference Sequence: NP 342459.1; SEQ ID NO: 55), major histone classes H1/H5, H2A, H2B, H3 and H4 (NCBI Reference Sequence: NP 066403.2, SEQ ID NO: 56), dsbA (NCBI Reference Sequence: NP 049858.1; SEQ ID NO: 57), Rad51 (NCBI Reference Sequence: NP 002866.2; SEQ ID NO: 58), sliding clamps and Topoisomerase V Mka (SEQ ID NO: 47) or a variant of any of these proteins. A variant of SEQ ID NO: 47, 49, 50, 51, 52, 53, 54, 55, 56, 57 or 58 typically has at least 50% homology to SEQ ID NO: 47, 49, 50, 51, 52, 53, 54, 55, 56, 57 or 58 based on amino acid identity over its entire sequence (or any of the % homologies discussed above in relation to helicases) and retains single stranded polynucleotide binding activity. A variant may differ from SEQ ID NO: 47, 49, 50, 51, 52, 53, 54, 55, 56, 57 or 58 in any of the ways discussed above in relation to helicases. In particular, a variant may have one or more conservative substitutions as shown in Tables 5 and 6. Most polymerases achieve processivity by interacting with sliding clamps. In general, these are multimeric proteins (homo-dimers or homo-trimers) that encircle dsDNA. These sliding clamps require accessory proteins (clamp loaders) to assemble them around the DNA helix in an ATP-dependent process. They also do not contact DNA directly, acting as a topological tether. As sliding clamps interact with their cognate polymerases in a specific manner via a polymerase domain, this fragment could be fused to the helicase in order to incite recruitment of helicases onto the sliding clamp. This interaction could be further stabilized by the generation of a covalent bond (introduction of cysteines or unnatural amino-acids).

Related to DNA sliding clamps, processivity factors are viral proteins that anchor their cognate polymerases to DNA, leading to a dramatic increase in the length of the fragments generated. They can be monomeric (as is the case for UL42 from Herpes simplex virus 1) or multimeric (UL44 from Cytomegalovirus is a dimer), they do not form closed rings around the DNA strand and they contact DNA directly. UL42 has been shown to increase processivity without reducing the rate of its corresponding polymerase, suggesting that it interacts with DNA in a different mode to SSBs. The UL42 preferably comprises the sequence shown in SEQ ID NO: 27 or SEQ ID NO: 32 or a variant thereof. A variant of SEQ ID NO: 27 or 32 is a protein that has an amino acid sequence which varies from that of SEQ ID NO: 27 or 32 and which retains polynucleotide binding activity. This can be measured as described above. A variant typically has at least 50% homology to SEQ ID NO: 27 or 32 based on amino acid identity over its entire sequence (or any of the % homologies discussed above in relation to helicases) and retains polynucleotide binding activity. A variant may differ from SEQ ID NO: 27 or SEQ ID NO: 32 in any of the ways discussed above in relation to helicases or below in relation to pores. A variant preferably comprises one or more substituted cysteine residues and/or one or more substituted Faz residues to facilitate attachment to the helicase as discussed above.

Attaching UL42 to a helicase could be done via genetic fusion or chemical attachment (cysteines, unnatural amino-acids). As the polymerase polypeptide that binds UL42 is visible in the crystal structure, these 35 amino acids (residues 1200-1235) could be fused onto the C-terminus of the helicase and the natural affinity between this polypeptide and the processivity factor used to form a complex. The interaction could be stabilized by introducing a covalent interaction (cysteines or unnatural amino-acids). One option is to utilize a natural UL42 cysteine (C300) that is located close to the polypeptide interaction site and introduce a point mutation into the polymerase polypeptide (e.g. L1234C).

A reported method of increasing polymerase processivity is by exploiting the interaction between *E. coli* thioredoxin (Trx) and the thioredoxin binding domain (TBD) of bacteriophage T7 DNA polymerase (residues 258-333). The binding of Trx to TBD causes the polypeptide to change conformation to one that binds DNA. TBD is believed to clamp down onto a DNA strand and limit the polymerase off-rate, thus increasing processivity. Chimeric polymerases have been made by transferring TBD onto a non-processive polymerase, resulting in 1000 fold increase in polymerised fragment length. There were no attempts to attach TBD to any other class of proteins, but a covalent link between TBD and Trx was engineered and can be used to stabilise the interaction.

Some helicases use accessory proteins in-vivo to achieve processivity (e.g. cisA from phage Φx174 and geneII protein from phage M13 for *E. coli* Rep helicase). Some of these proteins have been shown to interact with more than one helicase (e.g. MutL acts on both UvrD and Rep, though not to the same extent). These proteins have intrinsic DNA binding capabilities, some of them recognizing a specific DNA sequence. The ability of some of these accessory proteins to covalently attach themselves to a specific DNA sequence could also be used to create a set starting point for the helicase activity.

The proteins that protect the ends of chromosomes bind to telomeric ssDNA sequences in a highly specific manner. This ability could either be exploited as is or by using point mutations to abolish the sequence specificity.

Small DNA binding motifs (such as helix-turn-helix) recognize specific DNA sequences. In the case of the bacteriophage 434 repressor, a 62 residue fragment was engineered and shown to retain DNA binding abilities and specificity.

An abundant motif in eukaryotic proteins, zinc fingers consist of around 30 amino-acids that bind DNA in a specific manner. Typically each zinc finger recognizes only three DNA bases, but multiple fingers can be linked to obtain recognition of a longer sequence.

Proliferating cell nuclear antigens (PCNAs) form a very tight clamp (doughnut) which slides up and down the dsDNA or ssDNA. The PCNA from crenarchaeota is unique in being a hetero-trimer so it is possible to functionalise one subunit and retain activity. Its subunits are shown in SEQ ID NOs: 28, 29 and 30. The PCNA is preferably a trimer comprising the sequences shown in SEQ ID NOs: 28, 29 and 30 or variants thereof. PCNA sliding clamp (NCBI Reference Sequence: ZP 06863050.1; SEQ ID NO: 59) forms a dimer. The PCNA is preferably a dimer comprising SEQ ID NO: 59 or a variant thereof. A variant is a protein that has an amino acid sequence which varies from that of SEQ ID NO: 28, 29, 30 or 59 and which retains polynucleotide binding activity. This can be measured as described above. A variant is typically a trimer comprising sequences that have at least 50% homology to SEQ ID NOs: 28, 29 and 30 or a dimer comprising sequences that have at least 50% homology to SEQ ID NO: 59 based on amino acid identity over each entire sequence (or any of the % homologies discussed above in relation to helicases) and which retains polynucleotide binding activity. A variant may comprise sequences which differ from SEQ ID NO: 28, 29, 30 or 59 in any of the ways discussed above in relation to helicases or below in relation to pores. A variant preferably comprises one or more substituted cysteine residues and/or one or more substituted Faz residues to facilitate attachment to the helicase as discussed above. In a preferred embodiment, subunits 1 and 2 of the PCNA from crenarchaeota (i.e. SEQ ID NOs: 28 and 29 or variants thereof) are attached, such as genetically fused, and the resulting protein is attached to a helicase to form a construct of the invention. During use of the construct, subunit 3 (i.e. SEQ ID NO: 30 or a variant thereof) may be added to complete the PCNA clamp (or doughnut) once the construct has bound the polynucleotide. In a preferred embodiment, one monomer of the PCNA sliding clamp (i.e. SEQ ID NO: 59 or a variant thereof) is attached, such as genetically fused, to a helicase to form a construct of the invention. During use of the construct, the second monomer (i.e. SEQ ID NO: 59 or a variant thereof) may be added to complete the PCNA clamp (or doughnut) once the construct has bound the polynucleotide.

The polynucleotide binding motif may be selected from any of those shown in Table 3 below.

TABLE 3

Suitable polynucleotide binding motifs

| No. | Name | Class | Organism | Structure | Sequence | Functional form | MW (Da) | Notes |
|---|---|---|---|---|---|---|---|---|
| 1 | SSBEco | ssb | Escherichia coli | 1QVC, 1EYG | P0AGE0 | homo-tetramer | 18975 | |
| 2 | SSBBhe | ssb | Bartonella henselae | 3LGJ, 3PGZ | Q6G302 | homo-tetramer | 16737 | structure only |
| 3 | SSBCbu | ssb | Coxiella burnetii | 3TQY | Q83EP4 | homo-tetramer | 17437 | structure only |
| 4 | SSBTma | ssb | Thermathoga maritima | 1Z9F | Q9WZ73 | homo-dimer | 16298 | small, thermostable, salt independent DNA binding |
| 5 | SSBHpy | ssb | Helicobacter pylori | 2VW9 | O25841 | homo-tetramer | 20143 | |
| 6 | SSBDra | ssb | Deinococcus radiodurans | 1SE8 | Q9RY51 | homo-dimer | 32722 | |
| 7 | SSBTaq | ssb | Thermus aquaticus | 2FXQ | Q9KH06 | homo-dimer | 30026 | |
| 8 | SSBMsm | ssb | Mycobacterium smegmatis | 3A5U, 1X3E | Q9AFI5 | homo-tetramer | 17401 | tetramer more stable than E. coli, binding less salt dependent |
| 9 | SSBSso | ssb/RPA | Sulfolobus solfataricus | 1O7I | Q97W73 | homo-tetramer | 16138 | similarities with RPA |
| 10 | SSBMHsmt | ssb | Homo sapiens | 3ULL | Q04837 | homo-tetramer | 17260 | |
| 11 | SSBMle | ssb | Mycobacterium leprae | 3AFP | P46390 | homo-tetramer | 17701 | |
| 12 | gp32T4 | ssb | Bacteriohage T4 | 1GPC | P03695 | monomer | 33506 | Homo-dimer in the absence of DNA, monomer when binding DNA. |
| 13 | gp32RB69 | ssb | Bacteriophage RB69 | 2A1K | Q7Y265 | monomer | 33118 | |

TABLE 3-continued

Suitable polynucleotide binding motifs

| No. | Name | Class | Organism | Structure | Sequence | Functional form | MW (Da) | Notes |
|---|---|---|---|---|---|---|---|---|
| 14 | gp2.5T7 | ssb | Bacteriohage T7 | 1JE5 | P03696 | monomer | 25694 | |
| 15 | UL42 | processivity factor | Herpes virus 1 | 1DML | P10226 | monomer | 51159 | binds ssDNA dsDNA, structure shows link with polymerase |
| 16 | UL44 | processivity factor | Herpes virus 5 (cytomegalovirus) | 1YYP | P16790 | homo-dimer | 46233 | forms C shaped clamp on DNA |
| 17 | pf8 | processivity factor | KSHV | 3I2M | Q77ZG5 | homo-dimer | 42378 | |
| 18 | RPAMja | RPA | *Methanococcus jannaschii* | 3DM3 | Q58559 | monomer | 73842 | contains 4 OB folds. Structure of fragment |
| 19 | RPAMma | RPA | *Methanococcus maripaludis* | 3E0E, 2K5V | Q6LYF9 | monomer | 71388 | Core domain structure |
| 20 | RPAMth | RPA | *Methanothermobacter thermoautotrophicus* | | | monomer | 120000 | Shown to interact directly with Hel308. Sequence from paper. |
| 21 | RPA70Sce | RPA | *Saccharomyces cerevisiae* | 1YNX | P22336 | hetero-trimer | 70348 | unit has two OB folds and binds DNA |
| 22 | RPAMbu1 | RPA | *Methanococcoides burtonii* | | Q12V72 | ? | 41227 | three OB folds identified |
| 23 | RPAMbu2 | RPA | *Methanococcoides burtonii* | | Q12W96 | ? | 47082 | two OB folds identified |
| 24 | RPA70Hsa | RPA | *Homo sapiens* | 1JMC | P27694 | hetero-trimer | 68138 | |
| 25 | RPA14Hsa | RPA | *Homo sapiens* | 3KDF | P35244 | hetero-trimer | 13569 | in complex with RPA32 |
| 26 | gp45T4 | sliding clamp | Bacteriophage T4 | 1CZD | P04525 | homo-trimer | 24858 | ring shape threads DNA |
| 27 | BetaEco | sliding clamp | *E. coli* | 3BEP | P0A988 | homo-dimer | 40587 | ring shape threads DNA, may bind ssDNA in pocket |
| 28 | PCNASce | sliding clamp | *Saccharomyces cerevisiae* | 1PLQ, 3K4X | P15873 | homo-dimer | 28916 | ring shape threads DNA |
| 29 | PCNATko | sliding clamp | *Thermococcus kodakaraensis* | 3LX1 | Q5JF32 | homo-dimer | 28239 | |
| 30 | PCNAHvo | sliding clamp | *Haloferax volcanii* | 3IFV | D0VWY8 | homo-dimer | 26672 | |
| 31 | PCNAPfu | sliding clamp | *Pyrococcus furiosus* | 1GE8 | O73947 | homo-dimer | 28005 | |
| 32 | PCNAMbu | sliding clamp | *Methanococcoides burtonii* | | Q12U18 | homo-dimer | 27121 | Inferred from homology |
| 33 | BetaMtu | sliding clamp | *Mycobacterium tuberculosis* | 3P16 | Q50790 | homo-dimer | 42113 | |
| 34 | BetaTma | sliding clamp | *Thermotoga maritima* | 1VPK | Q9WYA0 | homo-dimer | 40948 | |
| 35 | BetaSpy | sliding clamp | *Streptococcus pyrogenes* | 2AVT | Q9EVR1 | homo-dimer | 41867 | |
| 36 | gp45RB69 | sliding clamp | Bacteriophage RB69 | 1B77 | O80164 | homo-trimer | 25111 | Structure shows interaction with polypeptide from polymerase |
| 37 | p55Hsa | DNA binding protein | *Homo sapiens* (mitochondrial) | 2G4C, 3IKL, 3IKM | Q9UHN | monomer | 54911 | interacts with specific polymerase domain |
| 38 | p55Dme | DNA binding protein | *Drosophylla melanogaster* | | Q9VJV8 | monomer | 41027 | associates with polymerase Gamma conferring salt tolerance, processivity and increased activity |
| 39 | p55Xla | DNA binding protein | *Xenopus laevis* | | Q9W6G7 | monomer | 52283 | |
| 40 | RepDSau | replication initiation protein | *Staphylococcus aureus* | | P08115 | homo-dimer | 37874 | increases processivity of PcrA, covalently and specifically links DNA |

TABLE 3-continued

Suitable polynucleotide binding motifs

| No. | Name | Class | Organism | Structure | Sequence | Functional form | MW (Da) | Notes |
|---|---|---|---|---|---|---|---|---|
| 41 | G2P | replication initiation protein | Enterobacteria phage 1 | | P69546 | monomer | 46168 | increases processivity of Rep, covalently and specifically links DNA |
| 42 | MutLEco | mismatch repair protein | Escherichia coli | 1BKN, 1B62, 1B63 | P23367 | homo-dimer | 67924 | increases processivity of UvrD (and Rep) |
| 43 | KuMtu | DNA repair protein | Mycobacterium tuberculosis | | O05866 | homo-dimer | 30904 | increases processivity of UvrD1. Structure available for human Ku |
| 44 | OnTEBP | telomere binding protein | Oxytricha nova-Alpha | 1OTC | P29549 | hetero-dimer | 56082 | Specific biding to 3' end T4G4T4G4. Alpha subunit may be enough |
| | | | Oxytricha nova-Beta | | P16458 | | 41446 | |
| 45 | EcrTEBP | telomere binding protein | Euplotes crassus | | Q06183 | monomer | 53360 | Homolog to OnTEBP with no Beta subunit in genome |
| 46 | TteTEBP | telomere binding protein | Tetrachymena termophila Alpha | | Q23FB9 | hetero-dimer | 53073 | Homolog to OnTEBP-Alpha |
| | | | Tetrachymena termophila Beta | | Q23FH0 | | 54757 | May be homolog to OnTEBP Beta |
| 47 | pot1Spo | telomere binding proteins | Schizosaccharomyces pombe | | O13988 | monomer | 64111 | related to TEBP |
| 48 | Cdc13pSce | telomere binding proteins | Saccharomyces cerevisiae | | C7GSV7 | monomer | 104936 | specific binding to telomeric DNA |
| 49 | C1 | repressor | Bacteriophage 434 | | P16117 | homo-dimer | 10426 | binds DNA specifically as homo-dimer |
| 50 | LexA | repressor | Escherichia coli | 1LEB | P0A7C2 | homo-dimer | 22358 | binds DNA specifically as homo-dimer |

The polynucleotide binding moiety is preferably derived from a polynucleotide binding enzyme. A polynucleotide binding enzyme is a polypeptide that is capable of binding to a polynucleotide and interacting with and modifying at least one property of the polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide binding moiety does not need to display enzymatic activity as long as it is capable of binding the polynucleotide and controlling its movement. For instance, the moiety may be derived from an enzyme that has been modified to remove its enzymatic activity or may be used under conditions which prevent it from acting as an enzyme.

The polynucleotide binding moiety is preferably derived from a nucleolytic enzyme. The enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are exonucleases, polymerases, helicases and topoisomerases, such as gyrases. Suitable exonucleases include, but are not limited to, exonuclease I from E. coli, exonuclease III enzyme from E. coli, RecJ from T. thermophilus and bacteriophage lambda exonuclease, TatD exonuclease and variants thereof.

The polymerase is preferably a member of any of the Moiety Classification (EC) groups 2.7.7.6, 2.7.7.7, 2.7.7.19, 2.7.7.48 and 2.7.7.49. The polymerase is preferably a DNA-dependent DNA polymerase, an RNA-dependent DNA polymerase, a DNA-dependent RNA polymerase or an RNA-dependent RNA polymerase. The polymerase may be PyroPhage®3173 DNA Polymerase (which is commercially available from Lucigen® Corporation), SD Polymerase (commercially available from Bioron®) or variants thereof. The polynucleotide binding moiety is preferably derived from Phi29 DNA polymerase (SEQ ID NO: 31). The moiety may comprise the sequence shown in SEQ ID NO: 101 or a variant thereof. A variant of SEQ ID NO: 31 is an enzyme that has an amino acid sequence which varies from that of SEQ ID NO: 31 and which retains polynucleotide binding activity. This can be measured as described above. The variant may include modifications that facilitate binding of the polynucleotide and/or facilitate its activity at high salt concentrations and/or room temperature.

Over the entire length of the amino acid sequence of SEQ ID NO: 31, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 31 over the entire sequence. There may be at least 80%, for example at least 85%, 90% or 95%, amino acid identity over a stretch of 200 or more, for example 230, 250, 270 or 280 or more, contiguous amino acids ("hard homology"). Homology is determined as described below. The variant may differ from the wild-type sequence in any of the ways discussed below with reference to SEQ ID NOs: 2 and 4.

The helicase may be any of those discussed above. Helicase dimers and multimers are discussed in detail below. The polynucleotide binding moiety may be a polynucleotide binding domain derived from a helicase. For instance, the polynucleotide binding moiety preferably comprises the sequence shown in SEQ ID NOs: 35 or 36 or a variant thereof. A variant of SEQ ID NOs: 35 or 36 is a protein that has an amino acid sequence which varies from that of SEQ ID NOs: 35 or 36 and which retains polynucleotide binding activity. This can be measured as described above. The variant may include modifications that facilitate binding of the polynucleotide and/or facilitate its activity at high salt concentrations and/or room temperature.

Over the entire length of the amino acid sequence of SEQ ID NOs: 35 or 36, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NOs: 35 or 36 over the entire sequence. There may be at least 80%, for example at least 85%, 90% or 95%, amino acid identity over a stretch of 40 or more, for example 50, 60, 70 or 80 or more, contiguous amino acids ("hard homology"). Homology is determined as described below. The variant may differ from the wild-type sequence in any of the ways discussed below with reference to SEQ ID NOs: 2 and 4.

The topoisomerase is preferably a member of any of the Moiety Classification (EC) groups 5.99.1.2 and 5.99.1.3.

The polynucleotide binding moiety may be any of the enzymes discussed above.

The moiety may be labelled with a revealing label. The label may be any of those described above.

The moiety may be isolated from any moiety-producing organism, such as *E. coli, T. thermophilus* or bacteriophage, or made synthetically or by recombinant means. For example, the moiety may be synthesized by in vitro translation and transcription as described below. The moiety may be produced in large scale following purification as described below.

Helicase Oligomers

As will be clear from the discussion above, the polynucleotide binding moiety is preferably derived from a helicase. For instance, it may be a polynucleotide domain from a helicase. The moiety more preferably comprises one or more helicases. The helicases may be any of those discussed above with reference to the constructs of the invention, including the helicases of the invention and helicases which are not modified in accordance with the invention. In such embodiments, the constructs of the invention of course comprise two or more helicases attached together. At least one of the helicases is preferably modified in accordance with the invention. The constructs may comprise two, three, four, five or more helicases. In other words, the constructs of the invention may comprise a helicase dimer, a helicase trimer, a helicase tetramer, a helicase pentamer and the like.

The two or more helicases can be attached together in any orientation. Identical or similar helicases may be attached via the same amino acid position or spatially proximate amino acid positions in each helicase. This is termed the "head-to-head" formation. Alternatively, identical or similar helicases may be attached via positions on opposite or different sides of each helicase. This is termed the "head-to-tail" formation. Helicase trimers comprising three identical or similar helicases may comprise both the head-to-head and head-to-tail formations.

The two or more helicases may be different from one another (i.e. the construct is a hetero-dimer, -trimer, -tetramer or pentamer etc.). For instance, the constructs of the invention may comprise (a) one or more helicases of the invention and one or more helicases which are not modified in accordance with the invention; (b) two or more different helicases of the invention; or (c) two or more helicases which are not modified in accordance with the invention. The construct may comprise two different variants of the same Dda helicase. For instance, the construct may comprise two variants of one of the helicases discussed above with one or more cysteine residues or Faz residues introduced at different positions in each variant. In this instance, the helicases can be in a head-to-tail formation.

Hetero-dimers can be formed in two possible ways. The first involves the use of a homo-bifunctional linker as discussed above. One of the helicase variants can be modified with a large excess of linker in such a way that one linker is attached to one molecule of the protein. This linker modified variant can then be purified away from unmodified proteins, possible homo-dimers and unreacted linkers to react with the other helicase variant. The resulting dimer can then be purified away from other species.

The second involves the use of hetero-bifunctional linkers. For example, one of the helicase variants can be modified with a first PEG linker containing maleimide or iodoacetamide functional group at one end and a cyclooctyne functional group (DIBO) at the other end. An example of this is shown below:

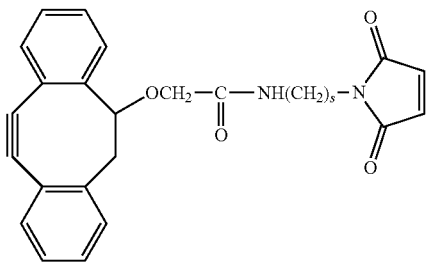

The second helicase variant can be modified with a second PEG linker containing maleimide or iodoacetamide functional group at one end and an azide functional group at the other end. An example is show below:

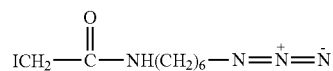

The two helicase variants with two different linkers can then be purified and clicked together (using copper free click chemistry) to make a dimer. Copper free click chemistry has been used in these applications because of its desirable properties. For example, it is fast, clean and not poisonous towards proteins. However, other suitable bio-orthogonal chemistries include, but are not limited to, Staudinger chemistry, hydrazine or hydrazide/aldehyde or ketone reagents (HyNic+4FB chemistry, including all Solulink™ reagents), Diels-Alder reagent pairs and boronic acid/salicyhydroxamate reagents.

These two ways of linking two different variants of the same helicase are also valid for any of the constructs discussed above in which the helicase and the moiety are different from one another, such as dimers of two different helicases and a helicase-polymerase dimer.

Similar methodology may also be used for linking different Faz variants. One Faz variant can be modified with a large excess of linker in such a way that one linker is attached to one molecule of the protein. This linker modified Faz variant can then be purified away from unmodified proteins, possible homo-dimers and unreacted linkers to react with the second Faz variant. The resulting dimer can then be purified away from other species.

Hetero-dimers can also be made by linking cysteine variants and Faz variants of the same helicase or different helicases. Hetero-bifunctional PEG linkers with maleimide or iodoacetamide functionalities at one end and DBCO functionality at the other end can be used in this combination of mutants. An example of such a linker is shown below (DBCO-PEG4-maleimide):

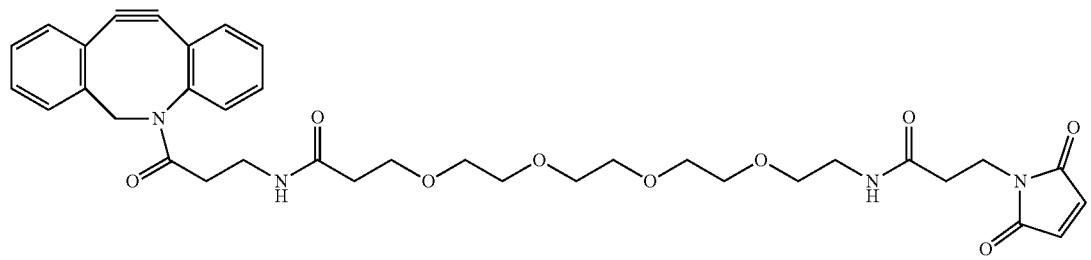 [SMILES: O=C(CCOCCOCCOCCOCCNC(=O)CCN1C(=O)C=CC1=O)NCCC(=O)N1Cc2ccccc2C#Cc2ccccc21]

The length of the linker can be varied by changing the number of PEG units between the two functional groups.

Helicase hetero-trimers can comprise three different types of helicases. The same is true for oligomers comprising more than three helicases. The two or more helicases within a construct may be different variants of the same helicase, such as different variants of any one of SEQ ID NOs: 8 to 23. The different variants may be modified at different positions to facilitate attachment via the different positions. The hetero-trimers may therefore be in a head-to-tail and head-to-head formation.

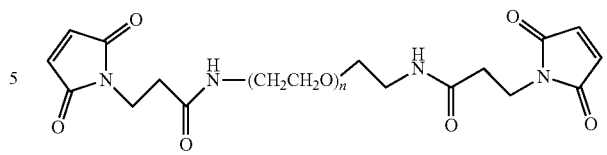

The length of the linker can be varied to suit the required applications. For example, n can be 2, 3, 4, 8, 11, 12, 16 or more. PEG linkers are suitable because they have favourable properties such as water solubility. Other non PEG linkers can also be used in cysteine linkage.

By using similar approaches, identical Faz variants can also be made into homo-dimers. Homo-bifunctional linkers with DIBO functional groups can be used to link two molecules of the same Faz variant to make homo-dimers using $Cu^{2+}$ free click chemistry. An example of a linker is given below:

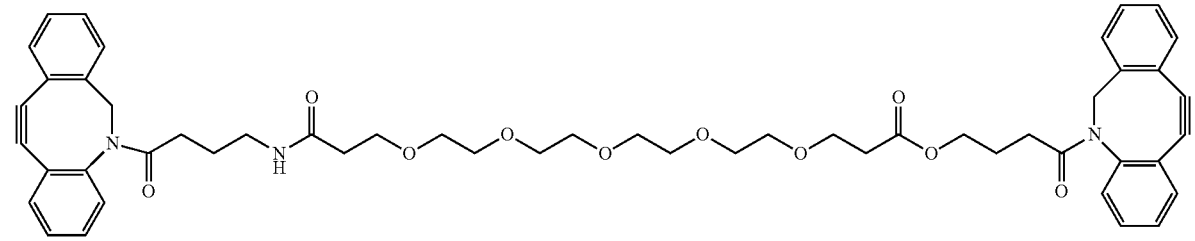

Maleimide linkers

The two or more helicases in the constructs of the invention may be the same as one another (i.e. the construct is a homo-dimer, -trimer, -tetramer or pentamer etc.) In such embodiments, the helicases are preferably attached using the same position in each helicase. The helicases are therefore attached head-to-head. The helicases may be linked using a cysteine residue or a Faz residue that has been substituted into the helicases at the same position. Cysteine residues in identical helicase variants can be linked using a homo-bifunctional linker containing thiol reactive groups such as maleimide or iodoacetamide. These functional groups can be at the end of a polyethyleneglycol (PEG) chain as in the following example:

The length of the PEG linker can vary to include 2, 4, 8, 12, 16 or more PEG units. Such linkers can also be made to incorporate a florescent tag to ease quantifications. Such fluorescence tags can also be incorporated into Maleimide linkers.

Homo-dimers or longer homo-oligomers may also be prepared in the head-to-tail formation if two or more cysteine residues or non-natural amino acids are introduced in the helicase in accordance with the invention and different cysteines or non-natural amino acids in the different helicase monomers are attached together. For instance, homo-oligomers may be formed from variants of SEQ ID NO: 8 comprising Y279C and G357C and the C at 279 in one monomer may be attached to the C at 357 in another monomer. Similarly, homo-oligomers may be formed from variants of SEQ ID NO: 8 comprising I281C and G357C and the C at 281 in one monomer may be attached to the C at 357 in another monomer. The same is true when Faz is introduced at these positions instead of C. Such C and Faz mutants allow series or trains of helicases to be created.

Polynucleotide Sequences

The invention provides a polynucleotide comprising a sequence which encodes a helicase of the invention, a polypeptide of the invention or a construct of the invention. The polynucleotide may consist of such a sequence. The polynucleotide may be any of those discussed above.

Any of the proteins described herein may be expressed using methods known in the art. Polynucleotide sequences may be isolated and replicated using standard methods in the art. Chromosomal DNA may be extracted from a helicase producing organism, such as *Methanococcoides burtonii*, and/or a SSB producing organism, such as *E. coli*. The gene encoding the sequence of interest may be amplified using PCR involving specific primers. The amplified sequences may then be incorporated into a recombinant replicable vector such as a cloning vector. The vector may be used to replicate the polynucleotide in a compatible host cell. Thus polynucleotide sequences may be made by introducing a polynucleotide encoding the sequence of interest into a replicable vector, introducing the vector into a compatible host cell, and growing the host cell under conditions which bring about replication of the vector. The vector may be recovered from the host cell. Suitable host cells for cloning of polynucleotides are known in the art and described in more detail below.

The polynucleotide sequence may be cloned into a suitable expression vector. In an expression vector, the polynucleotide sequence is typically operably linked to a control sequence which is capable of providing for the expression of the coding sequence by the host cell. Such expression vectors can be used to express a construct.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotide may be introduced into the vector.

The expression vector may then be introduced into a suitable host cell. Thus, a construct can be produced by inserting a polynucleotide sequence encoding a construct into an expression vector, introducing the vector into a compatible bacterial host cell, and growing the host cell under conditions which bring about expression of the polynucleotide sequence.

The vectors may be for example, plasmid, virus or phage vectors provided with an origin of replication, optionally a promoter for the expression of the said polynucleotide sequence and optionally a regulator of the promoter. The vectors may contain one or more selectable marker genes, for example an ampicillin resistance gene. Promoters and other expression regulation signals may be selected to be compatible with the host cell for which the expression vector is designed. A T7, trc, lac, ara or $\lambda_L$ promoter is typically used.

The host cell typically expresses the construct at a high level. Host cells transformed with a polynucleotide sequence will be chosen to be compatible with the expression vector used to transform the cell. The host cell is typically bacterial and preferably *E. coli*. Any cell with a λ DE3 lysogen, for example Rosetta2(DE3)pLys, C41 (DE3), BL21 (DE3), JM109 (DE3), B834 (DE3), TUNER, Origami and Origami B, can express a vector comprising the T7 promoter.

Series

The invention also provides a series of two or more helicases attached (or bound) to a polynucleotide, wherein at least one of the two or more helicases is a Dda helicase of the invention. The series may comprise any number of helicases such as 2, 3, 4, 5, 6, 7, 8, 9, 10 or more helicases. Any number of the helicases may be Dda helicases of the invention. All of the two or more helicases are preferably Dda helicases of the invention. The one or more Dda helicases of the invention may be any of those discussed above.

The two or more helicases may be the same helicase or may be different helicases. For instance, if the series comprises two or more Dda helicases of the invention, the Dda helicases of the invention may be the same or may be different.

The series may comprise any number and any combination of Dda helicases of the invention. The series of two or more helicases preferably comprises at least two Dda helicases of the invention. The series may comprise two or more Dda helicases each of which comprises a variant of SEQ ID NO: 8 comprising (or comprising only) (i) E94C/A360C, (ii) E94C/A360C and then (ΔM1)G1G2 (i.e. deletion of M1 and then addition G1 and G2), (iii) E94C/A360C/C109A/C136A, (iv) E94C/A360C/C109A/C136A and then (ΔM1)G1G2 (i.e. deletion of M1 and then addition G1 and G2), (v) E94C/A360C/W378A, (vi) E94C/A360C/W378A and then (ΔM1)G1G2 (i.e. deletion of M1 and then addition G1 and G2), (vii) E94C/A360C/C109A/C136A/W378A or (viii) E94C/A360C/C109A/C136A/W378A and then (ΔM1)G1G2 (i.e. deletion of M1 and then addition G1 and G2). One Dda helicase of the invention in the series preferably comprises a variant of SEQ ID NO: 8 comprising (or comprising only) one of (i) to (iv) and another Dda helicase of the invention in the series preferably comprises a variant of SEQ ID NO: 8 comprising (or comprising only) one of (v) to (viii).

In addition to one or more Dda helicases of the invention, the series may comprise one or more helicases which are not part of the invention. The one or more helicases may be or be derived from a Hel308 helicase, a RecD helicase, such as TraI helicase or a TrwC helicase, a XPD helicase or a Dda helicase. The one or more helicases may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013/098561); PCT/GB2013/051925 (published as WO 2014/013260); PCT/GB2013/051924 (published as WO 2014/013259) and PCT/GB2013/051928 (published as WO 2014/013262); and in UK Application No. 1318464.3 filed on 18 Oct. 2013. In particular, the one or more helicases are preferably modified to reduce the size of an opening in the polynucleotide binding domain through which in at least one conformational state the polynucleotide can unbind from the helicase. This is disclosed in WO 2014/013260.

The two or more helicases in the series may be separate from one another. The two or more helicases in the series may be brought together by a transmembrane pore as the polynucleotide moves through the pore. The two or more helicases in the series may contact one another.

The two or more helicases are preferably not attached to one another except via the polynucleotide. The two or more helicases are preferably not covalently attached to one another.

The two or more helicases may be attached or covalently attached to one another. The helicases may be attached in any order and using any method. A series of attached helicases may be called a train.

Polynucleotides to which the series of the invention may be attached/bound are discussed in more detail below.

Methods of the Invention

The invention provides a method of controlling the movement of a target polynucleotide. The method comprises contacting the target polynucleotide with a Dda helicase, a modified helicase of the invention or a construct of the invention and thereby controlling the movement of the polynucleotide. The method is preferably carried out with a potential applied across the pore. As discussed in more detail below, the applied potential typically results in the formation of a complex between the pore and the helicase or construct. The applied potential may be a voltage potential. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5.

The invention also provides a method of characterising a target polynucleotide. The method comprises (a) contacting the target polynucleotide with a transmembrane pore and a Dda helicase, a modified helicase of the invention or a construct of the invention such that the helicase or construct controls the movement of the target polynucleotide through the pore. The method also comprises (b) taking one or more measurements as the polynucleotide moves with respect to the pore wherein the measurements are indicative of one or more characteristics of the target polynucleotide and thereby characterising the target polynucleotide.

In all of the methods of the invention, the helicase may be any of those discussed above with reference to the constructs of the invention, including the modified Dda helicases of the invention and Dda helicases which are not modified in accordance with the invention.

Any number of Dda helicases of the invention may be used in these methods. For instance, 1, 2, 3, 4, 5, 6, 7, 8, 9, 10 or more helicases may be used. If two or more Dda helicases of the invention are used, they may be the same or different. Suitable numbers and combinations are discussed above with reference to the series of the invention. These equally apply to the methods of the invention.

If two or more helicases are used, they may be attached to one another. The two or more helicases may be covalently attached to one another. The helicases may be attached in any order and using any method. Preferred helicase constructs for use in the invention are described in International Application Nos. PCT/GB2013/051925 (published as WO 2014/013260); PCT/GB2013/051924 (published as WO 2014/013259) and PCT/GB2013/051928 (published as WO 2014/013262); and in UK Application No. 1318464.3 filed on 18 Oct. 2013.

If two or more helicases are used, they are preferably not attached to one another except via the polynucleotide. The two or more helicases are more preferably not covalently attached to one another.

Steps (a) and (b) are preferably carried out with a potential applied across the pore as discussed above. In some instances, the current passing through the pore as the polynucleotide moves with respect to the pore is used to determine the sequence of the target polynucleotide. This is Strand Sequencing.

The method of the invention is for characterising a target polynucleotide. A polynucleotide is defined above.

The whole or only part of the target polynucleotide may be characterised using this method. The target polynucleotide can be any length. For example, the polynucleotide can be at least 10, at least 50, at least 100, at least 150, at least 200, at least 250, at least 300, at least 400 or at least 500 nucleotide pairs in length. The polynucleotide can be 1000 or more nucleotide pairs, 5000 or more nucleotide pairs in length or 100000 or more nucleotide pairs in length.

The target polynucleotide is present in any suitable sample. The invention is typically carried out on a sample that is known to contain or suspected to contain the target polynucleotide. Alternatively, the invention may be carried out on a sample to confirm the identity of one or more target polynucleotides whose presence in the sample is known or expected.

The sample may be a biological sample. The invention may be carried out in vitro on a sample obtained from or extracted from any organism or microorganism. The organism or microorganism is typically archaeal, prokaryotic or eukaryotic and typically belongs to one of the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well in the membrane along which or into which hydrated ions may flow.

Any transmembrane pore may be used in the invention. The pore may be biological or artificial. Suitable pores include, but are not limited to, protein pores, polynucleotide pores and solid state pores.

Any membrane may be used in accordance with the invention. Suitable membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer.

The amphiphilic layer may be a monolayer or a bilayer. The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Examples. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004127 (published as WO 2009/077734).

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647).

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. Suitable apparatus and conditions are discussed below. The method of the invention is typically carried out in vitro.

The polynucleotide may be coupled to the membrane. This may be done using any known method. If the membrane is an amphiphilic layer, such as a lipid bilayer (as discussed in detail above), the polynucleotide is preferably coupled to the membrane via a polypeptide present in the membrane or a hydrophobic anchor present in the membrane. The hydrophobic anchor is preferably a lipid, fatty acid, sterol, carbon nanotube or amino acid.

The polynucleotide may be coupled directly to the membrane. The polynucleotide is preferably coupled to the membrane via a linker. Preferred linkers include, but are not limited to, polymers, such as polynucleotides, polyethylene glycols (PEGs) and polypeptides. If a polynucleotide is coupled directly to the membrane, then some data will be lost as the characterising run cannot continue to the end of the polynucleotide due to the distance between the membrane and the helicase. If a linker is used, then the polynucleotide can be processed to completion. If a linker is used, the linker may be attached to the polynucleotide at any position. The linker is typically attached to the polynucleotide at the tail polymer.

The coupling may be stable or transient. For certain applications, the transient nature of the coupling is preferred. If a stable coupling molecule were attached directly to either the 5' or 3' end of a polynucleotide, then some data will be lost as the characterising run cannot continue to the end of the polynucleotide due to the distance between the membrane and the helicase's active site. If the coupling is transient, then when the coupled end randomly becomes free of the membrane, then the polynucleotide can be processed to completion. Chemical groups that form stable or transient links with the membrane are discussed in more detail below. The polynucleotide may be transiently coupled to an amphiphilic layer, such as a lipid bilayer using cholesterol or a fatty acyl chain. Any fatty acyl chain having a length of from 6 to 30 carbon atoms, such as hexadecanoic acid, may be used.

In preferred embodiments, the polynucleotide is coupled to an amphiphilic layer. Coupling of polynucleotides to synthetic lipid bilayers has been carried out previously with various different tethering strategies. These are summarised in Table 4 below.

TABLE 4

| Attachment group | Type of coupling | Reference |
|---|---|---|
| Thiol | Stable | Yoshina-Ishii, C. and S. G. Boxer (2003). "Arrays of mobile tethered vesicles on supported lipid bilayers." J Am Chem Soc 125(13): 3696-7. |
| Biotin | Stable | Nikolov, V., R. Lipowsky, et al. (2007). "Behavior of giant vesicles with anchored DNA molecules." Biophys J 92(12): 4356-68 |
| Cholesterol | Transient | Pfeiffer, I. and F. Hook (2004). "Bivalent cholesterol-based coupling of oligonucletides to lipid membrane assemblies." J Am Chem Soc 126(33): 10224-5 |
| Lipid | Stable | van Lengerich, B., R. J. Rawle, et al. "Covalent attachment of lipid vesicles to a fluid-supported bilayer allows observation of DNA-mediated vesicle interactions." Langmuir 26(11): 8666-72 |

Polynucleotides may be functionalized using a modified phosphoramidite in the synthesis reaction, which is easily compatible for the addition of reactive groups, such as thiol, cholesterol, lipid and biotin groups. These different attachment chemistries give a suite of attachment options for polynucleotides. Each different modification group tethers the polynucleotide in a slightly different way and coupling is not always permanent so giving different dwell times for the polynucleotide to the membrane. The advantages of transient coupling are discussed above.

Coupling of polynucleotides can also be achieved by a number of other means provided that a reactive group can be added to the polynucleotide. The addition of reactive groups to either end of DNA has been reported previously. A thiol group can be added to the 5' of ssDNA using polynucleotide kinase and ATPγS (Grant, G. P. and P. Z. Qin (2007). "A facile method for attaching nitroxide spin labels at the 5' terminus of nucleic acids." Nucleic Acids Res 35(10): e77). A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." Anal Biochem 169(2): 376-82).

Alternatively, the reactive group could be considered to be the addition of a short piece of DNA complementary to one already coupled to the membrane, so that attachment can be achieved via hybridisation. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." Proc Natl Acad Sci USA 89(20): 9823-5). Alternatively either ssDNA or dsDNA could be ligated to native dsDNA and then the two strands separated by thermal or chemical denaturation. To native dsDNA, it is possible to add either a piece of ssDNA to one or both of the ends of the duplex, or dsDNA to one or both ends. Then, when the duplex is melted, each single strand will have either a 5' or 3' modification if ssDNA was used for ligation or a modification at the 5' end, the 3' end or both if dsDNA was used for ligation. If the polynucleotide is a synthetic strand, the coupling chemistry can be incorporated during the chemical synthesis of the polynucleotide. For instance, the polynucleotide can be synthesized using a primer with a reactive group attached to it.

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. By using an antisense primer that has a reactive group, such as a cholesterol, thiol, biotin or lipid, each copy of the amplified target DNA will contain a reactive group for coupling.

The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a lipid bilayer, to the other. The transmembrane protein pore allows a polynucleotide, such as DNA or RNA, to be moved through the pore.

The transmembrane protein pore may be a monomer or an oligomer. The pore is preferably made up of several repeating subunits, such as at least 6, at least 7, at least 8 or at least 9 subunits. The pore is preferably made up of 6, 7, 8 or 9 subunits. The pore is preferably a hexameric, heptameric, octameric or nonameric pore. The pore may be a homo-oligomer or a hetero-oligomer.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as Mycobacterium smegmatis porin (Msp), for example MspA, MspB, MspC or MspD, outer membrane porin F (OmpF), outer membrane porin G (OmpG), outer membrane phospholipase A and Neisseria autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) Nucleic Acids Research 12, p387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih.gov/).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. A variant of SEQ ID NO: 2 has the mutation L88N in addition to all the mutations of MS-(B1)8 and is called MS-(B2)8. The pore used in the invention is preferably MS-(B2)8. The further preferred variant comprises the mutations G75S/G77S/L88N/Q126R. The variant of SEQ ID NO: 2 has the mutations G75S/G77S/L88N/Q126R in addition to all the mutations of MS-(B1)8 and is called MS-(B2C)8. The pore used in the invention is preferably MS-(B2)8 or MS-(B2C)8.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 5 below. Where amino acids have similar polarity, this can also be determined by reference to the hydropathy scale for amino acid side chains in Table 6.

TABLE 5

Chemical properties of amino acids

| Ala | aliphatic, hydrophobic, neutral | Met | hydrophobic, neutral |
|---|---|---|---|
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

TABLE 6

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The monomers derived from Msp may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July; 4(7):497-505).

The monomer derived from Msp may be labelled with a revealing label. The revealing label may be any suitable label which allows the pore to be detected. Suitable labels are described above.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with NaBH$_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

The transmembrane protein pore is also preferably derived from α-hemolysin (α-HL). The wild type α-HL pore is formed of seven identical monomers or subunits (i.e. it is heptameric). The sequence of one monomer or subunit of α-hemolysin-NN is shown in SEQ ID NO: 4. The transmembrane protein pore preferably comprises seven monomers each comprising the sequence shown in SEQ ID NO: 4 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ ID NO: 4 form part of a constriction of the barrel or channel of α-HL.

In such embodiments, a pore comprising seven proteins or monomers each comprising the sequence shown in SEQ ID NO: 4 or a variant thereof are preferably used in the method of the invention. The seven proteins may be the same (homo-heptamer) or different (hetero-heptamer).

A variant of SEQ ID NO: 4 is a protein that has an amino acid sequence which varies from that of SEQ ID NO: 4 and which retains its pore forming ability. The ability of a variant to form a pore can be assayed using any method known in the art. For instance, the variant may be inserted into an amphiphilic layer, such as a lipid bilayer, along with other appropriate subunits and its ability to oligomerise to form a pore may be determined. Methods are known in the art for inserting subunits into amphiphilic layers, such as lipid bilayers. Suitable methods are discussed above.

The variant may include modifications that facilitate covalent attachment to or interaction with the helicase or construct. The variant preferably comprises one or more reactive cysteine residues that facilitate attachment to the helicase or construct. For instance, the variant may include a cysteine at one or more of positions 8, 9, 17, 18, 19, 44, 45, 50, 51, 237, 239 and 287 and/or on the amino or carboxy terminus of SEQ ID NO: 4. Preferred variants comprise a substitution of the residue at position 8, 9, 17, 237, 239 and 287 of SEQ ID NO: 4 with cysteine (A8C, T9C, N17C, K237C, S239C or E287C). The variant is preferably any one of the variants described in International Application No. PCT/GB09/001690 (published as WO 2010/004273), PCT/GB09/001679 (published as WO 2010/004265) or PCT/GB10/000133 (published as WO 2010/086603).

The variant may also include modifications that facilitate any interaction with nucleotides.

The variant may be a naturally occurring variant which is expressed naturally by an organism, for instance by a *Staphylococcus* bacterium. Alternatively, the variant may be expressed in vitro or recombinantly by a bacterium such as *Escherichia coli*. Variants also include non-naturally occurring variants produced by recombinant technology. Over the entire length of the amino acid sequence of SEQ ID NO: 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed above.

Amino acid substitutions may be made to the amino acid sequence of SEQ ID NO: 4 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4 may additionally be deleted from the polypeptides described above. Up to 1, 2, 3, 4, 5, 10, 20 or 30 residues may be deleted, or more.

Variants may be fragments of SEQ ID NO: 4. Such fragments retain pore-forming activity. Fragments may be at least 50, 100, 200 or 250 amino acids in length. A fragment preferably comprises the pore-forming domain of SEQ ID NO: 4. Fragments typically include residues 119, 121, 135. 113 and 139 of SEQ ID NO: 4.

One or more amino acids may be alternatively or additionally added to the polypeptides described above. An extension may be provided at the amino terminus or carboxy terminus of the amino acid sequence of SEQ ID NO: 4 or a variant or fragment thereof. The extension may be quite short, for example from 1 to 10 amino acids in length. Alternatively, the extension may be longer, for example up to 50 or 100 amino acids. A carrier protein may be fused to a pore or variant.

As discussed above, a variant of SEQ ID NO: 4 is a subunit that has an amino acid sequence which varies from that of SEQ ID NO: 4 and which retains its ability to form a pore. A variant typically contains the regions of SEQ ID NO: 4 that are responsible for pore formation. The pore forming ability of α-HL, which contains a β-barrel, is provided by β-strands in each subunit. A variant of SEQ ID NO: 4 typically comprises the regions in SEQ ID NO: 4 that form β-strands. The amino acids of SEQ ID NO: 4 that form β-strands are discussed above. One or more modifications can be made to the regions of SEQ ID NO: 4 that form 1-strands as long as the resulting variant retains its ability to form a pore. Specific modifications that can be made to the β-strand regions of SEQ ID NO: 4 are discussed above.

A variant of SEQ ID NO: 4 preferably includes one or more modifications, such as substitutions, additions or deletions, within its α-helices and/or loop regions. Amino acids that form α-helices and loops are discussed above.

The variant may be modified to assist its identification or purification as discussed above.

Pores derived from α-HL can be made as discussed above with reference to pores derived from Msp.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The transmembrane protein pore may be chemically modified by the attachment of any molecule. For instance, the pore may be chemically modified by attachment of a dye or a fluorophore.

Any number of the monomers in the pore may be chemically modified. One or more, such as 2, 3, 4, 5, 6, 7, 8, 9 or 10, of the monomers is preferably chemically modified as discussed above.

The reactivity of cysteine residues may be enhanced by modification of the adjacent residues. For instance, the basic groups of flanking arginine, histidine or lysine residues will change the pKa of the cysteines thiol group to that of the more reactive S group. The reactivity of cysteine residues may be protected by thiol protective groups such as dTNB. These may be reacted with one or more cysteine residues of the pore before a linker is attached.

The molecule (with which the pore is chemically modified) may be attached directly to the pore or attached via a linker as disclosed in International Application Nos. PCT/GB09/001690 (published as WO 2010/004273), PCT/GB09/001679 (published as WO 2010/004265) or PCT/GB10/000133 (published as WO 2010/086603).

The helicase or construct may be covalently attached to the pore. The helicase or construct is preferably not covalently attached to the pore. The application of a voltage to the pore and helicase or construct typically results in the formation of a sensor that is capable of sequencing target polynucleotides. This is discussed in more detail below.

Any of the proteins described herein, i.e. the helicases, the transmembrane protein pores or constructs, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the helicase, pore or construct. An example of this would be to react a gel-shift reagent to a cysteine engineered on the outside of the pore. This has been demonstrated as a method for separating hemolysin hetero-oligomers (Chem Biol. 1997 July; 4(7):497-505).

The helicase, pore or construct may be labelled with a revealing label. The revealing label may be any suitable label which allows the pore to be detected. Suitable labels include, but are not limited to, fluorescent molecules, radio-isotopes, e.g. $^{125}$I, $^{35}$S, enzymes, antibodies, antigens, polynucleotides and ligands such as biotin.

Proteins may be made synthetically or by recombinant means. For example, the helicase, pore or construct may be synthesized by in vitro translation and transcription (IVTT). The amino acid sequence of the helicase, pore or construct may be modified to include non-naturally occurring amino acids or to increase the stability of the protein. When a protein is produced by synthetic means, such amino acids may be introduced during production. The helicase, pore or construct may also be altered following either synthetic or recombinant production.

The helicase, pore or construct may also be produced using D-amino acids. For instance, the pore or construct may comprise a mixture of L-amino acids and D-amino acids. This is conventional in the art for producing such proteins or peptides.

The helicase, pore or construct may also contain other non-specific modifications as long as they do not interfere with pore formation or helicase or construct function. A number of non-specific side chain modifications are known in the art and may be made to the side chains of the protein(s). Such modifications include, for example, reductive alkylation of amino acids by reaction with an aldehyde followed by reduction with NaBH$_4$, amidination with methylacetimidate or acylation with acetic anhydride.

The helicase, pore and construct can be produced using standard methods known in the art. Polynucleotide sequences encoding a helicase, pore or construct may be derived and replicated using standard methods in the art. Polynucleotide sequences encoding a helicase, pore or construct may be expressed in a bacterial host cell using standard techniques in the art. The helicase, pore and/or construct may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, NY.

The helicase, pore and/or construct may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

The method of the invention involves measuring one or more characteristics of the target polynucleotide. The method may involve measuring two, three, four or five or more characteristics of the target polynucleotide. The one or more characteristics are preferably selected from (i) the length of the target polynucleotide, (ii) the identity of the target polynucleotide, (iii) the sequence of the target polynucleotide, (iv) the secondary structure of the target polynucleotide and (v) whether or not the target polynucleotide is modified. Any combination of (i) to (v) may be measured in accordance with the invention.

For (i), the length of the polynucleotide may be measured for example by determining the number of interactions between the target polynucleotide and the pore or the duration of interaction between the target polynucleotide and the pore.

For (ii), the identity of the polynucleotide may be measured in a number of ways. The identity of the polynucleotide may be measured in conjunction with measurement of the sequence of the target polynucleotide or without measurement of the sequence of the target polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the target polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the target polynucleotide is modified by methylation, by oxidation, by damage, with one or more proteins or with one or more labels, tags or spacers. Specific modifications will result in specific interactions with the pore which can be measured using the methods described below. For instance, methylcytosine may be distinguished from cytosine on the basis of the current flowing through the pore during its interaction with each nucleotide.

A variety of different types of measurements may be made. This includes without limitation: electrical measurements and optical measurements. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559.

In a preferred embodiment, the method comprises:
(a) contacting the target polynucleotide with a transmembrane pore and a helicase of the invention or a construct of the invention such that the target polynucleotide moves through the pore and the helicase or construct controls the movement of the target polynucleotide through the pore; and
(b) measuring the current passing through the pore as the polynucleotide moves with respect to the pore wherein the current is indicative of one or more characteristics of the target polynucleotide and thereby characterising the target polynucleotide.

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in International Application No. PCT/GB08/000562 (WO 2008/102120).

The methods may involve measuring the current passing through the pore as the polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the polynucleotide moves with respect to the pore. Suitable conditions for measuring ionic currents through transmembrane protein pores are known in the art and disclosed in the Examples. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. Hel308, XPD, RecD and TraI helicases surprisingly work under high salt concentrations. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffer include, but are not limited to, HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. 10 to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

The method may be carried out in the presence of free nucleotides or free nucleotide analogues and/or an enzyme cofactor that facilitates the action of the helicase or construct. The method may also be carried out in the absence of free nucleotides or free nucleotide analogues and in the absence of an enzyme cofactor. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the helicase or construct to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

The target polynucleotide may be contacted with the helicase or construct and the pore in any order. In is preferred that, when the target polynucleotide is contacted with the helicase or construct and the pore, the target polynucleotide firstly forms a complex with the helicase or construct. When the voltage is applied across the pore, the target polynucleotide/helicase or construct complex then forms a complex with the pore and controls the movement of the polynucleotide through the pore.

Other Methods

The invention also provides a method of forming a sensor for characterising a target polynucleotide. The method comprises forming a complex between a pore and a Dda helicase, a helicase of the invention or a construct of the invention. The helicase may be any of those discussed above with reference to the constructs of the invention, including the helicases of the invention and helicases which are not modified in accordance with the invention. Any number and combination of Dda helicases of the invention discussed above with reference to the series and methods of the invention may be used.

The complex may be formed by contacting the pore and the helicase or construct in the presence of the target polynucleotide and then applying a potential across the pore. The applied potential may be a chemical potential or a voltage potential as described above. Alternatively, the complex may be formed by covalently attaching the pore to the helicase or construct. Methods for covalent attachment are known in the art and disclosed, for example, in International Application Nos. PCT/GB09/001679 (published as WO 2010/004265) and PCT/GB10/000133 (published as WO 2010/086603). The complex is a sensor for characterising the target polynucleotide. The method preferably comprises forming a complex between a pore derived from Msp and a helicase of the invention or a construct of the invention. Any of the embodiments discussed above with reference to the methods of the invention equally apply to this method. The invention also provides a sensor produced using the method of the invention.

Kits

The present invention also provides a kit for characterising a target polynucleotide. The kit comprises (a) a pore and (b) a Dda helicase, a helicase of the invention or a construct of the invention. Any of the embodiments discussed above with reference to the method of the invention equally apply to the kits. The helicase may be any of those discussed above with reference to the constructs of the invention, including the helicases of the invention and helicases which are not modified in accordance with the invention. The kit may comprise any number and combination of Dda helicases of the invention discussed above with reference to the series and methods of the invention.

The kit may further comprise the components of a membrane, such as the phospholipids needed to form an amphiphilic layer, such as a lipid bilayer.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

Apparatus

The invention also provides an apparatus for characterising a target polynucleotide. The apparatus comprises a plurality of pores and a plurality of Dda helicases, a plurality of helicases of the invention or a plurality of constructs of the invention. The apparatus preferably further comprises instructions for carrying out the method of the invention. The apparatus may be any conventional apparatus for polynucleotide analysis, such as an array or a chip. Any of the embodiments discussed above with reference to the methods of the invention are equally applicable to the apparatus of the invention. The helicase may be any of those discussed above with reference to the constructs of the invention, including the helicases of the invention and helicases which are not modified in accordance with the invention. The apparatus may comprise any number and combination of Dda helicases of the invention discussed above with reference to the series and methods of the invention.

The apparatus is preferably set up to carry out the method of the invention.

The apparatus preferably comprises:
a sensor device that is capable of supporting the plurality of pores and being operable to perform polynucleotide characterisation using the pores and helicases or constructs; and
at least one port for delivery of the material for performing the characterisation.

Alternatively, the apparatus preferably comprises:
a sensor device that is capable of supporting the plurality of pores and being operable to perform polynucleotide characterisation using the pores and helicases or constructs; and
at least one reservoir for holding material for performing the characterisation.

The apparatus more preferably comprises:
a sensor device that is capable of supporting the membrane and plurality of pores and being operable to perform polynucleotide characterising using the pores and helicases or constructs;
at least one reservoir for holding material for performing the characterising;
a fluidics system configured to controllably supply material from the at least one reservoir to the sensor device; and
one or more containers for receiving respective samples, the fluidics system being configured to supply the samples selectively from one or more containers to the sensor device. The apparatus may be any of those described in International Application No. No. PCT/GB08/004127 (published as WO 2009/077734), PCT/GB10/000789 (published as WO 2010/122293), International Application No. PCT/GB10/002206 (published as WO 2011/067559) or International Application No. PCT/US99/25679 (published as WO 00/28312).

Methods of Producing Helicases of the Invention

The invention also provides methods of producing a modified helicase of the invention. The method comprises providing a Dda helicase and modifying the helicase to form a modified helicase of the invention.

The method preferably further comprises determining whether or not the helicase is capable of controlling the movement of a polynucleotide. Assays for doing this are described above. If the movement of a polynucleotide can be controlled, the helicase has been modified correctly and a helicase of the invention has been produced. If the movement of a polynucleotide cannot be controlled, a helicase of the invention has not been produced.

Methods of Producing Constructs of the Invention

The invention also provides a method of producing a construct of the invention. The method comprises attaching, preferably covalently attaching, a Dda helicase or a helicase of the invention to an additional polynucleotide binding moiety. Any of the helicases and moieties discussed above can be used in the methods. The site of and method of covalent attachment are selected as discussed above.

The method preferably further comprises determining whether or not the construct is capable of controlling the movement of a polynucleotide. Assays for doing this are described above. If the movement of a polynucleotide can be controlled, the helicase and moiety have been attached correctly and a construct of the invention has been produced. If the movement of a polynucleotide cannot be controlled, a construct of the invention has not been produced.

The following Examples illustrate the invention.

EXAMPLES

Example 1

This example describes how a T4 Dda E94C/A360C (SEQ ID NO: 8 with mutations E94C/A360C and then (ΔM1)G1G2) controlled the movement of intact DNA strands through a single MspA nanopore (MS(B1-G75S/G77S/L88N/Q126R)8 MspA (MspA B2C) (SEQ ID NO: 2 with mutations G75S/G77S/L88N/Q126R).

Materials and Methods

Prior to setting up the experiment, the Lambda DNA construct (SEQ ID NO: 60 attached by its 3' end to four iSpC3 spacers which are attached to the 5' end of SEQ ID NO: 61 which is attached at its 3' end to four iSPC3 spacers which are attached to the 5' end of SEQ ID NO: 62, the SEQ ID NO: 61 region of this construct is hybridised to SEQ ID NO: 63 (which has a 3' cholesterol tether) see FIG. 8 for a diagram of the construct) and T4 Dda E94C/A360C were pre-incubated together for 15 minutes at 23° C. in buffer (20 mM CAPS, pH 10.0, 500 mM NaCl, 5% Glycerol, 2 mM DTT).

Electrical measurements were acquired at 20° C. (by placing the experimental system on a cooler plate) from single MspA nanopores (MspA B2C) inserted in block co-polymer in buffer (600 mM KCl, 25 mM potassium phosphate, 75 mM Potassium Ferrocyanide (II), 25 mM Potassium ferricyanide (III), pH 8). After achieving a single pore inserted in the block co-polymer, then buffer (1 mL, 600 mM KCl, 25 mM potassium phosphate, 75 mM Potassium Ferrocyanide (II), 25 mM Potassium ferricyanide (III), pH 8) was flowed through the system to remove any excess MspA nanopores (MspA B2C) and finally experimental buffer was flowed into the system (2 mL 960 mM KCl, 25 mM potassium phosphate, 3 mM Potassium Ferrocyanide (II), 1 mM Potassium ferricyanide (III), pH 8). $MgCl_2$ (10 mM final concentration) and ATP (1 mM final concentration) were mixed together with buffer (960 mM KCl, 25 mM potassium phosphate, 3 mM Potassium Ferrocyanide (II), 1 mM Potassium ferricyanide (III), pH 8) and then added to the Lambda DNA construct (0.2 nM final concentration), T4 Dda E94C/A360C (10 nM final concentration) buffer (20 mM CAPS, pH 10.0, 500 mM NaCl, 5% Glycerol, 2 mM DTT) pre-mix. The pre-mix was then added to the single nanopore experimental system. Experiments were carried out for four hours following a potential flip process (+100 mV for 2 s, then 0 V for 2 s, then −120 mV for 14500s applied at the cis side) and helicase-controlled DNA movement was monitored.

Results and Discussion

Helicase controlled DNA movement was observed for the Lambda DNA construct, an example of a helicase-controlled DNA movement is shown in FIG. 1. The helicase-controlled DNA movement was 5170 seconds long and corresponded to the translocation of approximately 30 kB of the lambda construct through the nanopore. FIG. 2 shows zoomed in regions of the beginning (a) and end (b) of the helicase-controlled DNA movement.

Example 2

This example describes how a T4 Dda E94C/A360C exhibited tight binding to both linear (SEQ ID NO: 64) and circular (SEQ ID NO: 65) single-stranded DNA. The tight binding of the enzyme was measured using a fluorescence anisotropy-based assay.

Materials and Methods

Two custom fluorescent substrates were used to assess the ability of T4 Dda E94C/A360C helicase to bind to linear (SEQ ID NO: 64) and circular (SEQ ID NO: 65) single-stranded DNA. The 44 nt linear single-stranded DNA substrate (1 nM final, SEQ ID NO: 64) had a carboxyfluorescein (FAM) attached to the thymine base at position 37 in SEQ ID NO: 64. The 75 nt circular single-stranded DNA substrate (1 nM final, SEQ ID NO: 65) had a carboxyfluorescein (FAM) attached to a thymine base in SEQ ID NO: 65. As the helicase bound to either fluorescent substrate in a buffered solution (25 mM potassium phosphate, 151.5 mM KCl, pH8.0, 10 mM $MgCl_2$), the fluorescence anisotropy (a property relating to the speed of tumbling of the DNA substrate in solution) increased. The lower the amount of helicase needed to effect an increase in anisotropy, the tighter the binding affinity between the DNA and helicase (FIG. 3).

T4 Dda E94C/A360C was buffer exchanged into the binding buffer (25 mM potassium phosphate, 151.5 mM KCl, pH8.0, 10 mM $MgCl_2$) and then serially diluted over a concentration range of 0.02 nM to 750 nM. Each sample concentration was then mixed with linear or circular single-stranded DNA (1 nM of SEQ ID NO: 64 or 65) giving a final concentration range of T4 Dda E94C/A360C of 0.01 nM to 375 nM and the fluorescence anisotropy assessed over the course of 60 min at 25° C.

Results and Discussion

FIGS. 4 and 5 show the fluorescence binding assay data collected for the linear and circular single-stranded DNA binding experiments. FIG. 4 shows the change in anisotropy of the linear and circular single-stranded DNA oligonucleotides (SEQ ID NO: 64 or 65) with increasing amounts of T4 Dda E94C/A360C at the end of a 60 minute incubation period. FIG. 5 shows the equilibrium dissociation constants ($K_d$) for T4 Dda E94C/A360C binding to linear or circular single-stranded DNA after a 60 minute incubation, obtained through fitting one phase dissociation binding curves through the data shown in FIG. 4 using Graphpad Prism software (y-axis label dissociation constant Kd (nM), x-axis label Ref. Number, where Ref. Number 1 corresponded to the linear single-stranded DNA oligonucleotide and Ref. Number 2 corresponded to the circular single-stranded DNA oligonucleotide).

The T4 Dda E94C/A360C helicase was found to exhibit tight binding affinity (sub 15 nM binding affinity) to both circular and linear single-stranded DNA (see FIGS. 4 and 5).

Example 3

This example compared the helicase-controlled DNA movement of T4 Dda E94C/A360C with that of TrwC Cba (SEQ ID NO: 66). Both helicases move along the polynucleotide in a 5' to 3' direction. When the 5'end of the polynucleotide (the end away from which the helicases move) is captured by the pore, the helicases work with the direction of the field resulting from the applied potential and move the threaded polynucleotide into the pore and into the trans chamber. T4 Dda was observed to control the translocation of DNA through the nanopore smoothly without the DNA stepping back (i.e. towards its 3'end relative the pore), whereas TrwC Cba resulted in stepping back of the DNA between states as it controlled translocation of the DNA. In this Example, stepping back involves the DNA moving backwards relative to the the pore (i.e. towards its 5' and away from it 3' end in this Example). This phenomenon was called slipping in UK Application Nos. 1318464.3 and 1404718.7.

Materials and Methods

Prior to setting up the experiments, the DNA strand (3 uL of 20 nM, SEQ ID NO: 67 attached by its 3' end to four iSpC3 spacers which are attached to the 5' end of SEQ ID NO: 61 which is attached at its 3' end to four 5-nitroindoles the last of which is attached to the 5' end of SEQ ID NO: 68, in addition SEQ ID NO: 63 is hybridised to SEQ ID NO: 61) and TrwC Cba (SEQ ID NO: 66, 22.5 uL of 13.3 μM) were pre-incubated together for over an hour at room temperature in buffer (50 mM CAPS, pH 10.0, 100 mM NaCl). In a separate tube, 3 μL of MgCl2 (1 M) and 3 μL of dTTP (100 mM) were mixed with 260 μL of buffer (960 mM KCl, 3 mM potassium ferrocyanide (II), 1 mM potassium ferricyanide (III) and 25 mM potassium phosphate pH 8.0). After the hour pre-incubation, the DNA enzyme mix was added to MgCl2/dTTP mix giving final concentrations of reagents as follows DNA strand (0.2 nM), TrwC Cba (SEQ ID NO: 66, 1 M), MgCl2 (10 mM), dTTP (1 mM) in buffer (960 mM KCl, 3 mM potassium ferrocyanide (II), 1 mM potassium ferricyanide (III) and 25 mM potassium phosphate pH 8.0).

Prior to setting up the experiments, the DNA strand (0.2 uL of 300 nM, SEQ ID NO: 67 attached by its 3' end to four iSpC3 spacers which are attached to the 5' end of SEQ ID NO: 61 which is attached at its 3' end to four 5-nitroindoles the last of which is attached to the 5' end of SEQ ID NO: 68, in addition SEQ ID NO: 63 is hybridised to SEQ ID NO: 61) and T4 Dda E94C/A360C (0.1 uL of 3300 nM) were pre-incubated together for 15 minutes at room temperature. In a separate tube, MgCl2 (3 uL of 1M) and ATP (3 uL of 100 mM) were mixed with 294 μL of buffer (960 mM KCl, 3 mM potassium ferrocyanide (II), 1 mM potassium ferricyanide (III) and 25 mM potassium phosphate, pH 8.0). After the 15 minute pre-incubation, the DNA enzyme mix was added to MgCl2/ATP mix giving final concentrations of reagents as follows DNA strand (0.2 nM), T4 Dda E94C/A360C (1 nM), MgCl2 (10 mM), ATP (1 mM) in buffer (960 mM KCl, 3 mM potassium ferrocyanide (II), 1 mM potassium ferricyanide (III) and 25 mM potassium phosphate pH 8.0).

Electrical measurements were acquired at 20° C. (by placing the experimental system on a cooler plate) from single MspA nanopores (MspA B2C) inserted in block co-polymer in buffer (600 mM KCl, 25 mM potassium phosphate, 75 mM Potassium Ferrocyanide (II), 25 mM Potassium ferricyanide (III), pH 8). After achieving a single pore inserted in the block co-polymer, then buffer (3 mL, 960 mM KCl, 25 mM potassium phosphate, 3 mM Potassium Ferrocyanide (II), 1 mM Potassium ferricyanide (III), pH 8) was flowed through the system to remove any excess MspA nanopores (MspA B2C). Either the TrwC Cba (SEQ ID NO: 66) or the T4 Dda E94C/A360C pre-mix was then added to the single nanopore experimental system. Each experiment was carried out for 6 hours at a holding potential of −120 mV) and helicase-controlled DNA movement was monitored.

Results and Discussion

FIGS. 6 and 7 show helicase controlled DNA movements for the TrwC Cba (SEQ ID NO: 66) and T4 Dda E94C/A360C respectively. The upper trace of FIG. 6 shows two TrwC Cba (SEQ ID NO: 66) helicase controlled DNA movements (labelled 1 and 2) and the lower section shows zoomed in region X. The upper trace of FIG. 7 shows three T4 Dda E94C/A360C helicase controlled DNA movements (labelled 1, 2 and 3) and the lower section shows zoomed in region X. The Trwc Cba helicase controlled the movement of the DNA strand through the nanopore and the current changed as the DNA translocated. In the lower trace a number of current levels were labelled a to k which corresponded to consecutive current levels produced when the section of the DNA strand translocated through the pore. It was clear from zoomed in region X in FIG. 6 that the DNA stepped back so that levels corresponding to b, c, h and i were observed several times. Whereas, FIG. 7 lower trace shows that the T4 Dda E94C/A360C helicase controlled the movement of DNA through a nanopore such that stepping back was not observed and a single current level which corresponded to consecutive current levels a to k was observed. It was advantageous to have an enzyme which did not allow stepping back of the DNA strand as this meant it was much easier to map the changes in current to the sequence of the DNA strand when the enzyme moved in one direction along the strand. This made T4 Dda E94C/A360C an improved enzyme for DNA translocation when compared to TrwC Cba (SEQ ID NO: 66).

Example 4

This example describes how T4 Dda E94C/A360C, T4 Dda E94C/A360C/C109A/C136A (SEQ ID NO: 8 with mutations E94C/A360C/C109A/C136A and then (ΔM1) G1G2) and T4 Dda E94C/A360C/C114A/C171A/C421D (SEQ ID NO: 8 with mutations E94C/A360C/C114A/C171A/C421D and then (ΔM1)G1G2) controlled the movement of intact DNA strands through a single MspA nanopore. The helicase controlled movement speed of both region 1 and region 2 of the lambda DNA construct (shown in FIG. 8) was observed to decrease overtime for T4 Dda E94C/A360C and T4 Dda E94C/A360C/C114A/C171A/C421D. However, T4 Dda E94C/A360C/C109A/C136A exhibited improved helicase controlled DNA movement in comparison as the speed of movement remained high and fairly constant during the entire experimental run.

Materials and Methods

Prior to setting up the experiment, the DNA construct X (5.2 μL, 25 nM, SEQ ID NO: 67 attached by its 3' end to four iSpC3 spacers which are attached to the 5' end of SEQ ID NO: 61 which is attached at its 3' end to four 5-nitroindoles spacers which are attached to the 5' end of SEQ ID NO: 69, the SEQ ID NO: 61 region of this construct is hybridised to SEQ ID NO: 63 (which has a 3' cholesterol tether) this is a similar construct as shown in FIG. 8 except the region labelled A corresponds to SEQ ID NO: 67 and the region labelled E corresponds to SEQ ID NO: 69) in buffer (in 50 mM NaCl, 10 mM Tris pH7.5) was pre-incubated for 5 minutes at ambient temperature with either T4 Dda E94C/A360C, T4 Dda E94C/A360C/C109A/C136A or T4 Dda E94C/A360C/C114A/C171A/C421D in buffer (5.2 μL, 250 nM in 253 mM KCl, 50 mM potassium phosphate pH 8.0 2 mM EDTA). TMAD (2.6 μL, 500 μM) was then added to the DNA/enzyme pre-mix and incubated for a further 5 minutes. Finally, buffer (1241.5 μL, 25 mM potassium phosphate, 150 mM potassium ferrocyanide (II) and 150 mM potassium ferricyanide (III), pH 8.0) MgCl2 (13 μL, 1M) and ATP (32.5 μL, 100 mM) were added to the pre-mix.

Electrical measurements were acquired from single MspA nanopores inserted in block co-polymer in buffer (25 mM potassium phosphate, 150 mM potassium ferrocyanide (II), 150 mM potassium ferricyanide (III)) at a peltier temperature of 28° C. After achieving a single pore inserted in the block co-polymer, then buffer (2 mL, 25 mM potassium phosphate pH 8.0, 150 mM potassium ferrocyanide (II) and 150 mM potassium ferricyanide (III)) was flowed through the system to remove any excess MspA nanopores. The enzyme (either T4 Dda E94C/A360C, T4 Dda E94C/A360C/C109A/C136A or T4 Dda E94C/A360C/C114A/C421D (1 nM final concentration)), DNA (0.1 nM final concentration), fuel (MgCl2 10 nM final concentration, ATP 2.5 mM final concentration) pre-mix was then added to the single nanopore experimental system. Each experiment was carried out for 6 hours at a holding potential of 120 mV with potential flicks every hour with an applied potential of −120 mV and helicase-controlled DNA movement was monitored.

Results and Discussion

Helicase controlled DNA movement was observed for DNA construct X, with all mutant helicases investigated (T4 Dda E94C/A360C, T4 Dda E94C/A360C/C109A/C136A or T4 Dda E94C/A360C/C114A/C171A/C421D). Examples of T4 Dda E94C/A360C/C109A/C136A and T4 Dda E94C/A360C/C114A/C171A/C421D helicase-controlled DNA movements are shown in FIGS. 9 and 10 respectively.

The helicase controlled DNA movement speed was monitored through both region 1 and the region 2 of the lambda DNA construct X. For T4 Dda E94C/A360C and T4 Dda E94C/A360C/C114A/C171A/C421D the number of helicase controlled DNA movements per second was found to gradually decrease over the seven hour run time for both region 1 and 2 (See FIG. 11 for T4 Dda E94C/A360C and FIG. 12 for T4 Dda E94C/A360C/C114A/C171A/C421D). However, the T4 Dda E94C/A360C/C109A/C136A mutant helicase observed only a slight decrease in the number of helicase controlled DNA movements per second over the 7 hour experimental run for both region 1 and region 2 (see FIG. 13). The T4 Dda E94C/A360C/C109A/C136A mutant therefore showed improved helicase controlled DNA movement as the speed of movement remained high and fairly constant during the entire experimental run. This allowed increased throughput in comparison to the T4 Dda E94C/A360C which exhibited a gradual reduction in speed over time.

Example 5

This example describes how a T4 Dda E94C/C109A/C136A/A360C/W378A (SEQ ID NO: 8 with mutations E94C/C109A/C136A/A360C/W378A and then (ΔM1) G1G2) helicase can control the movement of intact DNA construct Z strands (shown in FIG. 14) through a single MspA nanopore.

Materials and Methods

Prior to setting up the experiment, the DNA construct Z (see FIG. 8 for a diagram of the construct and sequences, 1.2 µL) and T4 Dda E94C/C109A/C136A/A360C/W378A (2.84 µL) were pre-incubated together for 5 minutes at 23° C. in buffer (151 mM KCl, 25 mM potassium phosphate pH 8, 1 mM EDTA, 5% Glycerol). TMAD (500 µM, 0.92 µL) was added to the DNA enzyme mix and incubated at 23° C. for a further five minutes. Finally, buffer (282 µL of 500 mM KCl, 25 mM potassium phosphate pH 8), ATP (final concentration of 2 mM) and MgCL2 (final concentration 2 mM) were added to the mixture.

Electrical measurements were acquired as described in Example 1 using MspA nanopores inserted in block co-polymer in buffer (500 mM KCl, 25 mM potassium phosphate, pH 8). The pre-mix was added to the single nanopore experimental system and the experiment run at a holding potential of −120 mV for 6 hours (with potential flips to +60 mV for 2 seconds) and helicase-controlled DNA movement monitored.

Results and Discussion

Helicase controlled DNA movement was observed for DNA construct Z, an example of a helicase-controlled DNA movement is shown in FIG. 15. FIG. 16 shows the beginning of the helicase-controlled DNA movement in trace (A), shows a zoomed in region of trace A in trace (B) and shows the end of the helicase controlled DNA movement in trace (C).

Example 6

This example compared the use of a single T4 Dda-E94C/A360C or Ta Dda E94C/C109A/C136A/A360C to two T4 Dda E94C/A360C (SEQ ID NO: 24 with mutations E94C/A360C) or two T4 Dda E94C/C109A/C136A/A360C (SEQ ID NO: 24 with mutations E94C/C109A/C136A/A360C) helicases in order to control the movement of DNA construct X (shown in FIG. 17) through an MspA nanopore. When two helicases were used to control the movement of the construct through the nanopore then improved movement was observed in comparison to when the movement was controlled by a single helicase.

Materials and Methods

Prior to setting up the experiment, DNA construct X (see FIG. 17 for diagram and sequences used in construct X, final concentration added to the nanopore system 0.1 nM) was pre-incubated at room temperature for five minutes with T4 Dda E94C/A360C (final concentration added to the nanopore system 1 nM, SEQ ID NO: 24 with mutations E94C/A360C) or T4 Dda E94C/C109A/C136A/A360C (final concentration added to the nanopore system 1 nM, SEQ ID NO: 24 with mutations E94C/C109A/C136A/A360C, which was provided in buffer (253 mM KCl, 50 mM potassium phosphate, pH 8.0, 2 mM EDTA)). After five minutes, TMAD (1 µM final concentration added to the nanopore system) was added to the pre-mix and the mixture incubated for a further 5 minutes. Finally, MgCl2 (2 mM final premix concentration), ATP (2 mM final premix concentration) and buffer (25 mM potassium phosphate and 500 mM KCl pH 8.0) were added to the pre-mix.

Electrical measurements were acquired from single MspA nanopores inserted in block co-polymer in buffer (25 mM potassium phosphate, 150 mM potassium ferrocyanide (II), 150 mM potassium ferricyanide (III), pH 8.0). After achieving a single pore inserted in the block co-polymer, then buffer (2 mL, 25 mM potassium phosphate pH 8.0, 150 mM potassium ferrocyanide (II) and 150 mM potassium ferricyanide (III)) was flowed through the system to remove any excess MspA nanopores. The enzyme (T4 Dda E94C/A360C or T4 Dda E94C/C109A/C136A/A360C, 1 nM final concentration), DNA construct X (0.1 nM final concentration), fuel (MgCl2 2 mM final concentration, ATP 2 mM final concentration) pre-mix (300 µL total) was then flowed into the single nanopore experimental system and the experiment run at a holding potential of 120 mV for 6 hours and helicase-controlled DNA movement monitored.

Results

Figure 18A:
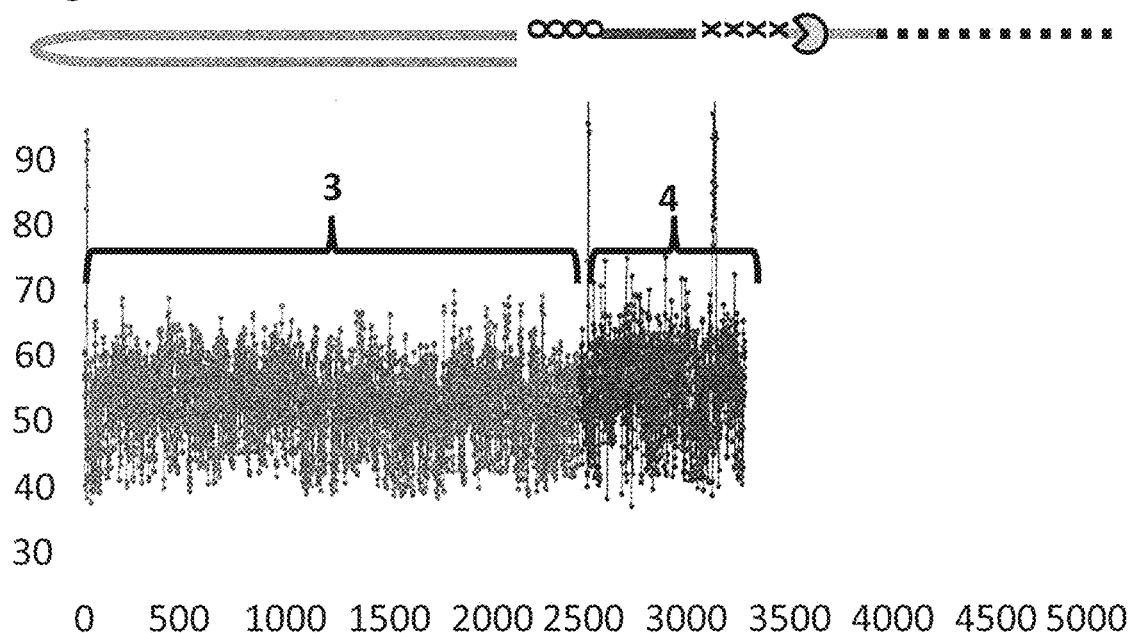
Figure 18B:
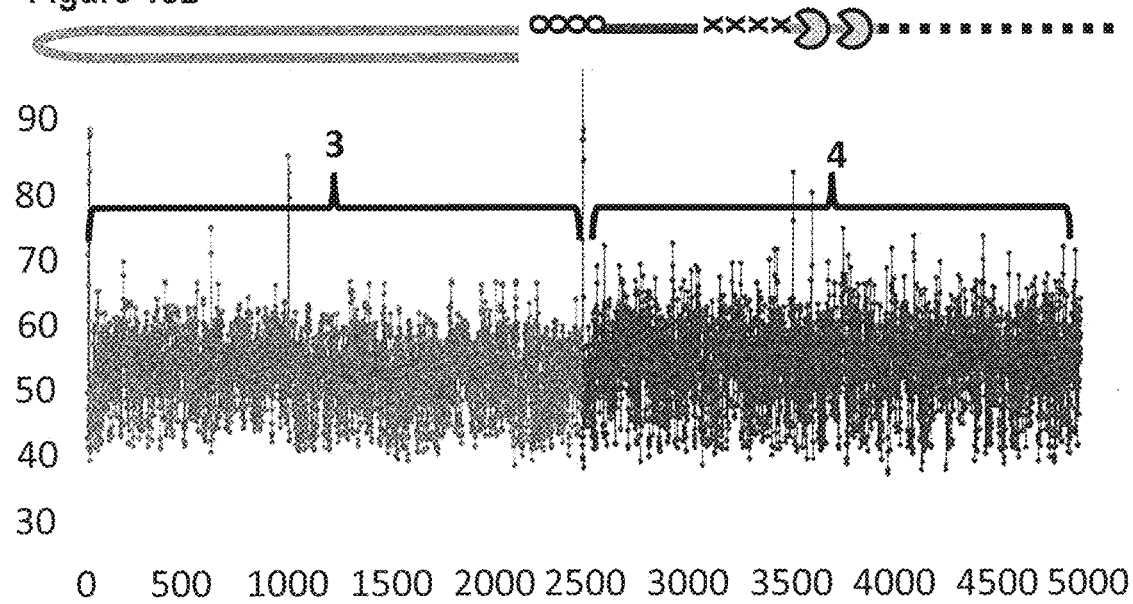

Helicase controlled DNA movement was observed for DNA construct X (FIG. 17) using T4 Dda E94C/A360C and T4 Dda E94C/C109A/C136A/A360C (see FIGS. 18A and 18B respectively). When a single enzyme was bound to DNA construct X (movement index shown in FIG. 18A), then helicase controlled DNA movement through the nanopore was observed for regions 3 and 4 (see FIG. 18). Region 3 moved through the pore in a controlled manner in which it was possible to observe a movement index (see FIG. 18's figure legend for description of movement index) for the region which was plotted in FIG. 18A. However, when region 4 translocated through the nanopore, the movement index plotted in FIG. 18A showed many less points than that produced for region 3. As region 3 and 4 were approximately the same length, the movement index observed for each region would have been expected to have had approximately the same number of points. This meant that the movement control of region 4 provided by a single enzyme (T4 Dda-E94C/A360C) resulted in less points and therefore less information was obtained for region 4 in comparison to region 3. Less information was obtained owing to the enzyme movement not being as consistent when region 4 was translocated through the nanopore (e.g. the DNA slipped forward along sections of region 4) that meant sections of DNA sequence were missed.

In this Example, the helicases move along the polynucleotide in a 5' to 3' direction. When the 5'end of the polynucleotide (the end away from which the helicases move) is captured by the pore, the helicases work with the direction of the field resulting from the applied potential and move the threaded polynucleotide into the pore and into the trans chamber. In this Example, slipping forward involves the DNA moving forwards relative to the the pore (i.e. towards its 3' and away from it 5' end in this Example) at least 4 consecutive nucleotides and typically more than 10 consecutive nucleotides. Slipping forward may involve movement forward of 100 consecutive nucleotides or more and this may happen more than once in each strand. This phenomenon was called skipping and slipping in UK Application Nos. 1406151.9.

FIG. 18B shows the movement index produced when the movement of DNA construct X (regions 3 and 4) was controlled using a "series" of enzymes, in this case two T4 Dda-E94C/A360C enzymes. The movement index of region 3 of DNA construct X was similar to that observed for the single enzyme. However, when region 4 translocated through the nanopore under the control of two enzymes then the DNA movement index was significantly different from that observed when a single T4 Dda-E94C/A360C helicase controlled the movement. A similar movement index was observed for region 4 as for region 3 when the movement was controlled using two T4 Dda-E94C/A360C enzymes, with both regions having approximately the same number of points. This illustrated that improved helicase-controlled DNA movement was observed when two T4 Dda-E94C/A360C enzymes in a "series" were used to control movement. This was because a similar amount of information was obtained for region 4 as region 3, whereas movement controlled using a single enzyme resulted in less information for region 4 than region 3. More information was obtained because the series of helicases resulted in more consistent movement of the DNA (e.g. slower movement or less slipping forward of the DNA region labelled 4). This meant that a series of T4 Dda E94C/A360C enzymes could be used to improve sequencing of a strand of DNA.

Figure 19A:
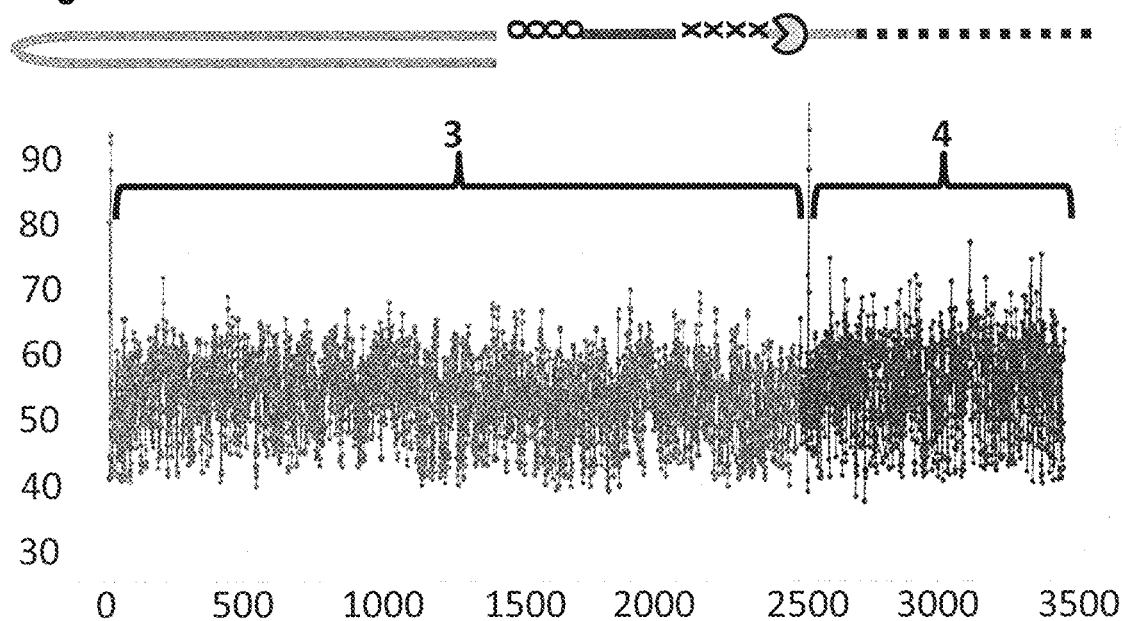
Figure 19B:
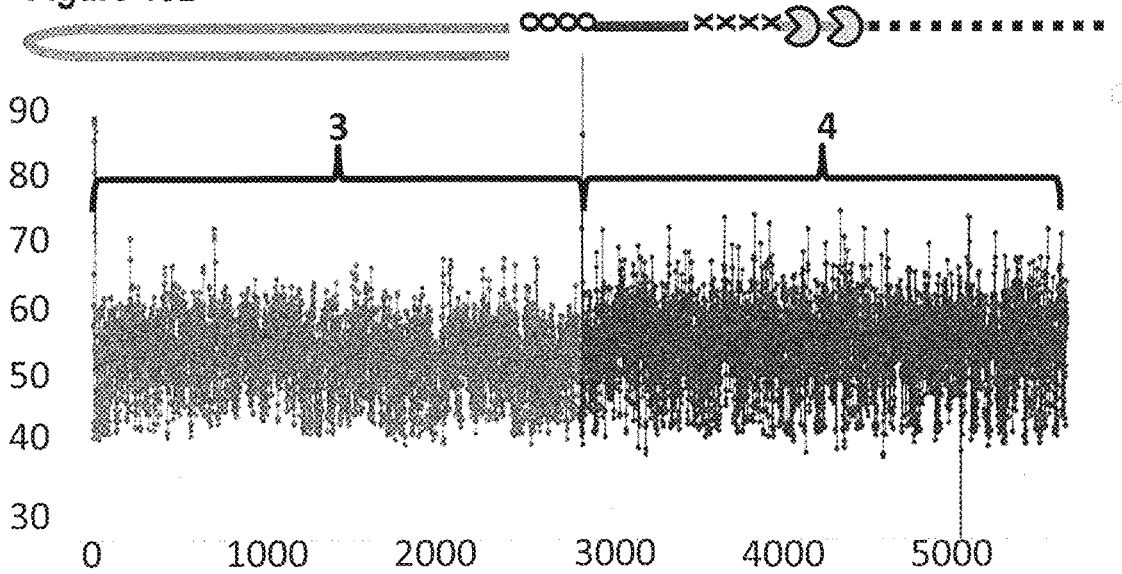

The same experiment was carried out using the helicase T4 Dda E94C/C109A/C136A/A360C to control the movement of DNA construct X through the nanopore. FIG. 19A shows the movement index for construct X when movement was controlled by a single T4 Dda E94C/C109A/C136A/A360C enzyme and FIG. 19B shows the movement index when the movement was controlled by two T4 Dda E94C/C109A/C136A/A360C helicases. As was observed for T4 Dda-E94C/A360C, a series of two T4 Dda E94C/C109A/C136A/A360C helicases resulted in more points being observed in the movement index when the movement of region 2 of the DNA was controlled by two enzymes, which indicated improved movement of this region (slower movement or less slipping forward). This meant that a series of T4 Dda E94C/C109A/C136A/A360C enzymes could be used to improve sequencing of a strand of DNA.

DNA construct X, shown and described in FIG. 17, has a section labelled b onto which two enzymes could bind. Control experiments where the length of section b was only sufficient to allow one enzyme to bind (10-12 T binding sites) were carried out for both T4 Dda E94C/A360C and T4 Dda E94C/C109A/C136A/A360C. In the control experiments, when region 4 translocated through the nanopore no strands with improved movement were detected when only a single enzyme bound to the construct and controlled the movement of the strand through the nanopore. In comparison, in the experiments above where two enzymes could have bound to the DNA, although we observed some strands with poor movement because only a single enzyme bound, it was also possible to identify strands with improved movement indexes which corresponded to DNA translocation controlled by two enzymes, rather than just one.

Example 7

This example compared the use of a single T4 Dda E94C/C109A/C136A/A360C or both T4 Dda E94C/C109A/C136A/A360C and T4 Dda E94C/C109A/C136A/A360C/W378A (SEQ ID NO: 24 with mutations E94C/C109A/C136A/A360C/W378A) in order to control the movement of DNA construct Z (shown in FIG. 20) through an MspA nanopore. T4 Dda E94C/C109A/C136A/A360C and T4 Dda E94C/C109A/C136A/A360C/W378A are both active helicases which moved along the DNA when provided with appropriate fuel. When these two different helicases were used to control the movement of the construct through the nanopore then improved movement was observed in comparison to when the movement was controlled by a single helicase (T4 Dda E94C/C109A/C136A/A360C).

Materials and Methods

The DNA construct Z (final concentration added to the nanopore system 0.1 nM) which either had both enzymes pre-bound (see FIG. 21B data) or only T4 Dda E94C/C109A/C136A/A360C pre-bound (control experiment, see FIG. 21A data) was added to buffer (final concentrations added to the nanopore system were 500 mM KCl, 25 mM potassium phosphate pH 8.0), ATP (final concentration added to the nanopore system 2 mM) and MgCL2 (final concentration added to the nanopore system 2 mM). This was the pre-mix which was then added to the nanopore system (total volume 150 µL).

Electrical measurements were acquired from single MspA nanopores inserted in block co-polymer in buffer (25 mM potassium phosphate, 75 mM potassium ferrocyanide (II), 25 mM potassium ferricyanide (III), 600 mM KCl, pH 8.0). After achieving a single pore inserted in the block co-polymer, then buffer (2 mL, 25 mM potassium phosphate, 75 mM potassium ferrocyanide (II), 25 mM potassium ferricyanide (III), 600 mM KCl, pH 8.0) was flowed through the system to remove any excess MspA nanopores. The enzyme pre-bound to construct Z (either a single T4 Dda E94C/C109A/C136A/A360C (control) or T4 Dda E94C/C109A/C136A/A360C and T4 Dda E94C/C109A/C136A/A360C/W378A), fuel (MgCl2 and ATP) pre-mix (150 µL total) was then flowed into the single nanopore experimental system and the experiment run at a holding potential of −120 mV for 6 hours (with potential flips to +60 mV for 2 seconds) and helicase-controlled DNA movement monitored.

Results

Helicase controlled DNA movements corresponding to controlled translocation by T4 Dda E94C/C109A/C136A/A360C only (control experiment, FIG. 21A) or both T4 Dda E94C/C109A/C136A/A360C and T4 Dda E94C/C109A/C136A/A360C/W378A (FIG. 22B) were observed. The trace shown in FIG. 21 section A showed an example movement index plot when only the helicase T4 Dda E94C/C109A/C136A/A360C controlled the translocation of DNA construct Z (see FIG. 20) through an MspA nanopore. When region 5 translocated through the nanopore, it was possible to observe the movement index for region 5. However, this figure showed that the movement index for region 6 had less points than for region 5 which indicated that less information was obtained for this region of DNA construct Y when it translocated through the nanopore. This resulted in DNA movement that was less consistent (e.g. more slipping forward of the DNA region labelled 6) and sections of DNA sequence were missed.

Figure 21B:
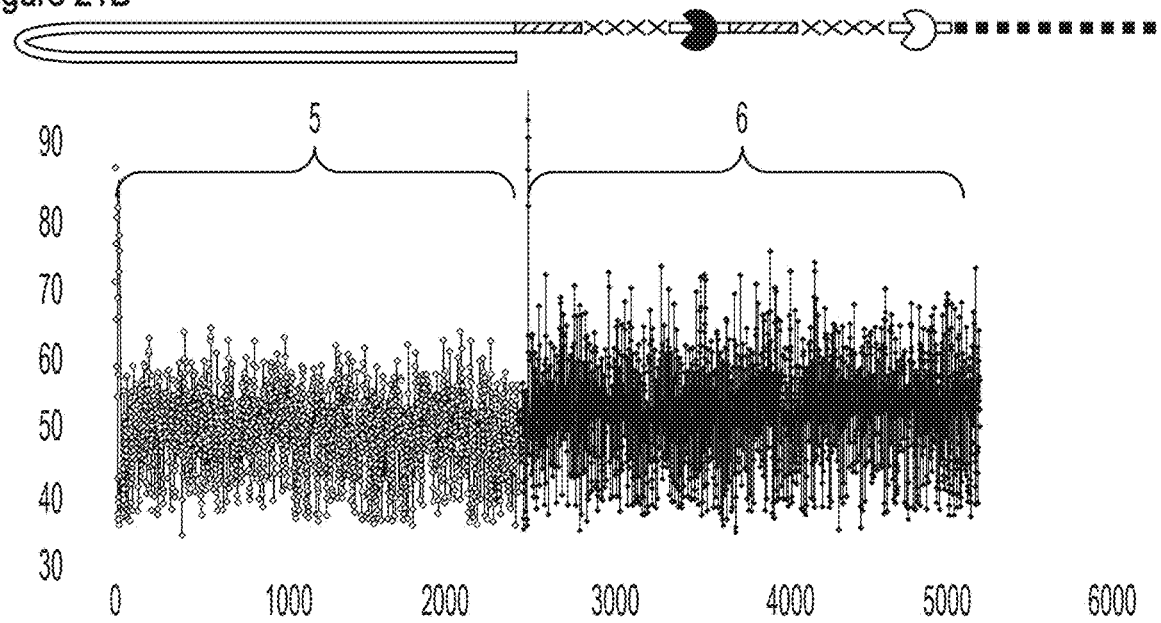

FIG. 21B shows the movement index when T4 Dda E94C/C109A/C136A/A360C and T4 Dda E94C/C109A/C136A/A360C/W378A controlled the translocation of DNA construct Z (see FIG. 20) through an MspA nanopore. When region 5 translocated through the nanopore under the control of T4 Dda E94C/C109A/C136A/A360C and T4 Dda E94C/C109A/C136A/A360C/W378A, it was possible to observe a movement index. Moreover, when region 6 translocated through the nanopore, the movement was again controlled by both T4 Dda E94C/C109A/C136A/A360C and T4 Dda E94C/C109A/C136A/A360C/W378A. When region 6 translocated through the nanopore under the control of the two enzymes (T4 Dda E94C/C109A/C136A/A360C and T4 Dda E94C/C109A/C136A/A360C/W378A) then the DNA movement was significantly different from that observed when a single T4 Dda E94C/C109A/C136A/A360C helicase controlled the movement of this region (see FIG. 21A section 6). This figure showed that the movement index for region 6, when the helicase movement was controlled using T4 Dda E94C/C109A/C136A/A360C and T4 Dda E94C/C109A/C136A/A360C/W378A, had many more points than for region 6 when the helicase movement was controlled by the single enzyme T4 Dda E94C/C109A/C136A/A360C which indicated that more information was obtained for this region of DNA construct Z when it translocated through the nanopore under the control of two different enzymes and that the DNA movement was more consistent (e.g. slower movement or less slipping forward of the DNA region labelled 6). This meant that the combination of T4 Dda E94C/C109A/C136A/A360C and T4 Dda E94C/C109A/C136A/A360C/W378A enzymes were used to improve sequencing of a strand of DNA.

Example 8

This example compared the use of either a single T4 Dda E94C/C109A/C136A/A360C/W378A or two T4 Dda E94C/C109A/C136A/A360C/W378A helicases (SEQ ID NO: 24 with mutations E94C/C109A/C136A/A360C/W378A) in order to control the movement of DNA construct Z (shown in FIG. 20) through an MspA nanopore. T4 Dda E94C/C109A/C136A/A360C/W378A is an active helicase which moved along the DNA when provided with appropriate fuel. When two helicases (T4 Dda E94C/C109A/C136A/A360C/W378A) were used to control the movement of the construct through the nanopore then improved movement was observed in comparison to when the movement was controlled by a single helicase (T4 Dda E94C/C109A/C136A/A360C/W378A).

Materials and Methods

The DNA construct Z (final concentration added to the nanopore system 0.1 nM) which either had two T4 Dda E94C/C109A/C136A/A360C/W378A helicases pre-bound (see FIG. 21B data) or a single T4 Dda E94C/C109A/C136A/A360C/W378A pre-bound (control experiment, see FIG. 21A data) was added to buffer (final concentrations added to the nanopore system were 500 mM KCl, 25 mM potassium phosphate pH 8.0), ATP (final concentration added to the nanopore system 2 mM) and MgCL2 (final concentration added to the nanopore system 2 mM). This was the pre-mix which was then added to the nanopore system (total volume 150 µL).

Electrical measurements were acquired from single MspA nanopores as described in Example 7 above, except either the DNA construct Z with a single T4 Dda E94C/C109A/C136A/A360C/W378A pre-bound (as a control experiment) or two T4 Dda E94C/C109A/C136A/A360C/W378A helicases pre-bound were added to the nanopore system.

Results

Helicase controlled DNA movements corresponding to controlled translocation by T4 Dda E94C/C109A/C136A/A360C/W378A only (control experiment, FIG. 22A) or two T4 Dda E94C/C109A/C136A/A360C/W378A helicases (FIG. 22B) were observed. The trace shown in FIG. 22 section A showed an example movement index plot when only a single helicase T4 Dda E94C/C109A/C136A/A360C/W378A controlled the translocation of DNA construct Z (see FIG. 20) through an MspA nanopore. When region 5 translocated through the nanopore, it was possible to observe the movement index for region 5. However, this figure showed that the movement index for region 6 had less points than for region 5 which indicated that less information was obtained for this region of DNA construct Z when it translocated through the nanopore. This resulted in DNA movement that was less consistent (e.g. more slipping forward of the DNA region labelled 6) and sections of DNA sequence were missed.

Figure 22B:
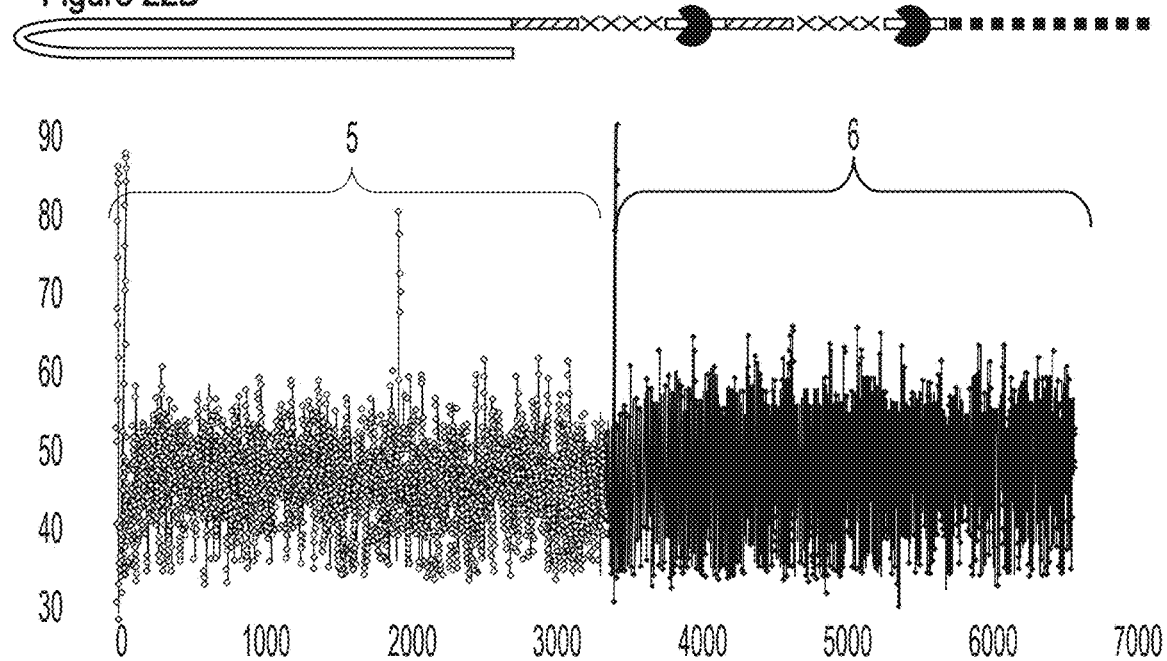

FIG. 22B shows the movement index when two T4 Dda E94C/C109A/C136A/A360C/W378A helicases controlled the translocation of DNA construct Z (see FIG. 20) through an MspA nanopore. When region 5 translocated through the nanopore under the control of two T4 Dda E94C/C109A/C136A/A360C/W378A helicases, it was possible to observe a movement index. Moreover, when region 6 translocated through the nanopore, the movement was again controlled by two T4 Dda E94C/C109A/C136A/A360C/W378A helicases. When region 6 translocated through the nanopore under the control of the two enzymes (two T4 Dda E94C/C109A/C136A/A360C/W378A helicases) then the DNA movement was significantly different from that observed when a single T4 Dda E94C/C109A/C136A/A360C/W378A helicase controlled the movement of region 6 (see FIG. 22A section 6). This figure showed that the movement index for region 6, when the helicase movement was controlled using two T4 Dda E94C/C109A/C136A/A360C/W378A helicases, had many more points than when the helicase movement was controlled by the single enzyme T4 Dda E94C/

C109A/C136A/A360C/W378A which indicated that more information was obtained for this region of DNA construct Z when it translocated through the nanopore under the control of two enzymes than was observed for the region 6 of construct Z under the control of a single T4 Dda E94C/C109A/C136A/A360C/W378A helicase. Furthermore, the DNA movement which was observed when DNA translocation was controlled by two T4 Dda E94C/C109A/C136A/A360C/W378A helicases was also more consistent (e.g. slower movement or less slipping forward of the DNA region labelled 8). This meant that the use of two T4 Dda E94C/C109A/C136A/A360C/W378A enzymes resulted in improved sequencing of a strand of DNA.

An alignment of the preferred Dda helicases of the invention (SEQ ID NOs: 8 to 23)

The invention claimed is:

1. A kit for characterising a target polynucleotide comprising:
   (a) a pore and
   (b) a helicase comprising:
      (i) a first polypeptide comprising the pin domain and the 1A domain from a Dda helicase and not comprising any other domains from a Dda helicase, wherein at least one cysteine residue and/or at least one non-natural amino acid have been introduced into the pin domain and/or the 1A domain, and
      (ii) a second polypeptide comprising the 2A domain, the tower domain and the hook domain from a Dda helicase and not comprising any other domains from a Dda helicase, wherein at least one cysteine residue and/or at least one non-natural amino acid have been introduced into the tower domain, wherein the helicase has the ability to control the movement of a polynucleotide;
   wherein two or more of the introduced cysteines and/or non-natural amino acids are connected to one another;
   wherein said first polypeptide is covalently attached to said second polypeptide; and
   wherein the pore is (1) a transmembrane protein pore, (2) a solid state pore, or (3) an oligomer pore.

2. The kit of claim 1, wherein the at least one non-natural amino acid in the first polypeptide and/or the at least one non-natural amino acid in the second polypeptide is 4-azido-L-phenylalanine (Faz).

3. The kit of claim 1, wherein the helicase comprises at least one introduced cysteine residue and at least one introduced non-natural amino acid.

4. The kit of claim 3, wherein the at least one introduced cysteine residue is connected to the at least one introduced non-natural amino acid.

5. The kit of claim 1, wherein the first polypeptide is covalently attached to the second polypeptide via an amino acid.

6. The kit of claim 1, wherein the helicase is further modified to increase or decrease its surface charge.

7. The kit of claim 1, wherein the helicase is further modified by the removal of one or more native cysteine residues.

8. The kit of claim 7, wherein the one or more cysteine residues are removed by substitution.

9. The kit of claim 1, wherein the helicase is covalently attached to the pore.

10. The kit of claim 1, wherein the pore is derived from Msp.

11. The kit of claim 1, wherein the pore is a MspA pore.

12. The kit of claim 1, further comprising an additional polynucleotide binding moiety, wherein the helicase is attached to the polynucleotide binding moiety.

13. The kit of claim 1, wherein the kit comprises two or more of the helicases.

14. The kit of claim 1, further comprising an additional polynucleotide binding moiety, wherein the pore is attached to the polynucleotide binding moiety.

15. The kit of claim 1, wherein the kit further comprises a chip comprising a amphiphilic membrane.

* * * * *

SEQUENCE LISTING

```
Sequence total quantity: 80
SEQ ID NO: 1              moltype = DNA  length = 558
FEATURE                   Location/Qualifiers
misc_feature              1..558
                          note = Mycobacterium smegmatis porin A
                           mutant(D90N/D91N/D93N/D118R/D134R/E139K)
source                    1..558
                          mol_type = other DNA
                          organism = unidentified
SEQUENCE: 1
atgggtctgg ataatgaact gagcctggtg gacggtcaag atcgtaccct gacggtgcaa    60
caatgggata cctttctgaa tggcgttttt ccgctggatc gtaatcgcct gacccgtgaa   120
tggtttcatt ccggtcgcgc aaaatatatc gtcgcaggcc cgggtgctga cgaattcgaa   180
ggcacgctgg aactgggtta tcagattggc tttccgttgc cactgggcgt tggtatcaac   240
ttctcgtaca ccacgccgaa tattctgatc aacaatggta acattaccgc accgccgttt   300
ggcctgaaca gcgtgattac gccgaacctg tttccggggtg ttagcatctc tgcccgtctg   360
ggcaatggtc cgggcattca agaagtggca acctttagtg tgcgcgtttc cggcgctaaa   420
ggcggtgtcg cggtgtctaa cgcccacggt accgttacgg gcgcggccgg cggtgtcctg   480
ctgcgtccgt tcgcgcgcct gattgcctct accggcgaca gcgttacgac ctatggcgaa   540
ccgtggaata tgaactaa                                                  558

SEQ ID NO: 2              moltype = AA  length = 184
FEATURE                   Location/Qualifiers
REGION                    1..184
                          note = Mycobacterium smegmatis porin A
                           mutant(D90N/D91N/D93N/D118R/D134R/E139K)
source                    1..184
                          mol_type = protein
                          organism = unidentified
SEQUENCE: 2
GLDNELSLVD GQDRTLTVQQ WDTFLNGVFP LDRNRLTREW FHSGRAKYIV AGPGADEFEG     60
TLELGYQIGF PWSLGVGINF SYTTPNILIN NGNITAPPFG LNSVITPNLF PGVSISARLG   120
NGPGIQEVAT FSVRVSGAKG GVAVSNAHGT VTGAAGGVLL RPFARLIAST GDSVTTYGEP   180
WNMN                                                                184

SEQ ID NO: 3              moltype = DNA  length = 885
FEATURE                   Location/Qualifiers
misc_feature              1..885
                          note = alpha-hemolysin mutant E111N/K147N
source                    1..885
                          mol_type = other DNA
                          organism = unidentified
SEQUENCE: 3
atggcagatt ctgatattaa tattaaaacc ggtactacag atattggaag caatactaca    60
gtaaaaacag gtgatttagt cacttatgat aaagaaaatg gcatgcacaa aaaagtgttt   120
tatagtttta tcgatgataa aaatcacaat aaaaaactgc tagttattag aacaaaaggt   180
accattgctg gtcaatatag agtttatagc gaagaaggtg ctaacaaaag tggtttagcc   240
tggccttcag cctttaaggt acagttgcaa ctacctgata tgaagtagc tcaaatatct   300
gattactatc caagaaattc gattgataca aaaaactata tgagtacttt aacttatgga   360
ttcaacggta atgttactgg tgatgataca ggaaaaattg gcggccttat tggtgcaaat   420
gtttcgattg gtcatacact gaactatgtt caacctgatt tcaaaacaat tttagagagc   480
ccaactgata aaaagtagg ctggaaagtg atatttaaca atatggtgaa tcaaaattgg   540
ggaccatacg atcgagattc ttggaacccg gtatatggca atcaactttt catgaaaact   600
agaaatggtt ctatgaaagc agcagataac ttccttgatc ctaacaaagc aagttctcta   660
ttatcttcag ggttttcacc agacttcgct acagttatta ctatggatag aaaagcatcc   720
aaacaacaaa caaatataga tgtaatatac gaacgagttc gtgatgatta ccaattgcat   780
tggacttcaa caaattggaa aggtaccaat actaaagata aatggacaga tcgttcttca   840
gaaagatata aaatcgattg ggaaaaagaa gaaatgacaa attaa                    885

SEQ ID NO: 4              moltype = AA  length = 293
FEATURE                   Location/Qualifiers
REGION                    1..293
                          note = alpha-hemolysin mutant E111N/K147N
source                    1..293
                          mol_type = protein
                          organism = unidentified
SEQUENCE: 4
```

```
ADSDINIKTG TTDIGSNTTV KTGDLVTYDK ENGMHKKVFY SFIDDKNHNK KLLVIRTKGT   60
IAGQYRVYSE EGANKSGLAW PSAFKVQLQL PDNEVAQISD YYPRNSIDTK NYMSTLTYGF  120
NGNVTGDDTG KIGGLIGANV SIGHTLNYVQ PDFKTILESP TDKKVGWKVI FNNMVNQNWG  180
PYDRDSWNPV YGNQLFMKTR NGSMKAADNF LDPNKASSLL SSGFSPDFAT VITMDRKASK  240
QQTNIDVIYE RVRDDYQLHW TSTNWKGTNT KDKWTDRSSE RYKIDWEKEE MTN         293

SEQ ID NO: 5              moltype = AA  length = 184
FEATURE                   Location/Qualifiers
source                    1..184
                          mol_type = protein
                          organism = Mycobacterium smegmatis
SEQUENCE: 5
GLDNELSLVD GQDRTLTVQQ WDTFLNGVFP LDRNRLTREW FHSGRAKYIV AGPGADEFEG   60
TLELGYQIGF PWSLGVGINF SYTTPNILID DGDITAPPFG LNSVITPNLF PGVSISADLG  120
NGPGIQEVAT FSVDVSGPAG GVAVSNAHGT VTGAAGGVLL RPFARLIAST GDSVTTYGEP  180
WNMN                                                               184

SEQ ID NO: 6              moltype = AA  length = 184
FEATURE                   Location/Qualifiers
source                    1..184
                          mol_type = protein
                          organism = Mycobacterium smegmatis
SEQUENCE: 6
GLDNELSLVD GQDRTLTVQQ WDTFLNGVFP LDRNRLTREW FHSGRAKYIV AGPGADEFEG   60
TLELGYQIGF PWSLGVGINF SYTTPNILID DGDITGPPFG LESVITPNLF PGVSISADLG  120
NGPGIQEVAT FSVDVSGPAG GVAVSNAHGT VTGAAGGVLL RPFARLIAST GDSVTTYGEP  180
WNMN                                                               184

SEQ ID NO: 7              moltype = AA  length = 183
FEATURE                   Location/Qualifiers
source                    1..183
                          mol_type = protein
                          organism = Mycobacterium smegmatis
SEQUENCE: 7
VDNQLSVVDG QGRTLTVQQA ETFLNGVFPL DRNRLTREWF HSGRATYHVA GPGADEFEGT   60
LELGYQVGFP WSLGVGINFS YTTPNILIDG GDITQPPFGL DTIITPNLFP GVSISADLGN  120
GPGIQEVATF SVDVKGAKGA VAVSNAHGTV TGAAGGVLLR PFARLIASTG DSVTTYGEPW  180
NMN                                                                183

SEQ ID NO: 8              moltype = AA  length = 439
FEATURE                   Location/Qualifiers
source                    1..439
                          mol_type = protein
                          note = Enterobacteria phage T4
                          organism = unidentified
SEQUENCE: 8
MTFDDLTEGQ KNAFNIVMKA IKEKKHHVTI NGPAGTGKTT LTKFIIEALI STGETGIILA   60
APTHAAKKIL SKLSGKEAST IHSILKINPV TYEENVLFEQ KEVPDLAKCR VLICDEVSMY  120
DRKLFKILLS TIPPWCTIIG IGDNKQIRPV DPGENTAYIS PFFTHKDFYQ CELTEVKRSN  180
APIIDVATDV RNGKWIYDKV VDGHGVRGFT GDTALRDFMV NYFSIVKSLD DLFENRVMAF  240
TNKSVDKLNS IIRKKIFETD KDFIVGEIIV MQEPLFKTYK IDGKPVSEII FNNGQLVRII  300
EAEYTSTFVK ARGVPGEYLI RHWDLTVETY GDDEYYREKI KIISSDEELY KFNLFLGKTA  360
ETYKNWNKGG KAPWSDFWDA KSQFSKVKAL PASTFHKAQG MSVDRAFIYT PCIHYADVEL  420
AQQLLYVGVT RGRYDVFYV                                               439

SEQ ID NO: 9              moltype = AA  length = 678
FEATURE                   Location/Qualifiers
source                    1..678
                          mol_type = protein
                          organism = Rhodothermus marinus
SEQUENCE: 9
MEELSNEQQR VLDHVLAWLE RNDAPPIFIL TGSAGTGKTL LIRHLVRALQ DRRIHYALAA   60
PTGRAARILS ERTGDHARTL HSLIYIFDRY QLVEEADRQT DEPLSLQLHF ALRSAEHDAR  120
LIIVDEASMV SDTAGEEELY RFGSGRLLND LLTFARLIPK RDRPPTTRLL FVGDPAQLPP  180
VGQSVSPALS AQYLRDTFGL SAETAHLRSV YRQRKGHPIL ETATALRNAL EKGHYHTFRL  240
PEQPPDLRPV GLEEAIETTA TDFRRQNPSV LLCRTNALAR KLNAAVRARL WGREGLPPQP  300
GDLLLVNRNA PLHGLFNGDL VLVETVGPLE HRRVGRRGRP PVDLYFRDVE LLYPHEKPRN  360
RIRCKLLENL LESPDGQLSP DIIQALLIDF YRRHPSLKHG SSEFRLMLAN DAYFNALHVR  420
YGYAMTVHKA QGGEWKRATV VFNDWRHFRH AEFFRWAYTA ITRAREELLT IGAPSFEALS  480
DMRWQPAPSV PAPEQAAENA TRFPLKALET YHQRLSEALT AAGIETTGVE LLQYAVRYHL  540
ARADRTTRIQ YYYRGDGQIS RIVTLGGADD PELTQQAYAL FERILSEPPA DSGELPENPL  600
LREFLERAHL RLEGSGIRIV HWKEMPYALR LYFSADGENV TIDFYYNRRG VWTHAQEVGR  660
SSSGALFARI QSLLQADS                                                678

SEQ ID NO: 10             moltype = AA  length = 496
FEATURE                   Location/Qualifiers
source                    1..496
                          mol_type = protein
                          note = Cyanothece ATCC51142
```

```
                                organism = unidentified
SEQUENCE: 10
MSQSVVVPDE LGEIITAVIE FYQDAVDKIE PKIVFLELRK NVVDWVSRTQ LKIEEKEIQA    60
TGLTRQQQTA YKEMINFIEN SSEQYFRLSG YAGTGKSFLM AKVIEWLKQE DYKYSVAAPT   120
NKAAKNLTQI ARSQGIKIEA TTVAKLLKLQ PTIDVDTGQQ SFEFNSEKEL ELKDYDVIII   180
DEYSMLNKDN FRDLQQAVKG GESKFIFVGD SSQLPPVKEK EPIVANHPDI RKSANLTQIV   240
RYDGEIVKVA ESIRRNPRWN HQTYPFETVA DGTIIKLNTE DWLQQALSHF EKEDWLSNPD   300
YVRMITWRNK TADKYNQAIR EALYGENVEQ LVVGDRLIAK KPVFRSLPGG KKKEKKIILN   360
NSEECKVIET PKINYNEKYK WEFYQVKVRT DEGGMIELRI LTSESEEKRQ KKLKELAKRA   420
REEENYSEKK KQWAIYYELD ELFDNMAYAY ALTCHKAQGS SIDNVFLLVS DMHYCRDKTK   480
MIYTGLTRAK KCCYVG                                                  496

SEQ ID NO: 11           moltype = AA   length = 421
FEATURE                 Location/Qualifiers
source                  1..421
                        mol_type = protein
                        organism = Salinibacter ruber
SEQUENCE: 11
MSTFADAPFT EDQEEAYDHV YDRLAQGERF TGLRGYAGTG KTYLVSRLVE QLLDEDCTVT    60
VCAPTHKAVQ VLSDELGDAP VQMQTLHSFL GLRLQPKQDG EYELVAEEER NFAEGVVIVD   120
EASMIGREEW SHIQDAPFWV QWLFVGDPAQ LPPVNEDPSP ALDVPGPTLE TIHRQAADNP   180
ILELATKIRT GADGRFGSTF EDGKGVAVTR NREEFLDSIL RAFDADAFAE DATHARVLAY   240
RNKTVRRYNR EIRAERYGAD ADRFVEGEWL VGTETWYYDG VQRLTNSEEV RVKKAQVETF   300
EADDQSEWTV WELKIRTPGR GLTRTIHVLH EEERERYENA LERRRGKAED DPSKWDRFFE   360
LRERFARVDY AYATTVHRAQ GSTYDTVFVD HRDLRVCRGE ERGALLYVAV TRPSRRLALL   420
V                                                                  421

SEQ ID NO: 12           moltype = AA   length = 500
FEATURE                 Location/Qualifiers
source                  1..500
                        mol_type = protein
                        note = Sulfurimonas gotlandica GD1
                        organism = unidentified
SEQUENCE: 12
MKILNKETYK LSLHQEEVFT QIVSQLDTKV SSILKSTNIE DYLLSLTGPA GTGKTFLTTQ    60
IAKYLVEKRK ESEYPMSSDF DFTITAPTHK AVGVLSKLLR ENNIQSSCKT IHSFLGIKPF   120
IDYTTGEEKF VVDKTNKRKD RTSILIVDES SMIGNTLYEY ILEAIEDKRV NVVLFIGDPY   180
QLLPIENSKN EIYDLPNRFF LSEVVRQAEN SYIIRVATKL RERIKNQDFI SLQQFFQENM   240
EDEITFFHNK EAFLEDFYKE EEWYKENKIL ATYKNKDVDA FNKIIRNKFW EQKGNTTPST   300
LLAGDMIRFK DAYTVGDITI YHNGQELQLG STEVKYHDSL HIEYWECKSI YALEQQVFRV   360
VNPDSEAVFN QKLQSLATKA KQAKFPDNKK LWKLYYETRN MFANVQYIHA STIHKLQGST   420
YDVSYIDIFS LVHNHYMSDE EKYRLLYVAI TRASKDIKIF MSAFDRTSDE KVIINNQNSE   480
TMNTLKQLHD IDIILKDLDL                                              500

SEQ ID NO: 13           moltype = AA   length = 450
FEATURE                 Location/Qualifiers
source                  1..450
                        mol_type = protein
                        note = Vibrio phage henriette 12B8
                        organism = unidentified
SEQUENCE: 13
MADFELTLGQ KTVLGEVIST ILKPVNLNDT SRFHTMHGPA GSGKTTVLQR IISQIPAYKT    60
IGFCSPTHKS VKVIRRMARE AGISHRVDIR TIHSALGLVM KPVRGDEVLV KEPFAEERIY   120
DVLIIDEAGM LNDELIMYIL ESQSSKVIFV GDMCQIGPIQ SNLPEEDGYT PTSTDDVSKV   180
FTEVEMMSAL TEVVRQAEGS PIIQLATEFR LAQDDIYADL PRIVTNTTPD GNGIITMPNG   240
NWVDSAVARF QSDQFKEDPD HCRIVCYTNA MVDLCNDLVR KRLFGADVPE WLEDEILVAQ   300
EMGSTWNNAD ELRIVSIDDH FDQQYEVPCW RMQLESVEDH KLHNALVVKG DYIEDFKFRL   360
NAIAERANTD KNMSGMHWKE FWGMRKKFNT FKNVYAGTAH KSQGSTFDYT YVFTPDFYKF   420
GATMTIKRLL YTAITRSRYT TYFAMNTGAQ                                   450

SEQ ID NO: 14           moltype = AA   length = 421
FEATURE                 Location/Qualifiers
source                  1..421
                        mol_type = protein
                        note = Vibrio phage phi-pp2
                        organism = unidentified
SEQUENCE: 14
MGLTNCQQGA MDAFLESDGH MTISGPAGSG KTFLMKSILE ALESKGKNVT MVTPTHQAKN    60
VLHKATGQEV STIHSLLKIH PDTYEDQKHF TQSGEVEGLD EIDVLVVEEA SMVDEELFQI   120
TGRTMPRKCR ILAVGDKYQL QPVKHDPGVI SPFFTKFTTF EMNEVVRQAK DNPLIQVATE   180
VRNGQWLRTN WSKERRQGVL HVPNVNKMLD TYLSKVNSPE DLLDYRILAY TNDCVDTFNG   240
IIREHVYNTS EPFIPGEYLV TQMPVMVSNG KYPVCVIENG EVVKILDVRQ KTIDGMLPKV   300
DNEAFDVAVL TVEKEDGNVY EFTVLWDDLQ KERFARYLSA AAGTYKSMRG NTKRYWRAFW   360
GLKEQMIETK SLGASTVHKS QGTTVKGVCL YTQDMGYAEP EILQQLVYVG LTRPTDWALY   420
N                                                                  421

SEQ ID NO: 15           moltype = AA   length = 434
FEATURE                 Location/Qualifiers
source                  1..434
```

```
                        mol_type = protein
                        note = Aeromonas phage 65
                        organism = unidentified
SEQUENCE: 15
MSESEITLTP SQNMAVNEVK NGTGHITISG PPGSGKTFLV KYLIKMLGDE LGTVLAAPTH    60
QAKIVLTEMS GIEACTIHSL MKIHPETLED IQIFDQSKLP DLSNIRYLIV EEASMHSKTL   120
FKITMKSIPP TCRIIAIGDK DQIQPEEHAQ GELSPYFTDP RFSQIRLTDI MRQSLDNPII   180
QVATKIREGG WIEPNWNRDT KTGVYKVSGI TDLVNSYLRA VKTPEDLTKY RFLAYTNKVV   240
NKVNSIVREH VYKTKLPFIE GEKIVLQEPV MVEHEDDTIE TIFTNGEVVT INEIEVFDRT   300
IRIDGSPEFK VNAAKLSVSS DYSGIEHDFC VLYGSESRLE FEYQLSESAG NIKQMGKGGN   360
QRSAWKSFWA AKKMFIETKS LGASTIHKSQ GSTVKGVWLA LHDIHYADEE LKQQLVYVGV   420
TRPTDFCLYF DGTK                                                    434

SEQ ID NO: 16           moltype = AA   length = 420
FEATURE                 Location/Qualifiers
source                  1..420
                        mol_type = protein
                        note = Aeromonas phage CC2
                        organism = unidentified
SEQUENCE: 16
MAVDAVQSGT GHITISGPPG SGKTFLVKYI IKMLGDELGT VLAAPTHQAK IVLTEMSGIE    60
ACTIHSLMKI HPETLEDIQI FDQSKMPDLS TVRYLIIEEA SMHSKALFNI TMKSIPPTCR   120
IIAIGDKDQI QPVDHAPGEL SPYFTDSRFT QIRMTDIMRQ SLDNPIIQVA TTIREGGWIY   180
QNWNKEKKSG VYKVKSITDL INSYLRVVKT PEDLTKYRFL AFTNKVVDKV NSIVRKHVYK   240
TDLPFIEGEK LVLQEPVMVE YDDDTIETIF TNGEVVTVDE IEVSDMNIRI DGSPAFSISV   300
AKLKVTSDFS GVTHDIMSVY GEDSKAEFNY QLSEAAAVIK QMQRGQTKAA WASFWDAKKT   360
FTETKSLGAC TIHKSQGSTV KGVWLGLHDI SYADTDLQQQ LVYVGVTRPT DFCLYFDGSK   420

SEQ ID NO: 17           moltype = AA   length = 443
FEATURE                 Location/Qualifiers
source                  1..443
                        mol_type = protein
                        note = Cronobacter phage vB CsaM GAP161
                        organism = unidentified
SEQUENCE: 17
MSELTFDDLS DDQKSAHDRV IHNIQNAIHT TITGGPGVGK TTLVKFVFNT LKGLGISGIW    60
LTAPTHQAKN VLAAATGMDA TTIHSALKIS PVTNEELRVF EQQKGKKAPD LSTCRVFVVE   120
EVSMVDMDLF RIIRRSIPSN AVILGLGDKD QIRPVNADGR VELSPFFDEE IFDVIRMDKI   180
MRQAEGNPII QVSRAVRDGK MLKPMSVGDL GVFQHANAVD FLRQYFRRVK TPDDLIENRM   240
FAYTNDNVDK LNATIRKHLY KTTEPFILDE VIVMQEPLVQ EMRLNGQIFT EIVYNNNEKI   300
RVLEIIPRRE VIKAEKCDEK IEIEFYLLKT VSLEEETEAQ IQVVVDPVMK DRLGNYLAYV   360
ASTYKRIKQQ TGYKAPWHSF WAIKNKFQDV KPLPVCTYHK SQGSTYDHAY MYTRDAYAFA   420
DYDLCKQLIY VGVTRARYTV DYV                                          443

SEQ ID NO: 18           moltype = AA   length = 442
FEATURE                 Location/Qualifiers
source                  1..442
                        mol_type = protein
                        note = Klebsiella phage KP15
                        organism = unidentified
SEQUENCE: 18
MSELTFDDLS EDQKNAHDRV IKNIRNKIHT TITGGPGVGK TTLVKFVFET LKKLGISGIW    60
LTAPTHQAKN VLSEAVGMDA TTIHSALKIS PVTNEELRVF EQQKGKKAAD LSECRVFVVE   120
EVSMVDKELF RIIKRTIPSC AVILGLGDKD QIRPVNTEGI TELSPFFDEE IFDVIRMDKI   180
MRQAEGNPII QVSRAIRDGK PLMPLMNGEL GVMKHENASD FLRRYFSRVK TPDDLNNNRM   240
FAYTNANVDK LNAVIRKHLY KTDQPFIVGE VVVMQEPLVT EGRVNGVSFV EVIYNNNEQI   300
KILEIIPRSD TIKADRCDPV QIDYFLMKTE SMFEDTKADI QVIADPVMQE RLGDYLNYVA   360
FQYKKMKQET GYKAPWYSFW QIKNKFQTVK ALPVCTYHKG QGSTYDHSYM YTRDAYAYAD   420
YELCKQLLYV GTTRARFTVD YV                                           442

SEQ ID NO: 19           moltype = AA   length = 438
FEATURE                 Location/Qualifiers
source                  1..438
                        mol_type = protein
                        note = Stenotrophomonas phage IME13
                        organism = unidentified
SEQUENCE: 19
MVTYDDLTVG QKDAIEKALQ AMRTKRHITI RGPAGSGKTT MTRFLLERLF QTGQQGIVLT    60
APTHQAKKEL SKHALRKSYT IQSVLKINPS TLEENQIFEQ KGTPDFSKTR VLICDEVSFY   120
TRKLFDILMR NVPSHCVVIG IGDKAQIRGV SEDDTHELSP FFTDNRFEQV ELTEVKRHQG   180
PIIEVATDIR NGKWIYEKLD DSGNGVKQPH TVKDFLSKYF ERTKTPNDLL ENRIMAYTNN   240
SVDKLNSVIR KQLYGANAAP FLPDEILVMQ EPLMFDIDIG GQTLKEVIFN NGQNVRVINV   300
KPSRKTLKAK GVGEIEVECT MLECESYEED EDDYRRAWFT VVHDQNTQYA INEFLSIIAE   360
KYRSREVFPN WKDFWAIRNT FVKVRPLGAM TFHKSQGSTF DNAYLFTPCL HQYCRDPDVA   420
QELIYVGNTR ARKNVCFV                                                438

SEQ ID NO: 20           moltype = AA   length = 442
FEATURE                 Location/Qualifiers
source                  1..442
```

```
                              mol_type = protein
                              note = Acinetobacter phage Ac42
                              organism = unidentified
SEQUENCE: 20
MNFEDLTEGQ KNAYTAAIKA IETVPSSSAE KRHLTINGPA GTGKTTLTKF LIAELIRRGE    60
RGVYLAAPTH QAKKVLSQHA GMEASTIHSL LKINPTTYED STTFEQKDVP DMSECRVLIC   120
DEASMYDLKL FQILMSSIPL CCTVIALGDI AQIRPVEPGA FEGQVSPFFT YEKFEQVSLT   180
EVMRSNAPII DVATSIRTGN WIYENVIDGA GVHNLTSERS VKSFMEKYFS IVKTPEDLFE   240
NRLLAFTNKS VDDLNKIVRK KIYNTLEPFI DGEVLVMQEP LIKSYTYEGK KVSEIVFNNG   300
EMVKVLCCSQ TSDEISVRGC STKYMVRYWQ LDLQSLDDPD LTGSINVIVD EAEINKLNLV   360
LGKSAEQFKS GAVKAAWADW WKLKRNFHKV KALPCSTIHK SQGTSVDNVF LYTPCIHKAD   420
SQLAQQLLYV GATRARHNVY YI                                           442

SEQ ID NO: 21                 moltype = AA   length = 442
FEATURE                       Location/Qualifiers
source                        1..442
                              mol_type = protein
                              note = Shigella phage SP18
                              organism = unidentified
SEQUENCE: 21
MIKFEDLNTG QKEAFDYITE AIQRRSGECI TLNGPAGTGK TTLTKFVIDH LVRNGVMGIV    60
LAAPTHQAKK VLSKLSGQTA NTIHSILKIN PTTYEDQNIF EQREMPDMSK CNVLVCDEAS   120
MYDGSLFKII CNSVPEWCTI LGIGDMHQLQ PVDPGSTQQK ISPFFTHPKF KQIHLTEVMR   180
SNAPIIEVAT EIRNGGWFRD CMYDGHGVQG FTSQTALKDF MVNYFGIVKD ADMLMENRMY   240
AYTNKSVEKL NNIIRRKLYE TDKAFLPYEV LVMQEPHMKE LEFEGKKFSE TIFNNGQLVR   300
IKDCKYTSTI LRCKGESHQL VINYWDLEVE SIDEDEEYQV DRIKVLPEDQ QPKFQAYLAK   360
VADTYKQMKA AGKRPEWKDF WKARRTFLKV RALPVSTIHK AQGVSVDKAF IYTPCIHMAE   420
ASLASQLAYV GITRARYDAY YV                                           442

SEQ ID NO: 22                 moltype = AA   length = 439
FEATURE                       Location/Qualifiers
source                        1..439
                              mol_type = protein
                              note = Yersinia phage phiR1-RT
                              organism = unidentified
SEQUENCE: 22
MITYDDLTDG QKSAFDNTME AIKNKKGHIT INGPAGTGKT TLTKFIIDHL IKTGEAGIIL    60
CAPTHQAKKV LSKLSGMDAS TIHSVLKINP TTYEENQIFE QREVPDLAAC RVLICDEASF   120
YDRKLFGIIL ATVPSWCTVI ALGDKDQLRP VTPGESEQQL SPFFSHAKFK QVHLTEIKRS   180
NGPIIQVATD IRNGGWLSEN IVDGEGVHAF NSNTALKDFM IRYFDVVKTA DDLIESRMLA   240
YTNKSVDKLN GIIRRKLYET DKPFINGEVL VMQEPLMKEL EFDGKKFHEI VFNNGQLVKI   300
LYASETSTFI SARNVPGEYM IRYWNLEVET ADSDDDYATS QIQVICDPAE MTKFQMFLAK   360
TADTYKNSGV KAYWKDFWSV KNKFKKVKAL PVSTIHKSQG CTVNNTFLYT PCIHMADAQL   420
AKQLLYVGAT RARTNLYYI                                               439

SEQ ID NO: 23                 moltype = AA   length = 441
FEATURE                       Location/Qualifiers
source                        1..441
                              mol_type = protein
                              note = Salmonella phage S16
                              organism = unidentified
SEQUENCE: 23
MITFEQLTSG QKLAFDETIR AIKEKKNHVT INGPAGTGKT TLTKFIMEHL VSTGETGIIL    60
TAPTHAAKKV LTKLSGMEAN TIHKILKINP TTYEESMLFE QKEVPDLASC RVLICDEASM   120
WDRKLFKILM ASIPKWCTIV AIGDVAQIRP VDPGETEAHI SPFFIHKDFK QLNLTEVMRS   180
NAPIIDVATD IRNGSWIYEK TVDGHGVHGF TSSTTALKDFM MQYFSIVKSP EDLFENRMLA   240
FTNKSVDKLN SIIRRRLYQT EEAFVVGEVI VMQEPLMREL VFEGKKFPHET LFTNGQYVRI   300
LSADYTSSFL GAKGVSGEHL IRHWVLDVET YDDEEYAREK INVISDEQEM NKFQFFLAKT   360
ADTYKNWNKG GKAPWSEFWD AKRKFHKVKA LPCSTFHKAQ GISVDSSFIY TPCIHVSSDN   420
KFKLELLYVG ATRGRHDVFF V                                            441

SEQ ID NO: 24                 moltype = AA   length = 65
FEATURE                       Location/Qualifiers
REGION                        1..65
                              note = preferred HhH domain
source                        1..65
                              mol_type = protein
                              organism = unidentified
SEQUENCE: 24
GTGSGAWKEW LERKVGEGRA RRLIEYFGSA GEVGKLVENA EVSKLLEVPG IGDEAVARLV    60
PGGSS                                                               65

SEQ ID NO: 25                 moltype = AA   length = 299
FEATURE                       Location/Qualifiers
source                        1..299
                              mol_type = protein
                              note = Bacteriophage RB69
                              organism = unidentified
SEQUENCE: 25
```

```
MFKRKSTADL AAQMAKLNGN KGFSSEDKGE WKLKLDASGN GQAVIRFLPA KTDDALPFAI    60
LVNHGFKKNG KWYIETCSST HGDYDSCPVC QYISKNDLYN TNKTEYSQLK RKTSYWANIL   120
VVKDPQAPDN EGKVFKYRFG KKIWDKINAM IAVDTEMGET PVDVTCPWEG ANFVLKVKQV   180
SGFSNYDESK FLNQSAIPNI DDESFQKELF EQMVDLSEMT SKDKFKSFEE LNTKFNQVLG   240
TAALGGAAAA AASVADKVAS DLDDFDKDME AFSSAKTEDD FMSSSSSDDG DLDDLLAGL    299

SEQ ID NO: 26           moltype = AA   length = 232
FEATURE                 Location/Qualifiers
source                  1..232
                        mol_type = protein
                        note = Bacteriophage T7
                        organism = unidentified
SEQUENCE: 26
MAKKIFTSAL GTAEPYAYIA KPDYGNEERG FGNPRGVYKV DLTIPNKDPR CQRMVDEIVK    60
CHEEAYAAAV EEYEANPPAV ARGKKPLKPY EGDMPFFDNG DGTTTFKFKC YASFQDKKTK   120
ETKHINLVVV DSKGKKMEDV PIIGGGSKLK VKYSLVPYKW NTAVGASVKL QLESVMLVEL   180
ATFGGGEDDW ADEVEENGYV ASGSAKASKP RDEESWDEDD EESEEADEDG DF           232

SEQ ID NO: 27           moltype = AA   length = 324
FEATURE                 Location/Qualifiers
source                  1..324
                        mol_type = protein
                        note = Herpes virus 1
                        organism = unidentified
SEQUENCE: 27
MDSPGGVAPA SPVEDASDAS LGQPEEGAPC QVVLQGAELN GILQAFAPLR TSLLDSLLVM    60
GDRGILIHNT IFGEQVFLPL EHSQFSRYRW RGPTAAFLSL VDQKRSLLSV FRANQYPDLR   120
RVELAITGQA PFRTLVQRIW TTTSDGEAVE LASETLMKRE LTSFVVLVPQ GTPDVQLRLT   180
RPQLTKVLNA TGADSATPTT FELGVNGKFS VFTTSTCVTF AAREEGVSSS TSTQVQILSN   240
ALTKAGQAAA NAKTVYGENT HRTFSVVVDD CSMRAVLRRL QVGGGTLKFF LTTPVPSLCV   300
TATGPNAVSA VFLLKPQKHH HHHH                                         324

SEQ ID NO: 28           moltype = AA   length = 251
FEATURE                 Location/Qualifiers
REGION                  1..251
                        note = subunit 1 of PCNA
source                  1..251
                        mol_type = protein
                        organism = unidentified
SEQUENCE: 28
MFKIVYPNAK DFFSFINSIT NVTDSIILNF TEDGIFSRHL TEDKVLMAIM RIPKDVLSEY    60
SIDSPTSVKL DVSSVKKILS KASSKKATIE LTETDSGLKI IRDEKSGAK STIYIKAEKG    120
QVEQLTEPKV NLAVNFTTDE SVLNVIAADV TLVGEEMRIS TEEDKIKIEA GEEGKRYVAF   180
LMKDKPLKEL SIDTSASSSY SAEMFKDAVK GLRGFSPATM VSFGENLPMK IDVEAVSGGH   240
MIFWIAPRLL E                                                       251

SEQ ID NO: 29           moltype = AA   length = 245
FEATURE                 Location/Qualifiers
REGION                  1..245
                        note = subunit 2 of PCNA
source                  1..245
                        mol_type = protein
                        organism = unidentified
SEQUENCE: 29
MKAKVIDAVS FSYILRTVGD FLSEANFIVT KEGIRVSGID PSRVVFLDIF LPSSYFEGFE    60
VSQEKEIIGF KLEDVNDILK RVLKDDTLIL SSNESKLTLT FDGEFTRSFE LPLIQVESTQ   120
PPSVNLEFPF KAQLLTITFA DIIDELSDLG EVLNIHSKEN KLYFEVIGDL STAKVELSTD   180
NGTLLEASGA DVSSSYGMEY VANTTKMRRA SDSMELYFGS QIPLKLRFKL PQEGYGDFYI   240
APRAD                                                              245

SEQ ID NO: 30           moltype = AA   length = 246
FEATURE                 Location/Qualifiers
REGION                  1..246
                        note = sununit 3 of PCNA
source                  1..246
                        mol_type = protein
                        organism = unidentified
SEQUENCE: 30
MKVVYDDVRV LKDIIQALAR LVDEAVLKFK QDSVELVALD RAHISLISVN LPREMFKEYD    60
VNDEFKFGFN TQYLMKILKV AKRKEAIEIA SESPDSVIIN IIGSTNREFN VRNLEVSEQE   120
IPEINLQFDI SATISSDGFK SAISEVSTVT DNVVVEGHED RILIKAEGES EVEVEFSKDT   180
GGLQDLEFSK ESKNSYSAEY LDDVLSLTKL SDYVKISFGN QKPLQLFFNM EGGGKVTYLL   240
APKVLE                                                             246

SEQ ID NO: 31           moltype = AA   length = 608
FEATURE                 Location/Qualifiers
source                  1..608
                        mol_type = protein
                        note = Bacillus subtilis phage phi29
```

```
                      organism = unidentified
SEQUENCE: 31
MKHMPRKMYS CAFETTTKVE DCRVWAYGYM NIEDHSEYKI GNSLDEFMAW VLKVQADLYF     60
HNLKFDGAFI INWLERNGFK WSADGLPNTY NTIISRMGQW YMIDICLGYK GKRKIHTVIY    120
DSLKKLPFPV KKIAKDFKLT VLKGDIDYHK ERPVGYKITP EEYAYIKNDI QIIAEALLIQ    180
FKQGLDRMTA GSDSLKGFKD IITTKKFKKV FPTLSLGLDK EVRYAYRGGF TWLNDRFKEK    240
EIGEGMVFDV NSLYPAQMYS RLLPYGEPIV FEGKYVWDED YPLHIQHIRC EFELKEGYIP    300
TIQIKRSRFY KGNEYLKSSG GEIADLWLSN VDLELMKEHY DLYNVEYISG LKFKATTGLF    360
KDFIDKWTYI KTTSEGAIKQ LAKLMLNSLY GKFASNPDVT GKVPYLKENG ALGFRLGEEE    420
TKDPVYTPMG VFITAWARYT TITAAQACYD RIIYCDTDSI HLTGTEIPDV IKDIVDPKKL    480
GYWAHESTFK RAKYLRQKTY IQDIYMKEVD GKLVEGSPDD YTDIKFSVKC AGMTDKIKKE    540
VTFENFKVGF SRKMKPKPVQ VPGGVVLVDD TFTIKSGGSA WSHPQFEKGG GSGGGSGGSA    600
WSHPQFEK                                                             608

SEQ ID NO: 32         moltype = AA  length = 318
FEATURE               Location/Qualifiers
source                1..318
                      mol_type = protein
                      note = Herpes virus 1
                      organism = unidentified
SEQUENCE: 32
TDSPGGVAPA SPVEDASDAS LGQPEEGAPC QVVLQGAELN GILQAFAPLR TSLLDSLLVM     60
GDRGILIHNT IFGEQVFLPL EHSQFSRYRW RGPTAAFLSL VDQKRSLLSV FRANQYPDLR    120
RVELAITGQA PFRTLVQRIW TTTSDGEAVE LASETLMKRE LTSFVVLVPQ GTPDVQLRLT    180
RPQLTKVLNA TGADSATPTT FELGVNGKFS VFTTSTCVTF AAREEGVSSS TSTQVQILSN    240
ALTKAGQAAA NAKTVYGENT HRTFSVVVDD CSMRAVLRRL QVGGGTLKFF LTTPVPSLCV    300
TATGPNAVSA VFLLKPQK                                                  318

SEQ ID NO: 33         moltype = AA  length = 233
FEATURE               Location/Qualifiers
source                1..233
                      mol_type = protein
                      note = Bacteriophage RB69
                      organism = unidentified
SEQUENCE: 33
KGFSSEDKGE WKLKLDASGN GQAVIRFLPA KTDDALPFAI LVNHGFKKNG KWYIETCSST     60
HGDYDSCPVC QYISKNDLYN TNKTEYSQLK RKTSYWANIL VVKDPQAPDN EGKVFKYRFG    120
KKIWDKINAM IAVDTEMGET PVDVTCPWEG ANFVLKVKQV SGFSNYDESK FLNQSAIPNI    180
DDESFQKELF EQMVDLSEMT SKDKFKSFEE LNTKFNQVLG TAALGGAAAA AAS            233

SEQ ID NO: 34         moltype = AA  length = 210
FEATURE               Location/Qualifiers
source                1..210
                      mol_type = protein
                      note = Bacteriophage T7
                      organism = unidentified
SEQUENCE: 34
AKKIFTSALG TAEPYAYIAK PDYGNEERGF GNPRGVYKVD LTIPNKDPRC QRMVDEIVKC     60
HEEAYAAAVE EYEANPPAVA RGKKPLKPYE GDMPFFDNGD GTTTFKFKCY ASFQDKKTKE    120
TKHINLVVVD SKGKKMEDVP IIGGGSKLKV KYSLVPYKWN TAVGASVKLQ LESVMLVELA    180
TFGGGEDDWA DEVEENGYVA SGSAKASKPR                                     210

SEQ ID NO: 35         moltype = AA  length = 99
FEATURE               Location/Qualifiers
source                1..99
                      mol_type = protein
                      note = Halorubrum lacusprofundi
                      organism = unidentified
SEQUENCE: 35
SGEELLDLAG VRNVGRKRAR RLFEAGIETR ADLREADKAV VLGALRGRER TAERILEHAG     60
REDPSMDDVR PDKSASAAAT AGSASDEDGE GQASLGDFR                            99

SEQ ID NO: 36         moltype = AA  length = 102
FEATURE               Location/Qualifiers
source                1..102
                      mol_type = protein
                      note = Haloferax volcanii
                      organism = unidentified
SEQUENCE: 36
SGEELLDLAG VRGVGRKRAR RLFEAGVETR ADLREADKPR VLAALRGRRK TAENILEAAG     60
RKDPSMDAVD EDDAPDDAVP DDAGFETAKE RADQQASLGD FE                       102

SEQ ID NO: 37         moltype = AA  length = 55
FEATURE               Location/Qualifiers
REGION                1..55
                      note = (HhH)2 domain
source                1..55
                      mol_type = protein
                      organism = unidentified
```

```
SEQUENCE: 37
WKEWLERKVG EGRARRLIEY FGSAGEVGKL VENAEVSKLL EVPGIGDEAV ARLVP          55

SEQ ID NO: 38            moltype = AA  length = 107
FEATURE                  Location/Qualifiers
REGION                   1..107
                         note = (HhH)2-(HhH)2 domain
source                   1..107
                         mol_type = protein
                         organism = unidentified
SEQUENCE: 38
WKEWLERKVG EGRARRLIEY FGSAGEVGKL VENAEVSKLL EVPGIGDEAV ARLVPGYKTL     60
RDAGLTPAEA ERVLKRYGSV SKVQEGATPD ELRELGLGDA KIARILG                  107

SEQ ID NO: 39            moltype = AA  length = 132
FEATURE                  Location/Qualifiers
source                   1..132
                         mol_type = protein
                         organism = Homo sapiens
SEQUENCE: 39
ESETTTSLVL ERSLNRVHLL GRVGQDPVLR QVEGKNPVTI FSLATNEMWR SGDSEVYQLG     60
DVSQKTTWHR ISVFRPGLRD VAYQYVKKGS RIYLEGKIDY GEYMDKNNVR RQATTIIADN    120
IIFLSDQTKE KE                                                       132

SEQ ID NO: 40            moltype = AA  length = 123
FEATURE                  Location/Qualifiers
source                   1..123
                         mol_type = protein
                         note = Bacillus subtilis phage phi29
                         organism = unidentified
SEQUENCE: 40
ENTNIVKATF DTETLEGGQIK IFNAQTGGGQ SFKNLPDGTI IEANAIAQYK QVSDTYGDAK    60
EETVTTIFAA DGSLYSAISK TVAEAASDLI DLVTRHKLET FKVKVVQGTS SKGNVFFSLQ   120
LSL                                                                 123

SEQ ID NO: 41            moltype = AA  length = 177
FEATURE                  Location/Qualifiers
source                   1..177
                         mol_type = protein
                         organism = Escherichia coli
SEQUENCE: 41
ASRGVNKVIL VGNLGQDPEV RYMPNGGAVA NITLATSESW RDKATGEMKE QTEWHRVVLF     60
GKLAEVASEY LRKGSQVYIE GQLRTRKWTD QSGQDRYTTE VVVNVGGTMQ MLGGRQGGGA   120
PAGGNIGGGQ PQGGWGQPQQ PQGGNQFSGG AQSRPQQSAP AAPSNEPPMD FDDDIPF      177

SEQ ID NO: 42            moltype = AA  length = 301
FEATURE                  Location/Qualifiers
source                   1..301
                         mol_type = protein
                         note = Enterobacteria phage T4
                         organism = unidentified
SEQUENCE: 42
MFKRKSTAEL AAQMAKLNGN KGFSSEDKGE WKLKLDNAGN GQAVIRFLPS KNDEQAPFAI     60
LVNHGFKKNG KWYIETCSST HGDYDSCPVC QYISKNDLYN TDNKEYSLVK RKTSYWANIL   120
VVKDPAAPEN EGKVFKYRFG KKIWDKINAM IAVDVEMGET PVDVTCPWEG ANFVLKVKQV   180
SGFSNYDESK FLNQSAIPNI DDESFQKELF EQMVDLSEMT SKDKFKSFEE LNTKFGQVMG   240
TAVMGGAAAT AAKKADKVAD DLDAFNVDDF NTKTEDDFMS SSSGSSSSAD DTDLDDLLND   300
L                                                                   301

SEQ ID NO: 43            moltype = AA  length = 177
FEATURE                  Location/Qualifiers
REGION                   1..177
                         note = EcoSSB-CterAla
source                   1..177
                         mol_type = protein
                         organism = unidentified
SEQUENCE: 43
ASRGVNKVIL VGNLGQDPEV RYMPNGGAVA NITLATSESW RDKATGEMKE QTEWHRVVLF     60
GKLAEVASEY LRKGSQVYIE GQLRTRKWTD QSGQDRYTTE VVVNVGGTMQ MLGGRQGGGA   120
PAGGNIGGGQ PQGGWGQPQQ PQGGNQFSGG AQSRPQQSAP AAPSNEPPMA FAAAIPF      177

SEQ ID NO: 44            moltype = AA  length = 177
FEATURE                  Location/Qualifiers
REGION                   1..177
                         note = EcoSSB-CterNGGN
source                   1..177
                         mol_type = protein
                         organism = unidentified
SEQUENCE: 44
```

```
ASRGVNKVIL VGNLGQDPEV RYMPNGGAVA NITLATSESW RDKATGEMKE QTEWHRVVLF    60
GKLAEVASEY LRKGSQVYIE GQLRTRKWTD QSGQDRYTTE VVVNVGGTMQ MLGGRQGGGA   120
PAGGNIGGGQ PQGGWGQPQQ PQGGNQFSGG AQSRPQQSAP AAPSNEPPMN FGGNIPF     177

SEQ ID NO: 45            moltype = AA   length = 152
FEATURE                  Location/Qualifiers
REGION                   1..152
                         note = EcoSSB-Q152del
source                   1..152
                         mol_type = protein
                         organism = unidentified
SEQUENCE: 45
ASRGVNKVIL VGNLGQDPEV RYMPNGGAVA NITLATSESW RDKATGEMKE QTEWHRVVLF    60
GKLAEVASEY LRKGSQVYIE GQLRTRKWTD QSGQDRYTTE VVVNVGGTMQ MLGGRQGGGA   120
PAGGNIGGGQ PQGGWGQPQQ PQGGNQFSGG AQ                                152

SEQ ID NO: 46            moltype = AA   length = 117
FEATURE                  Location/Qualifiers
REGION                   1..117
                         note = EcoSSB-G117del
source                   1..117
                         mol_type = protein
                         organism = unidentified
SEQUENCE: 46
ASRGVNKVIL VGNLGQDPEV RYMPNGGAVA NITLATSESW RDKATGEMKE QTEWHRVVLF    60
GKLAEVASEY LRKGSQVYIE GQLRTRKWTD QSGQDRYTTE VVVNVGGTMQ MLGGRQG      117

SEQ ID NO: 47            moltype = AA   length = 984
FEATURE                  Location/Qualifiers
source                   1..984
                         mol_type = protein
                         organism = Methanopyrus kandleri
SEQUENCE: 47
MALVYDAEFV GSEREFEEER ETFLKGVKAY DGVLATRYLM ERSSSAKNDE ELLELHQNFI    60
LLTGSYACSI DPTEDRYQNV IVRGVNFDER VQRLSTGGSP ARYAIVYRRG WRAIAKALDI   120
DEEDVPAIEV RAVKRNPLQP ALYRILVRYG RVDLMPVTVD EVPPEMAGEF ERLIERYDVP   180
IDEKEERILE ILRENPWTPH DEIARRLGLS VSEVEGEKDP ESSGIYSLWS RVVVNIEYDE   240
RTAKRHVKRR DRLLEELYEH LEELSERYLR HPLTRRWIVE HKRDIMRRYL EQRIVECALK   300
LQDRYGIRED VALCLARAFD GSISMIATTP YRTLKDVCPD LTLEEAKSVN RTLATLIDEH   360
GLSPDAADEL IEHFESIAGI LATDLEEIER MYEEGRLSEE AYRAAVEIQL AELTKKEGVG   420
RKTAERLLRA FGNPERVKQL AREFEIEKLA SVEGVGERVL RSLVPGYASL ISIRGIDRER   480
AERLLKKYGG YSKVREAGVE ELREDGLTDA QIRELKGLKT LESIVGDLEK ADELRKKYGS   540
ASAVRRLPVE ELRELGFSDD EIAEIKGIPK KLREAFDLET AAELYERYGS LKEIGRRLSY   600
DDLLELGATP KAAAEIKGPE FKFLLNIEGV GPKLAERILE AVDYDLERLA SLNPEELAEK   660
VEGLGEELAE RVVYAARERV ESRRKSGRQE RSEEEWKEWL ERKVGEGRAR RLIEYFGSAG   720
EVGKLVENAE VSKLLEVPGI GDEAVARLVP GYKTLRDAGL TPAEAERVLK RYGSVSKVQE   780
GATPDELREL GLGDAKIARI LGLRSLVNKR LDVDTAYELK RRYGSVSAVR KAPVKELREL   840
GLSDRKIARI KGIPETMLQV RGMSVEKAER LLERFDTWTK VKEAPVSELV RVPGVGLSLV   900
KEIKAQVDPA WKALLDVKGV SPELADRLVE ELGSPYRVLT AKKSDLMRVE RVGPKLAERI   960
RAAGKRYVEE RRSRRERIRR KLRG                                         984

SEQ ID NO: 48            moltype = AA   length = 299
FEATURE                  Location/Qualifiers
source                   1..299
                         mol_type = protein
                         organism = Methanopyrus kandleri
SEQUENCE: 48
SGRQERSEEE WKEWLERKVG EGRARRLIEY FGSAGEVGKL VENAEVSKLL EVPGIGDEAV    60
ARLVPGYKTL RDAGLTPAEA ERVLKRYGSV SKVQEGATPD ELRELGLGDA KIARILGLRS   120
LVNKRLDVDT AYELKRRYGS VSAVRKAPVK ELRELGLSDR KIARIKGIPE TMLQVRGMSV   180
EKAERLLERF DTWTKVKEAP VSELVRVPGV GLSLVKEIKA QVDPAWKALL DVKGVSPELA   240
DRLVEELGSP YRVLTAKKSD LMRVERVGPK LAERIRAAGK RYVEERRSRR ERIRRKLRG   299

SEQ ID NO: 49            moltype = AA   length = 853
FEATURE                  Location/Qualifiers
source                   1..853
                         mol_type = protein
                         organism = Escherichia coli
SEQUENCE: 49
MSAIENFDAH TPMMQQYLRL KAQHPEILLF YRMGDFYELF YDDAKRASQL LDISLTKRGA    60
SAGEPIPMAG IPYHAVENYL AKLVNQGESV AICEQIGDPA TSKGPVERKV VRIVTPGTIS   120
DEALLQERQD NLLAAIWQDS KGFGYATLDI SSGRFRLSEP ADRETMAAEL QRTNPAELLY   180
AEDFAEMSLI EGRRGLRRRP LWEFEIDTAR QQLNLQFGTR DLVGFGVENA PRGLCAAGCL   240
LQYAKDTQRT TLPHIRSITM EREQDSIIMD AATRRNLEIT QNLAGGAENT LASVLDCTVT   300
PMGSRMLKRW LHMPVRDTRV LLERQQTIGA LQDFTAGLQP VLRQVGDLER ILARLALRTA   360
RPRDLARMRH AFQQLPELRA QLETVDSAPV QALREKMGEF AELRDLLERA IIDTPPVLVR   420
DGGVIASGYN EELDEWRALA DGATDYLERL EVRERERTGL DTLKVGFNAV HGYYIQISRG   480
QSHLAPINYM RRQTLKNAER YIIPELKEYE DKVLTSKGKA LALEKQLYEE LFDLLLPHLE   540
ALQQSASALA ELDVLVNLAE RAYTLNYTCP TFIDKPGIRI TEGRHPVVEQ VLNEPFIANP   600
```

```
LNLSPQRRML IITGPNMGGK STYMRQTALI ALMAYIGSYV PAQKVEIGPI DRIFTRVGAA    660
DDLASGRSTF MVEMTETANI LHNATEYSLV LMDEIGRGTS TYDGLSLAWA CAENLANKIK    720
ALTLFATHYF ELTQLPEKME GVANVHLDAL EHGDTIAFMH SVQDGAASKS YGLAVAALAG    780
VPKEVIKRAR QKLRELESIS PNAAATQVDG TQMSLLSVPE ETSPAVEALE NLDPDSLTPR    840
QALEWIYRLK SLV                                                      853

SEQ ID NO: 50          moltype = AA   length = 64
FEATURE                Location/Qualifiers
source                 1..64
                       mol_type = protein
                       organism = Sulfolobus solfataricus
SEQUENCE: 50
MATVKFKYKG EEKEVDISKI KKVWRVGKMI SFTYDEGGGK TGRGAVSEKD APKELLQMLE    60
KQKK                                                                 64

SEQ ID NO: 51          moltype = AA   length = 99
FEATURE                Location/Qualifiers
source                 1..99
                       mol_type = protein
                       note = Sulfolobus solfataricus P2
                       organism = unidentified
SEQUENCE: 51
EKMSSGTPTP SNVVLIGKKP VMNYVLAALT LLNQGVSEIV IKARGRAISK AVDTVEIVRN    60
RFLPDKIEIK EIRVGSQVVT SQDGRQSRVS TIEIAIRKK                            99

SEQ ID NO: 52          moltype = AA   length = 88
FEATURE                Location/Qualifiers
source                 1..88
                       mol_type = protein
                       note = Sulfolobus solfataricus P2
                       organism = unidentified
SEQUENCE: 52
TEKLNEIVVR KTKNVEDHVL DVIVLFNQGI DEVILKGTGR EISKAVDVYN SLKDRLGDGV    60
QLVNVQTGSE VRDRRRISYI LLRLKRVY                                       88

SEQ ID NO: 53          moltype = AA   length = 107
FEATURE                Location/Qualifiers
source                 1..107
                       mol_type = protein
                       organism = Escherichia coli
SEQUENCE: 53
AQQSPYSAAM AEQRHQEWLR FVDLLKNAYQ NDLHLPLLNL MLTPDEREAL GTRVRIVEEL    60
LRGEMSQREL KNELGAGIAT ITRGSNSLKA APVELRQWLE EVLLKSD                  107

SEQ ID NO: 54          moltype = AA   length = 237
FEATURE                Location/Qualifiers
source                 1..237
                       mol_type = protein
                       note = Enterobacteria phage lambda
                       organism = unidentified
SEQUENCE: 54
MSTKKKPLTQ EQLEDARRLK AIYEKKKNEL GLSQESVADK MGMGQSGVGA LFNGINALNA    60
YNAALLAKIL KVSVEEFSPS IAREIYEMYE AVSMQPSLRS EYEYPVFSHV QAGMFSPELR    120
TFTKGDAERW VSTTKKASDS AFWLEVEGNS MTAPTGSKPS FPDGMLILVD PEQAVEPGDF    180
CIARLGGDEF TFKKLIRDSG QVFLQPLNPQ YPMIPCNESC SVVGKVIASQ WPEETFG       237

SEQ ID NO: 55          moltype = AA   length = 60
FEATURE                Location/Qualifiers
source                 1..60
                       mol_type = protein
                       note = Crenarchaea
                       organism = unidentified
SEQUENCE: 55
MSSGKKPVKV KTPAGKEAEL VPEKVWALAP KGRKGVKIGL FKDPETGKYF RHKLPDDYPI    60

SEQ ID NO: 56          moltype = AA   length = 136
FEATURE                Location/Qualifiers
source                 1..136
                       mol_type = protein
                       organism = Homo sapiens
SEQUENCE: 56
MARTKQTARK STGGKAPRKQ LATKAARKSA PATGGVKKPH RYRPGTVALR EIRRYQKSTE    60
LLIRKLPFQR LVREIAQDFK TDLRFQSSAV MALQEASEAY LVGLFEDTNL CAIHAKRVTI    120
MPKDIQLARR IRGERA                                                    136

SEQ ID NO: 57          moltype = AA   length = 89
FEATURE                Location/Qualifiers
source                 1..89
                       mol_type = protein
```

```
                        note = Enterobacteria phage T4
                        organism = unidentified
SEQUENCE: 57
MAKKEMVEFD EAIHGEDLAK FIKEASDHKL KISGYNELIK DIRIRAKDEL GVDGKMFNRL    60
LALYHKDNRD VFEAETEEVV ELYDTVFSK                                      89

SEQ ID NO: 58           moltype = AA  length = 339
FEATURE                 Location/Qualifiers
source                  1..339
                        mol_type = protein
                        organism = Homo sapiens
SEQUENCE: 58
MAMQMQLEAN ADTSVEEESF GPQPISRLEQ CGINANDVKK LEEAGFHTVE AVAYAPKKEL    60
INIKGISEAK ADKILAEAAK LVPMGFTTAT EFHQRRSEII QITTGSKELD KLLQGGIETG   120
SITEMFGEFR TGKTQICHTL AVTCQLPIDR GGGEGKAMYI DTEGTFRPER LLAVAERYGL   180
SGSDVLDNVA YARAFNTDHQ TQLLYQASAM MVESRYALLI VDSATALYRT DYSGRGELSA   240
RQMHLARFLR MLLRLADEFG VAVVITNQVV AQVDGAAMPA ADPKKPIGGN IIAHASTTRL   300
YLRKGRGETR ICKIYDSPCL PEAEAMFAIN ADGVGDAKD                         339

SEQ ID NO: 59           moltype = AA  length = 375
FEATURE                 Location/Qualifiers
source                  1..375
                        mol_type = protein
                        note = Citromicrobium bathyomarinum JL354
                        organism = unidentified
SEQUENCE: 59
MKATIERATL LRCLSHVQSV VERRNTIPIL SNVLIDADAG GGVKVMATDL DLQVVETMTA    60
ASVESAGAIT VSAHLLFDIA RKLPDGSQVS LETADNRMVV KAGRSRFQLP TLPRDDFPVI   120
VEGELPTSFE LPARELAEMI DRTRFAISTE ETRYYLNGIF LHVSDEARPV LKAAATDGHR   180
LARYTLDRPE GAEGMPDVIV PRKAVGELRK LLEEALDSNV QIDLSASKIR FALGGEGGVV   240
LTSKLIDGTF PDYSRVIPTG NDKLLRLDPK AFFQGVDRVA TIATEKTRAV KMGLDEDKVT   300
LSVTSPDNGT AAEEIAAEYK AEGFEIGFNA NYLKDILGQI DSDTVELHLA DAGAPTLIRR   360
DENSPALYVL MPMRV                                                   375

SEQ ID NO: 60           moltype = DNA  length = 50
FEATURE                 Location/Qualifiers
misc_feature            1..50
                        note = Synthetic Polynucleotide
source                  1..50
                        mol_type = other DNA
                        organism = synthetic construct
SEQUENCE: 60
tttttttttt tttttttttt tttttttttt tttttttttt tttttttttt               50

SEQ ID NO: 61           moltype = DNA  length = 27
FEATURE                 Location/Qualifiers
misc_feature            1..27
                        note = Synthetic Polynucleotide
source                  1..27
                        mol_type = other DNA
                        organism = synthetic construct
SEQUENCE: 61
ggttgtttct gttggtgctg atattgc                                        27

SEQ ID NO: 62           moltype = DNA  length = 97138
FEATURE                 Location/Qualifiers
misc_feature            1..97138
                        note = Synthetic Polynucleotide
source                  1..97138
                        mol_type = other DNA
                        organism = synthetic construct
SEQUENCE: 62
gctccactaa agggccgatt gacgggcggc gacctcgcgg gttttcgcta tttatgaaaa    60
ttttccggtt taaggcgttt ccgttcttct tcgtcataac ttaatgtttt tatttaaaat   120
accctctgaa aagaaaggaa acgacaggtg ctgaaagcga ggcttttttgg cctctgtcgt   180
ttcctttctc tgtttttgtc cgtggaatga acaatgaaag tcaacaaaaa gcagctggct   240
gacatttttcg gtgcgagtat ccgtaccatt cagaactggc aggaacaggg aatgcccgtt   300
ctgcgaggcg gtggcaaggg taatgaggtg ctttatgact ctgccgccgt cataaaatgg   360
tatgccgaaa gggatgctga aattgagaac gaaaagctgc gccgggaggt tgaagaactg   420
cggcaggcca gcgaggcaga tctccagcca ggaactattg agtacgaacg ccatcgactt   480
acgcgtgcgc aggccgacgc acaggaactg aagaatgcca gagactccgc tgaagtggtg   540
gaaaccgcat tctgtacttt cgtgctgtcg cggatcgcag gtgaaattgc cagtattctc   600
gacgggctcc ccctgtcggt gcagcggcgt tttccggaac tggaaaaccg acatgttgat   660
ttcctgaaac gggatatcat caaagccatg aacaaagcc ccgcgctgga tgaactgata   720
ccggggttgc tgagtgaata tatcgaacag tcaggttaac aggctgcggc attttgtccg   780
cgccgggctt cgctcactgt tcaggccgga gccacagacc gccgttgaat gggcggatgc   840
taattactat ctcccgaaag aatccgcata ccaggaaggg cgctgggaaa cactgccctt   900
tcagcgggcc atcatgaatg cgatgggcag cgactacatc cgtgaggtga atgtggtgaa   960
gtctgcccgt gtcggttatt ccaaaatgct gctgggtgtt tatgcctact ttatagagca  1020
```

```
taagcagcgc aacacccctta tctggttgcc gacggatggt gatgccgaga acttttatgaa  1080
aacccacgtt gagccgacta ttcgtgatat tccgtcgctg ctggcgctgg ccccgtggta   1140
tggcaaaaag caccgggata acacgctcac catgaagcgt ttcactaatg ggcgtggctt   1200
ctggtgcctg ggcggtaaag cggcaaaaaa ctaccgtgaa aagtcggtgg atgtggcggg   1260
ttatgatgaa cttgctgctt ttgatgatga tattgaacag gaaggctctc cgacgttcct   1320
gggtgacaag cgtattgaag gctcggtctg gccaaagtcc atccgtggct ccacgccaaa   1380
agtgagaggc acctgtcaga ttgagcgtgc agccagtgaa tccccgcatt ttatgcgttt   1440
tcatgttgcc tgcccgcatt gcggggagga gcagtatctt aaatttggcg acaaagagac   1500
gccgtttggc ctcaaatgga cgccgatga cccctccagc gtgttttatc tctgcgagca   1560
taatgcctgc gtcatccgcc agcaggagct ggactttact gatgcccgtt atatctgcga   1620
aaagaccggg atctgaccc gtgatggcat tctctggttt tcgtcatccg gtgaagagat   1680
tgagccacct gacagtgtga cctttcacat ctggacagcg tacagccgt tcaccacctg    1740
ggtgcagatt gtcaaagact ggatgaaaac gaaagggaga acgggaaaac gtaaaacctt   1800
cgtaaacacc acgtccggtg agacgtggga ggcgaaaatt cgaacgtc cggatgctga    1860
agtgatggca gagcggaaag agcattattc agcgcccgtt cctgaccgtg tggcttacct   1920
gaccgccggt atcgactccc agctggaccg ctacgaaatg cgcgtatggg gatgggggcc   1980
gggtgaggaa agctggctga ttgaccggca gattattatg ggccgccacg acgatgaaca   2040
gacgctgctg cgtgtggatg aggccatcaa taaaacctat acccgccgga atggtgcaga   2100
aatgtcgata tcccgtatct gctgggatac tggcggatt gacccgacca ttgtgtatga    2160
acgctcgaaa aacatggggc tgttccgggt gatcccatt aaaggggcat ccgtctacgg    2220
aaagccggtg gccagcatgc cacgtaagcg aaacaaaaac ggggttttacc ttaccgaaat   2280
cggtacggat accgcgaaag agcagattta taaccgcttc acactgacgc cggaagggga   2340
tgaaccgctt cccggtgccg ttcacttccc gaataacccg gatattttg atctgaccga    2400
agcgcagcag ctgactgctg aagagcaggt cgaaaaatgg gtggatggca ggaaaaaaat   2460
actgtgggac agcaaaaagc gacgcaatga ggcactcgac tgcttcgttt atgcgctggc   2520
ggcgctgctg atcagtattt cccgctgca gctggatctc agtgcgctgc tggcgagcct    2580
gcaggaagag gatggtgcag caaccaacaa gaaaacactg gcagattacg cccgtgcctt   2640
atccggagag gatgaatgac gcgacaggaa gaacttgccg ctgcccgtgc ggcactgcat   2700
gacctgatga caggtaaacg ggtggcaaca gtacagaaag acggacgaag ggtggagttt   2760
acggccactt ccgtgtctga cctgaaaaaa tatattgaag agctgaaggt gcagaccggc   2820
atgacacagc gacgcagggg acctgcagga ttttatgtat gaaaacgccc accattccca   2880
cccttctggg gccggacggc atgacatcgc tgcgcgaata tgccggttat cacggcggtg   2940
gcagcggatt tggagggcag ttgcggtcgt ggaacccacc gagtgaaagt gtggatgcag   3000
ccctgttgcc caactttacc cgtggcaatg cccgcgcaga cgatctggta cgcaataacg   3060
gctatgccgc caacgccatc cagctgcatc aggatcatat cgtcgggtct tttttccggc   3120
tcagtcatcg cccaagctgg cgctatctgg gcatcgggga ggaagaagcc cgtgccttt    3180
cccgcgaggt tgaagcggca tggaaagagt tgccgaggga tgactgctgc tgcattgacg   3240
ttgagcgaaa acgcacgttt accatgatga ttcgggaagg tgtggccatg cacgccttta   3300
acggtgaact gttcgttcag gccacctggg ataccagttc gtcgcggctt ttccggacac   3360
agttccggat ggtcagcccg aagcgcatca gcaacccgaa caataccggc gacagccgga   3420
actgccgtgc cggtgtgcag attaatgaca gcggtcgggc gctgggatat tacgtcagcg   3480
aggacgggta tcctggctgg atgccgcaga aatggacatg gataccccgt gagttacccg   3540
gcgggcgcgc ctcgttcatt cacgttttg aacccgtggg ggacgggcag actcgcggtg    3600
caaatgtgtt ttacagcgtg atggagcaga tgaagatgct cgacacgctg cagaacacgc   3660
agctgcagag cgccattgtg aaggcgatgt atgccgccac cattgagagt gagctggata   3720
cgcagtcagc gatggatttt attctgggcg cgaacagtca ggagcagcgg gaaaggctga   3780
ccggctggat tggtgaaatt gccgcgtatt acgccgcagc gccggtccgg ctgggaggcg   3840
caaaagtacc gcacctgatg ccgggtgact cactgaacct gcagacggct caggatacgg   3900
ataacggcta ctccgtgttt gagcagtcac tgctgcggta tatcgctgcc gggctggtg    3960
tctcgtatga gcagctttcc cggaattacg cccagatgag ctactccacg gcacgggcca   4020
gtgcgaacga gtcgtgggcg tactttatgg ggcggcgaaa attcgtcgca tcccgtcagg   4080
cgagccagat gtttctgtgc tggctgaaag aggccatcgt tcgccgcgtg gtgacgttac   4140
cttcaaaagc gcgcttcagt tttcaggaag cccgcagtgc ctgggggaac tgcgactgga   4200
taggctccgg tcgtatggcc atcgatggtc tgaaagaagt tcaggaagcg gtgatgctga   4260
tagaagccgg actgagtacc tacgaagaag agtgcgcaaa acgcggtgac gactatcagg   4320
aaatttttgc ccagcaggtc cgtgaaacga tggagcgccg tgcagccggt cttaaaccgc   4380
ccgcctgggc ggctgcagca tttgaatccg gctgcgaca atcaacagag gaggagaaga   4440
gtgacagcag agctgcgtaa tctcccgcat attgccagca tggcctttaa tgagccgctg   4500
atgcttgaac ccgcctatgc gcgggttttc ttttgtgcgc ttgcaggcca gcttgggag    4560
agcagcctga cggatgcggt gtccggcgac agcctgactg cccaggagge actcgcgacg   4620
ctggcattat ccggtgatga tgacggacca cgacaggccc gcagttatca ggtcatgaac   4680
ggcatcgccg tgctgccggt gtccggcacg ctggtcagcc ggacgcgggc gctgcagccg   4740
tactcgggga tgaccggtta caacggcatt atcgcccgtc tgcaacaggc tgccagcgat   4800
ccgatgtggg acggcattct gctcgatatg gacacgcgg gggatggt ggcgggggca     4860
tttgactgcg ctgacatcat cgccgtgtgt cgtgacataa aaccggtatg ggcgcttgcc   4920
aacgacatga actgcagtgc aggtcagttg cttgccagtg ccgcctcccg gcgtctggtc   4980
acgcagaccc cccggacagg ctccatcggc gtcatgatgg ctcacagtaa ttacggtgct   5040
gcgctggaga aacagggtgt ggaaatcacg ctgatttaca gcggcagcca taaggtggat   5100
gcaaccccct acagccatct tccggatgac gtccgggaga cactgcagtc cggcgatgga   5160
gcaacccgcc agatgtttgc gcagaaggtg tcggcatata ccggcctgtc cgtgcaggtt   5220
gtgctgata ccgaggctgc agtgtacagc ggtcaggagg ccattgatgc cggactggct    5280
gatgaacttg ttaacagcac cgatgcgatc accgtcatgc gtgatgcact ggatgcacgt   5340
aaatcccgtc tctcaggagg gcgaatgacc aaagagactc aatcaacaac tgtttcagcc   5400
actgcttcgc aggctgacgt tactgacgtg tgcgaggga gaacgccagc                5460
gcggcgcagc cggacgtgaa cgcgcagatc accgcagcgg ttgcggcaga aaacagccgc   5520
attatgggga tcctcaactg tgaggaggct cacggacgcg aagaacaggc acgcgtgctg   5580
gcagaaaccc ccggtatgac cgtgaaaacg gcccgccgca ttctggccgc agcaccacag   5640
agtgcacagg cgcgcagtga cactgcgctg atcgtctga tgcaggggc accggcaccg    5700
ctggctgcag gtaacccggc atctgatgcc gttaacgatt gctgaacac accagtgtaa    5760
```

```
gggatgttta tgacgagcaa agaaaccttt acccattacc agccgcaggg caacagtgac  5820
ccggctcata ccgcaaccgc gcccggcgga ttgagtgcga aagcgcctgc aatgaccccg  5880
ctgatgctgg acacctccag ccgtaagctg gttgcgtggg atggcaccac cgacggtgct  5940
gccgttggca ttcttgcggt tgctgctgac cagaccagca ccacgctgac gttctacaag  6000
tccggcacgt tccgttatga ggatgtgctc tggccggagg ctgccagcga cgagacgaaa  6060
aaacggaccg cgtttgccgg aacggcaatc agcatcgttt aactttaccc ttcatcacta  6120
aaggccgcct gtgcggcttt ttttacggga tttttttatg tcgatgtaca caaccgccca  6180
actgctggcg gcaaatgagc agaaatttaa gtttgatccg ctgtttctgc gtctcttttt  6240
ccgtgagagc tatcccttca ccacggagaa agtctatctc tcacaaattc cgggactggt  6300
aaacatggcg ctgtacgttt cgccgattgt ttccggtgag gttatccgtt cccgtggcgg  6360
ctccacctct gaatttacgc cgggatatgt caagccgaag catgaagtga atccgcagat  6420
gaccctgcgt cgcctgccgg atgaagatcc gcagaatctg gcggaccggg cttaccgccg  6480
ccgtcgcatc atcatgcaga acatgcgtga cgaagagctc gccattgctc aggtcgaaga  6540
gatgcaggca gtttctgccg tgcttaaggg caaatacacc atgaccggtg aagccttcga  6600
tccggttgag gtggatatgg gccgcagtga ggagaataac atcacgcagt ccggcggcac  6660
ggagtggagc aagcgtgaca agtccacgta tgacccgacc gacgatatcg aagcctacgc  6720
gctgaacgcc agcggtgtgg tgaatatcat cgtgttcgat ccgaaaggct gggcgctgtt  6780
ccgttccttc aaagccgtca aggagaagct ggataccgct cgtggctcta attccgagct  6840
ggagacagcg gtgaaagacc tgggcaaagc ggtgtcctat aaggggatgt atggcgatgt  6900
ggccatcgtc gtgtattccg gacagtacgt ggaaaacggc gtcaaaaaga acttcctgcc  6960
ggacaacacg atggtgctgg ggaacactca ggcacgcggt ctgcgcacct atggctgcat  7020
tcaggatgcg gacgcacagc gcgaaggcat taacgcctct gcccgttacc cgaaaaactg  7080
ggtgaccacc ggcgatccgg cgcgtgagtt caccatgatt cagtcagcac cgctgatgct  7140
gctggctgac cctgatgagt tcgtgtccgt acaactggcg taatcatggc ccttcggggc  7200
cattgttttct ctgtggagga gtccatgacg aaagatgaac tgattgcccg tctccgctcg  7260
ctgggtgaac aactgaaccg tgatgtcgac gcgacgggga cgaaagaaga actggcgctc  7320
cgtgtggcag agctgaaaga ggagcttgat gacacggatg aaactgccgg tcaggacacc  7380
cctctcagcc gggaaaatgt gctgaccgga catgaaaatg aggtgggatc agcgcagccg  7440
gataccgtga ttctggatac gtctgaactg gtcacggtcg tggcactggt gaagctgcat  7500
actgatgcac ttcacgccac gcgggatgaa cctgtgcgat ttgtgctgcc gggaaccgcg  7560
tttcgtgtct ctgccggtgt ggcagccgaa atgacagagc gcggcctggc cagaatgcaa  7620
taacgggagg cgctgtggct gatttcgata acctgttcga tgctgccatt gcccgcgccg  7680
atgaaacgat acgcgggtac atgggaacgt cagccaccat tacatccggt gagcagtcag  7740
gtgcggtgat acgtggtgtt tttgatgacc ctgaaaatat cagctatgcc ggacagggcg  7800
tgcgcgttga aggctccagc ccgtccctgt ttgtccggac tgatgaggtg cggcagctgc  7860
ggcgtggaga cacgctgacc atcggtgagg aaaattctg ggtagatcgg gtttcgccgg  7920
atgatgcgcg aagttgtcat ctctggcttg acggggcgt accgcctgcc gttaaccgtc  7980
gccgctgaaa ggggatgta tggccataaa aggtcttgag caggccgttg aaaacctcag  8040
ccgtatcagc aaaaccgcgg tgcctggtgc cgccgcaatc gccattaacc gcgttgcttc  8100
atccgcgata tcgcagtcgg cgtcacaggt tgcccgtgag acaaaggtac gccggaaact  8160
ggtaaaggaa agggccaggc tgaaaagggc cacggtcaaa aatccgcagg ccagaatcaa  8220
agttaaccgg ggggatttgc ccgtaatcaa gctgggtaat gcgcggggttg tccttttcgcg  8280
ccgcagcgt cgtaaaaagg ggcagcgttc atccctgaaa ggtggccgca gcgtgcttgt  8340
ggtgggtaac cgtcgtattc ccggcgcgtt tattcagcaa ctgaaaaatg gccggtggca  8400
tgtcatgcag cgtgtggctg ggaaaaaccg ttaccccatt gatgtggtga aaatcccgat  8460
ggcggtgccg ctgaccacgg cgtttaaaca aaatattgag cggatacggc gtgaacgtct  8520
tccgaaagag ctgggctatg cgctgcagca tcaactgagg atggtaataa agcgatgaaa  8580
catactgaac tccgtgcagc cgtactggat gcactgagaa agcatgacac cggggcgacg  8640
tttttttgatg tcgccccgc tgtttttgat gaggcggatt ttccggcagt tgccgtttat  8700
ctcaccggcg ctgaatacac gggcgaagag ctggacagcg ataccggca ggcggagctg  8760
catatcgaag ttttcctgcc tgctcaggtg ccggattcag agctggatgc gtggatggag  8820
tcccggattt atccggtgat gagcgatatc ccggcactgt cagatttgat caccagtatg  8880
gtggccagcg gctatgacta ccggcgcgac gatgatgcgg gcttgtggag ttcagccgat  8940
ctgacttatg tcattaccta tgaaatgtga ggacgctatg cctgtaccaa atcctacaat  9000
gccggtgaaa ggtgccggga ccaccctgtg ggttatatag gggacggtg accccttacgc  9060
gaatccgctt tcagacgttg actggtcgcg tctggcaaaa gttaaagacc tgacgcccgg  9120
cgaactgacc gctgagtcct atgacgacac ctatctcgat gatgaagatg cagactggac  9180
tgcgaccgga caggggcaga aatctgccgg agataccagc ttcacgctgg cgtggatgcc  9240
cggagagcag gggcagcagg cgctgctggc gtggtttaat gaaggcgata cccgtgccta  9300
taaaatccgc ttcccgaacg gcacggtcga tgtgttccgt ggctgggtca gcagtatcgg  9360
taaggcggtg acggcgaagg aagtgatcac ccgcacggtg aaagtcacca atgtgggacg  9420
tccgtcgatg gcagaagatc gcagcacggt aacagcggca accggcatga ccgtgacgcc  9480
tgccagcacc tcggtggtga agggcagag caccacgctg accgtggcct tcagccggaa  9540
gggcgtaacc gacaagagct ttcgtcgggt gtctgcggaa aaacaaaag ccaccgtcg  9600
ggtcagtggt atgaccatca ccgtgaacgg cgttgctgca ggcaaggtca acattccggt  9660
tgtatccggt aatggtgagt tgctgccggt tgcagaaatt accgtcaccg ccagttaatc  9720
cggagagtca gcgatgttcc tgaaaaccga atcatttgaa cataacggtg tgaccgtcac  9780
gcttttctga actgtcagccc tgcagcgcat tgagcatctc gccctgatga aacggcaggc  9840
agaacaggcg gagtcagaca caaccgaa gtttactgtg gaagacgcca tcagaaccgg  9900
cgcgtttctg gtggcgatgt ccctgtggca taaccatccg cagaagacgc agatgccgtc  9960
catgaatgaa gccgttaaac agattgagca ggaagtgctt accacctggc ccacggaggc 10020
aatttctcat gctgaaaacg tggtgtaccg gctgtctggt atgtatgagt ttgtggtgaa 10080
taatgccccct gaacagacag aggacgccgg gccccgcagag cctgtttctg cgggaaagtg 10140
ttcgacggtg agctgagttt tgccctgaaa ctggccgggg agatggggcg accggactgg 10200
cgtgccatgc ttgccgggat gtcatccacg gagtatgccg actggcaccg cttttacagt 10260
acccattatt ttcatgatgt tctgctggat atgcacttt ccgggctgac gtacaccgtg 10320
ctcagcctgt ttttcagcga tccggatatg catccgctgg atttcagtct gctgaaccgg 10380
cgcgaggctg acgaagagcc tgaagatgat gtgctgatga gaaagcggc agggcttgcc 10440
ggaggtgtcc gctttggccc ggacgggaat gaagttatcc ccgcttcccc ggatgtgcg 10500
```

```
gacatgacgg aggatgacgt aatgctgatg acagtatcag aagggatcgc aggaggagtc    10560
cggtatggct gaaccggtag gcgatctggt cgttgatttg agtctggatg cggccagatt    10620
tgacgagcag atggccagag tcaggcgtca tttttctggt acggaaagtg atgcgaaaaa    10680
aacagccgca gtcgttgaac agtcgctgag ccgacaggcg ctggctgcac agaaagcggg    10740
gatttccgtc gggcagtata aagccgccat gcgtatgccg cctgcacagt tcaccgacgt    10800
ggccacgcag cttgcaggcg ggcaaagtcc gtggctgatc ctgctgcaac agggggggca    10860
ggtgaaggac tccttcggcg ggatgatccc catgttcagg gggcttgccg gtgcgatcac    10920
cctgccgatg gtgggggcca cctcgctggc ggtggcgacc ggtgcgctgg cgtatgcctg    10980
gtatcagggc aactcaaccc tgtccgattt caacaaaacg ctggtccttt ccggcaatca    11040
ggcgggactg acggcagatc gtatgctggt cctgtccaga gccgggcagg cggcagggct    11100
gacgtttaac cagaccagcg agtcactcag cgcactggtt aaggcggggg taagcggtga    11160
ggctcagatt gcgtccatca gccagagtgt ggcgcgtttc tcctctgcat ccggcgtgga    11220
ggtggacaag gtcgctgaag ccttcgggaa gctgaccaca gacccgacgt cggggctgac    11280
ggcgatggct cgccagttcc ataacgtgtc ggccgagcag attgcgtatg ttgctcagtt    11340
gcagcgttcc ggcgatgaag ccggggcatt gcaggcggcg aacgaggccg caacgaaaggg   11400
gtttgatgac cagacccgcc gcctgaaaga gaacatgggc acgctggaga cctgggcaga    11460
caggactgcg cgggcattca aatccatgtg ggatgcggtg ctggatattg gtcgtcctga    11520
taccgcgcag gagatgctga ttaaggcaga ggctgcgtat aagaaagcag acgacatctg    11580
gaatctgcgc aaggatgatt attttgttaa cgatgaagcg cgggcgcgtt actgggatga    11640
tcgtgaaaag gcccgtcttg cgcttgaagc cgcccgaaag aaggctgagc agcagactca    11700
acaggacaaa aatgcgcagc agcagagcga taccgaagcg tcacggctga aatataccga    11760
agaggcgcag aaggcttacg aacggctgca gacgccgctg gagaaatata cgcccgtca    11820
ggaagaactg aacaaggcac tgaaagacgg gaaaatcctg caggcggatt acaacacgct    11880
gatggcggcg gcgaaaaagg attatgaagc gacgctgaaa aagccgaaac agtccagcgt    11940
gaaggtgtct gcgggcgatc gtcaggaaga cagtgctcat gctgccctgc tgacgcttca    12000
ggcagaactc cggacgctgg agaagcatgc cggagcagat gagaaaatca gccagcagcg    12060
ccgggatttg tggaaggcgg agagtcagtt cgcggtactg gaggaggcgg cgcaacgtcg    12120
ccagctgtct gcacaggaga aatccctgct ggcgcataaa gatgagacgc tggagtacaa    12180
acgccagctg gctgcacttg gcgacaaggt tacgtatcag gagcgcctga acgcgctggc    12240
gcagcaggcg gataaattcg cacagcagca acgggcaaaa cgggccgcca ttgatgcgaa    12300
aagccggggg ctgactgacc ggcaggcaga acgggaagcc acggaacagc gcctgaagga    12360
acagtatggc gataatccgc tggcgctgaa taacgtcatg tcagagcaga aaagacctg    12420
ggcggctgaa gaccagcttc gcgggaactg gatggcaggc ctgaagtccg gctggagtga    12480
gtggaaagag agcgccacgg acagtatgtc gcaggtaaaa agtgcagcca cgcagaccct    12540
tgatggtatt gcacagaata tggcggcgat gctgaccggc agtgacgaca actggcgcag    12600
cttcacccgt tccgtgctgt ccatgatgac agaaattctg cttaagcagg caatggtggg    12660
gattgtcggg agtatcggca gcgccattgg cggggctgtt ggtggcggcg catccgcgtc    12720
aggcggtaca gccattcagg ccgctgcggc gaaattccat tttgcaaccg gaggatttac    12780
gggaaccggc ggcaaatatg agccagcggg gattgttcac cgtggtgagt ttgtcttcac    12840
gaaggaggca accagccgga ttggcgtggg gaatctttac cggctgatgc gcggctatgc    12900
caccggcggt tatgtcggta caccgggcag catggcagac agccggtcgc aggcgtccgg    12960
gacgtttgag cagaataacc atgtggtgat taacaacgac ggcacgaacg ggcagatagg    13020
tccggctgct ctgaaggcgg tgtatgacat ggcccgcaag ggtgcccgtg atgaaattca    13080
gacacagatg cgtgatggtg gcctgttctc cggaggtgga cgatgaagac cttccgctgg    13140
aaaagtgaaac ccggtatgga tgtggcttcg gtcccttctg taagaaaggt gcgctttggt   13200
gatggctatt ctcagcgagc gcctgccggg ctgaatgcca acctgaaaac gtacagcgtg    13260
acgctttctg tcccccgtga ggaggccacg gtactggagt cgtttctgga agagcacggg    13320
ggctggaaat cctttctgtg gacgccgcct tatgagtggc ggcagataaa ggtgacctgc    13380
gcaaaatggt cgtcgcgggt cagtatgctg cgtgttgagt tcagcgcaga gtttgaacag    13440
gtggtgaact gatgcaggat atccggcagg aaacactgaa tgaatgcacc cgtgcggagc    13500
agtcgccag cgtggtgctc tgggaaatcg acctgacaga ggtcggttga gaacgttatt    13560
ttttctgtaa tgagcagaac gaaaaaggtg agccggtcac ctggcagggg cgacagtatc    13620
agccgtatcc cattcagggg agcggttttg aactgaatgg caaaggcacc agtacgcgcc    13680
ccacgctgac ggtttctaac ctgtacggta tggtcaccgg gatggcggaa gatatgcaga    13740
gtctggtcgg cggaacggtg gtccggcgta aggtttacgc ccgttttctg gatgcggtga    13800
acttcgtcaa cggaaacagt tacgccgatc cggagcagga ggtgatcagc cgctggcgca    13860
ttgagcagtg cagcgaactg agcgcggtga gtgcctcctt tgtactgtcc acgccgacgg    13920
aaaacggatg cgctgttttt ccgggacgta tcatgctggc caacacctgc acctggacct    13980
atcgcggtga cgagtcgcgt tatagcggtc cggctgtccg ggatgaatat gaccagccaa    14040
cgtccgatat cacgaaggat aaatgcctgag cggttgtaag ttccgcaata    14100
acgtcggcaa ctttgcggc ttcctttcca ttaacaaact ttcgcagtaa atcccatgac    14160
acagacagaa tcagcgattc tggcgcacgc ccggcgatgt gcgccagcgg agtcgtgcgg    14220
cttcgtggta agcacgccgg agggggaaag atatttcccc tgcgtgaata tctccggtga    14280
gccggagctg atttccgtat gtcgccgaaa gactggctgg aggcagaaat gcagggtgag    14340
attgtggcgc tggtccacag ccaccccggt ggtctgccct ggctgagtga ggccgaccgg    14400
cggctgcagg tgcagagtga tttgccgtgg tggctggtct gccgggggac gattcataag    14460
ttccgctgtg tgccgcatct caccgggcgg cgctttgagc acggtgtgac ggactgttac    14520
acactgttcc gggatgctta tcatctggcg gggattgaga tgccggactt tcatcgtgag    14580
gatgactggt ggcgtaacgg ccagaatctc tatctggatg atctggaggc gacggggctg    14640
tatcaggtgc cgttgtcagc ggcacagccg ggcgatgtgc tgctgtgctg ttttggttca    14700
tcagtgccga atcacgccgc aatttactgc ggcgacggcg agctgctgca ccatattcct    14760
gaacaactga gcaaacgaga gaggtacacc gacaaatggc agcgacgcac acactccctc    14820
tggcgtcacc gggcatggcg cgcatctgcc tttacgggga tttacaacga tttggtcgcc    14880
gcatcgacct tcgtgtgaaa acggggggctg aagccatccg ggcactggcc acacagctcc    14940
cggcgttttcg tcagaaactg agcgacggct ggtatcaggt acggattgcc gggcgggacg    15000
tcagcacgtc cgggttaacg gcgcagttac atgagactct gcctgatggc gctgtaattc    15060
atattgttcc cagagtcgcc ggggccaagt caggtggcgt attccagatt gtcctggggg    15120
ctgccgccat tgccggatca ttctttaccg ccggagccac ccttgcagca tgggggggcag    15180
ccattggggc cggtggtatg accggcatcc tgtttttctct cggtgccagt atggtgctcg    15240
```

```
gtggtgtggc gcagatgctg gcaccgaaag ccagaactcc ccgtatacag acaacggata  15300
acggtaagca gaacacctat ttctcctcac tggataacat ggttgcccag ggcaatgttc  15360
tgcctgttct gtacgggaaa atgcgcgtgg ggtcacgcgt ggtttctcag gagatcagca  15420
cggcagacga aggggacggt ggtcaggttg tggtgattgg tcgctgatgc aaaatgtttt  15480
atgtgaaacc gcctgcgggc ggttttgtca tttatggagc gtgaggaatg ggtaaaggaa  15540
gcagtaaggg gcatacccgc cgcgaagcga aggacaacct gaagtccacg cagttgctga  15600
gtgtgatcga tgccatcagc gaagggccga ttgaaggtcc ggtggatggc ttaaaaagcg  15660
tgctgctgaa cagtacgccg gtgctggaca ctgaggggaa taccaacata tccggtgtca  15720
cggtggtgtt ccgggctggt gagcaggagc agactccgcc ggagggattt gaatcctccg  15780
gctccgagac ggtgctgggt acgaagtga aatatgacac gccgatcacc cgcaccatta  15840
cgtctgcaaa catcgaccgt ctgcgcttta ccttcggtgt acaggcactg gtggaaacca  15900
cctcaaaggg tgacaggaat ccgtcggaag tccgcctgct ggttcagata caacgtaacg  15960
gtggctgggg gacggaaaaa gacatcacca ttaagggcaa aaccacctcg cagtatctgg  16020
cctcggtggt gatgggtaac ctgccgccgc gcccgtttaa tatccggatg cgcaggatga  16080
cgccggacag caccacagac cagctgcaga acaaaacgct ctggtcgtca tacactgaaa  16140
tcatcgatgt gaaacagtgc tacccgaaca cggcactggt cggcgtgcag gtggactcgg  16200
agcagttcgg cagccagcag gtgagccgta attatcatct gcgcgggcgt attctgcagg  16260
tgccgtcgaa ctataacccg cagacgcggc aatcagcgg tatctggac ggaacgttta  16320
aaccggcata cagcaacaac atggcctggt gtctgtggga tatgctgacc catccgcgct  16380
acggcatggg gaaacgtctt ggtcggcggc atgtggataa atgggcgctg tatgtcatcg  16440
gccagtactg cgaccagtca gtgccggacg gcttggcgg cacggagccg cgcatccacct  16500
gtaatgcgta cctgaccaca cagcgtaagg cgtgggatgt gctcagcgat ttctgctcgg  16560
cgatgcgctg tatgccggta tggaacgggc agacgctgac gttcgtgcag gaccgaccgt  16620
cggataagac gtggacctat aaccgcagta atgtggtgat gccggatgat ggcgcgccgt  16680
tccgctacag cttcagcgcc ctgaaggacc gccataatgc cgttgaggtg aactggattg  16740
acccgaacaa cggctgggag acgctgttga agatacgcag gccattgccc  16800
gttacggtcg taatgttacg aagatggatg cctttggctg taccagccgg gggcaggcac  16860
accgcgccgg gctgtggctg attaaaacag aactgctgga aacgcagacc gtggatttca  16920
gcgtcggcgc agaagggctt cgccatgtac cgggcgatgt tattgaaatc tgcgatgatg  16980
actatgccgg tatcagcacc ggtggtcgtg tgctggcggt gaacagccag acccggacgc  17040
tgacgctcga ccgtgaaatc acgctgccat cctccggtac cgcgctgata agcctggttg  17100
acggaagtgg caatccggtc agcgtggagg ttcagtccgt caccgacggc gtgaaggtaa  17160
aagtgagccg tgttcctgac ggtgttgctg aatacagcgt atgggagctg aagctgccga  17220
cgctgcgcgc cgactgttc cgctgcgtga gtatccgtga gaacgacgac ggcacgtatg  17280
ccatcaccgc cgtgcagcat gtgccggaaa aagaggccat cgtggataac cggggcgcact  17340
ttgacggcga acagagtggc acggtgaatg gtgtcacgcc gccagcggtg cagcacctga  17400
ccgcagaagt cactgcagac agcggggaat atcaggtgct ggcgcgatgg gacacaccga  17460
aggtggtgaa gggcgtgagt ttcctgctcc gtctgaccgt aacagcggac gacggcagtg  17520
agcggctggt cagcacggcc cggacgacgg aaaccacata ccgcttcacg caactggcgg  17580
tggggaacta caggctgaca gtccgggcgg taaatgcgtg ggggcagcag ggcgatccgg  17640
cgtcggtatc gttccggatt gccgcaccgg cagcaccgtc gaggattgag ctgacgccgg  17700
gctattttca gataaccgcc acgccgcatc ttgccgtttta tgacccgacg gtacagtttg  17760
agttcggtt ctcggaaaag cagattgcgg atatcagaca ggttgaaacc gcacgcgtt  17820
atcttggtac ggcgctgtac tggatagccg ccagtatcaa tatcaaaccg ggccatgatt  17880
attacttta tatccgcagt gtgaacaccg ttggcaaatc ggcattcgtg gaggccgtcg  17940
gtcgggcag cgatgatgcg gaaggttacc tggattttt caaaggcaag ataaccgaat  18000
cccatctcgg caaggagctg ctggaaaaag tcgagctgac ggaggataac gccagcagac  18060
tggaggagtt ttcgaaagag tggaaggatg ccagtgataa gtggaatgcc atgtgggctg  18120
tcaaaattga gcagaccaaa gacggcaaac attatgtcgc gggtattggc ctcagcatgg  18180
aggacacgga ggaaggcaaa ctgagccagt ttctggttgc cgccaatcgt atcgcattta  18240
ttgaccccgg caaacgggaat gaaacgccga tgtttgtgcg gcagggcaac cagatattga  18300
tgaacgacgt gttcctgaag cgcctgacgg cccccaccat taccagcggc ggcaatcctc  18360
cggcctttc cctgacaccg gacggaaagc tgaccgctaa aaatgcggat atcagtggca  18420
gtgtgaatgc gaactccggg acgctcagta atgtgacgat agctgaaaac tgtacgaaaa  18480
acggtacgct gagggcggaa aaaatcgtcg gggacattgt aaaggcgggg agcgcggctt  18540
ttccgcgcca gcgtgaaagc agtgtggact ggccgtcagg tacccgtact gtcaccgtga  18600
ccgatgacca tcctttgat cgccagatag tggtgcttcc gctgacgttt cgcggaagta  18660
agcgtactgt cagcggcagg acaacgtatt cgatgtgtta tctgaaagta ctgatgaacg  18720
gtgcggtgat ttatgatggc gcggcgaacg aggcggtaca ggtgttctcc cgtattgttg  18780
acatgccagc gggtcgggga aacgtgatcc tgacgttcac gcttacgtcc acacggcatt  18840
cggcagatat tccgccgtat acgtttgcca gcgatgtgca ggttatggtg attaagaaac  18900
aggcgctggg catcagcgtg gtctgagtgt gttacagagg ttcgtccggg aacgggcgtt  18960
ttattataaa acagtgagag gtgaacgatg cgtaatgtgt gtattgccgt tgctgtcttt  19020
gccgcacttg cggtgacagt cactccggcc cgtgcgaaag gtggacatgg tacgttttacg  19080
gtgggctatt tcaagtgaa accgggtaca ttgccgtcgt tgtcgggcgg ggataccggt  19140
gtgagtcatc tgaaagggat taacgtgaag taccgttatg agctgacgga cagtgtgggg  19200
gtgatggctt cctggggtt cgccgcgtcg aaaaagagca gcacagtgat gaccggggag  19260
gatacgtttc actatgagag cctgcgtgga cgttatgtga gcgtgatggc cggaccggtt  19320
ttacaaatca gtaagcaggt cagtgctac gccatggccg gggtgctca cagtcggtgg  19380
tccggcagta caatggatta ccgtaagacg gaaatcactc ccgggtatat gaaagagacg  19440
accactgcca gggacgaaag tgcaatgcgg catacctcag tggcgtggag tgcaggtata  19500
cagattaatc cggcagcgtc cgtcgttgtt gatattgctt atgaaggctc cggcagtggc  19560
gactggcgta ctgacggatt catcgtttggg gtcggttata aattcgatt agccaggtaa  19620
gtgttacagtg tgacagcccg ccggaaccgg tgggcttttt tgtgggggtga atatggcagt  19680
aaagatttca ggagtcctga agacgcgcac aggaaaaccg gtacagaact gcaccattca  19740
gctgaaagcc agacgtaaca gcaccacggt ggtggtgaac acgtgggct cagagaatcc  19800
ggatgaagcc gggcgttaca gcatggatgt ggagtacggt cagtacagtg tcatcctgca  19860
ggttgacggt tttccaccat cgcacgccgg gaccatcacc gtgtatgaag attcacaacc  19920
ggggacgctg aatgattttc tctgtgccat gacggaggat gatgcccggc cggaggtgct  19980
```

```
gcgtcgtctt gaactgatgg tggaagaggt ggcgcgtaac gcgtccgtgg tggcacagag   20040
tacggcagac gcgaagaaat cagccggcga tgccagtgca tcagctgctc aggtcgcggc   20100
ccttgtgact gatgcaactg actcagcacg cgccgccagc acgtccgccg gacaggctgc   20160
atcgtcagct caggaagcgt cctccggcgc agaagcggca tcagcaaagg ccactgaagc   20220
ggaaaaaagt gccgcagccg cagagtcctc aaaaaacgcg gcggccacca gtgccggtgc   20280
ggcgaaaacg tcagaaacga atgctgcagc gtcacaacaa tcagccgcca cgtctgcctc   20340
caccgcggcc acgaaagcgt cagaggccgc cacttcagca cgagatgcgg tggcctcaaa   20400
agaggcagca aaatcatcag aaacgaacgc atcatcaagt gccggtcgtg cagcttcctc   20460
ggcaacggcg gcagaaaatt ctgccagggc ggcaaaaacg tccgagacga atgccaggtc   20520
atctgaaaca gcagcggaac ggagcgcctc tgccgcggca gacgcaaaaa cagcggcggc   20580
ggggagtgcg tcaacggcat ccacgaaggc gacagaggct gcgggaagtg cggtatcagc   20640
atcgcagagc aaaagtgcgg cagaagcggc ggcaatacgt gcaaaaaatt cggcaaaacg   20700
tgcagaagat atagcttcag ctgtcgcgct tgaggatgcg gacacaacga gaagggggat   20760
agtgcagctc agcagtgcaa ccaacagcac gtctgaacag cttgctgcaa cgccaaaggc   20820
ggttaaggtg gtaatggatg aaacgaacag aaaagcccac tggacagtcc ggcactgacc   20880
ggaacgccaa cagcaccaac cgcgctcagg gaacaaaca atacccagat tgcgaacacc   20940
gcttttgtac tggccgcgat tgcagatgtt atcgacgcgt cacctgacgc actgaatacg   21000
ctgaatgaac tggccgcagc gctcgggaat gatccagatt ttgctaccac catgactaac   21060
gcgcttgcgg gtaaacaacc gaagaatgcg cactgacgg cgctggcagg gctttccacg   21120
gcgaaaaata aattaccgta ttttgcggaa aatgatgccg ccagcctgac tgaactgact   21180
caggttggca gggatattct ggcaaaaaat tccgttgcag atgttcttga ataccttggg   21240
gccggtgaga attcggcctt tccggcaggt gcgccgatcc cgtggccatc agatatcgtt   21300
ccgtctggct acgtcctgat gcaggggcag gcgtttgaca aatcagccta cccaaaactt   21360
gctgtcgcgt atccatcggg tgtgcttcct gatatgcgag gctggacaat caggggaaa    21420
cccgccagcg gtcgtgctgt attgtctcag gaacaggatg gaattaagtc gcacacccac   21480
agtgccgtg catccggtac ggatttgggg acgaaaacca catcgtcgtt tgattacggg   21540
acgaaaacaa caggcagttt cgattacggc accaaatcga cgaataacac ggggggctcat  21600
gctcacagtc tgagcggttc aacaggggcc gcggtgctc atgcccacac aagtggttta   21660
aggatgaaca gttctggctg gagtcagtat ggaacagcaa ccattacagg aagtttatcc   21720
acagttaaag gaaccagcac acagggtatt gcttatttat cgaaaacgca cagtcagggc   21780
agccacagtc actcattgtc cggtacagcc gtgagtgccg gtgcacatgc gcatacagtt   21840
ggtattggtg cgcaccagca tccggttgtt atcggtgctc atgcccattc tttcagtatt   21900
ggttcacacg gacacaccat caccgttaac gctgcgggta acgcggaaaa caccgtcaaa   21960
aacattgcat ttaactatat tgtgaggctt gcataatggc attcagaatg agtgaacaac   22020
cacggaccat aaaaatttat aatctgctgg ccggaactaa tgaatttatt ggtgaaggtg   22080
acgcatatat tccgcctcat accggtctgc ctgcaaacag taccgatatt gcaccgccag   22140
atattccggc tggctttgtg gctgtttttca acagtgatga ggcatcgtgg catctcgttg   22200
aagaccatcg gggtaaaacc gtctatgacg tggcttccgg cgacgcgtta tttatttctg   22260
aactcggtcc gttaccggaa aattttacct ggttatcgcc gggaggggaa tatcagaagt   22320
ggaacgcac agcctgggtg aaggatacgg aagcagaaaa actgttccgg atccgggagg   22380
cggaagaaac aaaaaaaaagc ctgatgcagg tagccagtga gcatattgcg ccgcttcagg   22440
atgctgcaga tctggaaatt gcaacgaagg aagaaaacctc gttgctggaa gcctggaaga   22500
agtatcgggt gttgctgaac cgtgttgata catcaactgc acctgattatt gagtggcctg   22560
ctgtccctgt tatggagtaa tcgttttgtg atatgccgca gaaacgttgt atgaaataac   22620
gttctgcggt tagttagtat attgtaaagc tgagtattgg tttatttggc gattattatc   22680
ttcaggagaa taatggaagt tctatgactc aattgttcat agtgttttaca tcaccgccaa   22740
ttgcttttaa gactgaacgc atgaaatatg gttttcgtc atgttttgag tctgctgttg   22800
atatttctaa agtcggtttt ttttcttcgt ttctctaac tattttccat gaaatacatt    22860
tttgattatt atttgaatca attccaatta cctgaagtct ttcatctata attggcattg   22920
tatgtattgg tttattggag tagatgcttg cttttctgag ccatagctct gatatccaaa   22980
tgaagccata ggcatttgtt attttggctc tgtcagctgc ataacgccaa aaaatattt    23040
tatctgcttg atcttcaaat gttgtattga ttaaatcaat tggatggaat tgtttatcat   23100
aaaaaattaa tgtttgaatg tgataaccgt ccttttaaaa agtcgtttct gcaagcttgg   23160
ctgtatagtc aactaactct tctgtcgaag tgatatttt aggcttatct accagtttta    23220
gacgctcttt aatatcttca ggaattattt tattgtcata ttgtatcatg ctaaatgaca   23280
atttgcttat ggagtaatct tttaatttta aataagttat tctcctggct tcatcaaata   23340
aagagtcgaa tgatgttggc gaaatcacat cgtcacccat tggattgttt atttgtatgc   23400
caagagagtt acagcagtta tacattctgc catagattat agctaaggca tgtaataatt   23460
cgtaatcttt tagcgtatta gcgacccatc gtctttctga tttaataata gatgattcag   23520
ttaaatatga aggtaatttc ttttgtgcaa gtctgactaa ctttttttata ccaatgttta   23580
acatactttc atttgtaata aactcaatgt cattttcttc aatgtaagat gaaataagag   23640
tagcctttgc ctcgctatac atttctaaat cgccttgttt ttctatcgta ttgcgagaat   23700
ttttagccca agcattaat ggatcatttt tccattttc aataacatta ttgttataacc    23760
aaatatcata tcctataatc tggtttttgt tttttgaat aataaatgtt actgtcttg    23820
cggtttggag gaattgattc aaattcaagc gaaataattc agggtcaaaa tatgtatcaa   23880
tgcagcattt gagcaagtgc gataaatctt taagtcttct ttcccatggt ttttagtca    23940
taaaactctc catttgata ggtttgcatgc tagatgctga tatattttag aggtgataaa   24000
attaactgct taactgtcaa tgtaataca gttgtttgat ctttgcaatg attcttatca    24060
gaaaccatat agtaaattag ttacacagga aatttttaat attattatta tcattcatta   24120
tgtattaaaa ttagagttgt ggcttggctc tgctaacacg ttgctcatag gagatatggt   24180
agagccgcag acacgtcgta tgcaggaacg tgctgcggct ggctggtgaa cttccgatag   24240
tgcgggtgtt gaatgatttc cagttgctac cgatttttaca tatttttgc atgagagaat   24300
ttgtaccacc tcccaccgac catctatgac tgtacgccac tgtccctagg actgctatgt   24360
gccggacgg acattacaaa cgtccttctc ggtgcatgcc actgttgcca atgacctgcc    24420
taggaattgg ttagcaagtt actaccggat tttgtaaaaa cagccctcct catataaaaa    24480
gtattcgttc acttccgata agcgtcgtaa ttttctatct ttcatcatat tctagatccc   24540
tctgaaaaa tcttccgagt ttgctaggca ctgatacata actctttttcc aataattggg   24600
gaagtcattc aaatctataa taggtttcag atttgcttca ataaattctg actgtagctg   24660
ctgaaacgtt gcggttgaac tatatttcct tataacttttt acgaaagagt ttcttgagt    24720
```

```
aatcacttca ctcaagtgct tccctgcctc caaacgatac ctgttagcaa tatttaatag   24780
cttgaaatga tgaagagctc tgtgtttgtc ttcctgcctc cagttcgccg ggcattcaac   24840
ataaaaactg atagcacccg gagttccgga aacgaaattt gcatataccc attgctcacg   24900
aaaaaaaatg tccttgtcga tatagggatg aatcgcttgg tgtacctcat ctactgcgaa   24960
aacttgacct ttctctccca tattgcagtc gcggcacgat ggaactaaat taataggcat   25020
caccgaaaat tcaggataat gtgcaatagg aagaaaatga tctatatttt ttgtctgtcc   25080
tatatcacca caaaatggac attttttcacc tgatgaaaca agcatgtcat cgtaatatgt   25140
tctagcgggt ttgttttttat ctcggagatt attttcataa agcttttcta atttaacctt   25200
tgtcaggtta ccaactacta aggttgtagg ctcaagaggg tgtgtcctgt cgtaggtaaa   25260
taactgacct gtcgagctta atattctata ttgttgttct ttctgcaaaa aagtgggaa    25320
gtgagtaatg aaattatttc taacattat ctgcatcata ccttccgagc atttattaag    25380
catttcgcta taagttctcg ctggaagagg tagtttttc attgtacttt accttcatct    25440
ctgttcatta tcatcgcttt taaaacggtt cgaccttcta atcctatctg accattataa   25500
tttttaagaa tggtttcata agaaagctct gaatcaacgg actgcgataa taagtggtgg   25560
tatccagaat ttgtcacttc aagtaaaaac acctcacgag ttaaaacacc taagttctca   25620
ccgaatgtct caatatccgg acggataata tttattgctt ctcttgaccg taggactttc   25680
cacatgcagg attttggaac ctcttgcagt actactgggg aatgagttgc aattattgct   25740
acaccattgc gtgcatcgag taagtcgctt aatgttcgta aaaaagcaga gagcaaaggt   25800
ggatgcagat gaacctctgg ttcatcgaat aaaactaatg acttttcgcc aacgacatct   25860
actaatcttg tgatagtaaa taaaacaatt gcatgtccag agctcattcg aagcagatat   25920
ttctggatat tgtcataaaa caatttagtg aatttatcat cgtccacttg aatctgtggt   25980
tcattacgtc ttaactcttc atatttagaa atgaggctga tgagttccat atttgaaaag   26040
ttttcatcac tacttagttt tttgatagct tcaagccaga gttgtctttt tctatctact   26100
ctcatacaac caataaatgc tgaaatgaat tctaagcgga gatcgcctag tgattttaaa   26160
ctattgctgg cagcattctt gagtccaata taaaagtatt gtgtacctt tgctgggtca    26220
ggttgttctt taggaggagt aaaaggatca aatgcactaa acgaaactga acaagcgat    26280
cgaaaatatc cctttgggat tcttgactcg ataagtctat tattttcaga gaaaaaatat   26340
tcattgtttt ctgggttggt gattgcacca atcattccat tcaaaattgt tgttttacca   26400
cacccattcc gcccgataaa agcatgaatg ttcgtgctgg gcatagaatt aaccgtcacc   26460
tcaaaaggta tagttaaatc actgaatccg ggagcacttt ttctattaaa tgaaaagtgg   26520
aaatctgaca attctggcaa accatttaac acacgtgcga actgtccatg aatttctgaa   26580
agagttaccc ctctaagtaa tgaggtgtta aggacgcttt cattttcaat gtcggctaat   26640
cgatttggcc atactactaa atcctgaata gctttaagaa ggttatgttt aaaaccatcg   26700
cttaatttgc tgagattaac atagtagtca atgcttccac ctaaggaaaa aaacatttca   26760
gggagttgac tgaatttttt atctattaat gaataagtgc ttacttcttc tttttgacct   26820
acaaaaccaa ttttaacatt tccgatatcg catttttcac catgctcatc aaagacagta   26880
agataaaaca ttgtaacaaa ggaatagtca ttccaaccat ctgctcgtag gaatgcctta   26940
tttttttcta ctgcaggaat ataccccgcct cttttcaataa cactaaactc caacatatag   27000
taaccctttaa ttttattaaa ataaccgcaa tttatttggc ggcaacacag gatctctctg    27060
ttaagttact ctctattaca tacgttttcc atctaaaaat tagtagtatt gaacttaacg   27120
gggcatcgta ttgtagtttt ccatatttag cttttctgctt ccttttggat aacccactgt   27180
tattcatgtt gcatggtgca ctgttatac caacgtatata gtctattaat gcatatatag   27240
tatcgccgaa cgattagctc ttcaggcttc tgaagaagcg tttcaagtac taataagccg   27300
atagatagcc acggacttcg tagccatttt tcataagtgt taacttccgc tcctcgctca   27360
taacagacat tcactacagt tatggcgaaa aggtatgcat gctgggtgtg gggaagtcgt   27420
gaaagaaaag aagtcagctg cgtcgtttga catcactgct atcttcttac tggttatgca   27480
ggtcgtagtg ggtggcacac aaagctttgt actggattgc gaggcttttgt gcttctctgg   27540
agtgcgacag gtttgatgac aaaaaattag cgcaagaaga caaaaatcac cttgcgctaa   27600
tgctctgtta caggtcacta ataccatcta agtagttgat tcatagtgac tgcatatgtt   27660
gtgttttaca gtattatgta gtctgttttt tatgcaaaat ctaatttaat atattgatat   27720
ttatatcatt ttacgtttct cgttcagctt ttttatacta agttggcatt ataaaaaagc   27780
attgcttatc aatttgttgc aacgaacagg tcactatcag tcaaaataaa atcattattt   27840
gatttcaatt ttgtcccact ccctgcctct gtcatcacga tactgtgatg ccatggtgtc   27900
cgacttatgc ccgagaagat gttgagcaaa cttatcgctt atctgcttct catagagtct   27960
tgcagacaaa ctgcgcaact cgtgaaaggt aggcggatcc ccttcgaagg aaagacctga   28020
tgcttttcgt gcgcgcataa aataccttga tactgtgccg gatgaaagcg gttcgcgacg   28080
agtagatgca attatggttt ctccgccaag aatctctttg catttatcaa gtgtttcctt   28140
cattgatatt ccgagagcat caatatgcaa tgctgttggg atggcaattt ttacgcctgt   28200
tttgctttgc tcgacataaa gatatccatc tacgatatca gaccacttca tttcgcataa   28260
atcaccaact cgttgcccgg taacaacagc cagttccatt gcaagtctga gccaacatgg   28320
tgatgattct gctgcttgat aaattttcag gtattcgtca gccgtaagtc ttgatctcct   28380
tacctctgat tttgctgcgc gagtggcagc gacatggttt ttgttatat ggccttcagc    28440
tattgcctct cggaatgcat cgctcagtgt tgatctgatt aacttggctg acgccgcctt   28500
gccctcgtct atgtatccat tgagcattgc cgcaatttct tttgtggtga tgtcttcaag   28560
tggagcatca ggcagacccc tccttattgc tttaattttg ctcatgtaat ttatgagtgt   28620
cttctgcttg attcctctgc tggccaggat ttttcgtag cgatcaagcc atgaatgtaa    28680
cgtaacggaa ttatcactgt tgattctcgc tgtcagaggc ttgtgtttgt gtcctgaaaa   28740
taactcaatg ttggcctgta tagcttcagt gattgcgaat cgcctgtctc tgcctaatcc   28800
aaactcttta cccgtcccttg ggtccctgta gcagtaatat ccattgtttc ttatataaag   28860
gttagggggt aaatcccggc gctcatgact tcgccttctt cccatttctg atcctctttca  28920
aaaggccacc tgttactggt cgatttaagt caaccttttac cgctgattcg tggaacagat   28980
actctcttcc atccttaacc ggaggtggga atatcctgca ttcccgaacc catcgacgaa   29040
ctgtttcaag gcttcttgga cgtcgctggc gtgcgttcca ctcctgaagt gtcaagtaca   29100
tcgcaaagtc tccgcaatta cacgcaagaa ccaggcggct tggtgttctt   29160
tcagttcttc aattcgaata ttggttacgt ctgcatgtgc tatctgcgcc catatcatcc   29220
agtggtcgta gcagtcgttg atgttctccg cttcgataac tctgttgaat ggctctccat   29280
tccattctcc tgtgactcgg aagtgcattt atcatctcca taaaacaaaa cccgccgtag   29340
cgagttcaga taaaataaat ccccgcgagt gcgaggatta ttatgtaata ttgggtttaa   29400
tcatctatat gttttgtaca gagagggcaa gtatcgtttc caccgtactc gtgataataa   29460
```

```
ttttgcacgg tatcagtcat ttctcgcaca ttgcagaatg gggatttgtc ttcattagac   29520
ttataaacct tcatggaata tttgtatgcc gactctatat ctataccttc atctacataa   29580
acaccttcgt gatgtctgca tggagacaag acaccggatc tgcacaacat tgataacgcc   29640
caatctttt gctcagactc taactcattg atactcattt ataaactcct tgcaatgtat   29700
gtcgtttcag ctaaacggta tcagcaatgt ttatgtaaag aaacagtaag ataatactca   29760
acccgatgtt tgagtacggt catcatctga cactacagac tctggcatcg ctgtgaagac   29820
gacgcgaaat tcagcatttt cacaagcgtt atcttttaca aaaccgatct cactctcctt   29880
tgatgcgaat gccagcgtca gacatcatat gcagatactc acctgcatcc tgaacccatt   29940
gacctccaac cccgtaatag cgatgcgtaa tgatgtcgat agttactaac gggtcttgtt   30000
cgattaactg ccgcagaaac tcttccaggt caccagtgca gtgcttgata acaggagtct   30060
tcccaggatg gcgaacaaca agaaactggt ttccgtcttc acggacttcg ttgctttcca   30120
gtttagcaat acgcttactc ccatccgaga taacaccttc gtaatactca cgctgctcgt   30180
tgagtttga ttttgctgtt tcaagctcaa cacgcagttt ccctactgtt agccgcaatat  30240
cctcgttctc ctggtcgcgg cgtttgatgt attgctggtt tctttcccgt tcatccagca   30300
gttccagcac aatcgatggt gttaccaatt catggaaaag gtctgcgtca aatccccagt   30360
cgtcatgcat tgcctgctct gccgcttcac gcagtgcctg agagttaatt tcgctcactt   30420
cgaacctctc tgtttactga taagttccag atcctcctgg caacttgcac aagtccgaca   30480
accctgaacg accaggcgtc ttcgttcatc tatcggatcg ccacactcac aacaatgagt   30540
ggcagatata gcctggtggt tcaggcggcg catttttatt gctgtgttgc gctgtaattc   30600
ttctatttct gatgctgaat caatgatgtc tgccatcttt cattaatccc tgaactgttg   30660
gttaatacgc ttgagggtga atgcgaataa taaaaaagga gcctgtagct ccctgatgat   30720
tttgcttttc atgttcatcg ttccttaaag acgccgttta acatgccgat tgccaggctt   30780
aaatgagtcg gtgtgaatcc catcagcgtt accgtttcgc ggtgcttctt cagtacgcta   30840
cggcaaatgt catcgacgtt tttatccgga aactgctgtc tggctttttt tgatttcaga   30900
attagcctga cgggcaatgc tgcgaagggc gttttcctgc tgaggtgtca ttgaacaagt   30960
cccatgtcga caagcataag cacacagaat atgaagccg ctgccagaaa aatgcattcc    31020
gtggttgtca tacctggttt ctctcatctg cttctgcttt cgccaccatc atttccagct   31080
tttgtgaaag ggatgcggct aacgtatgaa attcttcgtc tgtttctact ggtattggca   31140
caaacctgat tccaatttga gcaaggctat gtgccatctc gatactcgtt cttaactcaa   31200
cagaagatgc tttgtgcata cagcccctcg tttattattt atctcctcag ccagccgtca   31260
tgctttcagt ggatttcgga taacagaaag gccgggaaat acccagcctc gctttgtaac   31320
ggagtagacg aaagtgattg cgcctaccg gatattatcg tgaggatgcg tcatcgccat    31380
tgctccccaa atacaaaacc aatttcagcc agtgcctcgt ccattttttc gatgaactcc   31440
ggcacgatct cgtcaaaact cgccatgtac ttttcatccc gctcaatcac gacataatgc   31500
aggccttcac gcttcatacg cgggtcatag ttggcaaagt accaggcatt ttttcgcgtc   31560
acccacatgc tgtactgcac ctgggccatg taagctgact ttatggcctc gaaaccaccg   31620
agccggaact tcatgaaatc ccgggaggta acgggcatt tcagttcaag gccgttgccg    31680
tcactgcata aaccatcggg agagcaggcg gtacgcatac tttcgtcgcg atagatgatc   31740
ggggattcag taacattcac gccggaagtg aattcaaaca gggttctgc gtcgttctcg    31800
tactgtttc cccaggccag tgctttagcg ttaacttccg gagccacacc ggtgcaaacc    31860
tcagcaagca gggtgtggaa gtaggacatt ttcatgtcag gccacttctt tccggagcgg   31920
ggttttgcta tcacgttgtg aacttctgaa gcggtgatga cgccgagccg taatttgtgc   31980
cacgcatcat ccccctgttc gacagctctc acatcgatcc ggtacgctg caggataatg    32040
tccggtgtca tgctgccacc ttctgctctg cggctttctg tttcaggaat ccaagagctt   32100
ttactgcttc ggcctgtgtc agttctgacg atgcacgaat gtcgcggcga aatatctggg   32160
aacagagcgg caataagtcg tcatcccatg ttttatccag ggcgatcagc agagtgttaa   32220
tctcctgcat ggtttcatcg ttaaccggag tgatgtcgcg ttccggctga cgttctgcag   32280
tgtatgcagt attttcgaca atgcgctcgg cttcatcctt gtcatagata ccagcaaatc   32340
cgaaggccag acgggcacac tgaatcatgg ctttatgacg taacatccgt ttgggatgcg   32400
actgccacg ccccgtgatt tctctgcctt cgcgagtttt gaatggttcg cggcggcatt    32460
catccatcca ttcggtaacg cagatcggat gattacgtgc cttgcggtaa atccggcatg   32520
tacaggattc attgtcctgc tcaaagtcca tgccatcaaa ctgctggttt tcattgatga   32580
tgcgggacca gccatcaacg cccaccaccg gaacgatgcc attctgctta tcaggaaagg   32640
cgtaaatttc tttcgtccac ggattaaggc cgtactggtt ggcaacgatc agtaatgcga   32700
tgaactgcgc atcgctggca tcacctttaa atgccgtcg gcgaagagtg gtgatcagtt    32760
cctgtgggtc gacagaatcc atgccgacac gttcagccag cttcccagcc agcgttgcga   32820
gtgcagtact cattcgtttt ataccctga atcaatatca acctggtggt gagcaatggt   32880
ttcaaccatg taccggatgt gttctgccat gcgctcctga aactcaacat cgtcatcaaa   32940
cgcacgggta atggattttt tgctggcccc gtggcgttgc aaatgatcga tcatagcga   33000
ttcaaacagg tgctggggca ggccttttc catgtcgtct gccagttctg cctcttttc     33060
ttcacgggcg agctgctggt agtgacgcgc ccagctctga gcctcaagac gatcctgaat   33120
gtaataagcg ttcatggctg aactcctgaa atagctgtga aaatatcgcc cgcgaaatgc   33180
cgggctgatt aggaaaacag gaaaggggt tagtgaatgc ttttgcttga tctcagtttc    33240
agtattaata tccatttttt ataagcgtca acggcttcac acggcttgaat tcatcgcca   33300
ataaaagtgg cgatagtgaa tttagtctgg atagccataa gtgtttgatc cattctttgg   33360
gactcctggc tgattaagta tgtcgataag gcgtttccat ccgtcacgta atttacgggt   33420
gattcgttca agtaaagatt cggaagggca gccagcaaca ggccaccctg caatggcata   33480
ttgcatggtg tgctccttat ttatacataa cgaaaaacgc ctcgagtgaa gcgttattgg   33540
tatgcggtaa aaccgcactc aggcggcctt gatagtcata tcatctgaat caaatattcc   33600
tgatgtatcg atatcggtaa ttcttattcc ttcgctacca tccattggag gccatccttc   33660
ctgaccattt ccatcattcc agtcgaactc acacacaaca ccatatgcat ttaagtcgct   33720
tgaaattgct ataagcagag catgttgcgc cagcatgatt aatacagcat ttaatacaga   33780
gccgtgttta ttgagtcggt attcagagtc tgaccagaaa ttattaatct ggtgaagttt   33840
ttcctctgtc attacgtcat gtgcgatttc aatttctatt gatgctttcc agtcgtaatc   33900
aatgatgtat tttttgatgt ttgacatctg ttcatatcct cacagataaa aaatcgccct   33960
cacactggag ggcaaagaag atttccaata atcagaacaa gtcggctcct gtttagttac   34020
gagcgacatt gctccgtgta ttcactcgtt ggaatgaata cacagtgcag tgtttattct   34080
gttatttatg ccaaaaataa aggccactat caggcagctt gttgttctg tttaccaagt    34140
tctctggcaa tcattgccgt cgttcgtatt gccatttat cgacatattt cccatcttcc    34200
```

```
attacaggaa acatttcttc aggcttaacc atgcattccg attgcagctt gcatccattg   34260
catcgcttga attgtccaca ccattgattt ttatcaatag tcgtagtcat acggatagtc   34320
ctggtattgt tccatcacat cctgaggatg ctcttcgaac tcttcaaatt cttcttccat   34380
atatcacctt aaatagtgga ttgcggtagt aaagattgtg cctgtctttt aaccacatca   34440
ggctcggtgg ttctcgtgta cccctacagc gagaaatcga ataaactatt acaaccccta   34500
cagtttgatg agtatagaaa tggatccact cgttattctc ggacgagtgt tcagtaatga   34560
acctctggag agaaccatgt atatgatcgt tatctgggtt ggacttctgc ttttaagccc   34620
agataactgg cctgaatatg ttaatgagag aatcggtatt cctcatgtgt ggcatgtttt   34680
cgtcttttgct cttgcatttt cgctagcaat taatgtgcat cgattatcag ctattgccag   34740
cgccagatat aagcgattta agctaagaaa acgcattaag atgcaaaacg ataaagtgcg   34800
atcagtaatt caaaaccttta cagaagagca atctatggtt ttgtgcgcag cccttaatga   34860
aggcaggaag tatgtggtta catcaaaaca attcccatac attagtgagt tgattgagct   34920
tggtgtgttg aacaaaactt tttcccgatg gaatggaaag catatattat tccctattga   34980
ggatatttac tggactgaat tagttgccag ctatgatcca tataatattg agataaagcc   35040
aaggccaata tctaagtaac tagataagag gaatcgattt tcccttaatt ttctggcgtc   35100
cactgcatgt tatgccgcgt tcgccaggct tgctgtacca tgtgcgctga ttcttgcgct   35160
caatacgttg caggttgctt tcaatctgtt tgtggtattc agccagcact gtaaggtcta   35220
tcggatttag tgcgctttct actcgtgatt tcggtttgcg attcagcgag agaataggc    35280
ggttaactgg ttttgcgctt accccaacca acaggggatt tgctgctttc cattgagcct   35340
gtttctctgc gcgacgttcg cggcggcgtg tttgtcatc catctggatt ctcctgtcag    35400
ttagctttgg tggtgtgtgg cagttgtagt cctgaacgaa aacccccgc gattggcaca    35460
tggcagcta atccggaatc gcacttacgg ccaatgcttc gtttcgtatc acacacccca   35520
aagccttctg ctttgaatgc tgcccttctt cagggcttaa ttttttaagag cgtcaccttc   35580
atggtggtca gtgcgtcctg ctgatgtgct cagtatcacc gccagtggta tttatgtcaa   35640
caccgccaga gataatttat caccgcagat ggttatctgt atgtttttta tatgaattta   35700
ttttttgcag gggggcattg tttggtaggt gagagatctg aattgctatg tttagtgagt   35760
tgtatctatt tatttttcaa taaatacaat tggttatgtg ttttgggggc gatcgtgagg   35820
caaagaaaac ccggcgctga ggccgggtta ttccttgttct ctggtcaaat tatatagttg   35880
gaaaacaagg atgcatatat gaatgaacga tgcagaggca atgccgatgg cgatagtggg   35940
tatcatgtag ccgcttatgc tggaaagaag caataacccg cagaaaaaca aagctccaag    36000
ctcaacaaaa ctaagggcat agacaataac taccgatgtc atataccat actctctaat   36060
cttggccagt cggcgcgttc tgcttccgat tagaaacgtc aaggcagcaa tcaggattgc   36120
aatcatggtt cctgcatatg atgacaatgt cgccccaaga ccatctctat gagctgaaaa   36180
agaaacacca ggaatgtagt ggcggaaaag gagatagcaa atgcttacga taacgtaagg   36240
aattattact atgtaaacac caggcatgat tctgttccgc ataattactc ctgataatta   36300
atccttaact ttgcccacct gccttttaaa acattccagt atatcacttt tcattcttgc    36360
gtagcaatat gccatctctt cagctatctc agcattggtg accttgttca gaggcgctga   36420
gagatggcct ttttctgata gataatgttc tgttaaaata tctccggcct catcttttgc   36480
ccgcaggcta atgtctgaaa attggatgga cgggttaaaa ataatatcct tggcaacctt    36540
tttatatcc cttttaaatt ttggcttaat gactatatcc aatgagtcaa aaagctcccc   36600
ttcaatatct gttgcccta agacctttaa tatatcgcca aatacaggta gcttggcttc    36660
taccttcacc gttgttcggc cgatgaaatg catatgcata acatcgtctt tggtggttcc   36720
cctcatcagt ggctctatct gaacgcgctc tccactgctt aatgacattc ctttcccgat   36780
taaaaaatct gtcagatcgg atgtggtcgg cccgaaaaca gttctggcaa accaatggt    36840
gtcgccttca acaaacaaaa aagatgggaa tcccaatgat tcgtcatctg cgaggctgtt   36900
cttaatatct tcaactgaag ctttagagcg atttatcttc tgaaccagac tcttgtcatt   36960
tgttttggta aagagaaaag ttttttccatc gattttatga atatacaaat aattggagc    37020
aacctgcagg tgatgattat cagccagcag agaattaagg aaaacagaca ggtttattga   37080
gcgcttatct ttcccttttat ttttgctgcg gtaagtcgca taaaaccat tcttcataat    37140
tcaatccatt tactatgtta tgttctgagg ggagtgaaaa ttcccctaat tcgatgaaga   37200
ttcttgctca attgttatca gctatgcgcc gaccagaaca ccttgccgat cagccaaacg    37260
tctcttcagg ccactgacta gcgataactt tccccacaac ggaacaactc tcattgcatg   37320
ggatcattgg gtactgtggg tttagtggtt gtaaaacac ctgaccgcta tccctgatca    37380
gtttcttgaa ggtaaactca tcaccccaa gtctggctat gcagaaatca cctggctcaa    37440
cagcctgctc agggtcaacg agaattaaca ttccgtcaag aaagcttggc ttggagcctg   37500
ttggtgcggt catggaatta ccttcaacct caagccagaa tgcagaatca ctggcttttt    37560
tggttgtgct tacccatctc tccgcatcac ctttggtaaa ggttctaagc ttaggtgaga   37620
acatccctgc ctgaacatga gaaaaaacag ggtactcata ctcacttcta agtgacggct   37680
gcatactaac cgcttcatac atctcgtaga ttttctggc gattgaaggg ctaaattctt    37740
caacgctaac tttgagaatt tttgtaagca atgcggcgtt ataagcattt aatgcattga    37800
tgccattaaa taaagcacca acgcctgact gccccatccc catcttgtct gcgacagatt   37860
cctgggataa gccaagttca ttttctttt tttcataaat tgctttaagg cgacgtgcgt   37920
cctcaagctg ctcttgtgtt aatggtttct tttttgtgct catacgttaa atctatcacc   37980
gcaaggata aatatctaac accgtgcgtg ttgactattt tacctctggc ggtgataatg   38040
gttgcatgta ctaaggaggt tgtatggaac aacgcataac cctgaaagat tatgcaatgc    38100
gctttgggca aaccaagaca gctaaagatc tcggcgtata tcaaagcgcg atcaacaagg    38160
ccattcatgc aggccgaaag attttttttaa ctataaacgc tgatggaagc gtttatgcgg   38220
aagaggtaag gcccttcccg agtaacaaaa aaacaacagc ataaataacc ccgctcttac   38280
acattccagc cctgaaaaag gcatcaaatt taaaccacac ctatggtgta tgcatttatt   38340
tgcatacatt caatcaattg ttatctaagg aaatacttac atatggttcg tgcaaacaaa   38400
cgcaacgagg ctctacgaat cgagagtgcg ttgcttaaca aaatcgcaat gcttggaact   38460
gagaagacag cggaagctgt gggcgttgat aagtcgcaga tcagcaggtg gaagagggac   38520
tggattccaa agttctcaat gctgcttgct gttcttgaat gggggggtcgt tgacgacgac   38580
gccgat tggcgcgaca agttgctgcg attctcacta ataaaaaacg cccggcggca       38640
accgagcgtt ctgaacaaat ccagatggag ttctgaggtc attactggat ctatcaacag   38700
gagtcattat gacaaataca gcaaaatac tcaacttcgg cagaggtaac tttgccggac    38760
aggagcgtaa tgtggcagat ctcgatgatg gttacgccag actatcaaat atgctgcttg   38820
aggcttattc gggcgcagat ctgaccaagc gacagtttaa agtgctgctt gccattctgc   38880
gtaaaaccta tgggtggaat aaaccaatgg acagaatcac cgattctcaa cttagcgaga   38940
```

```
ttacaaagtt acctgtcaaa cggtgcaatg aagccaagtt agaactcgtc agaatgaata   39000
ttatcaagca gcaaggcggc atgtttggac caaataaaaa catctcagaa tggtgcatcc   39060
ctcaaaacga gggaaaatcc cctaaaacga gggataaaac atccctcaaa ttgggggatt   39120
gctatccctc aaaacagggg gacacaaaag acactattac aaaagaaaaa agaaaagatt   39180
attcgtcaga gaattctggc gaatcctctg accagccaga aaacgacctt tctgtggtga   39240
aaccggatgc tgcaattcag agcggcagca agtgggggac agcagaagac ctgaccgccg   39300
cagagtggat gtttgacatg gtgaagacta tcgcaccatc agccagaaaa ccgaattttg   39360
ctgggtgggc taacgatatc cgcctgatgc gtgaacgtga cggacgtaac caccgcgaca   39420
tgtgtgtgct gttccgctgg gcatgccagg acaacttctg gtccggtaac gtgctgagcc   39480
cggccaaact ccgcgataag tggacccaac tcgaaatcaa ccgtaacaag caacaggcag   39540
gcgtgacagc cagcaaacca aaactcgacc tgacaaacac agactggatt tacggggtgg   39600
atctatgaaa aacatcgccg cacagatggt taactttgac cgtgagcaga tgcgtcggat   39660
cgccaacaac atgccggaac agtacgacga aaagccgcag gtacagcagg tagcgcagat   39720
catcaacggt gtgttcagcc agttactggc aactttcccg gcgagcctgg ctaaccgtga   39780
ccagaacgaa gtgaacgaaa tccgtcgcca gtgggttctg gcttttcggg aaaacgggat   39840
caccacgatg gaacaggtta acgcaggaat gcgcgtagcc cgtcggcaga atcgaccatt   39900
tctgccatca cccgggcagt tgttgcatg gtgccgggaa gaagcatccg ttaccgccgg   39960
actgccaaac gtcagcgagc tggttgatat ggtttacgag tattgccgga agcgaggcct   40020
gtatccggat gcggagtctt atccgtgaaa atcaaacgcg cactactggc tggttaccaa   40080
cctgtatcag aacatgcggg ccaatgcgct tactgatgcg gaattacgcc gtaaggccgc   40140
agatgagctt gtccatatga ctgcgagaat taaccgtggt gaggcgatcc ctgaaccagt   40200
aaaacaactt cctgtcatgg gcggtagacc tctaaatgct gcacaggctc tggcgaagat   40260
cgcagaaatc aaagctaagt tcggactgaa aggagcaagt gtatgacggg caaagaggca   40320
attattcatt acctggggac gcataatagc ttctgtgcgc cggacgttgc cgcgctaaca   40380
ggcgcaacag taaccagcat aaatcaggcc gcggctaaaa tggcacgggc aggtcttctg   40440
gttatcgaag gtaaggtctg gcgaacggtg tattaccggt ttgctaccag ggaagaacgg   40500
gaaggaaaga tgagcacgaa cctggttttt aaggagtgtc gccagagtgc cgcgatgaaa   40560
cgggtattgg cggtatatgg agttaaaaga tgaccatcta cattactgag ctaataacag   40620
gcctgctggt aatcgcaggc cttttattt ggggagagg gaagtcatga aaaaactaac   40680
ctttgaaatt cgatctccag cacatcagca aaacgctatt cacgcagtac agcaaatcct   40740
tccagaccca accaaaccaa tcgtagtaac cattcaggaa cgcaaccgca gcttagacca   40800
aaacaggaag ctatgggcct gcttaggtga cgtctctcgt caggttgaat ggcatggtcg   40860
ctggctggat gcagaaagct ggaagtgtgt gtttaccgca gcattaaagc agcaggatgt   40920
tgttcctaac cttgccggga atggcttttgt ggtaataggc cagtcaacca gcaggatgc   40980
tgtaggcgaa tttgcggagc tattagagct tatacaggca ttcggtacag agcgtggcgt   41040
taagtggtca gacgaagcga gactggctct ggagtggaaa gcgagatggg gagacagggc   41100
tgcatgataa atgtcgttag tttctccggt ggcaggacgt cagcatattt gctctggcta   41160
atggagcaaa agcgacgggc aggtaaagac gtgcattacg ttttcatgga tacaggttgt   41220
gaacatccaa tgacatatcg gtttgtcagg gaagttgtga agttctggga tatccgctc   41280
accgtattgc aggttgatat caacccggag cttggacaga caaatggtta tacggtatgg   41340
gaaccaaagg atattcagac gcgaatgcct gttctgaagc catttatcga tatggtaaag   41400
aaatatggca ctccatacgt cggcggcgcg ttctgcactg acagattaaa actcgttccc   41460
ttcaccaaat actgtgatga ccatttcggg cgagggaatt acaccacgtg gattggcatc   41520
agagctgatg aaccgaagcg gctaaagcca aagcctggaa tcagatatct tgctgaactg   41580
tcagactttg agaaggaaga tatcctcgca tggtggaagc aacaaccatt cgatttgcaa   41640
ataccggaac atctcggtaa ctgcatattc tgcattaaaa aatcaacgca aaaaatcgga   41700
cttgcctgca aagatgagga gggattgcag cgtgttttta atgaggtcat cacgggatcc   41760
catgtgcgtg acggacatcg ggaaacgcca aaggagatta tgtaccgagg aagaatgtcg   41820
ctggacggta tcgcgaaaat gtattcagaa aatgattatc aagccctgta tcaggacatg   41880
gtacgagcta aaagattcga taccggctct tgttctgagt catgcgaaat atttggaggg   41940
cagcttgatt tcgacttcgg gagggaagct gcatgatacg atgttatcgg tgcggtgaat   42000
gcaaagaaga taaccgcttc cgaccaaatc aaccttactg gaatcgatgg tgtctccggt   42060
gtgaaagaac accaacaggg gtgttaccac taccgcagga aaaggaggac gtgtggcgag   42120
acagcgacga agtatcaccg acataatctg cgaaaactgc aaatacccttc caacgaaacg   42180
caccagaaat aaacccaagc caatcccaaa agaatctgac gtaaaaacct tcaactacac   42240
ggctcacctg tgggatatcc ggtggctaag acgtcgtgcg aggaaaacaa ggtgattgac   42300
caaaatcgaa gttacgaaca agaaagcgtc gagcgagctt taacgtgcgc taactgcggt   42360
cagaagctgc atgtgctgga agttcacgtg tgtgagcact gctgcgcaga actgatgagc   42420
gatccgaata gctcgatgca cgaggaagaa gatgatggct aaaccagcgc gaagacgatg   42480
taaaaacgat gaatgccggg aatggtttca ccctgcattc gctaatcagt ggtggtgctc   42540
tccagagtgt ggaaccaaga tagcactcga acgacgaagt aaaagaacgcg aaaaagcgga   42600
aaaagcagca gagaagaaac gacgacgaga ggagcagaaa cagaaagata aacttaagat   42660
tcgaaaactc gccttaaagc cccgcagtta ctggattaaa caagcccaac aagccgtaaa   42720
cgccttcatc agagaaaagag accgcgactt accatgtatc tcgtgcggaa cgctcacgtc   42780
tgctcagtgg gatgccggac attaccggac aactgctgcg gcacctcaac tccgatttaa   42840
tgaacgcaat attcacaagc aatgcgtggt gtgcaaccag cacaaaagcg gaaatctcgt   42900
tccgtatcgc gtcgaactga ttagccgcat cgggcaggaa gcagtagacg aaatcgaatc   42960
aaaccataac cgccatcgct ggactatcga agagtgcaag gcgatcaagg cagagtacca   43020
acagaaactc aaagacctgc gaaatagcag aagtgaggcc gcatgacgtt ctcagtaaaa   43080
accattccag acatgctcgt tgaaacatac ggaaatcaga cagaagtagc acgcagactg   43140
aaatgtagtc gcggtacggt cagaaaatac gttgatgata aagacgggaa aatgcacgcc   43200
atcgtcaacg acgttctcat ggttcatcgc ggatggagtg aaagagatgc gctattacga   43260
aaaaattgat ggcagcaaat accgaaatat ttgggtagtt ggcgatctgc acggatgcta   43320
cacgaactcg atgaacaaac tggatacgat tggattcgac aacaaaaaag acctgcttat   43380
ctcggtgggc gatttggttg atcgtggtgc agagaacgtt gaatgcctgg aattaatcac   43440
attcccctgg ttcagagctg tacgtggaaa ccatgagcaa atgatgattg atggcttatc   43500
agagcgtgga aacgttaatc actggctgct taatggcggt ggctggttct ttaatctcga   43560
ttacgacaaa gaaattctgg ctaaagctct tgccctaaaa gcagatgaac ttccgttaat   43620
catcgaactg gtgagcaaag ataaaaaaata tgttatctgc cacgccgatt atccctttga   43680
```

```
cgaatacgag tttggaaagc cagttgatca tcagcaggta atctggaacc gcgaacgaat   43740
cagcaactca caaaacggga tcgtgaaaga aatcaaaggc gcggacacgt tcatctttgg   43800
tcatacgcca gcagtgaaac cactcaagtt tgccaaccaa atgtatatcg ataccggcgc   43860
agtgttctgc ggaaacctaa cattgattca ggtacaggga gaaggcgcat gagactcgaa   43920
agcgtagcta aatttcattc gccaaaaagc ccgatgatcg gcgactcacc acgggccacg   43980
gcttctgact ctcttttccgg tactgatgtg atggctgcta tggggatggc gcaatcacaa   44040
gccggattcg gtatgctgc attctgcggt aagcacgaac tcagccagaa cgacaaacaa   44100
aaggctatca actatctgat gcaatttgca cacaaggtat cggggaaata ccgtggtgtg   44160
gcaaagcttg aaggaaatac taaggcaaag gtactgcaag tgctcgcaac attcgcttat   44220
gcggattatt gccgtagtgc cgcgacgccg ggggcaagat gcagagattg ccatggtaca   44280
ggccgtgcgg ttgatattgc caaaacagag ctgtggggga gagttgtcga gaaagagtgc   44340
ggaagatgca aaggcgtcgg ctattcaagg atgccagcaa gcgcagcata tcgcgctgtg   44400
acgatgctaa tcccaaacct tacccaaccc acctggtcac gcactgttaa gccgctgtat   44460
gacgctctgg tggtgcaatg ccacaaagaa gagtcaatcg cagacaacat tttgaatgcg   44520
gtcacacgtt agcagcatga ttgccacgga tggcaacata ttaacggcat gatattgact   44580
tattgaataa aatttgggtaa atttgactca acgatgggtt aattcgctcg ttgtggtagt   44640
gagatgaaaa gaggcggcgc ttactaccga ttccgcctag ttggtcactt cgacgtatcg   44700
tctggaactc caaccatcgc aggcagagag gtctgcaaaa tgcaatcccg aaacagttcg   44760
caggtaatag ttagagcctg cataacggtt tcgggatttt ttatatctgc acaacaggta   44820
agagcattga gtcgataatc gtgaaagagtc ggcgagcctg gttagccagt gctctttccg   44880
ttgtgctgaa ttaagcgaat accggaagca gaaccggatc accaaatgcg tacaggcgtc   44940
atcgccgccc agcaacagca caacccaaac tgagccgtag ccactgtctg tcctgaattc   45000
attagtaata gttacgctgc ggcctttac acatgacctt cgtgaaagcg ggtggcagga   45060
ggtcgcgcta acaacctcct gccgttttgc ccgtgcatat cggtcacgaa caaatctgat   45120
tactaaacac agtagcctgg atttgttcta tcagtaatcg accttattcc taattaaata   45180
gagcaaatcc ccttattggg ggtaagacat gaagatgcca gaaaaacatg acctgttggc   45240
cgccattctc gcggcaaagg aacaaggcat cggggcaatc cttgcgtttg caatggctgga   45300
ccttcgcggc agatataatg gcggtgcgtt tacaaaaaca gtaatcgacg caacgatgtg   45360
cgccattatc gcctagttca ttcgtgacct tctcgacttc gccggactaa gtagcaatct   45420
cgcttatata acgagcgtgt ttatcggcta catcggtact gactcgattg gttcgcttat   45480
caaacgcttc gctgctaaaa aagccggagt agaagatggt agaaatcaat aatcaacgta   45540
aggcgttcct cgatatgctg gcgtggtcgg agggaactga taacgacgt cagaaaacca   45600
gaaatcatgt ttatgacgtc attgtaggcg gagagctatt tactgattac tccgatcacc   45660
ctcgcaaact tgtcacgcta aacccaaaac tcaaatcaac aggcgccgga cgctaccagc   45720
ttctttcccg ttggtgggat gcctaccgca agcagcttgg cctgaaagac ttctctccga   45780
aaagtcagga cgctgtggca ttgcagcaga ttaaggagcg tggcgcttta cctatgattg   45840
atcgtggtga tatccgtcag gcaatcgacc gttgcagcaa tatctgggct tcactgccgg   45900
gcgctggtta tggtcagttc gagcataagg ctgacagcct gattgcaaaa ttcaaagaag   45960
cgggcggaac ggtcagagag attgatgtat gagcagagtc accgcgatta tctccgctct   46020
ggttatctgc atcatcgtct gcctgtcatg ggctgttaat cattaccgtg ataacgccat   46080
tacctacaaa gcccagcgcg acaaaaatgc cagagaactg aagctggcga acgcggcaat   46140
tactgacatg cagatgcgtc agcgtgatgt tgctgcgctc gatgcaaaat acacgaagga   46200
gttagctgat gctaaagctg aaaatgatgc tctgcgtgat gatgttgccg ctggtcgtca   46260
tcggttgcac atcaaagcag tctgtcagtc agtgcgtgaa gccaccaccg cctccggcgt   46320
ggataatgca gcctcccccc gactggcaga caccgctgaa cgggattatt tcacccctcag   46380
agagaggctg atcactatgc aaaaacaact ggaaggaacc cagaagtata ttaatgagca   46440
gtgcagatag agttgcccat atcgatgggc aactcatcga attattgtga gcaatacaca   46500
cgcgcttcca gcggagtata aatgcctaaa gtaataaaac cgagcaatcc atttacgaat   46560
gtttgctggg tttctgtttt aacaacattt tctgcgccgc cacaaatttt ggctgcatcg   46620
acagttttct tctgcccaat tccagaaacg aagaaatgat gggtgatggt ttcctttggt   46680
gctactgctc ccggtttgtt ttgaacagta aacgtctgtt gagcacatcc tgtaataagc   46740
agggccagcg cagtagcgag tagcattttt ttcatggtgt tattcccgat gcttttgaa   46800
gttcgcagaa tcgtatgtgt agaaaattaa acaaaccccta aacaatgagt tgaaatttca   46860
tattgttaat atttattaat gtatgtcagg tcgatgaat cgtcattgta ttcccggatt   46920
aactatgtcc acagccctga cggggaactt ctctgcggga gtgtccggga ataattaaaa   46980
cgatgcacac agggtttagc gcgtacacgt attgcattat gccaacgccc cggtgctgac   47040
acggaagaaa ccggacgtta tgatttagcg tggaaagatt tgtgtagtgt tctgaatgct   47100
ctcagtaaat agtaatgaat tatcaaaggt atagtaatat ctttatgtt catggatatt   47160
tgtaacccat cggaaaactc ctgctttagc aagatttttcc tctattgct gaaatgtgat   47220
ttctcttgat ttcaacctat cataggacgt ttctataaga tgcgtgtttc ttgagaattt   47280
aacatttaca accttttttaa gtccttttat taacacggtg ttatcgtttt ctaacacgat   47340
gtgaatatta tctgtggcta gatagtaaat ataatgtgag acgttgtgac gttttagttc   47400
agaataaaac aattcacagt ctaaatcttt tcgcacttga tcgaatattt cttttaaaaat   47460
ggcaacctga gccattggta aaaccttcca tgtgatacga gccgcgtag tttgcattat   47520
cgttttttatc gtttcaatct ggtctgacct ccttgtgttt tgttgatgat ttatgtcaaa   47580
tattaggaat gttttcactt aatagtattg gttgcgtaac aaagtgcggt cctgctggca   47640
ttctggaggg aaatacaacc gacagatgta tgtaaggcca acgtgctcaa atcttcatac   47700
agaaagattt gaagtaatat tttaaccgct agatgaagag caagcgcatg gagcgacaaa   47760
atgaataaag aacaatctgc tgatgatccc tccgtggatc tgattcgtgt aaaaaatg   47820
cttaatagca ccattttctat gagttaccct gatgttgtaa ttgcatgtat agaacataag   47880
gtgtctctgg aagcattcag agcaattgag gcagcgttgg tgaagcacga taataatatg   47940
aaggattatt ccctggtggt tgactgatca ccataactgc taatcattca aactatttag   48000
tctgtgacag agccaacacg cagtctgtca ctgtcaggaa agtggtaaaa ctgcaactca   48060
attactgcaa tgccctcgta attaagtgaa tttacaatat cgtcctgttc ggagggaaga   48120
acgcgggatg ttcattcttc atcacttta attgatgtat atgctctctt ttctgacgtt   48180
agtctccgac ggcaggcttc aatgacccag gctgagaaat tcccgacccc ttttgctca   48240
agagcgatgt taatttgttc aatcatttgg ttaggaaagc ggatgttgcg ggttgttgtt   48300
ctgcgggttc tgttcttcgt tgacatgagg ttcccggta ttcagtgtcg ctgatttgta   48360
ttgtctgaag ttgttttttac gttaagttga tgcagatcaa ttaatacgat acctgcgtca   48420
```

```
taattgatta tttgacgtgg tttgatggcc tccacgcacg ttgtgatatg tagatgataa 48480
tcattatcac tttacgggtc ctttccggtg atccgacagg ttacggggcg gcgacctcgt 48540
tctgtttatg tttcttgttt gttagccttt tggctaacaa acaagaaaca taaacagaac 48600
gcgtaacctg tcggatcacc ggaaaggacc cgtaaagtga taatgattat catctacata 48660
tcacaacgtg cgtggaggcc atcaaaccac gtcaaataat caattatgac gcaggtatcg 48720
tattaattga tctgcatcaa cttaacgtaa aaacaacttc agacaataca aatcagcgac 48780
actgaatacg gggcaacctc atgtcaacga agaacagaac ccgcagaaca caacccgca 48840
acatccgctt tcctaaccaa atgattgaac aaattaacat cgctcttgag caaaaagggt 48900
ccgggaattt ctcagcctgg gtcattgaag cctgccgtcg gagactaacg tcagaaaaga 48960
gagcatatac atcaattaaa agtgatgaag aatgaacatc ccgcgttctt ccctccgaac 49020
aggacgatat tgtaaattca cttaattacg agggcattgc agtaattgag ttgcagtttt 49080
accactttcc tgacagtgac agactgcgtg ttggctctgt cacagactaa atagtttgaa 49140
tgattagcag ttatggtgat cagtcaacca ccagggaata atccttcata ttattatcgt 49200
gcttcaccaa cgctgcctca attgctctga atgcttccag agacaccttt tgttctatac 49260
atgcaattac aacatcaggg taactcatag aaatggtgct attaagcata tttttttacac 49320
gaatcagatc cacggaggga tcatcagcag attgttcttt attcattttg tcgctccatg 49380
cgcttgctct tcatctagcg gttaaaatat tacttcaaat cttctgtat gaagatttga 49440
gcacgttggc cttacataca tctgtcggtt gtatttccct ccagaatgcc agcaggaccg 49500
cactttgtta cgcaaccaat actattaagt gaaaacattc ctaatatttg acataaatca 49560
tcaacaaaac acaaggaggt cagaccagat tgaaacgata aaaacgataa tgcaaactac 49620
gcgcccctcgt atcacatgga aggttttacc aatggctcag gttgccattt ttaaagaaat 49680
attcgatcaa gtgcgaaaag atttagactg tgaattgttt tattctgaac taaaacgtca 49740
caacgtctca cattatattt actatctagc cacagataat attccatcg tgttagaaaa 49800
cgataacacc gtgttaataa aaggacttaa aaaggttgta aatgttaaat tctcaagaaa 49860
cacgcatctt atagaaacgt cctatgatag gttgaaatca agagaaatca catttcagca 49920
atacagggaa aatcttgcta aagcaggagt ttttccgatg gttacaaata tccatgaaca 49980
taaaagatat tactataacct ttgataattc attactattt actgagagca ttcagaaaac 50040
tacacaaatc tttccacgct aaatcataac gtccggtttc ttccgtgtca gcaccggggc 50100
gttggcataa tgcaatacgt gtacgcgcta aaccctgtgt gcatcgtttt aattattccc 50160
ggacactccc gcagagaagt tccccgtcag ggctgtgaac atagttaatc cgggaataca 50220
atgacgattc atcgcacctg acatacatta ataaatatta acaatatgaa atttcaactc 50280
attgtttagg gtttgtttaa ttttctacac atacgattct gcgaacttca aaaagcatcg 50340
ggaataacac catgaaaaaa atgctactcg ctactgcgct ggcctgctt attacaggat 50400
gtgctcaaca gacgttact gttcaaaaca aaccggcagc agtagcacca aaggaaacca 50460
tcacccatca tttcttcgtt tctgaaattg ggcagaagaa aactgtcgat gcagccaaaa 50520
tttgtggcgg cgcagaaaat gttgttaaaa cagaaaccca gcaaacattc gtaaatggat 50580
tgctcggttt tattacttta ggcatttata ctccgctgga agcgcgtgtg tattgctcac 50640
aataattgca tgagttgccc atcgatatgg gcaactctat ctgcactgct cattaatata 50700
cttctgggtt ccttccagtt gtttttgcat agtgatcagc ctctctctga gggtgaaata 50760
atcccgttca gcggtgtctg ccagtcgggg ggaggctgca ttatccacgc cggaggcggt 50820
ggtggcttca cgcactgact gacagactgc tttgatgtgc aaccgacgac gaccagcggc 50880
aacatcatca cgcagagcat cattttcagc tttagcatca gctaactcct tcgtgtattt 50940
tgcatcgagc gcagcaacat cacgctgacg catctgcatg tcagtaattg ccgcgttcgc 51000
cagcttcagt tctctggcat ttttgtcgcg ctgggctttg taggtaatgg cgttatcacg 51060
gtaatgatta acagcccatg acaggcagac gatgatgcag ataaccagag cggagataat 51120
cgcggtgact ctgctcatac atcaatctct ctgaccgttc cgcccgcttc tttgaatttt 51180
gcaatcagac tgtcagcctt atgctcgaac tgaccataac cagcgcccgg cagtgaagcc 51240
cagatattgc tgcaacggtc gattgcctga cggatatcac cacgatcaat cataggtaaa 51300
gcgccacgct ccttaatctg ctgcaatgcc acagcgtcct gacttttcgg agagaagtct 51360
ttcaggccaa gctgcttgcg gtaggcatcc caccaacggg aaagaagctg gtagcgtccg 51420
gcgcctgttg atttgagttt tgggtttagc gtgacaagtt tgcgagggtg atcggagtaa 51480
tcagtaaata gctctccgcc tacaatgacg tcataaccat gatttctggt tttctgacgt 51540
ccgttatcag ttccctccga ccacgccagc atatcgagga acgccttacg ttgattattg 51600
atttctacca tcttctactc cggctttttt agcagcgaag cgtttgataa gcgaaccaat 51660
cgagtcagta ccgatgtagc cgataaacac gctcgttata taagcgagat tgctacttag 51720
tccggcgaag tcgagaaggt cacgaatgaa ctaggcgata atggcgcaca tcgttgcgtc 51780
gattactgtt tttgtaaacg caccgccatt atatctgccg cgaaggtacg ccattgcaaa 51840
cgcaaggatt gccccgatgc cttgttcctt tgccgcgaga atggcggcca acaggtcatg 51900
tttttctggc atcttcatgt cttaccccca ataagggat ttgctctatt taattaggaa 51960
taaggtcgat tactgataga acaaatccag gctactgtgt ttagtaatca gatttgttcg 52020
tgaccgatat gcacgggcaa aacggcagga ggttgttagc gcgacctcct gccacccgct 52080
ttcacgaagg tcatgtgtaa aaggccgcag cgtaactatt actaatgaat tcaggacaga 52140
cagtggctac ggctcagttt gggttgtgct gttgctgggc ggcgatgacg cctgtacgcg 52200
tttggtgatc cggttctgct tccggtattc gcttaattca gcacaacgga aagagcactg 52260
gctaaccagg ctcgccgact cttcacgatt atcgactcaa tgctcttacc tgttgtgcag 52320
atataaaaaa tcccgaaacc gttatgcagg ctctaactat tacctgcgaa ctgtttcggg 52380
attgcatttt gcagacctct ctgcctgcga tggttggagt tccagacgat acgtcgaagt 52440
gaccaactag gcggaatcgg tagtaagcgc cgcctctttt catctcacta ccacaacgag 52500
cgaattaacc catcgttgag tcaaatttac ccaattttat tcaataagtc aatatcatgc 52560
cgttaatatg ttgccatccg tggcaatcat gctgctaacg tgtgaccgca ttcaaaatgt 52620
tgtctgcgat tgactcttct ttgtggcatt gcaccaccag agcgtcatac agcggcttaa 52680
cagtgcgtga ccaggtgggt tgggtaaggt ttgggattag catcgtcaca gcgcgatatg 52740
ctgcgcttgc tggcatcctt gaatagccga cgcctttgca tcttccgcac tctttctcga 52800
caactctccc cacagctct gttttgcaa tatcaaccgc aggcctgta ccatggcaat 52860
ctctgcatct tgcccccggc gtcgcggcac tacggcaata atccgcataa gcgaatgttc 52920
cgagcacttg cagtacctttt gccttagtat ttccttcaag ctttgccaca ccacggtatt 52980
tcccgatac cttgtgtgca aattgcatca gatagttgat agcctttttgt ttgtcgttct 53040
ggctgagttc gtgcttaccg cagaatgcag ccataccgaa tccggcttgt gattgcgcca 53100
tccccatagc agccatcaca tcagtaccgg aaagagagtc agaagccgtg gcccgtggtg 53160
```

```
agtcgctcat catcgggctt tttggcgaat gaaatttagc tacgctttcg agtctcatgc    53220
gccttctccc tgtacctgaa tcaatgttag gtttccgcag aacactcgcg cggtatcgat    53280
atacatttgg ttggcaaact tgagtggttt cactgctggc gtatgaccaa agatgaacgt    53340
gtccgcgcct ttgatttctt tcacgatccc gttttgtgag ttgctgattc gttcgcggtt    53400
ccagattacc tgctgatgat caactggctt tccaaactcg tattcgtcaa agggataatc    53460
ggcgtggcag ataacatatt ttttatcttt gctcaccagt tcgatgatta acggaagttc    53520
atctgcttta tgggcaagag cttttagcca aatttctttg tcgtaatcga gattaaagaa    53580
ccagccaccg ccattaagca gccagtgatt aacgtttcca cgctctgata agccatcaat    53640
catcatttgc tcatggtttc cacgtacagc tctgaaccag gggaatgtga ttaattccag    53700
gcattcaacg ttctctgcac cacgatcaac caaatcgccc accgagataa gcaggtcttt    53760
tttgttgtcg aatccaatcg tatccagttt gttcatcagg ttcgtgtagc atccgtgcag    53820
atcgccaact acccaaatat ttcggtattt gctgccatca atttttttcgt aatagcgcat    53880
ctctttcact ccatccgcga tgaaccatga gaacgtcgtt gacgatggcg tgcatttcc    53940
cgtctttatc atcaacgtat tttctgaccg taccgcgact acatttcagt ctgcgtgcta    54000
cttctgtctg atttccgtat gtttcaacga gcatgtctgg aatggttttt actgagaacg    54060
tcatgcggcc tcacttctgc tatttcgcag gtctttgagt ttctgttggt actctgcctt    54120
gatcgccttg cactcttcga tagtccagcg atggcggtta tggtttgatt cgatttcgtc    54180
tactgcttcc tgcccgatgc ggctaatcag ttcgacgcga tacggaacga gatttccgct    54240
tttgtgctgg ttgcacacca cgcattgctt gtgaatattg cgttcattaa atcggagttg    54300
aggtgccgca gcagttgtcc ggtaatgtcc ggcatcccac tgagcagacg tgagcgttcc    54360
gcacgagata catggtaagt cgcggtctct ttctctgatg aaggcgttta cggcttgttg    54420
ggcttgttta atccagtaac tgcggggctt taaggcgagt tttcgaatct taagtttatc    54480
tttctgtttc tgctcctctc gtcgtcgttt cttctctgct gctttttccg ctttttcgcg    54540
ttctttactt cgtcgttcga gtgctatctt ggttccacac tctggagagc accaccactg    54600
attagcgaat gcagggtgaa accattcccg gcattcatcg ttttttacatc gtcttcgcgc    54660
tggtttagcc atcatcttct tcctcgtgca tcgagctatt cggatcgctc atcagttctg    54720
cgcagcagtg ctcacacacg tgaacttcca gcacatgcaa cttctgaccg cagttagcgc    54780
acgttaaagc tcgctcgacg ctttcttgtt cgtaacttcg attttggtca atcaccttgt    54840
tttcctcgca cgacgtctta gccaccggat atcccacagg tgagccgtgt agttgaaggt    54900
tttacgtca gattcttttg ggattggctt gggttttatt ctggtgcgtt tcgttggaag    54960
gtatttgcag ttttcgcaga ttatgtcggt gatacttcgt cgctgtctcg ccacacgtcc    55020
tccttttcct gcgtagtgg taacacccct gttggtgttc tttcacaccg gagacaccat    55080
cgattccagt aaggttgatt tggtcggaag cggttatctt ctttgcattc accgcaccga    55140
taacatcgca tcatgcagct tccctcccga agtcgaaatc aagctgccct ccaaatattt    55200
cgcatgactc agaacaagag ccggtatcga atctttagc tcgtaccatg tcctgataca    55260
gggcttgata atcatttcct gaatacattt tcgcgatacc gtccagcgac attcttcctc    55320
ggtacataat ctcctttggc gtttcccgat gtccgtcacg cacatgggat cccgtgatga    55380
cctcattaaa aacacgctgc aatccctcct catctttgca ggcaagtccg atttttttgcg    55440
ttgatttttt aatgcagaat atgcagttac cgagatgttc cggtatttgc aaatcgaatg    55500
gttgttgctt ccaccatgcg aggatatctt ccttctcaaa gtctgacagt tcagcaagat    55560
atctgattcc aggctttggc tttagccgct tcggttcatc agctctgatg ccaatccacg    55620
tggtgtaatt ccctcgcccg aaatggtcat cacagtattt ggtgaaggga acgagtttta    55680
atctgtcagt gcagaacgcg ccgccgacgt atggagtgcc atatttcttt accatatcga    55740
taaatggctt cagaacaggc attcgcgtct gaatatcctt tggttcccat accgtataac    55800
catttggctg tccaagctcc gggttgatat caacctgcaa tacggtgagc ggtatatccc    55860
agaacttcac aacttccctg acaaaccgat atgtcattgg atgttcacaa cctgtatcca    55920
tgaaaacgta atgcacgtct ttacctgccc gtcgcttttg ctccattagc cagagcaaat    55980
atgctgacgt cctgccaccg gagaaactaa cgacatttat catgcagccc tgtctcccca    56040
tctcgctttc cactccagag ccagtctcgc ttcgtctgac cacttaacgc cacgctctgt    56100
accgaatgcc tgtataagct ctaatagctc cgcaaattcg cctacacgca tcctgctggt    56160
tgactggcct attaccacaa agccattccc ggcaaggtta ggaacaacat cctgctgctt    56220
taatgctgcg gtaaacacac acttccagct ttctgcatcc agccagcgac catgccattc    56280
aacctgacga gagacgtcac ctaagcaggc ccatagcttc ctgtttttggt ctaagctgcg    56340
gttgcgttcc tgaatggtta ctacgattgg tttggttggg tctggaagga tttgctgtac    56400
tgcgtgaata gcgttttgct gatgtgctgg agatcgaatt tcaaaggtta gttttttcat    56460
gacttccctc tcccccaaat aaaaaggcct gcgattacca gcaggcctgt tattagctca    56520
gtaatgtaga tggtcatctt ttaactccat ataccgccaa tacccgtttc atcgcggcac    56580
tctggcgaca ctccttaaaa accaggttcg tgctcatctt tccttcccgt tcttccctgg    56640
tagcaaaccg gtaatacacc gttcgccaga ccttacctttc gataaccaga agacctgccc    56700
gtgccatttt agccgcgggcc tgatttatgc tggttactgt tgcgcctgtt agcgcgtgcaa    56760
cgtccgcgc acagaagcta ttatgcgtcc ccaggtaatg aataattgcc tctttgcccg    56820
tcatacactt gctcctttca gtccgaactt agctttgatt tctgcgatct tcgccagagc    56880
ctgtgcacga tttagaggtc taccgccat gacaggaagt tgttttactg gttcagggat    56940
cgcctcacca cggttaattc tcgcagtcat atggacaagc tcatctgcgg ccttacggcg    57000
taattccgca tcagtaagcg cattggcccg catgttctga tacaggttgg taaccagcca    57060
gtagtcgcg tttgatttcc acggataaga ctccgcatcc ggatacaggc ctcgcttccg    57120
gcaatactcg taaccatat caaccagctc gctgacgttt ggcagtccgg cggtaacgga    57180
tgcttcttcc cggcaccatg caacaaactg cccgggtgat ggcagaaatg gtcgattctg    57240
ccgacgggct acgcgcatc ctgcgttaac ctgttcccag gtggtgatcc cgttttcccg    57300
aaaagccaga acccactggc gacggatttc gttcacttcg ttctggtcac ggttagccag    57360
gctcgccggg aaagttgcca gtaactggct gaacacaccg ttgatgatct gcgctacctg    57420
ctgtacctgc ggcttttcgt cgtactgttc cggcatgttg ttggcgatcc gacgcatctg    57480
ctcacggtca aagttaacca tctgtgcggc gatgtttttt atagatccac cccgtaaatc    57540
gcgtctgt ttgtcaggtc gagttttggt ttgctgccgc caccgcctgc cgttgcttg    57600
ttacggttga tttcgagttg ggtccactta tcgcggagtt tggccgggct cagcacgtta    57660
ccggaccaga agttgtcctg gcatgcccag cggaacagca cacacatgtc gcggtggtta    57720
cgtccgtcac gttcacgcat caggcggata tcgttagccc acccagcaaa attcggtttt    57780
ctggctgatg gtgcgatagt cttcaccatg tcaaacatcg actctgcggc ggtcaggtct    57840
tctgctgtcc cccacttgct gccgctctga attgcagcat ccggtttcac cacagaaagg    57900
```

-continued

```
tcgttttctg gctggtcaga ggattcgcca gaattctctg acgaataatc tttctttttt  57960
tcttttgtaa tagtgtcttt tgtgtccccc tgttttgagg gatagcaatc ccccaatttg  58020
agggatgttt tatccctcgt tttagggtat tttccctcgt tttgagggat gcaccattct  58080
gagatgtttt tatttggtcc aaacatgccg ccttgctgct tgataatatt cattctgacg  58140
agttctaact tggcttcatt gcaccgtttg acaggtaact ttgtaatctc gctaagttga  58200
gaatcggtga ttctgtccat tggtttattc cacccatagg ttttacgcag aatggcaagc  58260
agcactttaa actgtcgctt ggtcagatct gcgcccgaat aagcctcaag cagcatattt  58320
gatagtctgg cgtaaccatc atcgagatct gccacattac gctcctgtcc ggcaaagtta  58380
cctctgccga agttgagtat ttttgctgta tttgtcataa tgactcctgt tgatagatcc  58440
agtaatgacc tcagaactcc atctggattt gttcagaacg ctcggttgcc gccgggcgtt  58500
ttttattggt gagaatcgca gcaacttgtc gcgccaatcg agccatgtcg tcgtcaacga  58560
cccccccattc aagaacagca agcagcattg agaactttgg aatccagtcc ctcttccacc  58620
tgctgatctg cgacttatca acgcccacag cttccgctgt cttctcagtt ccaagcattg  58680
cgattttgtt aagcaacgca ctctcgattc gtagagcctc gttgcgtttg tttgcacgaa  58740
ccatatgtaa gtatttcctt agataacaat tgattgaatg tatgcaaata aatgcataca  58800
ccataggtgt ggtttaattt gatgcccttt tcagggctg gaatgtgtaa gagcggggtt  58860
atttatgctg ttgttttttt gttactcggg aagggcttta cctcttccgc ataaacgctt  58920
ccatcagcgt ttatagttaa aaaaatcttt cggcctgcat gaatggcctt gttgatcgcg  58980
ctttgatata cgccgagatc tttagctgtc ttggtttgcc caaagcgcat tgcataatct  59040
ttcagggtta tgcgttgttc catacaacct ccttagtaca tgcaaccatt atcaccgcca  59100
gaggtaaaat agtcaacacg cacggtgtta gatatttatc ccttgcgtgt atagatttaa  59160
cgtatgagca caaaaaagaa accattaaca caagagcagc ttgaggacgc acgtcgcctt  59220
aaagcaattt atgaaaaaaa gaaaatgaa cttggcttat cccaggaatc tgtcgcagac  59280
aagatgggga tggggcagtc aggcgttggt gctttattta atggcatcaa tgcattaaat  59340
gcttataacg ccgcattgct tacaaaaatt ctcaaagtta gcgttgaaga atttagccct  59400
tcaatcgcca gagaaatcta cgagatgtat gaagcggtta gtatgcagcc gtcacttaga  59460
agtgagtatg agtaccctgt tttttctcat gttcaggcag ggatgttctc acctaagctt  59520
agaacctta ccaaaggtga tgcggagaga tgggtaagca caaccaaaaa agccagtgat  59580
tctgcattct ggcttgaggt tgaaggtaat tccatgaccg caccaacagg ctccaagcca  59640
agctttcctg acggaatgtt aattctcgtt gaccctgagc aggctgttga gccaggtgat  59700
ttctgcatag ccagacttgg gggtgatgag tttaccttca agaaactgat cagggatagc  59760
ggtcaggtgt ttttacaacc actaaaccca cagtacccaa tgatcccatg caatgagagt  59820
tgttccgttg tggggaaagt tatcgctagt cagtggcctg aagagacgtt tggctgatcg  59880
gcaaggtgtt ctggtcggcg catgctgat aacaattgag caagaatctt catcgaatta  59940
ggggaatttt cactccctc agaacataac atagtaaatg gattgaatta tgaagaatgg  60000
tttttatgcg acttaccgca gcaaaaataa agggaaagat aagcgctcaa taaacctgtc  60060
tgttttcctt aattctctgc tggctgataa tcatcacctg caggttggct ccaattattt  60120
gtatattcat aaaatcgatg gaaaaacttt tctctttacc aaaacaaatg acaagagtct  60180
ggttcagaag ataaatcgct ctaaagcttc agttgaagat attaagaaca gcctcgcaga  60240
tgacgaatca ttgggattcc catctttttt gtttgttgaa ggcgacacca ttggttttgc  60300
cagaactgtt ttcgggccga ccacatccga tctgacagat ttttttaatcg ggaaaggaat  60360
gtcattaagc agtggagagc gcgttcagat agagccactg atgaggggaa ccaccaaaga  60420
cgatgttatg catatgcatt tcatcggccg aacaacggta aagtagaag ccaagctacc  60480
tgtatttggc gatatattaa aggtcttagg ggcaacagat attgaagggg agcttttttga  60540
ctcattggat atagtcatta agccaaaatt taaaagggat ataaaaaagg ttgccaagga  60600
tattatttt aacccgtcac ctcaattttc agacattagc ctgcgggcaa aagatgaggc  60660
cggagatatt ttaacagaac attatctcta agaaaaagcc catctctcag cgcctctgaa  60720
caaggtcacc aatgctgaga tagctgaaga gatggcatat tgctacgcaa gaatgaaaag  60780
tgatatactg gaatgtttta aaaggcaggt gggcaaagtt aaggattaat tatcaggagt  60840
aattatgcga aacagaatca tgcctggtgt ttacatagta ataattcctt acgttatcgt  60900
aagcatttgc tatctccttt tccgccacta cattcctggt gttttctttt cagctcatag  60960
agatggtctt ggggcgacat tgtcatcata tgcaggaacc atgattgcaa tcctgattgc  61020
tgccttgacg tttctaatcg gaagcagaac gcgccgactg gccaagatta gagagtatgg  61080
gtatatgaca tcggtagtta ttgtctatgc ccttagtttt gttgagcttg gagctttgtt  61140
tttctgcggg ttattgcttc tttccagcat aagcggctac atgatacccca ctatcgccat  61200
cggcattgcc tctgcatcgt tcattcatat atgcatcctt gttttccaac tatataattt  61260
gaccagagaa caagaataac ccggcctcag cgccgggttt tctttgcctc acgatcgccc  61320
ccaaaacaca taaccaattg tatttattga aaaataaata gatacaactc actaaacata  61380
gcaattgaca tctctcacct accaaacaat gcccccctgc aaaaaataaa ttcatataaa  61440
aaacatacag ataaccatct gcggtgataa attatctctg gcggtgttga cataaatacc  61500
actggcggtg atactgagca catcagcagg acgcactgac caccatgaag gtgacgctct  61560
taaaaattaa gccctgaaga agggcagcat tcaaagcaga aggctttggg gtgtgtgata  61620
cgaaacgaag cattggccgt aagtgcgatt ccggattagc tgccaatgtg ccaatcgcgg  61680
ggggttttcg ttcaggacta caactgccac acaccaccaa agctaactga caggagaatc  61740
cagatgatg cacaaacacg ccgccgcgaa cgtcgcgcag agaaacaggc tcaatgcaaa  61800
gcagcaaatc ccctgttggt tgggtaagc gcaaaaccag ttaaccgccc tattctctcg  61860
ctgaatcgca aaccgaaatc acgagtagaa agcgcactaa atccgataga ccttacagtg  61920
ctggctgaat accacaaaca gattgaaagc aacctgcaac gtattgagcg caagaatcag  61980
cgcacatggt acagcaagcc tggcgaacgc ggcataacat gcagtggacg ccagaaaatt  62040
aagggaaat cgattcctct tatctagtta cttagatatt ggccttggct ttatctcaat  62100
attatatgga tcatagctgg caactaattc agtccagtaa atatcctcaa tagggaataa  62160
tatatgcttt ccattccatc gggaaaaagt tttgttcaac acaccaagct caatcaactc  62220
actaatgtat gggaattgtt tgatgtaac cacatacttc ctgccttcat taagggctgc  62280
gcacaaaacc atagatgct cttctgtaag gttttgaatt actgatcgca ctttatcgtt  62340
ttgcatctta atgcgtttc ttagcttaaa tcgcttatat ctggcgctgg caatagctga  62400
taatcgatgc acattaattg ctagcgaaaa tgcaagagca aagacgaaaa catgccacac  62460
atgaggaata ccgattctct cattaacata ttcaggccag ttatctgggc ttaaaagcag  62520
aagtccaacc cagataacga tcatatacat ggttctctcc agaggttcat tactgaacac  62580
tcgtccgaga ataacgagtg gatccatttc tatactcatc aaactgtagg ggttgtaata  62640
```

```
gtttatccga tttctcgctg taggggtaca cgagaaccac cgagcctgat gtggttaaaa  62700
gacaggcaca atctttacta ccgcaatcca ctatttaagg tgatatatgg aagaagaatt  62760
tgaagagttc gaagagcatc ctcaggatgt gatggaacaa taccaggact atccgtatga  62820
ctacgactat tgataaaaat caatggtgtg gacaattcaa gcgatgcaat ggatgcaagc  62880
tgcaatcgga atgcatggtt aagcctgaag aaatgtttcc tgtaatgaaa gatgggaaat  62940
atgtcgataa atgggcaata cgaacgacgg caatgattgc cagagaactt ggtaaacaga  63000
acaacaaagc tgcctgatag tggcctttat ttttggcata aataacagaa taaacactgc  63060
actgtgtatt cattccaacg agtgaataca cggagcaatg tcgctcgtaa ctaaacagga  63120
gccgacttgt tctgattatt ggaaatcttc tttgccctcc agtgtgaggg cgatttttta  63180
tctgtgagga tatgaacaga tgtcaaacat caaaaaatac atcattgatt acgactggaa  63240
agcatcaata gaaattgaaa tcgaccatga cgtaatgaca gaggaaaaac ttcaccagat  63300
taataatttc tggtcagact ctgaataccg actcaataaa cacggctctg tattaaatgc  63360
tgtattaatc atgctggcgc aacatgctct gcttatagca atttcaagcg acttaaatgc  63420
atatggtgtt gtgtgtgagt tcgactggaa tgatgaaaat ggtcaggaag gatggcctcc  63480
aatggatggt agcgaaggaa taagaattac cgatatcgat acatcaggaa tatttgattc  63540
agatgatatg actatcaagg ccgcctgagt gcggttttac cgcataccaa taacgcttca  63600
ctcgaggcgt ttttcgttat gtataaataa ggagcacacc atgcaatatg ccattgcagg  63660
gtggcctgtt gctggctgcc cttccgaatc tttacttgaa cgaatcaccc gtaaattacg  63720
tgacggatgg aaacgcctta tcgacatact taatcagcca ggagtcccaa agaatggatc  63780
aaacacttat ggctatccag actaaattca ctatcgccac ttttattggc gatgaaaaga  63840
tgtttcgtga agccgtcgac gcttataaaa aatgatatt aatactgaaa ctgagatcaa  63900
gcaaaagcat tcactaaccc cctttcctgt tttcctaatc agcccggcat ttcgcgggcg  63960
atattttcac agctatttca ggagttcagc catgaacgct tattacattc aggatcgtct  64020
tgaggctcag agctgggcgc gtcactacca gcagctcgcc cgtgaagaga aagaggcaga  64080
actggcagag gacatggaaa aaggcctgcc ccagcacctg tttgaatcgc tatgcatcga  64140
tcatttgcaa cgccacgggg ccagcaaaaa atccattacc cgtgcgtttg atgacgatgt  64200
tgagtttcag gagcgcatgg cagaacacat ccggtacatg gttgaaacca ttgctcacca  64260
ccaggttgat attgattcag aggtataaaa cgaatgagta ctgcactcgc aacgctggct  64320
gggaagctgg ctgaacgtgt cggcatggat tctgtcgacc cacaggaact gatcaccact  64380
cttcgccaga cggcatttaa aggtgatgcc agcgatgcgc agttcatcgc attactgatc  64440
gttgccaacc agtacggcct taatccgtgg acgaaagaaa tttacgcctt tcctgataag  64500
cagaatggca tcgttccggt ggtgggcgtt gatggctggt cccgcatcat caatgaaaac  64560
cagcagtttg atggcatgga ctttgagcag gacaatgaat cctgtacatg ccggatttac  64620
cgcaaggacc gtaatcatcc gatctgcgtt accgaatgga tggatgaaga ccgccgcgaa  64680
ccattcaaaa ctcgcgaagg cagagaaatc acggggccgt ggcagtcgca tcccaaacgg  64740
atgttacgtc ataaagccat gattcagtgt gcccgtctgg ccttcggatt tgctggtatc  64800
tatgacaagg atgaagccga gcgcattgtc gaaaatactg catacactgc agaacgtcag  64860
ccggaacgcg acatcactcc ggttaacgat gaaaccatgc aggagattaa cactctgctg  64920
atcgcctctg ataaaacatg ggatgacgac ttattgccgc tctgttccca gatatttcgc  64980
cgcgacattc gtgcatcgtc agaactgaca caggccgaag cagtaaaagc tcttggattc  65040
ctgaaacaga aagccgcaga gcagaaggtg gcagcatgac accggacatt atcctgcagc  65100
gtaccgggat cgatgtgaga gctgtcgaac agggggatga tgcgtggcac aaattacggc  65160
tcggcgtcat caccgcttca gaagttcaca acgtgatagc aaaacccgc tccggaaaga  65220
agtggcctga catgaaaatg tcctacttcc acacctgct tgctgaggtt tgcaccggtg  65280
tggctccgga agttaacgct aaagcactgg cctggggaaa acagtacgag aacgacgcca  65340
gaaccctgtt tgaattcact tccggcgtga atgttactga atcccgatc atctatcgcg  65400
acgaaagtat gcgtaccgcc tgctctcccg atggtttatg cagtgacggc aacggcctg  65460
aactgaaatg cccgtttacc tcccgggatt tcatgaagtt ccggctcggt ggtttcgagg  65520
ccataaagtc agcttacatg gcccaggtgc agtacagcat gtgggtgacg cgaaaaaatg  65580
cctggtactt tgccaactat gacccgcgta tgaagcgtga aggcctgcat tatgtcgtga  65640
ttgagcggta tgaaaagtac atggcgagtt ttgacgagat cgtgccggag ttcatcgaaa  65700
aaatggacga ggcactggct gaaattggtt ttgtatttgg ggagcaatgg cgatgacgca  65760
tcctcacgat aatatccggg taggcgcaat cactttcgtc tactccgtta caaagcgagg  65820
ctgggtattt cccggccttt ctgttatccg aaatccactg aaagcacagc ggctggctga  65880
ggagataaat aataaacgag gggctgtatg cacaaagcat cttctgttga gttaagaacg  65940
agtatcgaga tggcacatag ccttgctcaa attggaatca ggtttgtgcc aataccagta  66000
gaaacagacg aagaatttca tacgttagcc gcatcccttt cacaaaagct ggaaatgatg  66060
gtggcgaaag cagaagcaga tgagagaaac caggtatgac aaccacgaa tgcatttttc  66120
tggcagcggg cttcatattc tgtgtgctta tgcttgccga catgggactt gttcaatgac  66180
acctcagcag gaaaacgccc ttcgcagcat tgcccgtcag gctaattctg aaatcaaaaa  66240
aagccagaca gcagtttccg gataaaaacg tcgatgacat ttgccgtagc gtactgaaga  66300
agcaccgcga aacggtaacg ctgatgggat tcacaccgac tcatttaagc ctggcaatcg  66360
gcatgttaaa cggcgtcttt aaggaacgat gaacatgaaa agcaaaatca tcagggagct  66420
acaggctcct ttttattat tcgcattcac cctcaagcgt attaaccaac agttcaggga  66480
ttaatgaaag atggcagaca tcattgattc agcatcagaa atagaagaat tacagcgcaa  66540
cacagcaata aaaatgcgcc gcctgaacca ccaggctata tctgccactc attgttgtga  66600
gtgtggcgat ccgatagatg aacgaagacg cctggtcgtt cagggttgtc ggacttgtgc  66660
aagttgccag gaggatctgg aacttatcag taaacagaga ggttcgaagt gagcgaaatt  66720
aactctcagg cactgcgtga agcggcagag caggcaatgc atgacgactg gggatttgac  66780
gcagaccttt tccatgaatt ggtaacacca tcgattgtgc tggaactgct ggatgaacgg  66840
gaaagaaacc agcaatacat caaacgccgc gaccaggaga acgaggatat tgcgctaaca  66900
gtagggaaac tgcgtgttga gcttgaaaca gcaaatcaa aactcaacga gcagcgtgag  66960
tattacgaag gtgttatctc ggatgggagt aagcgtattg ctaaactgga aagcaacgaa  67020
gtccgtgaag acggaaacca gtttcttgtt gttcgccatc gtggaagac tcctgttatc  67080
aagcactgca ctggtgacct ggaagagttt ctgcggcagt taatcgaaca agacccgtta  67140
gtaactatcg acatcattac gcatcgctat tacggggttg gaggtcaatg ggttcaggat  67200
gcaggtgagt atctgcatat gatgtctgac gctggcattc gcatcaaagg agagtgagat  67260
cggttttgta aaagataacg cttgtgaaaa tgctgaattt cgcgtcgtct tcacagcgat  67320
gccagagtct gtagtgtcag atgatgaccg tactcaaaca tcgggttgag tattatctta  67380
```

```
ctgtttctttt acataaacat tgctgatacc gtttagctga aacgacatac attgcaagga 67440
gtttataaat gagtatcaat gagttagagt ctgagcaaaa agattgggcg ttatcaatgt 67500
tgtgcagatc cggtgtcttg tctccatgca gacatcacga aggtgtttat gtagatgaag 67560
gtatagatat agagtcggca tacaaatatt ccatgaaggt ttataagtct aatgaagaca 67620
aatccccatt ctgcaatgtg cgagaaatga ctgataccgt gcaaaattat tatcacgagt 67680
acggtggaaa cgatacttgc cctctctgta caaaacatat agatgattaa acccaatatt 67740
acataacaat cctcgcactc gcggggattt attttatctg aactcgctac ggcgggtttt 67800
gttttatgga gatgataaat gcacttccga gtcacaggag aatggaatgg agagccattc 67860
aacagagtta tcgaagcgga gaacatcaac gactgctacg accactggat gatatgggcg 67920
cagatagcac atgcagacgt aaccaatatt cgaattgaag aactgaaaga acaccaagcc 67980
gcctgatggc ggttttttct tgcgtgtaat tgcggagact ttgcgatgta cttgacactt 68040
caggagtgga acgcacgcca gcgacgtcca agaagccttg aaacagttcg tcgatgggtt 68100
cgggaatgca ggatattccc acctccggtt aaggatggaa gagagtatct gttccacgaa 68160
tcagcggtaa aggttgactt aaatcgacca gtaacaggtg gccttttgaa gaggatcaga 68220
aatgggaaga aggcgaagtc atgagcgccg ggatttaccc cctaaccttt atataagaaa 68280
caatggatat tactgctaca gggacccaag gacgggtaaa gagtttggat taggcagaga 68340
caggcgaatc gcaatcactg aagctataca ggccaacatt gagttatttt caggacacaa 68400
acacaagcct ctgacagcga gaatcaacag tgataattcc gttacgttac attcatggct 68460
tgatcgctac gaaaaaatcc tggccagcag aggaatcaag cagaagacac tcataaatta 68520
catgagcaaa attaaagcaa taggaggggg tctgcctgat gctccacttg aagacatcac 68580
cacaaaagaa attgcggcaa tgctcaatgg atacatagac gagggcaagg cggcgtcagc 68640
caagttaatc agatcaacac tgagcgatgc attccgagac gcaatagctg aaggccatat 68700
aacaacaaac catgtcgctg ccactcgcgc agcaaaatca gaggtaagga gatcaagact 68760
tacggctgac gaatacctga aaatttatca agcagcagaa tcatcaccat gttggctcag 68820
acttgcaatg gaactggctg ttgttaccgg gcaacgagtt ggtgatttat gcgaaatgaa 68880
gtggtctgat atcgtagatg gatatcttta tgtcgagcaa agcaaaacag gcgtaaaaat 68940
tgccatccca acagcattgc atattgatgc tctcggaata tcaatgaagg aaacacttga 69000
taaatgcaaa gagattcttg gcggagaaac cataattgca tctactcgtc gcgaaccgct 69060
ttcatccggc acagtatcaa ggtattttat gcgcgcacga aaagcatcag gtctttcctt 69120
cgaaggggat ccgcctacct ttcacgagtt gcgcagtttg tctgcaagac tctatgagaa 69180
gcagataagc gataagtttg ctcaacatct tctcgggcat aagtcggaca ccatggcatc 69240
acagtatcgt gatgacagag gcagggagtg ggacaaaatt gaaatcaaat aatgattta 69300
ttttgactga tagtgacctg ttcgttgcaa caaattgata agcaatgctt ttttataatg 69360
ccaacttagt ataaaaaagc tgaacgagaa acgtaaaatg atataaatat caatatatta 69420
aattagattt tgcataaaaa acagactaca taatactgta aaacacaaca tatgcagtca 69480
ctatgaatca actacttaga tggtattagt gacctgtaac agagcattag cgcaaggtga 69540
tttttgtctt cttgcgctaa tttttgtca tcaaacctgt cgcactccag agaagcacaa 69600
agcctcgcaa tccagtgcaa agctttgtgt gccacccact acgacctgca taaccagtaa 69660
gaagatagca gtgatgtcaa acgacgcagc tgacttcttt tcttcacga cttccccaca 69720
cccagcatgc ataccttcc gccataactg tagtgaatgt ctgttatgag cgaggagcgg 69780
aagttaacac ttatgaaaaa tggctacgaa gtccgtggct atctatccgg ttattagtac 69840
ttgaaacgct tcttcagaag cctgaagagc taatcgttcg gcgatactat atatgcatta 69900
atagactata tcgttggtat aaacagtgca ccatgcaaca tgaataacag tgggttatcc 69960
aaaaggaagc agaaagctaa atatggaaaa ctacaatacg atgccccgtt aagttcaata 70020
ctactaattt ttagatggaa aacgtatgta atagagagta acttaaaaga gagatcctgt 70080
gttgccgcca aataaattgc ggttattta ataaaattaa gggttactat atgttggagt 70140
ttagtgttat tgaaagaggc gggtatattc ctgcagtaga aaaaaataag gcattcctac 70200
gagcagatgg ttgaatgac tattcctttg ttacaatgtt ttatcttact gtctttgatg 70260
agcatggtga aaaatgcgat atcggaaatg ttaaaattgg ttttgtaggt caaaagaag 70320
aagtaagcac ttattcatta atagataaaa aattcagtca actccctgaa atgtttttt 70380
cctaggtga aagcattgac tactatgtta atctcagcaa attaagcgat ggttttaaac 70440
ataaccttct taaagctatt caggatttag tagtatggcc aaatcgatta gccgacattg 70500
aaaatgaaag cgtcctcaac acctcattac ttagagggt aactctttca gaaatcatg 70560
gacagttcgc acgtgtgtta aatggttgc cagaattgtc agatttccac ttttcattta 70620
atagaaaaag tgctccccgga ttcagtgatt taactatacc tttgaggtg acggttaatt 70680
ctatgcccag cacgaacatt catgcttta tcgggcggaa tgggtgtggt aaaacaacaa 70740
ttttgaatgg aatgattggt gcaatcacca acccagaaaa caatgaatat tttttctctg 70800
aaaataatag acttatcgag tcaagaatcc caaagggata tttcgatcg cttgtttcag 70860
tttcgtttag tgcatttgat cctttttactc ctcctaaaga acaacctgac ccagcaaaag 70920
gtacacaata ctttttatat ggactcaaga atgctgccag caatagttta aaatcactag 70980
gcgatctccg cttagaattc atttcagcat ttattggttg tatgagagta gatagaaaaa 71040
gacaactctg gcttgaagct atcaaaaaac taagtagtga tgaaactttt tcaaatatgg 71100
aactcatcag cctcatttct aaatatgaag agttaagacg taatgaacca cagattcaag 71160
tggacgatga taaattcact aaattgtttt atgacaatat ccagaaatat ctgcttcgaa 71220
tgagctctgg acatgcaatt gttttattta ctatcacaag attagtagat gtcgttggcg 71280
aaaagtcatt agtttattc gatgaaccag aggttcatct gcatccacct ttgctctctg 71340
cttttttacg aacattaagc gacttactcg atgcacgcaa tggtgtagca ataattgcaa 71400
ctcattcccc agtagtactg caagaggttc caaaatcctg catgtggaaa gtcctacggt 71460
caagagaagc aataaatatt atccgtccgg atattggag atctcggtgag aacttaggtg 71520
ttttaactcg tgaggtgttt tacttgaag tgacaaattc tggataccac cacttattat 71580
cgcagtccgt tgattcagag cttttcttatg aaaccattct aaaaaattat aatggtcaga 71640
taggattaga aggtcgaacc gttttaaaag cgatgataat gaacagagat gaaggtaaag 71700
tacaatgaaa aaactccctc ttccagcgag aacttatagc gaaatgctta ataaatgctc 71760
ggaaggtatg atgcagataa atgttagaaa taatttcatt actcacttcc ccacttttt 71820
gcagaaagaa caacaatata gaatattaag ctcgacaggt cagttattta cctacgacag 71880
gacacaccct cttgagccta caaccttagt agttggtaac ctgacaaagg ttaaattaga 71940
aaagctttat gaaaataatc tccgagataa aaacaaaccc gctagaacat attacgatga 72000
catgcttgtt tcatcaggtg aaaaatgtcc attttgtggt gatataggac agacaaaaaa 72060
tatagatcat tttcttccta ttgcacatta tcctgaattt tcggtgatgc ctattaattt 72120
```

```
agttccatcg tgccgcgact gcaatatggg agagaaaggt caagttttcg cagtagatga  72180
ggtacaccaa gcgattcatc cctatatcga caaggacatt ttttttcgtg agcaatgggt  72240
atatgcaaat ttcgtttccg gaactccggg tgctatcagt tttatgttg aatgcccggc   72300
gaactggagg caggaagaca aacacagagc tcttcatcat ttcaagctat taaatattgc  72360
taacaggtat cgttttggagg cagggaagca cttgagtgaa gtgattactc aaagaaactc  72420
tttcgtaaaa gttataagga aatatagttc aaccgcaacg tttcagcagc tacagtcaga  72480
atttattgaa gcaaatctga aacctattat agatttgaat gacttcccca attattggaa  72540
aagagttatg tatcagtgcc tagcaaactc ggaagatttt ttcagaggga tctagaatat  72600
gatgaaagat agaaaattac gacgcttatc ggaagtgaac gaatacttt tatatgagga   72660
gggctgtttt tacaaaatcc ggtagtaact tgctaaccaa ttcctaggca ggtcattggc   72720
aacagtggca tgcaccgaga aggacgtttg taatgtccgc tccggcacat agcagtccta   72780
gggacagtgg cgtacagtca tagatggtcg gtgggaggtg gtacaaattc tctcatgcaa   72840
aaaatatgta aaatcggtag caactggaaa tcattcaaca cccgcactat cggaagttca   72900
ccagccagcc gcagcacgtt cctgcatacg acgtgctcgc ggctctacca tatctcctat   72960
gagcaacgtg ttagcagagc caagccacaa ctctaatttt aatacataat gaatgataat   73020
aataatatta aaaatttcct gtgtaactaa tttactatat ggtttctgat aagaatcatt   73080
gcaaagatca aacaacttgt attacattga cagttaagca gttaattta tcacctctaa    73140
aatatatcag catctagcat gcaacctatc aaaatggaga gttttatgac taaaaaacca   73200
tgggaaagaa gacttaaaga tttatcgcac ttgctcaaat gctgcattga tacatatttt   73260
gaccctgaat tatttcgctt gaatttgaat caattcctcc aaaccgcaag aacagtaaca   73320
tttattattc aaaaaaacaa aaaccagatt ataggatatg acatttggta taacaataat   73380
gttattgaaa aatggaaaaa tgatccatta atggcttggg ctaaaaattc tcgcaatacg   73440
atagaaaaac aaggcgattt agaaatgtat agcgaggcaa aggctactct tatttcatct   73500
tacattgaag aaaatgacat tgagtttatt acaaatgaaa gtatgttaaa cattggtata   73560
aaaaagttag tcagacttgc acaaaagaaa ttaccttcat atttaactga atcatctatt   73620
attaaatcga aaagacgatg ggtcgctaat acgctaaaag attacgaatt attacatgcc   73680
ttagctataa tctatggcag aatgtataac tgctgtaact ctcttggcat acaaataaac   73740
aatccaatgg gtgacgatgt gatttcgcca acatcattcg actctttatt tgatgaagcc   73800
aggagaataa cttatttaaa attaaagat tactccataa gcaaattgtc atttagcatg    73860
atacaatatg acaataaaat aattcctgaa gatattaaag agcgtctaaa actggtagat   73920
aagcctaaaa atatcacttc gacagaaagg ttagttgact atacagccaa gcttgcagaa   73980
acgactttt taaggacgg ttatcacatt caaacattaa tttttatga taaacaattc     74040
catccaattg atttaatcaa tacaacttt gaagatcaag cagataaata tatttttgg    74100
cgttatgcag ctgacagagc caaaataaca aatgcctatg gcttcatttg gatatcagag   74160
ctatggctca gaaaagcaag catctactcc aataaaccaa tacatacaat gccaattata   74220
gatgaaagac ttcaggtaat tggaattgat tcaatataa atcaaaaatg tatttcatgg   74280
aaaatagtta gagaaaacga agaaaaaaaa ccgactttag aaatatcaac agcagactca   74340
aaacatgacg aaaaaaccata tttcatgcgt tcagtcttaa aagcaattgg cggtgatgta   74400
aacactatga acaattgagt catagaactt ccattattct cctgaagata ataatcgaca   74460
aataaaccaa tactcagctt tacaatatac taactaaccg cagaacgtta tttcatacaa   74520
cgtttctgcg gcatatcaca aaacgattac tccataacag ggacagcagg ccactcaata   74580
tcaggtgcag ttgatgtatc aacacggttc agcaacaccc gatacttctt ccaggcttcc   74640
agcaacgagg tttcttcctt cgttgcaatt tccagatctg cagcatcctg aagcggcgca   74700
atatgctcac tggctacctg catcaggctt ttttttgttt cttccgcctc ccggatccgg   74760
aacagttttt ctgcttccgt atccttcacc caggctgtgc cgttccactt ctgatattcc   74820
cctcccggcg ataaccaggt aaaatttcc ggtaacggac cgagttcaga aataaataac    74880
gcgtcgccgg aagccacgtc atagacgagtt ttaccccgat ggcttcaac gagatgccac   74940
gatgcctcat cactgttgaa aacagccaca aagccagccg gaatatctgg cggtgcaata   75000
tcggtactgt ttgcaggcag accggtatga ggcggaatat atgcgtcacc ttcaccaata   75060
aattcattag ttccggccag cagattataa attttatgg tccgtggttg ttcactcatt    75120
ctgaatgcca ttatgcaagc ctcacaatat agttaaatgc aatgttttg acggtgttt     75180
ccgcgttacc cgcagcgtta acggtgatgg tgtgtccgtg tgaaccaata ctgaaagaat   75240
gggcatgagc accgataaca accggatgct ggtgcgcacc aataccaact gtatgcgcat   75300
gtgcaccggc actcacggct gtaccggaca atgagtgact gtggctgccc tgactgtccg   75360
ttttcgataa ataagcaata ccctgtgtgc tggttccttt aactgtggat aaacttcctg   75420
taatggttgc tgttccatac tgactccagc cagaactgtt catccttaaa ccacttgtgt   75480
gggcatgagc acccgcggcc cctgttgaac cgctcagact gtgagcatga gccccgtgt    75540
tattcgtcga tttggtgccg taatcgaaac tgcctgttgt tttcgtcccg taatcaaacg   75600
acgatgtggt tttcgtcccc aaatccgtac cggatgccat ggcactgtgg gtgtgcgact   75660
taattccatc ctgttcctga gacaatacag cacgaccgct ggcgggtttc cccttgattg   75720
tccagcctcg catatcagga agcacacccg atggatacgc gacagcaagt tttgggtagg   75780
ctgatttgtc aaacgcctgc ccctgcatca ggacgtagcc agacggaacg atatctgatg   75840
gccacgggat cggcgcacct gccggaaagg ccgaattctc accggcccca aggtattcaa   75900
gaacatctgc acggaattt tttgccagaa tatccctgcc aacctagtca gttcagtca    75960
ggctggcggc atcatttcc gcaaaatacg gtaatttatt tttcgccgtg gaaagccctg    76020
ccagcgccgt cagtgtcgca ttcttcggtt gtttacccgc aagcgcgtta gtcatggtgg   76080
tagcaaaatc tggatcattc ccgagcgctg cggccagttc attcagcgta ttcagtcgt    76140
caggtgacgc gtcgataaca tctgcaatcg cggccagtac aaaagcggtg ttcgcaatct   76200
gggtattgtt tgttccctg agcgcgggttg gtgctgttgg cgttccggtc agtgccggac   76260
tgtccagtgg gcttttctgt tcgtttcatc cattaccacc ttaaccgcct ttggcgttgc   76320
agcaagcgtt tcagacgtgc tgttggttgc actgctgagc tgcactatcc cctttctcgt   76380
tgtgtccgca tcctcaagcg cgacagctga agctatatct tctgcacgtt tgccgaatt    76440
ttttgcacgt attgccgccg cttctgccgc acttttgctc tgcgatgctg ataccgcact   76500
tcccgacctg tctgtgcct tcgtggatgc cgttgacgca ctccccgccg ccgctgtttt   76560
tgcgtctgcc gcggcagagg cgctccgttc cgctgctgtt tcagatgacc tggcattcgt   76620
ctcgacgtt tttgccgccc tggcagaatt ttctgccgcc gttgccgagg aagctgcacg    76680
accggcactt gatgatgcgt tcgtttctga tgatttgct gcctcttttg aggccaccgc    76740
atctcgtgct gaagtggcgg cctctgacgc tttcgtggcc gcggtggagg cagacgtggc   76800
ggctgattgt tgtgacgctg cagcattcgt ttctgacgtt ttcgccgcac cggcactggt   76860
```

-continued

```
ggccgccgcg ttttttgagg actctgcggc tgcggcactt ttttccgctt cagtggcctt   76920
tgctgatgcc gcttctgcgc cggaggacgc ttcctgagct gacgatgcag cctgtccggc   76980
ggacgtgctg gcggcgcgtg ctgagtcagt tgcatcagtc acaagggccg cgacctgagc   77040
agctgatgca ctggcatcgc cggctgattt cttcgcgtct gccgtactct gtgccaccac   77100
ggacgcgtta cgcgccacct cttccaccat cagttcaaga cgacgcagca cctccggccg   77160
ggcatcatcc tccgtcatgg cacagagaaa atcattcagc gtccccggtt gtgaatcttc   77220
atacacggtg atggtcccgg cgtgcgatgg tggaaaaccg tcaacctgca ggatgacact   77280
gtactgaccg tactccacat ccatgctgta acgcccggct tcatccggat tctctgagcc   77340
caccgtgttc accaccaccg tggtgctgtt acgtctggct ttcagctgaa tggtgcagtt   77400
ctgtaccggt tttcctgtgc cgtctttcag gactcctgaa atctttactg ccatattcac   77460
cccacaaaaa agcccaccgg ttccggcggg ctgtcataac actgtgttac ctggctaatc   77520
agaatttata accgaccca acgatgaatc cgtcagtacg ccagtcgcca ctgccggagc   77580
cttcataagc aatatcaaca acgacggacg ctgccggatt aatctgtata cctgcactcc   77640
acgccactga ggtatgccgc attgcacttt cgtccctggc agtggtcgtc tctttcatat   77700
acccgggagt gatttccgtc ttacggtaat ccattgtact gccggaccac cgactgtgag   77760
ccactccggc catggcgtac gcactgacct gcttactgat ttgtaaaacc ggtccggcca   77820
tcacgctcac ataacgtcca cgcaggctct catagtgaaa cgtatcctcc ccggtcatca   77880
ctgtgctgct cttttttcgac gcggcgaacc ccagggaagc catcaccccc acactgtccg   77940
tcagctcata acgtacttc acgttaatcc ctttcagatg actcacaccg gtatccccgc   78000
ccgacaacga cggcaatgta cccggtttca cttgaaaata gcccaccgta aacgtaccat   78060
gtccaccttc cgcacgggcc ggagtgactg tcaccgcaag tgcggcaaag acagcaacgg   78120
caatacacac attacgcatc gttcacctct cactgttttta taataaaacg cccgttcccg   78180
gacgaacctc tgtaacacac tcagaccacg ctgatgccca gcgcctgttt cttaatcacc   78240
ataacctgca catcgctggc aaacgtatac ggcggaatat ctgccgaatg ccgtgtggac   78300
gtaagcgtga acgtcaggat cacgtttccc cgacccgctg gcatgtcaac aatacggag   78360
aacacctgta ccgcctcgtt cgccgcgcca tcataaatca ccgcaccgtt catcagtact   78420
ttcagataac acatcgaata cgttgtcctg ccgctgacag tacgcttact tccgcgaaac   78480
gtcagcggaa gcaccactat ctggcgatca aaaggatggt catcggtcac ggtgacagta   78540
cgggtacctg acggccagtc cacactgctt tcacgctggc gcggaaaagc cgcgctcgcc   78600
gccttacaa tgtccccgac gatttttcc gccctcacga taccgtttat cgtacagttt   78660
tcagctatcg tcacattact gagcgtcccg gagttcgcat tcacactgcc actgatatcc   78720
gcatttttag cggtcagctt tccgtccggt gtcaggaaaa aggccggagg attgccgccg   78780
ctggtaatgg tgggggccgt caggcgcttc aggaacacgt cgttcatgaa tatctggttg   78840
ccctgcgcca caaacatcgg cgtttcattc ccgtttgccg ggtcaataaa tgcgatacga   78900
ttggcggcaa ccagaaactg gctcagtttg ccttcctccg tgtcctccat gctgaggcca   78960
atacccgcga cataatgttt gccgtctttg gtctgctcaa ttttgacagc ccacatggca   79020
ttccacttat cactggcatc cttccactct ttcgaaaact cctccagtct gctggcgtta   79080
tcctccgtca gctcgacttt ttccagcagc tccttgccga gatgggattc ggttatcttg   79140
cctttgaaaa aatccaggta accttccgca tcatcgctcc cccgaccgac ggcctccacg   79200
aatgccgatt tgccaacggt gttcacactg cggatataaa agtaatatc atggcccggt   79260
ttgatattga tactggcggc tatccagtac agcgccgtac caagataacg cgtgctggtt   79320
tcaacctgtc tgatatccgc aatctgcttt tccgagaacc agaactcaaa ctgtaccgtc   79380
gggtcataaa cggcaagatg cggcgtggcg gttatctgaa catagcccgg cgtcagctca   79440
atcctcgacg gtgctgccgg tgcggcaatc cggaacgata ccgacgccgg atcgccctgc   79500
tgcccccacg catttaccgc ccggactgtc agcctgtagt tccccagcgc cagttgcgtg   79560
aagcggtatg tggtttccgt cgtccgggcc gtgctgacca gccgctcact gccgtcgtcc   79620
gctgttacgg tcagacggag caggaaactc acgcccttca ccaccttcgg tgtgtcccat   79680
cgcgccagca cctgatattc cccgctgtct gcagtgactt ctgcggtcag gtgctgcacc   79740
gctggcggca tgacaccatt caccgtgcca ctctgttcgc cgtcaaagtg cgccccgtta   79800
tccacgatgg cctctttttc cggcacatgc tgcacgcgcg tgatgcata cgtgccgtcg   79860
tcgttctcac ggatactcac gcagcggaac agtcgctggc gacgcgtcgg cagcttcagc   79920
tcccatacgc tgtattcagc aacaccgtca ggaacacggc tcacttttac cttcacgccg   79980
tcggtgacgg actgaacctc cacgctgacc ggattgccac ttccgtcaac caggcttatc   80040
agcgcggtac cggaggatgg cagcgtgatt tcacggtcga gcgtcagcgt ccgggtctgg   80100
ctgttcaccg ccagcacacg accaccggtg ctgatccggg catagtcatc atcgcagatt   80160
tcaataacat cgcccggtac atggcgaagc ccttctgcgc cgacgctgaa atccaccggtc   80220
tgcgtttcca gcagttctgt tttaatcagc cacagcccgg cgcggtgtgc ctgccccgg   80280
ctggtacagc caaaggcatc catcttcgta acattacgac cgtaacgggc aatgcctgc   80340
gtatcttcaa caagctctgt cgccgtctcc cagccgttgt tcgggtcaat ccagttcacc   80400
tcaacggcat tatgcggtc cttcagggcg ctgaagctgt agcggaacgg cgcgccatca   80460
tccggcatca ccacattact gcggttatag gtccacgtct tatccgacgg tcggtcctgc   80520
acgaacgtca gcgtctgccc gttccatacc ggcatacagc gcatcgccga gcagaaatcg   80580
ctgagcacat cccacgcctt acgctgtgtg gtcaggtacg cattacaggt gatgcgcggc   80640
tccgtgccgc caaagccgtc ggcactgac tggtcgcagt actggccgat gacatacagc   80700
gcccattat ccacatccgc cgcaccaaga cgtttcccca tgccgtagcg cggatgggtc   80760
agcatatccc acagacacca ggccatgttg ttgctgtatg ccggtttaaa cgttccgtcc   80820
cagataccgc tgtattgccg cgtctgcggg ttatagttcg acggcacctg cagaatacgc   80880
ccgcgcagat gataattacg gctcacctgc tggctgccga actgctccga gtccacctgc   80940
agccgaccca gtgccgtgtt cgggtagcac tgtttcacat cgatgatttc agtgtatgac   81000
gaccagagcg ttttgttctg cagctggtct gtggtgctgt ccggcgtcat cctgcgcatc   81060
cggatattaa acgggcgcgg cggcaggtta cccatcacca ccgaggccag atactgcgag   81120
gtggttttgc ccttaatggt gatgtctttt tccgtcaccc agccaccgtt acgttgtatc   81180
tgaaccagca ggcggacttc cgacggattc ctgtcaccct ttgaggtggt ttccaccagt   81240
gcctgtacac cgaaggtaaa gcgcagacgg tcgatgtttg acgtagtaat ggtgcgggtg   81300
atcggcgtgt catatttcac ttccgtaccc agcaccgtct cggagccgga ggattcaaat   81360
ccctccggcg gagtctgctc ctgctcacca gcccggaaca ccaccgtgac accggatatg   81420
ttggtattcc cctcagtgtc cagcaccggc gtactgttca gcagcacgct ttttaagcca   81480
tccaccggac cttcaatcgg cccttcgctg atggcatcga tcacactcag caactgcgtg   81540
gacttcaggt tgtccttcgc ttcgcgcggg gtatgcccct tactgcttcc tttacccatt   81600
```

```
cctcacgctc cataaatgac aaaaccgccc gcaggcggtt tcacataaaa cattttgcat  81660
cagcgaccaa tcaccacaac ctgaccaccg tccccttcgt ctgccgtgct gatctcctga  81720
gaaaccacgc gtgacccac gcgcatttcc ccgtacagaa caggcagaac attgccctgg  81780
gcaaccatgt tatccagtga ggagaaatag gtgttctgct taccgttatc cgttgtctgt  81840
atacggggag ttctggcttt cggtgccagc atctgcgcca caccaccgag caccatactg  81900
gcaccgagag aaaacaggat gccggtcata ccaccggccc caatggctgc cccccatgct  81960
gcaagggtgg ctccggcggt aaagaatgat ccggcaatgg cggcagcccc caggacaatc  82020
tggaatacgc cacctgactt ggccccggcg actctgggaa caatatgaat tacagcgcca  82080
tcaggcagag tctcatgtaa ctgcgccgtt aacccggacg tgctgacgtc ccgcccggca  82140
atccgtacct gataccagcc gtcgctcagt ttctgacgaa acgccgggag ctgtgtggcc  82200
agtgcccgga tggcttcagc ccccgttttc acacgaaggt cgatgcgcg accaaatcgt  82260
tgtaaatccc cgtaaaggca gatgcgcgcc atgcccggtg acgccagagg gagtgtgtgc  82320
gtcgctgcca tttgtcggtg tacctctctc gtttgctcag ttgttcagga atatggtgca  82380
gcagctcgcc gtcgccgcag taaattgcgg cgtgattcgg cactgatgaa ccaaaacagc  82440
acagcagcac atcgcccggc tgtgccgctg acaacggcac ctgatacagc ccgtcgcct  82500
ccagattatc cagatagaga ttctggccgt tacgccacca gtcatcctca cgatgaaagt  82560
ccggcatctc aatccccgcc agatgataag catcccggaa cagtgtgtaa cagtccgtca  82620
caccgtgctc aaagcgccgc ccggtgagat gcggcacaca gcggaactta tgaatcgtcc  82680
cccggcagac cagccaccac ggcaaatcac tctgcacctg cagccgccgg tcggcctcac  82740
tcagccaggg cagaccaccg gggtggctgt ggaccagcgc cacaatctca ccctgcattt  82800
ctgcctgcag ccagtcttcc ggcgacatac ggaaatagcc tccggctcac cggagatatt  82860
cacgcagggg aaatatcttt cccctccgg cgtgcttacc acgaagccgc acgactccgc  82920
tggcgcacat cgccgggcgt gcgccagaat cgctgattct gtctgtgtca tgggatttac  82980
tgcgaaagtt tgttaatgga aaggaagccg ccaaagttgc cgacgttatt gcggaactta  83040
caaccgctca ggcatttgct gcatttatcc ttcgtgatat cggacgttgg ctggtcatat  83100
tcatccgcga cagccggacc gctataaccg cactcgtcac cgcgataggt ccaggtgcag  83160
gtgttggcca gcatgatacg tcccggaaaa acagcgccat ccgtttccgt cggcgtggac  83220
agtacaaagg aggcactcac cgcgctcagt tcgctgcact gctcaatgcg ccagcggctg  83280
atcacctcct gctccggatc ggcgtaactg tttccgttga cgaagttcac cgcatccaga  83340
aaacggggcgt aaaccttacg ccggaccacc gttccgccga ccagactctg catatcttcc  83400
gccatcccgg tgaccatacc gtacaggtta gaaaccgtca gcgtggggcg cgtactggtg  83460
cctttgccat tcagttcaaa accgctcccc tgaatgggat acggctgata ctgtcgcccc  83520
tgccaggtga ccggctcacc tttttcgttc tgctcattac agaaaaaata acgttctcca  83580
ccgacctctg tcaggtcgat ttcccagagc accacgctgg ccgactgctc cgcacgggtg  83640
cattcattca gtgtttcctg ccggatatcc tgcatcagtt caccacctgt tcaaactctg  83700
cgctgaactc aacacgcagc atactgaccc gcgacgacca ttttgcgcag gtcacccttta  83760
tctgccgcca ctcataaggc ggcgtccaca gaaaggattt ccagccccg tgctcttcca  83820
gaaacgactc cagtaccgtg gcctcctcac ggggggacaga aagcgtcacg ctgtacgttt  83880
tcaggttggc attcagcccg gcaggcgctc gctgagaata gccatcacca aagcgcacct  83940
ttcttacaga agggaccgaa gccacatcca taccgggttt cactttccag cggaaggtct  84000
tcatcgtcca cctccggaga acaggccacc atcacgcatc tgtgtctgaa tttcatcacg  84060
ggcacccttg cgggccatgt catacaccgc cttcagagca gccggaccta tctgcccgtt  84120
cgtgccgtcg ttgttaatca ccacatggtt attctgctca aacgtcccgg acgcctgcga  84180
ccggctgtct gccatgctgc ccggtgtacc gacataaccg ccggtggcat agccgcgcat  84240
cagccggtaa agattcccca cgccaatccg gctggttgcc tccttcgtga agacaaactc  84300
accacgtga acaatcccg ctggctcata tttgccgccg gttcccgtaa atcctccggt  84360
tgcaaaatgg aatttcgccg cagcggcctg aatggctgta ccgcctgacg cggatgcgcc  84420
gccaccaaca gccccgccaa tggcgctgcc gatactcccg acaatcccca ccattgcctg  84480
cttaagcaga attttctgtca tcatggacag cacggaacgg gtgaagctgc gccagttctg  84540
ctcactgccg gtcagcatcg ccgccatatt ctgtgcaata ccatcaaagg tctgcgtggc  84600
tgcactttttt acctgcgaca tactgtccgt ggcgctctct tcccactcac tccagccgga  84660
cttcaggcct gccatccagt tcccgcgaag ctggtcttca gccgcccagg tcttttttctg  84720
ctctgacatg acgttattca gcgccagcgg attatcgcca tactgttcct tcaggcgctg  84780
ttccgtggct tcccgttctg cctgccggtc agtcagcccc cggcttttcg catcaatggc  84840
ggcccgtttt gcccgttgct gctgtgcgaa tttatccgcc tgctgcgcca gcgcgttcag  84900
gcgctcctga tacgtaacct tgtcgccaag tgcagccagc tggcgtttgt actccagcgt  84960
ctcatcttta tgcgccagca gggatttctc ctgtgcagac agctggcgac gttgcgccgc  85020
ctcctccagt accgcgaact gactctccgc cttccacaaa tcccgcgct gctggctgat  85080
tttctcattt gctccgtgcat gcttctccag cgtccggagt tctgcctgaa gcgtcagcag  85140
ggcagcatga gcactgtctt cctgacgatc gcccgcagac accttcacgc tggactgttt  85200
cggcttttttc agcgtcgctt cataatcctt tttcgccgcc gccatcagcg tgttgtaatc  85260
cgcctgcagg attttcccgt ctttcagtgc cttgttcagt tcttcctgac gggcggtata  85320
tttctccagc ggcgtctgca gccgttcgta agccttctgc gcctcttcgg tatatttcag  85380
ccgtgacgct tcggtatcgc tctgctgctg cgcattttttg tcctgttgga tctgctgcca  85440
agccttcttt cgggcggctt caagcgcaag acgggccttt tcacgatcat cccagtaacg  85500
cgcccgcgct tcatcgttaa caaaataatc atccttgcgc agattccaga tgtcgtctgc  85560
tttcttatac gcagcctctg ccttaatcag catctcctgc gcggtatcag gacgaccaat  85620
atccagcacc gcatcccaca tggatttgaa tgcccgcgca gtcctgtctg cccaggtctc  85680
cagcgtgccc atgttctctt tcaggcggcg ggtctggtca tcaaacccttt tcgttggtga  85740
ctcgttcgcc gcctgcaatg ccccggcttc atcgccggaa cgctgcaact gagcaacata  85800
cgcaatctgc tccgccgaca cgttatgaa ctggcgagcc atgccgtca gccccgacgt  85860
cgggtctgtg gtcagcttcc cgaaggcttc agcgaccttg tccacctcca cgccggatgc  85920
agaggagaaa cgcgccacac tctggctgat ggacgcaatc tgagcctcac cgcttacccc  85980
cgccttaacc agtgcgctga gtgactcgct ggtctggtta aacgtcagcc ctgccgcctg  86040
cccggctctg gacaggacca gcatacgatc tgccgtcagt cccgcctgat tgccggaaag  86100
gaccagcgtt ttgttgaaat cggacagggt tgagttgccc tgataccagg catacgccag  86160
cgcaccggtc gccaccgcca gcgaggtggc cccaccatc ggcagggtga tcgcaccggc  86220
aagccccctg aacatgggga tcatcccgcc gaaggagtcc ttcacctgcc ccccctgttg  86280
cagcaggatc agccacggac tttgcccgcc tgcaagctgc gtgccacgt cggtgaactg  86340
```

```
tgcaggcagc atacgcatgg cggctttata ctgcccgacg gaaatcccg ctttctgtgc  86400
agccagcgcc tgtcggctca gcgactgttc aacgactgcc gctgttttt tcgcatcact  86460
ttccgtacca gaaaaatgac gcctgactct ggccatctgc tcgtcaaatc tggccgcatc  86520
cagactcaaa tcaacgacca gatcgcctac cggttcagcc ataccggact cctcctgcga  86580
tcccttctga tactgtcatc agcattacgt catcctccgt catgtccgca acatccgggg  86640
aagcggggat aacttcattc ccgtccgggc caaagcggaa acctccggca agccctgccg  86700
ctttctgcat cagcacatca tcttcaggct cttcgtcagc ctcgcgccgg ttcagcagac  86760
tgaaatccag cggatgcata tccggatcgc tgaaaaacag gctgagcacg gtgtacgtca  86820
gcccggaaaa gtgcatatcc agcagaacat catgaaaata atgggtactg taaaagcggt  86880
gccagtcggc atactccgtg gatgacatcc cggcaagcat ggcacgccag tcgggtcgcc  86940
ccatctcacg cgccagtttc agggcaaaac tcagctcacc gtcgaacact ttcccgcaga  87000
aacaggctct gcgggcccgg cgtcctctgt ctgttcaggg gcattattca ccacaaactc  87060
atacatacca gacagccggt acaccacgtt ttcagcatga gaaattgcct ccgtgggcca  87120
ggtggtaagc acttcctgct caatctgttt aacggcttca ttcatgacg gcatctgcgt  87180
cttctgcgga tggttatgcc acagggacat cgccaccaga aacgcgccgg ttctgatggc  87240
gtcttccaca gtaaacttcc ggttgctgtc tgactccgcc tgttctgcct gccgtttcat  87300
cagggcgaga tgctcaatgc gctgcagggc tgacagttca gaaagcgtga cggtcacacc  87360
gttatgttca aatgattcgg ttttcaggaa catcgctgac tctccggatt aactggcggt  87420
gacggtaatt tctgcaaccg cagcaaactc accattaccg gatacaaccg gaatgttgac  87480
cttgcctgca gcaacgccgt tcacggtgat ggtcatacca ctgaccgaca cggtggcttt  87540
tgttttatcc gcagacaccg cacgaaagct cttgtcggtt acgccctccg gctggaaggc  87600
cacggtcagc gtggtgctct gcccttcac caccgaggtg ctggcaggcg tcacggtcat  87660
gccggttgcc gctgttaccg tgctgcgatc ttctgccatc gacggacgtc ccacattggt  87720
gactttcacc gtgcgggtga tcacttcctt cgccgtcacc gccttaccga tactgctgac  87780
ccagccacgg aacacatcga ccgtgccgtt cgggaagcgg attttatagg cacgggtatc  87840
gccttcatta aaccacgcca gcagcgcctg ctgcccctgc tctccgggca tccacgccag  87900
cgtgaagctg gtatctccgg cagatttctg cccctgccg gtcgcagtcc agtctgcatc  87960
ttcatcatcg agatagctgt cgtcatagga ctcagcggtc agttcgccgg cgtcaggtc  88020
tttaactttt gccagacgcg accagtcaac gtctgaaagc ggattcgcgt aagggtcacc  88080
gctccccta taacccaca gggtggtccc ggcacctttc accggcattg taggatttgg  88140
tacaggcata gcgtcctcac atttcatagg taatgacata agtcagatcg gctgaactcc  88200
acaagcccgc atcatcgtcg cgccggtagt catagccgct ggccaccata ctggtgatca  88260
aatctgacag tgccgggata tcgctcatca ccggataaat ccgggactcc atccacgcat  88320
ccagctctga atccggcacc tgagcaggca ggaaaacttc gatatgcagc tccgactccg  88380
aggtatcgct gtccagctct tcgcccgtgt attcagcgcc ggtgagataa acggcaactg  88440
ccggaaaatc cgcctcatca aaaacagcgg ggcgaccatc aaaaaacgtc gccccggtgt  88500
catgcttctc cagtgcatcc agtacggctg cacggagttc agtatgtttc atcgctttat  88560
taccatcctc agttgatgct gcagcgcata gcccagctct ttcggaagac gttcacgccg  88620
tatccgctca atattttgtt taaaccgcgt ggtcagcggc accgccatcg ggattttcac  88680
cacatcaatg gggtaacggt ttttcccagc cacacgctgc atgacatgcc accggccatt  88740
tttcagttgc tgaataaacg cgccgggaat acgacggtta cccaccacaa gcacgctgcc  88800
gccacctttc agggatgaac gctgcccctt tttacgacg ctgcggcgcg aaaggacaac  88860
ccgcgcatta cccagcttga ttacgggcaa atccccccgg ttaactttga ttctggcctg  88920
cggattttg accgtggccc ttttcagcct ggccctttcc tttaccagtt tccggcgtac  88980
ctttgtctca cgggcaacct gtgacgccga ctgcgatatc gcggatgaag caacgcggtt  89040
aatgccatt gcggcggcac caggcaccgc cgttttgctg atacggctga ggttttcaac  89100
ggcctgctca agaccttta tggccataca tccccctttc agcgggcacg gttaacggca  89160
ggcggtacgc cccgtccaag ccagagatga caacttccgc catcatccgg cgaaacccga  89220
tctacccaga aattttcctc accgatggtc agcgtgtctc cacgccgcag ctgccgcacc  89280
tcatcagtcc ggacaaacag ggacgggctg gagccttcaa cgcgcacgcc ctgtccggca  89340
tagctgatat tttcagggtc atcaaaaaca ccacgtatca ccgcacctga ctgctcaccg  89400
gatgtaatgg tggctgacgt tccatgtac ccgcgtatcg tttcatcggc gcgggcaatg  89460
gcagcatcga acaggttatc gaaatcagcc acagcgcctc ccgttattgc attctggcca  89520
ggccgcgctc tgtcatttcg gctgccacac cggcagagac acgaaacgcc gttcccggca  89580
gcacaaatgc cacaggttca tcccgcgtgg cgtgaagtgc atcagtatgc agcttcacca  89640
gtgccacgac cgtgaccagt tcagacgtat ccagaatcac ggtatccggc tgcgctgatc  89700
ccacctcatt ttcatgtccg gtcagcacat ttttcccggct gagaggggtg tcctgaccgg  89760
cagtttcatc cgtgtcatca agctcctctt tcagctctgc cacacggagc gccagttctt  89820
ctttcgtccc cgtcaggctg acatcacggt tcagttgttc accagcgag cggagacggg  89880
caatcagttc atctttcgtc atggactcct ccacagaaa acaatggccc cgaagggcca  89940
tgattacgcc agttgtacgg acacgaactc atcagggtca gccagcagca tcagcggtgc  90000
tgactgaatc atggtgaact cacgcgccgg atcgccggtg tcacccagt ttttcgggta  90060
acgggcagag gcgttaatgc cttcgcgctg tgcgtccgca tcctgaatgc agccataggt  90120
gcgcagaccg cgtgcctgag tgttcccag caccatcgtg ttgtccggca ggaagttctt  90180
tttgacgccg ttttccacgt actgtccgga atacacgacg atggccacat cgccatacat  90240
cccctttatag gacaccgctt tgcccaggtc tttcaccgct gtctccagct cggaattaga  90300
gccacgacgg gtatccagct tctccttgac ggctttgaag gaacgaaaca gcgcccagcc  90360
tttcggatcg aacacgatga tattcaccac accgctggcg ttcagcgcgt aggcttcgat  90420
atcgtcggtc gggtcatacg tggacttgtc acgcttcgtc cactccgtgc cgccggactg  90480
cgtgatgtta ttctcctcac tgcggcccat atccacctca accggatcga aggcttcacc  90540
ggtcatggtg tatttgccct taagcacggc agaaactgcc tgcatctctt cgacctgagc  90600
aatgccagc tcttcgtcac gcatgttctg catgatgatg cgacggcggc ggtaagccgg  90660
gtccgccaga ttctgcggat cttcatccgg caggcgacgc agggtcatct gcggattcac  90720
ttcatgcttg gccttgacat atcccgcgt aaattcagag ggtggacgcc cacgggaacg  90780
gataaccctca ccggaaacaa tcggcgaaac gtacagcgcc atgttaccca gtcccggaat  90840
ttgtgagaga tagactttct ccgtggtgaa gggatagctc tcacgaaaaa agagacgcag  90900
aaacagcgga tcaaacttaa attctgctc atttgccgcc agcagttggg cggttgtata  90960
catcgacata aaaaaatccc gtaaaaaaag ccgcacaggc ggcctttagt gatgaagggt  91020
aaagttaaac gatgctgatt gccgttccgg caaacgcggt ccgttttttc gtctcgtcgc  91080
```

```
tggcagcctc cggccagagc acatcctcat aacggaacgt gccggacttg tagaacgtca   91140
gcgtggtgct ggtctggtca gcagcaaccg caagaatgcc aacggcagca ccgtcggtgg   91200
tgccatccca cgcaaccagc ttacggctgg aggtgtccag catcagcggg gtcattgcag   91260
gcgctttcgc actcaatccg ccgggcgcgg ttgcggtatg agccgggtca ctgttgccct   91320
gcggctggta atgggtaaag gttcttttgc tcgtcataaa catcccttac actggtgtgt   91380
tcagcaaatc gttaacggca tcagatgccg ggttacctgc agccagcggt gccggtgccc   91440
cctgcatcag acgatccagc gcagtgtcac tgccgcgctg tgcactctgt ggtgctgcgg   91500
ccagaatgcg gcgggccgtt ttcacggtca taccgggggt ttctgccagc acgcgtgcct   91560
gttcttcgcg tccgtgagcc tcctcacagt tgaggatccc cataatgcgg ctgttttctg   91620
ccgcaaccgc tgcggtgatc tgcgcgttca cgtccggctg cgccgcgctg gcgttctcgc   91680
cctccgtcgc tggcaccacg tcagtaacgt cagcctgcga agcagtggct gaaacagttg   91740
ttgattgagt ctctttggtc attcgccctc ctgagagacg ggatttacgt gcatccagtg   91800
catcacgcat gacggtgatc gcatcggtgc tgttaacaag ttcatcagcc agtccggcat   91860
caatgcctc ctgaccgctg tacactgcag cctcggtatc cagcacaacc tgcacggaca   91920
ggccggtata tgccgacacc ttctgcgcaa acatctggcg ggttgcgtcc atccgggact   91980
gcagtgtctc ccggacgtca tccggaagat ggctgtaggg gttgccatcc acctttatggc   92040
tgccgctgta aatcagcgtg atttccacac cctgtttctc cagcgcagca ccgtaattac   92100
tgtgagccat catgacgccg atggaacctg tccgggcggt ctgcgtgacc agacgccggg   92160
aggcggcact ggcaagcaac tgacctgcac tgcagttcat gtcgttggca agcgcccata   92220
ccggttttat gtcacgcaca cgggcgatga tgtcagcgca gtcaaatgcc cccgccacca   92280
tcccgccggg cgtgtccata tcgagcagaa tgccgtccac catcggatcg ctggcagcct   92340
gttgcagacg ggcgataatg ccgttgtaac cggtcatccc cgagtacggc tgcagccgcc   92400
gcgtccggct gaccagcgtg ccggacaccg gcagcacgcc gatgccgttc atgacctgat   92460
aactgcgggc ctgtcgtggt ccgtcatcat caccggataa tgccagcgtc gcgagtgcct   92520
cctgggcagt caggctgtcg ccggacaccg catccgtcag gctgctgatc caagctggc   92580
ctgcaagcgc acaaaagaaa acccgcgcaat aggcgggttc aagcatcagc ggctcattaa   92640
aggccatgct ggcaatatgc gggagattac gcagctctgc tgtcactctt ctcctcctct   92700
gttgattgtc gcagcccgga ttcaaatgct gcagccgccc aggcgggcgg tttaagaccg   92760
gctgcacggc gctccatcgt ttcacggacc tgctgggcaa aaatttcctg atagtcgtca   92820
ccgcgttttg cgcactcttt ctcgtaggta ctcagtccgg cttctatcag catcaccgct   92880
tcctgaactt ctttcagacc atcgatggcc atacgaccgg agcctatcca gtcgcagttc   92940
ccccaggcac tgcgggcttc ctgaaaactg aagcgcgctt ttgaaggtaa cgtcaccacg   93000
cggcgaacga tggcctcttc cagccagcac agaaacatct ggctcgcctg acgggatgcg   93060
acgaatttc gccgcccat aaagtacgcc cacgactcgt tcgcactggc ccgtgccgtg   93120
gagtagctca tctgggcgta attccggaa agctgctcat acgagacacc cagcccggca   93180
gcgatatacc gcagcagtga ctgctcaaac acggagtagc cgttatccgt atcctgagcc   93240
gtctgcaggt tcagtgagtc acccggcatc aggtgcggta cttttgcgcc tcccagccgg   93300
accggcgctg cggcgtaata cgcggcaatt tcaccaatcc agccggtcag cctttcccgc   93360
tgctcctgac tgttcgcgcc cagaataaaa tccatcgctg actgcgtatc cagctcactc   93420
tcaatggtgg cggcatacat cgccttcaca atgcgctct gcagctgcgt gttctgcagc   93480
gtgtcgagca tcttcatctg ctccatcacg ctgtaaaaca catttgcacc gcgagtctgc   93540
ccgtcctcca cgggttcaaa aacgtgaatg aacgaggcgc gcccgccggg taactcacgg   93600
ggtatccatg tccatttctg cggcatccag ccaggataac cgtcctcgct gacgtaatat   93660
cccagcgccg caccgctgtc attaatctgc acaccggcac ggcagttccg gctgtcgccg   93720
gtattgttcg ggttgctgat gcgcttcggg ctgaccatcc ggaactgtgt ccggaaaagc   93780
cgcgacgaac tggtatccca ggtggcctga cgaacagtt caccgttaaa ggcgtgcatg   93840
gccacacctt cccgaatcat catggtaaac gtgcgtttc gctcaacgtc aatgcagcag   93900
cagtcatcct cggcaaactc tttccatgcc gcttcaacct cgcgggaaaa ggcacgggct   93960
tcttcctccc cgatgcccag atagcgccag cttgggcgat gactgagccg gaaaaaagac   94020
ccgacgatat gatcctgatg cagctggatg gcgttggcgg catagccgtt attgcgtacc   94080
agatcgtctg cgcgggcatt gccacgggta aagttgggca acagggctgc atccacactt   94140
tcactcggtg ggttccacga ccgcaactgc cctccaaatc cgctgccacc gccgtgataa   94200
ccggcatatt cgcgcagcga tgtcatgccg tccggcccca gaagggtggg aatggtgggc   94260
gtttcatac ataaaatcct gcaggtcccc tgcgtcgctg tgtcatgccg gtctgcactt   94320
ccagctctgc aatatatttt ttcaggtcag acacggaagt ggcgtaaac tccacccttc   94380
gtccgtctt ctgtactgtt gccaccgtt tacctgtcat caggtcatgc agtgccgcac   94440
gggcagcggc aagttcttcc tgtcgcgtca ttcatcctct ccggataagg cacgggcgta   94500
atctgccagt gttttcttgt tggttgctgc accatcctct tcctgcaggc tgccagcag   94560
cgcactgaga tccagctgcc agcgggaaat actgatgcgc agcgccgcca gcgcataaac   94620
gaagcagtcg agtgcctcat tgcgtcgctt tttgctgtcc cacagtattt ttttcctgcc   94680
atccacccat ttttcgacct gctcttcagc agtcagctgc tgcgcttcgg tcagatcaaa   94740
aatatccggg ttattcggga agtgaacggc accgggaagc ggttcatccc cttccggcgt   94800
cagtgtgaag cggttataaa tctgctcttt cgcggtatcc gtaccgattt cggtaaggta   94860
aaccccgttt ttgtttcgct tacgtggcat gctggccacc gctggcatg agacggatgc   94920
cccttaatg gggatcaccc ggaacagccc atgttttttc gagcgttcat acacaatgcc   94980
cgggtcaatc ccgccagtat cccagcagat acggatatc gacattctg caccattccg   95040
gcgggtatag gttttattga tggcctcatc cacacgcagc agcgtctgtt catcgtcgtg   95100
gcggcccata ataatctgcc ggtcaatcag ccagcttcc tcaccggcc cccatcccca   95160
tacgcgcatt tcgtagcggt ccagtcggga gtcgataccg gcggtcaggt aagcacacg   95220
gtcaggaacg ggcgctgaat aatgctcttt ccgctctgcc atcacttcag catccggacg   95280
ttcgccaatt ttcgcctccc acgtctcacc gagcgtggtg tttacgaagg ttttacgttt   95340
tcccgtatcc cctttcgttt tcatccagtc tttgacaatc tgcacccagg tggtgaacgg   95400
gctgtacgct gtccagatgt gaaaggtcac actgtcaggt ggctcaatct cttcaccgga   95460
tgacgaaaac cagagaatgc catcacgggt ccagatccgg tcttttcgc agatataagg   95520
ggcatcagta aagtccagct cctgctggcg gatgacgcag gcattatgct cgcagagata   95580
aaacacgctg gagggtcat ccggcgtcca tttgaggcca aacggcgtct ctttgtcgcc   95640
aaatttaaga tactgctcct ccccgcaatg cgggcaggca acatgaaaac gcataaaatg   95700
cggggattca ctggctgcac gctcaatctg acaggtgcct ctcactttg gcgtggagcc   95760
acggatggac tttggccaga ccgagccttc aatacgcttg tcacccagga acgtcggaga   95820
```

-continued

```
gccttcctgt tcaatatcat catcaaaagc agcaagttca tcataacccg ccacatccac    95880
cgactttca  cggtagtttt ttgccgcttt accgccagg  caccagaagc cacgcccatt    95940
agtgaaacgc ttcatggtga gcgtgttatc ccggtgcttt ttgccatacc acggggccag    96000
cgccagcagc gacggaatat cacgaatagt cggctcaacg tgggttttca taagttctc     96060
ggcatcacca tccgtcggca accagataag ggtgttgcgc tgcttatgct ctataaagta    96120
ggcataaaca cccagcagca ttttggaata accgacacgg gcagacttca ccacattcac    96180
ctcacggatg tagtcgctgc ccatcgcatt catgatggcc cgctgaaagg gcagtgtttc    96240
ccagcgccct tcctggtatg cggattcttt cgggagatag taattagcat ccgcccattc    96300
aacggcggtc tgtggctccg gcctgaacag tgagcgaagc ccggcgcgca caaaatgccg    96360
cagcctgtta acctgactgt tcgatatatt cactcagcaa ccccggtatc agttcatcca    96420
gcgcggctgc tttgttcatg gctttgatga tatcccgttt caggaaatca acatgtcggt    96480
tttccagttc cggaaaacgc cgctgcaccg acaggggag  cccgtcgaga atactggcaa    96540
tttcacctgc gatccgcgac agcacgcaaag tacagaatgc ggtttccacc acttcagcgg    96600
agtctctggc attcttcagt tcctgtgcgt cggcctggcc acgcgtaagt cgatggccgtt   96660
cgtactcaat agttcctggc tggagatctg cctcgctggc ctgccagt   tcttcaacct    96720
cccggcgcag ctttcgttc  tcaatttcag catccctttc ggcataccat tttatgacgg    96780
cggcagagtc ataaagcacc tcattaccct tgccaccgcc tcgcagaacg ggcattccct    96840
gttcctgcca gttctgaatg gtacggatac tcgcaccgaa aatgtcagcc agctgctttt    96900
tgttgacttc cattgttcat tccacggaca aaaacagaga aaggaaacga cagaggccaa    96960
aaagcctcgc tttcagcacc tgtcgtttcc ttctttca    gagggtattt taataaaaa    97020
cattaagtta tgacgaagaa gaacgaaac  gccttaaacc ggaaaatttt cataaatagc    97080
gaaaacccgc gaggtcgccg cccaggtcgc cgccgtcaa  tcggccctttt agtggagc     97138
```

```
SEQ ID NO: 63              moltype = DNA   length = 28
FEATURE                    Location/Qualifiers
misc_feature               1..28
                           note = Synthetic Polynucleotide
source                     1..28
                           mol_type = other DNA
                           organism = synthetic construct
SEQUENCE: 63
gcaatatcag caccaacaga aacaacct                                        28

SEQ ID NO: 64              moltype = DNA   length = 44
FEATURE                    Location/Qualifiers
misc_feature               1..44
                           note = Synthetic Polynucleotide
misc_feature               37
                           note = Carboxyfluorescein (FAM) attached to T
source                     1..44
                           mol_type = other DNA
                           organism = synthetic construct
SEQUENCE: 64
tttttttttt tttttttttt tttttttttt tttttttt tttt                        44

SEQ ID NO: 65              moltype = DNA   length = 75
FEATURE                    Location/Qualifiers
misc_feature               1..75
                           note = Synthetic Polynucleotide
misc_feature               1..75
                           note = Carboxyfluorescein (FAM) attached to one T in
                            sequence
source                     1..75
                           mol_type = other DNA
                           organism = synthetic construct
SEQUENCE: 65
tttttttttt tttttttttt tttttttttt tttttttttt tttttttttt tttttttttt    60
tttttttttt ttttt                                                     75

SEQ ID NO: 66              moltype = AA   length = 970
FEATURE                    Location/Qualifiers
source                     1..970
                           mol_type = protein
                           organism = Clostridium botulinum
SEQUENCE: 66
MLSVANVRSP SAAASYFASD NYYASADADR SGQWIGDGAK RLGLEGKVEA RAFDALLRGE     60
LPDGSSVGNP GQAHRPGTDL TFSVPKSWSL LALVGKDERI IAAYREAVVE ALHWAEKNAA    120
ETRVVEKGMV VTQATGNLAI GLFQHDTNRN QEPNLHFHAV IANVTQGKDG KWRTLKNDRL    180
WQLNTTLNSI AMARFRVAVE KLGYEPGPVL KHGNFEARGI SREQVMAFST RRKEVLEARR    240
GPGLDAGRIA ALDTRASKEG IEDRATLSKQ WSEAAQSIGL DLKPLVDRAR TKALGQMEA     300
TRIGSLVERG RAWLSRFAAH VRGDPADPLV PPSVLKQDRQ TIAAAQAVAS AVRHLSQREA    360
AFERTALYKA ALDFGLPTTI ADVEKRTRAL VRSGDLIAGK GEHKGWLASR DAVVTEQRIL    420
SEVAAGKGDS SPAITPQKAA ASVQAAALTG QGFRLNEGQL AAARLILISK DRTIAVQGIA    480
GAGKSSVLKP VAEVLRDEGH PVIGLAIQNT LVQMLERDTG IGSQTLARFL GGWNKLLDDP    540
GNVALRAEAQ ASLKDHVLVL DEASMVSNED KEKLVRLANL AGVHRLVLIG DRKQLGAVDA    600
GKPFALLQRA GIARAEMATN LRARDPVVRE AQAAAQAGDV RKALRHLKSH TVEARGDGAQ    660
VAAETWLALD KETRARTSIY ASGRAIRSAV NAAVQQGLLA SREIGPAKMK LEVLDRVNTT    720
REELRHLPAY RAGRVLEVSR KQQALGLFIG EYRVIGQDRK GKLVEVEDKR GKRFRFDPAR    780
IRAGKGDDNL TLLEPRKLEI HEGDRIRWTR NDHRRGLFNA DQARVVEIAN GKVTFETSKG    840
```

```
DLVELKKDDP MLKRIDLAYA LNVHMAQGLT SDRGIAVMDS RERNLSNQKT FLVTVTRLRD    900
HLTLVVDSAD KLGAAVARNK GEKASAIEVT GSVKPTATKG SGVDQPKSVE ANKAEKELTR    960
SKSKTLDFGI                                                           970

SEQ ID NO: 67           moltype = DNA   length = 46
FEATURE                 Location/Qualifiers
misc_feature            1..46
                        note = Synthetic Polynucleotide
source                  1..46
                        mol_type = other DNA
                        organism = synthetic construct
SEQUENCE: 67
tttttttttt tttttttttt tttttttttt tttttttttt tttttt                   46

SEQ ID NO: 68           moltype = DNA   length = 1292
FEATURE                 Location/Qualifiers
misc_feature            1..1292
                        note = Synthetic Polynucleotide
source                  1..1292
                        mol_type = other DNA
                        organism = synthetic construct
SEQUENCE: 68
gccatcagat tgtgtttgtt agtcgctttt tttttttgga attttttttt tggaattttt    60
ttttgacgc tcagtaatgt gacgatagct gaaaactgta cgataaacgg tacgctgagg    120
gcggaaaaaa tcgtcgggga cattgtaaag gcggcgagcg cggcttttcc cgccagcgt    180
gaaagcagtg tggactggcc gtcaggtacc cgtactgtca ccgtgaccga tgaccatcct    240
tttgatcgcc agatagtggt gcttccgctg acgtttcgcg gaagtaagcg tactgtcagc    300
ggcaggacaa cgtattcgat gtgttatctg aaagtactga tgaacggtgc ggtgatttat    360
gatgcgcgg cgaacgaggc ggtacaggtg ttctcccgta ttgttgacat gccagcgggt    420
cggggaaacg tgatcctgac gttcacgctt acgtccacac ggcattcggc agatattccg    480
ccgtatacgt ttgccagcga tgtgcaggtt atggtgatta agaaacaggc gctgggcatc    540
agcgtggtct gagtgtgttt tttttttgga attttttttt tggaattttt ttttcatcg    600
tcgtgagtag tgaaccgtaa gctgcgttct gtttcggatg tatgaaaaca tacatccgaa    660
acagaacgca gcttacggtt cactactcac gacgatgaaa aaaaaaattc caaaaaaaaa    720
attccaaaaa aaaaacacac tcagaccacg ctgatgccca cgcctgtttt cttaatcacc    780
ataacctgca catcgctggc aaacgtatac ggcggaatat ctgccgaatg ccgtgtggac    840
gtaagcgtga acgtcaggat cacgtttccc cgacccgctg gcatgtcaac aatacgggag    900
aacacctgta ccgcctcgtt cgccgcgcca tcataaatca ccgaccgtt catccagtact    960
ttcagataac acatcgaata cgtttgtcctg ccgctgacga tacgcttact tccgcgaaac   1020
gtcagcggaa gcaccactat ctggcgatca aaaggatggt catcggtcac ggtgacagta   1080
cgggtacctg acgccagtc cactactgctt tcacgctggc gcggaaaagc cgcgctcgcc   1140
gcctttacaa tgtccccgac gatttttttcc gccctcagcg taccgtttat cgtacagttt   1200
tcagctatcg tcacattact gagcgtcaaa aaaaaaattc caaaaaaaaa attccaaaaa   1260
aaaaaagcga ctaacaaaca caatctgatg gc                                 1292

SEQ ID NO: 69           moltype = DNA   length = 7240
FEATURE                 Location/Qualifiers
misc_feature            1..7240
                        note = Synthetic Polynucleotide
source                  1..7240
                        mol_type = other DNA
                        organism = synthetic construct
SEQUENCE: 69
gccatcagat tgtgtttgtt agtcgctgcc atcagattgt gtttgttagt cgcttttttt    60
ttttggaatt ttttttttgg aatttttttt ttgcgctaac aacctcctgc cgttttgccc   120
gtgcatatcg gtcacgaaca aatctgatta ctaaacacag tagcctggat ttgttctatc   180
agtaatcgac cttattccta attaaataga gcaaatcccc ttattggggg taagacatga   240
agatgccaga aaaacatgac ctgttggccg ccattctcgc ggcaaaggaa caaggcatcg   300
gggcaatcct tgcgtttgca atggcatacc ttcgcggcaa atataatggc ggtgcgttta   360
caaaaacagt aatcgacgca acgatgtgcc ccattatcgc ctagttcatt cgtgaccttc   420
tcgacttcgc cggactaagt agcaatctcg cttatataac gagcgtgttt atcggctaca   480
tcggtactga ctcgattggt tgcttatcaa acgcttcgc tgctaaaaaa gccggagtag    540
aagatggtag aaatcaataa tcaacgtaag gcgttcctcg atatgctggc gtggtcgag    600
ggaactgata acgacgtca gaaaaccaga aatcatggct atgacgtcat tgtaggcgga    660
gagctatttta ctgattactc cgatcaccct cgcaaacttg tcacgctaaa cccaaaactc    720
aaatcaacag gcgccggacg ctaccagctt cttttcccgtt ggtgggatgc ctaccgcaag    780
cagcttggcc tgaaagactt ctctccgaaa agtcaggacg ctgtggcatt gcagcagatt    840
aaggagcgtg gcgctttacc tatgattgat cgtggtgata tccgtcaggc aatcgaccgt    900
tgcagcaata tctgggcttc actgccgggc gctggttatg gtcagttcga catataggct    960
gacagcctga ttgcaaaatt caagaagcg ggcggaacgg tcagagagat tgatgtatga   1020
gcagagtcac cgcgattatc tccgctctgg ttatctgcat catcgtctgc ctgtcatggg   1080
ctgttaatca ttaccgtgat aacgccatta cctacaaagc ccagcgcgac aaaaatgcca   1140
gagaactgaa gctggcgaac gcggcaatta ctgacatgca gatgcgtcag cgtgatgttg   1200
ctgcgctcga tgcaaaatac acgaaggagt tagctgatga aatgatgcto   1260
tgcgtgatga tgttgccgct ggtcgtcgtc ggttgcacat caaagcagtc tgtcagtcag   1320
tgcgtgaagc caccaccgcc tccggcgtgg ataatgcagc ctcccccgga ctggcagaca   1380
ccgctgaacg ggattatttc accctcagag agaggctgat cactatgcaa aaacaactgg   1440
aaggaaccca gaagtatatt aatgagcagt gcagatagag ttgcccatat cgatgggcaa   1500
ctcatgcaat tattgtgagc aatacacacg cgcttccagc ggagtataaa tgcctaaagt   1560
```

```
aataaaaccg agcaatccat ttacgaatgt ttgctgggtt tctgttttaa caacattttc 1620
tgcgccgcca caaattttgg ctgcatcgac agttttcttc tgcccaattc cagaaacgaa 1680
gaaatgatgg gtgatggttt cctttggtgc tactgctgcc ggtttgtttt gaacagtaaa 1740
cgtctgttga gcacatcctg taataagcag ggccagcgca gtagcgagta gcattttttt 1800
catggtgtta ttcccgatgc ttttttgaagt tcgcagaatc gtatgtgtag aaaattaaac 1860
aaaccctaaa caatgagttg aaatttcata ttgttaatat ttattaatgt atgtcaggtg 1920
cgatgaatcg tcattgtatt cccggattaa ctatgtccac agccctgacg gggaacttct 1980
ctgcgggagt gtccgggaat aattaaaacg atgcacacag ggtttagcgc gtacacgtat 2040
tgcattatgc caacgccccg gtgctgacac ggaagaaacc ggacgttatg atttagcgtg 2100
gaaagatttg tgtagtgttc tgaatgctct cagtaaatag taatgaatta tcaaaggtat 2160
agtaatatct tttatgttca tggatatttt taacccatcg gaaaactcct gctttagcaa 2220
gattttccct gtattgctga aatgtgattt ctcttgattt caacctatca taggacgttt 2280
ctataagatg cgtgtttctt gagaatttaa catttacaac cttttttaagt ccttttatta 2340
acacggtgtt atcgttttct aacacgatgt gaatattatc tgtggctaga tagtaaatat 2400
aatgtgagac gttgtgacgt tttagttcag aataaaacaa ttcacagtct aaatcttttc 2460
gcacttgatc gaatatttct ttaaaaatgg caacctgagc cattggtaaa accttccatg 2520
tgatacgagg gcgcgtagtt tgcattatcg tttttatcgt ttcaatctgg tctgacctcc 2580
ttgtgttttg ttgatgattt atgtcaaata ttaggaatgt tttcacttaa tagtattggt 2640
tgcgtaacaa agtgcggtcc tgctggcatt ctggagggaa atacaaccga cagatgtatg 2700
taaggccaac gtgctcaaat cttcatacag aaagatttga agtaatattt taaccgctag 2760
atgaagagca agcgcatgga gcgacaaaat gaataaagaa caatctgctg atgatccctc 2820
cgtggatctg attcgtgtaa aaaatatgct taatagcacc atttctatga gttacccctga 2880
tgttgtaatt gcatgtatag aacataaggt gtctctggaa gcattcagag caattgaggc 2940
agcgttggtg aagcacgata ataatatgaa ggattattcc ctggtggttg actgatcacc 3000
ataactgcta atcattcaaa ctatttagtc tgtgacagag ccaacacgca gtctgtcact 3060
gtcaggaaag tggtaaaact gcaactcaat tactgcaatg ccctcgtaat taagtgaatt 3120
tacaatatcg tcctgttcgg agggaagaac gcgggatgtt cattcttcat cactttttaat 3180
tgatgtatat gctctctttt ctgacgttag tctccgacgg caggcttcaa tgacccaggc 3240
tgagaaattc ccgaccctt tttgctcaag agcgatgtta atttgttcaa tcatttggtt 3300
aggaaagcgg atgttgcggg ttgttgttct gcgggttctg ttcttcgttg acatgaggtt 3360
gccccgtatt cagtgtcgct gatttgtatt gtctgaagtt gtttttacgt taagttgatg 3420
cagatcaatt aatacgatac ctgcgtcata attgattatt tgacgtggtt tgatggcctc 3480
cacgcacgtt gtgatatgta gatgataatc attatcactt tacgggtcct ttccggtgaa 3540
aaaaaggta ccaaaaaaaa catcgtcgtg agtagtgaac cgtaagcacg ttctgttat 3600
gtttcttgtt tgttagcctt ttggctaaca aacaagaaac ataaacagaa cgtgcttacg 3660
gttcactact cacgacgatg ttttttttgg tacctttttt ttcaccggaa aggaccgta 3720
aagtgataat gattatcatc tacatatcac aacgtgcgtg gaggccatca aaccacgtca 3780
aataatcaat tatgacgcag gtatcgtatt aattgatctg catcaactta acgtaaaaac 3840
aacttcagac aatacaaatc agcgacactg aatacggggc aacctcatgt caacgaagaa 3900
cagaacccgc agaacaacaa cccgcaacat ccgctttcct aaccaaatga ttgaacaaat 3960
taacatcgct cttgagcaaa aagggtccgg gaatttctca gcctgggtca ttgaagcctg 4020
ccgtcggaga ctaacgtcag aaaagagagc atatacatca attaaaagtg atgaagaatg 4080
aacatcccgc gttcttccct ccgaacagga cgatattgta aattcactta attacgaggg 4140
cattgcagta attgagttgc agttttacca cttttcctgac agtgacagac tgcgtgttgg 4200
ctctgtcaca gactaaatag tttgaatgat tagcagttat ggtgatcagt caaccaccag 4260
ggaataatcc ttcatattat tatcgtgctt caccaacgct gcctcaattg ctctgaatgc 4320
ttccagagac acctttatgt ctatacatgc aattacaaca tcagggtaac tcatagaaat 4380
ggtgctatta agcatatttt ttacacgaat cagatccacg gagggatcat cagcagattg 4440
ttctttattc atttttgtcgc tccatgcgct tgctcttcat ctagcggtta aaatattact 4500
tcaaatcttt ctgtatgaag atttgagcac gttggcctta catacatctg tcggttgtat 4560
ttccctccag aatgccagca ggaccgcact ttgttacgca accaatacta ttaagtgaaa 4620
acattcctaa tatttgacat aaatcatcaa caaaacacaa ggaggtcaga ccagattgaa 4680
acgataaaaa cgataatgca aactacgcgc cctcgtatca catggaaggt tttaccaatg 4740
gctcaggttg ccattttaa agaaatattc gatcaagtgc gaaaagattt agactgtgaa 4800
ttgttttatt ctgaactaaa acgtcacaac gtctcacatt atatttacta tctagccaca 4860
gataatattc acatcgtgtt agaaaacgat aacaccgtgt taataaaagg acttaaaaag 4920
gttgtaaatg ttaaattctc aagaaacacg catcttatag aaacgtccta tgataggttg 4980
aaatcaagag aaatcacatt tcagcaatac agggaaaatc ttgctaaagc aggagttttc 5040
cgatgggtta caaatatcca tgaacataaa agatattact ataccttga taattcatta 5100
ctatttactg agagcattca gaacactaca caaatctttc cacgctaaat cataacgtcc 5160
ggtttcttcc gtgtcagcac cggggcgttg gcataatgca atacgtgtac gcgctaaacc 5220
ctgtgtgcat cgtttaatt attcccggac actcccgcag agaagttccc cgtcagggct 5280
gtggacatag ttaatccggg aatacaatga cgattcatcg cacctgacat acattaataa 5340
atattaacaa tatgaaattt caactcattg ttttagggtt gtttaatttt ctacacatac 5400
gattctgcga acttcaaaaa gcatcggaaa taacaccatg aaaaaaatgc tactcgctac 5460
tgcgctggcc ctgcttatta caggatgtgc tcaacagacg tttactgttc aaaacaaacc 5520
ggcagcagta gcaccaaagg aaaccatcac ccatcatttc ttcgtttctg gaattgggca 5580
gaagaaaact gtcgatgcag ccaaaatttg tggcggcgca gaaaatgttg ttaaaacaga 5640
aacccagcaa acattcgtaa atggattgct cggttttatt actttaggca tttatactcc 5700
gctggaagcg cgtgtgtatt gctcacaata attgcatgag ttgcccatcg atatgggcaa 5760
ctctatctgc actgctcatt aatatacttc tgggttcctt ccagttgttt ttgcatagtg 5820
atcagcctct ctctgagggt gaaataatcc cgttcagcgg tgtctgccag tcgggggag 5880
gctgcattat ccacgccgga ggcggtggtg gcttcacgca ctgactgaca gactgctttg 5940
atgtgcaacc gacgacgacc agcggcaaca tcatcacgca gagcatcatt ttcagcttta 6000
gcatcagcta actccttcgt gtattttgca tcgagcgcag caacatcacg ctgacgcatc 6060
tgcatgtcag taattgccgc gttcgccagc ttcagttctc tggcattttt gtcgcgctgg 6120
gctttgtagg taatggcgtt atcacggtaa tgattaacag cccatgacag gcagacgatg 6180
atgcagataa ccagagcgga gataatcgcg gtgactctgc tcatcatcca atctctctga 6240
ccgttccgcc cgcttctttg aattttgcaa tcaggctgtc agcctatgc tcgaactgac 6300
```

```
cataaccagc gcccggcagt gaagcccaga tattgctgca acggtcgatt gcctgacgga  6360
tatcaccacg atcaatcata ggtaaagcgc cacgctcctt aatctgctgc aatgccacag  6420
cgtcctgact tttcggagag aagtctttca ggccaagctg cttgcggtag gcatcccacc  6480
aacgggaaag aagctggtag cgtccggcgc ctgttgattt gagttttggg tttagcgtga  6540
caagtttgcg agggtgatcg gagtaatcag taaatagctc tccgcctaca atgacgtcat  6600
aaccatgatt tctggttttc tgacgtccgt tatcagttcc ctccgaccac gccagcatat  6660
cgaggaacgc cttacgttga ttattgattt ctaccatctt ctactccggc ttttttagca  6720
gcgaagcgtt tgataagcga accaatcgag tcagtaccga tgtagccgat aaacacgctc  6780
gttatataag cgagattgct acttagtccg gcgaagtcga gaaggtcacg aatgaactag  6840
gcgataatgg cgcacatcgt tgcgtcgatt actgttttg taaacgcacc gccattatat  6900
ctgccgcgaa ggtacgccat tgcaaacgca aggattgccc cgatgccttg ttcctttgcc  6960
gcgagaatgc cggccaacag gtcatgtttt tctggcatct tcatgtctta cccccaataa  7020
ggggatttgc tctatttaat taggaataag gtcgattact gatagaacaa atccaggcta  7080
ctgtgtttag taatcagatt tgttcgtgac cgatatgcac gggcaaaacg gcaggaggtt  7140
gttagcgcaa aaaaaaaatt ccaaaaaaaa aattccaaaa aaaaaaagcg actaacaaac  7200
acaatctgat ggcagcgact aacaaacaca atctgatggc                        7240

SEQ ID NO: 70           moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 70
tttttttttt tttttttttt                                               20

SEQ ID NO: 71           moltype = DNA   length = 7240
FEATURE                 Location/Qualifiers
misc_feature            1..7240
                        note = Synthetic Polynucleotide
source                  1..7240
                        mol_type = other DNA
                        organism = synthetic construct
SEQUENCE: 71
gccatcagat tgtgtttgtt agtcgctgcc atcagattgt gtttgttagt cgcttttttt    60
ttttggaatt ttttttttgg aatttttttt ttgcgctaac aacctcctgc gttttgccc   120
gtgcatatcg gtcacgaaca aatctgatta ctaaacacag tagcctggat tgttctatc   180
agtaatcgac cttattccta attaaataga gcaaatcctc ttattggggg taagacatga   240
agatgccaga aaaacatgac ctgttggccg ccattctcgc ggcaaaggaa caaggcatcg   300
gggcaatcct tgcgtttgca atggcgtacc ttcgcggcag atataatggc ggtgcgttta   360
caaaaacagt aatcgacgca acgatgtgcg ccattatcgc ctagttcatt cgtgaccttc   420
tcgacttcgc cggactaagt agcaatctcg cttatataac gagcgtgttt atcggctaca   480
tcggtactga ctcgattggt tcgcttatca aacgcttcgc tgctaaaaaa gccggagtag   540
aagatggtag aaatcaataa tcaacgtaag gcgttcctcg atatgctggc gtggtcggag   600
ggaactgata acggacgtca gaaaaccaga aatcatggtt atgacgtcat gtaggcggaa   660
gagctattta ctgattactc cgatcaccct cgcaaacttg tcacgctaaa cccaaaactc   720
aaatcaacag gcgccggacg ctaccagctt ctttcccgtt ggtgggatgc ctaccgcaag   780
cagcttggcc tgaaagactt ctctccgaaa agtcaggacg ctgtggcatt gcagcagatt   840
aaggagcgtg gcgctttacc tatgattgat cgtggtgata tccgtcaggc aatcgaccgt   900
tgcagcaata tctgggcttc actgccgggc gctggttatg gtcagttcga gcataaggct   960
gacagcctga ttgcaaaatt caaagaagcg ggcggaacgg tcagagagat tgatgtgatga 1020
gcagagtcac cgcgattatc tccgctctgg ttatctgcat catcgtctgc ctgtcatggg  1080
ctgttaatca ttaccgtgat aacgccatta cctacaaagc ccagcgcgac aaaaatgcca  1140
gagaactgaa gctggcgaac gcggcaatta ctgacatgca gatcgtcag cgtgatgttg  1200
ctgcgctcga tgcaaaatac acgaaggagt tagctgatgc taaagctgaa aatgatgctc  1260
tgcgtgatga tgttgccgct ggtcgtcgtc ggttgcacat caaagcagtc tgtcagtcag  1320
tgcgtgaagc caccaccgcc tccggcgtgg ataatgcagc ctcccccga ctggcagaca  1380
ccgctgaacg ggattattc accctcagag agaggctgat cactatgcaa aaacaactgg  1440
aaggaaccca gaagtatatt aatgagcagt gcagataga ttgcccatat cgatgggcaa  1500
ctcatgcaat tattgtgagc aatacacacg cgcttccagc ggagtataaa tgcctaaagt  1560
aataaaaccg agcaatccat ttacgaatgt ttgctgggtt tctgttttaa caacattttc  1620
tgcgccgcca caaattttgg ctgcatcgac agttttcttc tgcccaattc cagaaacgaa  1680
gaaatgatgg gtgatggttt cctttggtgc tactgctgc ggtttgttt gaacagtaaa  1740
cgtctgttga gcacatcctg taataagcag ggcagcgca gtagcgagta gcattttttt  1800
catggtgtta ttcccgatgc tttttgaagt tcgcagaatc gtatgtgtag aaaattaaac  1860
aaaccctaaa caatgagttg aaatttcata ttgttaatat ttattaatgt atgtcaggtg  1920
cgatgaatcg tcattgtatt cccggattaa ctatgtccac agccctgacg gggaacttct  1980
ctgcgggagt gtccggcgaa aattaaaacg atgcacacag gcttagccg gtacacgtat  2040
tgcattatgc caacgcccg gtgctgacac ggaagaaacc ggacgttatg atttagcgtg  2100
gaaagatttg tgtagtgttc tgaatgctct cagtaaatag taatgaatta caaaggtat  2160
agtaatatct tttatgttca tggatatttg taacccatcg gaaaactcct gctttagcaa  2220
gattttccct gtattgctga aatgtgattt ctcttgattt caacctatca taggacgttt  2280
ctataagatg cgtgtttctt gagaatttaa catttacaac ctttttaagt cctttatta  2340
acacggtgtt atcgttttct aacacgatgt gaatattatc tgtggctaga tagtaaatat  2400
aatgtgagac gttgtgacgt tttagttcag aataaaacaa ttcacagtct aaatcttttc  2460
gcacttgatc gaatatttct ttaaaaatgg caacctgagc cattggtaaa accttccatg  2520
tgatacgagg gcgcgtagtt tgcattatcg ttttatcgt ttcaatctgg tctgacctcc  2580
ttgtgttttg ttgatgattt atgtcaaata ttaggaatgt tttcacttaa tagtattggt  2640
```

```
tgcgtaacaa agtgcggtcc tgctggcatt ctggagggaa atacaaccga cagatgtatg 2700
taaggccaac gtgctcaaat cttcatacag aaagatttga agtaatattt taaccgctag 2760
atgaagagca agcgcatgga gcgacaaaat gaataaagaa caatctgctg atgatccctc 2820
cgtggatctg attcgtgtaa aaaatatgct taatagcacc atttctatga gttaccctga 2880
tgttgtaatt gcatgtatag aacataaggt gtctctggga gcattcagag caattgaggc 2940
agcgttggtg aagcacgata ataatatgaa ggattattcc ctggtggttg actgatcacc 3000
ataactgcta atcattcaaa ctatttagtc tgtgacagag ccaacacgca gtctgtcact 3060
gtcaggaaag tggtaaaact gcaactcaat tactgcaatg ccctcgtaat taagtgaatt 3120
tacaatatcg tcctgttcgg agggaagaac gcgggatgtt cattcttcat cacttttaat 3180
tgatgtatat gctctctttt ctgacgttag tctccgacgg caggcttcaa tgacccaggc 3240
tgagaaattc ccggaccctt tttgctcaag agcgatgtta atttgttcaa tcatttggtt 3300
aggaaagcgg atgttgcggg ttgttgttct gcgggttctg ttcttcgttg acatgaggtt 3360
gccccgtatt cagtgtcgct gatttgtatt gtctgaagtt gttttacgt taagttgatg 3420
cagatcaatt aatacgatac ctgcgtcata attgattatt tgacgtggtt tgatggcctc 3480
cacgcacgtt gtgatatgta gatgataatc attatcactt tacgggtcct ttccggtgaa 3540
aaaaaaggta ccaaaaaaaa catcgtcgtg agtagtgaac cgtaagcacg ttctgtttat 3600
gtttcttgtt tgttagcctt ttggctaaca aacaagaaac ataaacagaa cgtgcttacg 3660
gttcactact cacgacgatg ttttttttgg taccttttt ttcaccggaa aggacccgta 3720
aagtgataat gattatcatc tacatatcac aacgtgcgtg gaggccatca aaccacgtca 3780
aataatcaat tatgacgcag gtatcgtatt aattgatctg catcaactta acgtaaaaac 3840
aacttcgac aatacaaatc agcgacactg aatacgggc aacctcatgt caacgaagaa 3900
cagaacccgc agaacaacaa cccgcaacat ccgctttcct aaccaaatga ttgaacaaat 3960
taacatcgct cttgagcaaa aagggtccgg gaatttctca gcctgggtca ttgaagcctg 4020
ccgtcggaga ctaacgtcag aaaagagagc atatacatca attaaaagtg atgaagaatg 4080
aacatcccgc gttcttccct ccgaacagga cgatattgta aattcactta attacgaggg 4140
cattgcagta attgagttgc agttttacca ctttcctgac agtgacagac tgcgtgttgg 4200
ctctgtcaca gactaaatag tttgaatgat tagcagttat ggtgatcagt caaccaccag 4260
ggaataatcc ttcatattat tatcgtgctt caccaacgct gcctcaattg ctctgaatgc 4320
ttccagagac accttatgtt ctatacatgc aattacaaca tcagggtaac tcatagaaat 4380
ggtgctatta agcatatttt ttacacgaat cagatccacg cagggatcat cagcagattg 4440
ttctttattc attttgtcgc tccatgcgct tgctcttcat ctagcggtta aaatattact 4500
tcaaatcttt ctgtatgaag atttgagcac gttggcctta catacatctg tcggttgtat 4560
ttccctccag aatgccagca ggaccgcact tgttacgca accaatacta ttaagtgaaa 4620
acattcctaa tatttgacat aaatcatcaa caaaacacaa ggaggtcaga ccagattgaa 4680
acgataaaaa cgataatgca aactacgcgc cctcgtatca catggaaggt tttaccaatg 4740
gctcaggttg ccatttttaa agaaatattc gatcaagtgc gaaagattt agactgtgaa 4800
ttgtttattt ctgaactaaa acgtcacaac gtctcacatt atatttacta tctagccaca 4860
gataatattc acatcgtgtt agaaaacgat aacaccgtgt taataaaagg acttaaaaag 4920
gttgtaaatg ttaaattctc aagaaacacg catcttatag aaacgtccta tgataggttg 4980
aaatcaagag aaatcacatt tcagcaatac agggaaaatc ttgctaaagc aggagttttc 5040
cgatgggtta caaatatcca tgaacataaa agatattact ataccttga taattcatta 5100
ctatttactg agagcattca gaacactaca caaatctttc cacgctaaat cataacgtcc 5160
ggtttcttcc gtgtcagcac cggggcgttg gcataatgca atacgtgtac gcgctaaacc 5220
ctgtgtgcat cgtttttaatt attcccggac actcccgcag agaagttccc cgtcagggct 5280
gtggacatag ttaatccggg aatacaatga cgattcatcg cacctgacat acattaataa 5340
atattaacaa tatgaaattt caactcattg tttagggttt gtttaatttt ctacacatac 5400
gattctgcga acttcaaaaa gcatcgggaa taacaccatg aaaaaaatgc tactcgctac 5460
tgcgctggcc ctgcttatta caggatgtgc tcaacagacg tttactgttc aaaacaaacc 5520
ggcagcagta gcaccaaagg aaaccatcac ccatcatttc ttcgtttctg gaattgggca 5580
gaagaaaact gtcgatgcag ccaaaatttg tggcggcgca gaaaatgttg ttaaaacaga 5640
aacccagcaa acattcgtaa atggattgct cggttttatt actttaggca tttatactcc 5700
gctggaagcg cgtgtgtatt gctcacaata attgcatgag ttgcccatcg atatgggcaa 5760
ctctatctgc actgctcatt aatatacttc tgggttcctt ccagttgttt ttgcatagtg 5820
atcagcctct ctctgagggt gaaataatcc cgttcagcgg tgtctgccag tcgggggag 5880
gctgcattat ccacgccgga ggcggtggtg gcttcacgca ctgactgaca gactgctttg 5940
atgtgcaacc gacgacgacc agcggcaaca tcatcacgcg gagcatcatt ttcagcttta 6000
gcatcagcta actccttcgt gtattttgca tcgagcgcag caacatcacg ctgacgcatc 6060
tgcatgtcag taattgccgc gttcgccagc ttcagttctc tggcatttt gtcgcgctgg 6120
gctttgtagg taatggcgtt atcacggtaa tgattaacag cccatgacag gcagacgatg 6180
atgcagataa ccagagcgga gataatcgcg gtgactctgc tcatacatca atctctctga 6240
ccgttccgcc cgcttctttg aattttgcaa tcaggctgtc agcctttatgc tcgaactgac 6300
cataaccagc gcccggcagt gaagcccaga tattgctgca acgtcgatt gcctgacgga 6360
tatcaccacg atcaatcata ggtaaagcgc cacgctcctt aatctgctgc aatgccacag 6420
cgtcctgact tttcggagag aagtctttca ggccaagctg cttggtag gcatcccaacc 6480
aacggggaaag aagctggtag cgtccggcgc ctgttgattt gagttttggg tttagcgtga 6540
caagtttgcg agggtgatcg gagtaatcag taaatagctc tccgcctaca atgacgtcat 6600
aaccatgatt tctggttttc tgacgtccgt tatcagttcc ctccgaccac gccagcatat 6660
cgaggaacgc cttacgttga ttattgattt ctaccatctt ctactccggc ttttttagca 6720
gcgaagcgtt tgataagcga accaatcgag tcagtaccga tgtagccgat aaacacgctc 6780
gttatataag cgagattgct acttagtccg gcgaagtcga gaaggtcacg aatgaactag 6840
gcgataatgg cgcacatcgt tgcgtcgatt actgttttg taaacgcacc gccattatat 6900
ctgccgcgaa ggtacgccat tgcaaacgca aggattgccc cgatgccttg ttcctttgcc 6960
gcgagaatgg cggccaacag gtcatgtttt tctggcatct tcatgtctta ccccaataaa 7020
ggggatttgc tctatttaat taggaataag gtcgattact gatagaacaa atccaggcta 7080
ctgtgtttag taatcagatt tgttcgtgac cgatatgcac gggcaaaacg gcaggaggtt 7140
gttagcgcaa aaaaaaaatt ccaaaaaaaa aattccaaaa aaaaaaagcg actaacaaac 7200
acaatctgat ggcagcgact aacaaacaca atctgatggc                      7240

SEQ ID NO: 72          moltype = DNA   length = 3653
```

| FEATURE | Location/Qualifiers |
|---|---|
| misc_feature | 1..3653 |
| | note = Synthetic Polynucleotide |
| misc_feature | 3648 |
| | note = n is uridine |
| source | 1..3653 |
| | mol_type = other DNA |
| | organism = synthetic construct |

SEQUENCE: 72

```
gccatcagat tgtgtttgtt agtcgctgcc atcagattgt gtttgttagt cgcttttttt    60
ttttggaatt ttttttttgg aatttttttt ttgcgctaac aacctcctgc cgttttgccc   120
gtgcatatcg gtcacgaaca aatctgatta ctaaacacag tagcctggat ttgttctatc   180
agtaatcgac cttattccta attaaataga gcaaatcccc ttattggggg taagacatga   240
agatgccaga aaaacatgac ctgttggccg ccattctcgc ggcaaaggaa caaggcatcg   300
gggcaatcct tgcgtttgca atggcgtacc ttcgcggcag atataatggc ggtgcgttta   360
caaaaacagt aatcgacgca acgatgtgcg ccattatcgc ctagttcatt cgtgaccttc   420
tcgacttcgc cggactaagt agcaatctcg cttatataac gagcgtgttt atcggctaca   480
tcggtactga ctcgattggt tcgcttatca aacgcttcgc tgctaaaaaa gccggagtag   540
aagatggtag aaatcaataa tcaacgtaag gcgttcctcg atatgctggc gtggtcggag   600
ggaactgata acgacgtcag aaaaccagaa aatcatggtt atgacgtcat gtaggcgga   660
gagctatta ctgattactc cgatcaccct cgcaaacttg tcacgctaaa cccaaaactc   720
aaatcaacag gcgccggacg ctaccagctt ctttcccgtt ggtgggatgc ctaccgcaag   780
cagcttggcc tgaaagactt ctctccgaaa agtcaggacg ctgtggcatt cagcagatt   840
aaggagcgtg gcgctttacc tatgattgat cgtggtgata tccgtcaggc aatcgaccgt   900
tgcagcaata tctgggcttc actgccgggc gctggtatg tcagttcga gcataaggct   960
gacagcctga ttgcaaaatt caaagaagcg ggcggaacg tcagagagt tgatgtatga  1020
gcagagtcac cgcgattatc tccgctctgg ttatctgcat catcgtctgc ctgtcatggg  1080
ctgttaatca ttaccgtgat aacgccatta cctacaaagc ccagcgcgac aaaaatgcca  1140
gagaactgaa gctggcgaac gcggcaatta ctgacatgca gatgcgtcag cgtgatgttg  1200
ctgcgctcga tgcaaaatac acgaaggagt tagctgatgc taaagctgaa aatgatgctc  1260
tgcgtgatga tgttgccgct ggtcgtcgtc ggttgcacat caaagcagtc tgtcagtcag  1320
tgcgtgaagc caccaccgcc tccggcgtgg ataatgcagc ctcccccga ctggcagaca  1380
ccgctgaacg ggattatttc accctcagag agaggctgat cactatgcaa aaacaactgg  1440
aaggaaccca gaagtatatt aatgagcagt gcagatagag ttgcccatat cgatgggcaa  1500
ctcatgcaat tattgtgagc aatacacacg cgcttccagc ggagtataaa tgcctaaagt  1560
aataaaaccg agcaatccat ttacgaatgt tgctgggtt tctgttttaa caacatttc  1620
tgcgccgcca caattttgg ctgcatcgac agttttcttc tgcccaattc cagaaacgaa  1680
gaaatgatgg gtgatggttt cctttggtgc tactgctgcc ggttgtttt gaacagtaaa  1740
cgtctgttga gcacatcctg taataagcag ggccagcgca gtagcgagta gcatttttt  1800
catggtgtta ttcccgatgc tttttgaagt tcgcagaatc gtatgtgtag aaaattaaac  1860
aaaccctaaa caatgagttg aaatttcata ttgttaatat ttattaatgt atgtcaggtg  1920
cgatgaatcg tcattgtatt cccggattaa ctatgtccac agccctgacg gggaacttct  1980
ctgcgggagt gtccgggaat aattaaaacg atgcacacag gttttagcgc gtacacgtat  2040
tgcattatgc caacgccccg gtgctgacac ggaagaaacc ggacgttatg atttagcgtg  2100
gaaagatttg tgtagtgttc tgaatgctct cagtaaatag taatgaatta tcaaaggtat  2160
agtaatatct tttatgttca tggatatttg taacccatcg gaaaactcct gctttagcaa  2220
gatttttccct gtattgctga aatgtgattt ctcttgattt caacctatca taggacgttt  2280
ctataagatg cgtgttctt gagaatttaa catttacaac cttttaagt cctttatta  2340
acacggtgtt atcgttttct aacacgatgt gaatattatc tgtggctaga tagtaaatat  2400
aatgtgagac gttgtgacgt tttagttcag aataaaacaa ttcacagtct aaatcttttc  2460
gcacttgatc gaatattct ttaaaaatgg caacctgagc cattggtaaa accttccatg  2520
tgatacgagg gcgcgtagtt tgcattatcg tttttatcgt ttcaatctgg tctgacctcc  2580
ttgtgttttg ttgatgattt atgtcaaata ttaggaatgt tttcacttaa tagtattggt  2640
tgcgtaacaa agtgcggtcc tgctggcatt ctggagggaa atacaaccga cagatgtatg  2700
taaggccaac gtgctcaaat cttcatacag aaagatttga agtaatattt taaccgctag  2760
atgaagagca agcgcatgga gcgacaaaat gaataaagaa caatctgctg atgatccctc  2820
cgtggatctg attcgtgtaa aaaatatgct taatagcacc atttctatga gttaccctga  2880
tgttgtaatt gcatgtatag aacataaggt gtctctggaa gcattcagag caattgaggc  2940
agcgttggtg aagcacgata ataatatgaa ggattattcc ctggtggttg actgatcacc  3000
ataactgcta atcattcaaa ctatttagtc tgtgacagag ccaacacga gtcgtcact  3060
gtcaggaaag tggtaaaact gcaactcaat tactgcaatg ccctcgtaat taagtgaatt  3120
tacaatatcg tcctgttcgg agggaagaac gcgggatgtt cattcttcat cacttttaat  3180
tgatgtatat gctctctttt ctgacgttag tctccgacgg caggcttcaa tgacccaggc  3240
tgagaaattc ccggaccctt tttgctcaag agcgatgtta attttccaa tcatttggtt  3300
aggaaagcgg atgttgcggg ttgttgttct gcggggttctg ttcttcgttg acatgaggtt  3360
gccccgtatt cagtgtcgct gatttgtatt gtctgaagtt gtttttacgt taagttgatg  3420
cagatcaatt aatacgatac ctgcgtcata attgattatt tgacgtggtt tgatggcctc  3480
cacgcacgtt gtgatatgta gatgataatc attatcactt tacgggtcct ttccggtgaa  3540
aaaaaggta ccaaaaaaaa catcgtcgtg agtagtgaac cgtaagcagc gacggctgag  3600
aagttccact caagcctctg acactgattg cacggtttta gtgaacnttt ttt          3653
```

| SEQ ID NO: 73 | moltype = DNA length = 3643 |
|---|---|
| FEATURE | Location/Qualifiers |
| misc_feature | 1..3643 |
| | note = Synthetic Polynucleotide |
| source | 1..3643 |
| | mol_type = other DNA |
| | organism = synthetic construct |

SEQUENCE: 73

```
cttctcaatg tgtacgtgtc ctctagaggc ttgagtggaa cttctcagcc gtcgctgctt    60
acggttcact actcacgacg atgttttttt tggtaccttt tttttcaccg gaaaggaccc   120
gtaaagtgat aatgattatc atctacatat cacaacgtgc gtggaggcca tcaaaccacg   180
tcaaataatc aattatgacg caggtatcgt attaattgat ctgcatcaac ttaacgtaaa   240
aacaacttca gacaatacaa atcagcgaca ctgaatacgg ggcaacctca tgtcaacgaa   300
gaacagaacc cgcagaacaa caacccgcaa catccgcttt cctaaccaaa tgattgaaca   360
aattaacatc gctcttgagc aaaaagggtc cgggaatttc tcagcctggg tcattgaagc   420
ctgccgtcgg agactaacgt cagaaaagag agcatataca tcaattaaaa gtgatgaaga   480
atgaacatcc cgcgttcttc cctccgaaca ggacgatatt gtaaattcac ttaattacga   540
gggcattgca gtaattgagt tgcagtttta ccactttcct gacagtgaca gactgcgtgt   600
tggctctgtc acagactaaa tagtttgaat gattagcagt tatggtgatc agtcaaccac   660
cagggaataa tccttcatat tattatcgtg cttccaccaac gctgcctcaa ttgctctgaa   720
tgcttccaga gacaccttat gttctataca tgcaattaca acatcagggt aactcataga   780
aatggtgcta ttaagcatat tttttacacg aatcagatcc acggagggat catcagcaga   840
ttgttcttta ttcattttgt cgctccatgc gcttgctctt catctagcgg ttaaaatatt   900
acttcaaatc tttctgtatg aagatttgag cacgttggcc ttacatacat ctgtcggttg   960
tatttccctc cagaatgcca gcaggaccgc actttgttac gcaaccaata ctattaagtg  1020
aaaacattcc taatatttga cataaatcat caacaaaaca caaggaggtc agaccagatt  1080
gaaacgataa aaacgataat gcaaactacg cgccctcgta tcacatggaa ggttttacca  1140
atggctcagg ttgccatttt taagaaaata ttcgatcaag tgcgaaaaga tttagactgt  1200
gaattgtttt attctgaact aaaacgtcac aacgtctcac attatattta ctatctagcc  1260
acagataata ttcacatcgt gttagaaaac gataacacg tgttaataaa aggacttaaa  1320
aaggttgtaa atgttaaatt ctcaagaaac acgcatctta tagaaacgtc ctatgatagg  1380
ttgaaatcaa gagaaatcac atttcagcaa tacaggaaaa atcttgctaa agcaggagtt  1440
ttccgatggg ttacaaatat ccatgaacat aaaagatatt actataccct tgataattca  1500
ttactattta ctgagagcat tcagaacact cacacaaatc tttccacgcta aatcataacg  1560
tccggttctct tccgtgtcag caccggggcg ttggcataat gcaatacgtg tacgcgctaa  1620
accctgtgtg catcgtttta attattcccg gacactccg cagagaagtt ccccgtcagg   1680
gctgtgggaca tagttaatcc gggaatacaa tgacgattca tcgcacctga catacattaa  1740
taaatattaa caatatgaaa tttcaactca ttgtttaggg tttgtttaat tttctacaca  1800
tacgattctg cgaacttcaa aaagcatcgg gaataacacc atgaaaaaaa tgctactcgc  1860
tactgcgctg gccctgctta ttacaggatg tgctcaacag acgtttactg ttcaaaacaa  1920
accggcagca gtagcaccaa aggaaaccat cacccatcat ttcttcgttt ctggaattgg  1980
gcagaagaaa actgtcgatg cagccaaaat ttgtggcggc gcagaaaatg ttgttaaaac  2040
agaaacccag caaacattcg taaatggatt gctcggtttt attactttag gcatttatac  2100
tccgctggaa gcgcgtgtgt attgctcaca ataattgcat gagttgccca tcgatatggg  2160
caactctatc tgcactgctc attaatatac ttctgggttc cttccagttg tttttgcata  2220
gtgatcagcc tctctctgag ggtgaaaataa tcccgttcag cggtgtctgc cagtcggggg  2280
gaggctgcat tatccacgcc ggaggcggtg gtggcttcac gcactgactg acagactgct  2340
ttgatgtgca accgacgacg accagcggca acatcatcac gcagagcatc attttcagct  2400
ttagcatcag ctaactcctt cgtgtatttt gcatcgagcg cagcaacatc acgctgacgc  2460
atctgcatgt cagtaattgc cgcgttcgcc agcttcagtt ctctggcatt tttgtcgcgc  2520
tgggctttgt aggtaatggc gttatcacgg taatgattaa cagcccatga caggcagacg  2580
atgatgcaga taaccagagc ggagataatc gcggtgactc tgctcataca tcaatctctc  2640
tgaccgttcc gcccgcttct ttgaattttg caatcaggct gtcagcctta tgctcgaact  2700
gaccataacc agcgcccggc agtgaagccc agatattgct gcaacggtcg attgcctgac  2760
ggatatcaac acgatcaatc ataggtaaag cgccacgctc cttaatctgc tgcaatgcca  2820
cagcgtcctg acttttcgga gagaagtctt tcaggccaag ctgcttgcgg taggcatccc  2880
accaacggga aagaagctgg tagcgtcgg cgcctgttga tttgagtttt gggtttagcg  2940
tgacaagttt gcgagggtga tcggagtaat cagtaaatag ctctccgcct acaatgacgt  3000
cataacccatg atttctggtt ttctgacgtc cgttatcagt tccctccgac cacgccagca  3060
tatcgaggaa cgccttacgt tgattattga tttctaccat cttctactcc ggcttttttta  3120
gcagcgaagc gtttgataag cgaaccaatc gagtcagtac cgatgtagcc gataaacacg  3180
ctcgttatat aagcgagatt gctacttagt ccggcgaagt cgagaaggtc acgaatgaac  3240
taggcgataa tggcgcacat cgttgcgtcg attactgttt ttgtaaacgc accgccatta  3300
tatctgccgc gaaggtacgc cattgcaaac gcaaggattg ccccgatgcc ttgttccttt  3360
gccgcgagaa tggcggccaa caggtcatgt ttttctggca tcttcatgtc ttaccccaaa  3420
taagggggatt tgctctattt aattaggaat aaggtcgatt actgatagaa caaatccagg  3480
ctactgtgtt tagtaatcag atttgttcgt gaccgatatg cacgggcaaa acggcaggag  3540
gttgttagcg caaaaaaaaa attccaaaaa aaaaattcca aaaaaaaaaa gcgactaaca  3600
aacacaatct gatggcagcg actaacaaac acaatctgat ggc                    3643

SEQ ID NO: 74             moltype = DNA  length = 45
FEATURE                   Location/Qualifiers
misc_feature              1..45
                          note = Synthetic Polynucleotide
source                    1..45
                          mol_type = other DNA
                          organism = synthetic construct
SEQUENCE: 74
gcaatatcag caccaacaga aacaaccttt gaggcgagcg gtcaa                   45

SEQ ID NO: 75             moltype = DNA  length = 15
FEATURE                   Location/Qualifiers
misc_feature              1..15
                          note = Synthetic Polynucleotide
source                    1..15
                          mol_type = other DNA
                          organism = synthetic construct
```

```
SEQUENCE: 75
ttgaccgctc gcctc                                                       15

SEQ ID NO: 76           moltype = DNA   length = 10
FEATURE                 Location/Qualifiers
misc_feature            1..10
                        note = Synthetic Polynucleotide
source                  1..10
                        mol_type = other DNA
                        organism = synthetic construct
SEQUENCE: 76
tttttttttt                                                             10

SEQ ID NO: 77           moltype = DNA   length = 59
FEATURE                 Location/Qualifiers
misc_feature            1..59
                        note = Synthetic Polynucleotide
source                  1..59
                        mol_type = other DNA
                        organism = synthetic construct
SEQUENCE: 77
ggttgtttct gttggtgctg atattgcact gagtgaccaa tcagctacgt tttttttt        59

SEQ ID NO: 78           moltype = DNA   length = 3636
FEATURE                 Location/Qualifiers
misc_feature            1..3636
                        note = Synthetic Polynucleotide
source                  1..3636
                        mol_type = other DNA
                        organism = synthetic construct
SEQUENCE: 78
ggttgtttct gttggtgctg atattgctgc catcagattg tgtttgttag tcgcttttt       60
tttttggaat tttttttttg gaattttttt tttgcgctaa caacctcctg ccgttttgcc      120
cgtcgatatc ggtcacgaac aaatctgatt actaaacaca gtagcctgga tttgttctat     180
cagtaatcga ccttattcct aattaaaatag agcaaatccc cttattgggg gtaagacatg    240
aagatgccag aaaaacatga cctgttggcc gccattctcg cggcaaagga acaaggcatc     300
ggggcaatcc ttgcgtttgc aatggcgtac cttcgcggca gatataatgg cggtgcgttt     360
acaaaaacag taatcgacgc aacgatgtgc gccattatcg cctagttcat tcgtgacctt    420
ctcgacttcg ccggactaag tagcaatctc gcttatataa cgagcgtgtt tatcggctac    480
atcggtactg actcgattgg ttcgcttatc aaacgcttcg ctgctaaaaa agccggagta    540
gaagatggta gaaatcaata atcaacgtaa ggcgttcctc gatatgctgg cgtggtcgga   600
gggaactgat aacggacgtc agaaaaccag aaatcatggt tatgacgtca ttgtaggcgg    660
agagctattt actgattact ccgatcaccc tcgcaaactt gtcacgctaa acccaaaact    720
caaatcaaca ggcgccggac gctaccagct tctttcccgt tggtgggatg cctaccgcaa    780
gcagcttggc ctgaaagact tctctccgaa aagtcaggac gctgtggcat tgcagcagat    840
taaggagcgt ggcgctttac ctatgattga tcgtggtgat atccgtcagg caatcgaccg    900
ttgcagcaat atctgggctt cactgccggg cgctggttat gtcagttcg agcataaggc    960
tgacagcctg attgcaaaat tcaaagaagc gggcggaacg gtcagagaga ttgatgtatg    1020
agcagagtca ccgcgattat ctccgctctg gttatctgca tcatcgtctg cctgtcatgg   1080
gctgttaatc attaccgtga taacgccatt acctacaaag cccagcgcga caaaaatgcc    1140
agagaactga agctggcgaa cgcggcaatt actgacatgc agatgcgtca gcgtgatgtt    1200
gctgcgctcg atgcaaaata cacgaaggag ttagctgatg ctaaagctga aaatgatgct    1260
ctgcgtgatg atgttgccgc tggtcgtcgt cggttgcaca tcaaagcagt ctgtcagtca    1320
gtgcgtgaag ccaccaccgc ctccggcgtg gataatgcag cctcccccg actggcagac    1380
accgctgaac gggattattt caccctcaga gagggctga tcactatgca aaaacaactg    1440
gaaggaaccc agaagtatat taatgagcag tgcagataga gttgcccata tcgatgggca   1500
actcatgcaa ttattgtgag caatacacac gcgcttccag cggagtataa atgcctaaag    1560
taataaaacc gagcaatcca tttacgaatg tttgctgggt ttctgtttta acaacatttt    1620
ctgccgcgcc acaaattttg gctgcatcga cagttttctt ctgcccaatt ccagaaacga    1680
agaaatgatg ggtgatggtt tcctttggtg ctactgctgc cggtttgttt tgaacagtaa    1740
acgtctgttg agcacatcct gtaataagca gggccagcgc agtagcgagt gcatttttt    1800
tcatggtgtt attcccgatg cttttttgaag ttcgcagaat cgtatgtgta gaaaattaaa   1860
caaacccctaa acaatgagtt gaaatttcat attgttaata tttattaatg tatgtcaggt    1920
gcgatgaatc gtcattgtat tcccggatta actatgtcca cagccctgac ggggaactte    1980
tctgcgggag tgtccgggaa taattaaaac gatgcacaca gggtttagcg cgtacgtaa    2040
ttgcattatg ccaacgcccc ggtgctgaca cggaagaaac cggacgttat gatttagcgt    2100
ggaaagattt gtgtagtgtt ctgaatgctc tcagtaaata gtaatgaatt atcaaaggta    2160
tagtaatatc ttttatgttc atggatattt gtaacccatc ggaaaactcc tgctttagca    2220
agatttttccc tgtattgctg aaatgtgatt tctccttgatt tcaacctatc ataggacgtt    2280
tctataagat gcgtgttctt tgagaattta acattttacaa ccttttttaag tcctttttatt   2340
aacacggtgt tatcgttttc taacacgatg tgaatattat ctgtggctag atagtaaata    2400
taatgtgaga cgttgtgacg tttagttcaa gaataaaaca attcacagtc taaatctttt    2460
cgcacttgat cgaatttttc tttaaaaatg gcaacctgag ccattggtaa aaccttccat    2520
gtgatacgag ggcgcgtagt ttgcattatc gtttttatcg gtctgacctc                2580
cttgtgtttt gttgatgatt tatgtcaaat attaggaatg ttttcactta atagtattgg   2640
ttgcgtaaca aagtcgggtc ctgctggcat tctggaggga aatacaaccg acagatgtat    2700
gtaaggccaa cgtgctcaaa tcttcataca gaaagatttg aagtaatatt ttaaccgcta    2760
gatgaagagc aagcgcatgg agcgacaaaa tgaataaaga acaatctgct gatgatccct    2820
ccgtggatct gattcgtgta aaaaatatgc ttaatagcac catttctatg agttaccctg    2880
```

```
atgttgtaat tgcatgtata gaacataagg tgtctctgga agcattcaga gcaattgagg    2940
cagcgttggt gaagcacgat aataatatga aggattattc cctggtggtt gactgatcac    3000
cataactgct aatcattcaa actatttagt ctgtgacaga gccaacacgc agtctgtcac    3060
tgtcaggaaa gtggtaaaac tgcaactcaa ttactgcaat gccctcgtaa ttaagtgaat    3120
ttacaatatc gtcctgttcg gagggaagaa cgcgggatgt tcattcttca tcacttttaa    3180
ttgatgtata tgctctcttt tctgacgtta gtctccgacg gcaggcttca atgacccagg    3240
ctgagaaatt cccggaccct ttttgctcaa gagcgatgtt aatttgttca atcatttggt    3300
taggaaagcg gatgttgcgg gttgttgttc tgcgggttct gttcttcgtt gacatgaggt    3360
tgcccgtat tcagtgtcgc tgatttgtat tgtctgaagt tgttttttacg ttaagttgat    3420
gcagatcaat taatacgata cctgcgtcat aattgattat ttgacgtggt ttgatggcct    3480
ccacgcacgt tgtgatatgt agatgataat cattatcact ttacgggtcc tttccggtga    3540
aaaaaaaggt accaaaaaaa acatcgtcgt gagtagtgaa ccgtaagccg tcctgtcgct    3600
gtgtctcgga cactgattga cacggtttag tagagc                              3636

SEQ ID NO: 79          moltype = DNA  length = 52
FEATURE                Location/Qualifiers
misc_feature           1..52
                       note = Synthetic Polynucleotide
source                 1..52
                       mol_type = other DNA
                       organism = synthetic construct
SEQUENCE: 79
tttttttttt tttttttttt tttttttttcg agacacagcg acaggacgtc ct            52

SEQ ID NO: 80          moltype = DNA  length = 83
FEATURE                Location/Qualifiers
misc_feature           1..83
                       note = Synthetic Polynucleotide
source                 1..83
                       mol_type = other DNA
                       organism = synthetic construct
SEQUENCE: 80
cgtagctgat tgaggtcact cagtgcaata tcagcaccaa cagaaacaac ctttgaggcg     60
agcggtcaag cgacgaggtg tcc                                             83
```